United States Patent
Lederman et al.

(10) Patent No.: US 9,403,755 B2
(45) Date of Patent: *Aug. 2, 2016

(54) ISOMETHEPTENE ISOMER

(71) Applicant: TONIX PHARMACEUTICALS INC., New York, NY (US)

(72) Inventors: Seth Lederman, New York, NY (US); Bruce Daugherty, Mendham, NJ (US); Leland J. Gershell, New York, NY (US); Darryl Rideout, Parkton, MD (US); Andrew Kawasaki, San Diego, CA (US)

(73) Assignee: TONIX PHARMA HOLDINGS LIMITED (BERMUDA), Hamilton (BM)

( * ) Notice: Subject to any disclaimer, the term of this patent is extended or adjusted under 35 U.S.C. 154(b) by 60 days.

This patent is subject to a terminal disclaimer.

(21) Appl. No.: 14/158,735

(22) Filed: Jan. 17, 2014

(65) Prior Publication Data

US 2014/0212486 A1 Jul. 31, 2014

Related U.S. Application Data

(60) Provisional application No. 61/926,739, filed on Jan. 13, 2014, provisional application No. 61/814,664, filed on Apr. 22, 2013, provisional application No. 61/793,456, filed on Mar. 15, 2013, provisional application No. 61/754,281, filed on Jan. 18, 2013.

(51) Int. Cl.
  *C07C 211/21* (2006.01)
  *C07C 59/285* (2006.01)
  (Continued)

(52) U.S. Cl.
  CPC .............. *C07C 211/21* (2013.01); *A61K 31/047* (2013.01); *A61K 31/131* (2013.01);
  (Continued)

(58) Field of Classification Search
  CPC ............ A61K 2300/00; A61K 31/131; A61K 31/167; A61K 31/192; A61K 31/4152; A61K 31/522; A61K 31/047; A61K 31/4045; A61K 31/616; A61K 45/06; C07B 53/00; C07B 2200/07; C07C 211/21; C07C 59/285
  USPC ............. 424/463, 464; 514/263.34, 404, 671; 562/582; 564/509
  See application file for complete search history.

(56) References Cited

U.S. PATENT DOCUMENTS 1,972,450 A   9/1934   Klavehn
2,230,753 A   2/1941   Klavehn et al.
(Continued)

FOREIGN PATENT DOCUMENTS

EP   0780389 A1   6/1997
KR   1020000031737   6/2000

OTHER PUBLICATIONS

PubChem Substance Record for SID 50125852 (National Center for Biotechnology Information. PubChem Substance Database; SID=50125852, https://pubchem.ncbi.nlm.nih.gov/substance/50125852, available to the public on Aug. 12, 2008, and accessed Aug. 20, 2015, p. 1-6.*

(Continued)

*Primary Examiner* — Fereydoun G Sajjadi
*Assistant Examiner* — Amy C Bonaparte
(74) *Attorney, Agent, or Firm* — Withers Bergman LLP

(57) ABSTRACT

The invention relates to a purified Isometheptene compound comprising the structure according to Formula (I),

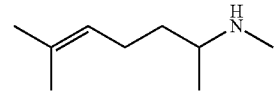

(6-methylamino-2-methylheptene)

or a hydrochloride, or a pharmaceutically acceptable addition salt thereof. In particular, the disclosure relates to the synthesis, purification and characterization of an Isometheptene isomer mucate crystal 2, wherein the Isometheptene isomer 2 is stereochemically characterized as (R)-enantiomer, respectively. The Isometheptene (R)-enantiomer activity indicates a selective centrally acting selective ligand for Imidazoline subtype 1 (I1) receptor sites; and more specifically, the disclosure provides an antihypertensive composition for treatment of migraine and other neurovascular or neurogenic pain from abdominal distress. (R)-Isometheptene enantiomer or isomer 2 may be an anti-hypertensive agent with lower side effects than the racemate form. Therefore (R)-Isometheptene is believed to be effective against episodic tension-type headaches (ETTH). The (R)-Isometheptene enantiomer or isomer 2 is believed to effectively lower blood pressure, used alone or together with other headache ameliorating drugs. Methods of synthesis and treatment are described. Regarding (R)-Isometheptene crystals data of X-ray crystallography are presented.

7 Claims, 24 Drawing Sheets

(51) Int. Cl.
   A61K 31/131    (2006.01)
   A61K 45/06     (2006.01)
   C07B 53/00     (2006.01)
   A61K 31/167    (2006.01)
   A61K 31/192    (2006.01)
   A61K 31/522    (2006.01)
   A61K 31/4152   (2006.01)
   A61K 31/047    (2006.01)
   A61K 31/4045   (2006.01)
   A61K 31/616    (2006.01)

(52) U.S. Cl.
   CPC ............. *A61K31/167* (2013.01); *A61K 31/192* (2013.01); *A61K 31/4045* (2013.01); *A61K 31/4152* (2013.01); *A61K 31/522* (2013.01); *A61K 31/616* (2013.01); *A61K 45/06* (2013.01); *C07B 53/00* (2013.01); *C07C 59/285* (2013.01); *C07B 2200/07* (2013.01)

(56)                References Cited

U.S. PATENT DOCUMENTS 4,522,827    A    6/1985   Marlettini et al.
   2015/0258197 A1*  9/2015   Lederman ............ A61K 31/131
                                                        514/162

OTHER PUBLICATIONS

PubChem Compound Summary for CID 24871315 (National Center for Biotechnology Information. PubChem Compound Database; CID=24871315, https://pubchem.ncbi.nlm.nih.gov/compound/24871315, created Aug. 12, 2008 and accessed Aug. 20, 2015, p. 1-14.*
Cocolas, George et al., "Synthetic Spasmolytic Amines", Journal of Medicinal Chemistry, Nov. 1, 1965, 875-877, vol. 8, No. 6.
Ellis, Sydney et al., "Effect of amines on blood sugar of the rat", Chemical Abstracts Service, Columbus, Ohio, US, retrieved from STN, Database accession No. 1951: 24810, 1951.
Jacome, Daniel E. et al., "The Non-epileptiform Basilar Artery Migraine", Headache, Oct. 1, 1986, 447-450, vol. 26, No. 9.
Johnston, Blair D. et al., "Facile syntheses of the enantiomers of sulcatol", Canadian Journal of Chemistry, Jan. 15, 1979, 233-235, vol. 57, No. 2.
Lyris, Emmanouil et al., "Metabolism of isometheptene in human urine and analysis by gas chromatography-mass spectrometry in doping control", J. Chromatogr. B., 2005, 199-204, vol. 827.
Plakogiannis, Fotios M et al., "Simultaneous GLC Determination of Acetaminophen, Dichloralantipyrine, and Isometheptene Mucate", J. Pharm. Sci., 1977, 604-605, vol. 66(4).
Samaan, Karam et al., "Mode of action of methyloctenylamine hydrochloride (octinum)", Chemical Abstracts Service, Columbus, Ohio, US, retrieved from STN, Database accession No. 1937: 19086. 1936.
Taylor, Wesley G. et al., "Preparation of two metabolites of isometheptene", Can J. Chem 1979, 2103-2107, vol. 57.
Willems, Edwin et al., "Pharmacological profile of the mechanisms involved in the external carotid vascular effects of the antimigraine agent isometheptene in anaesthetised dogs", Naunyn-Schmiedeberg's Archives of Pharmacology, Jul. 1, 2001, 27-32, vol. 364, No. 1.
Horton, BT, et al. A new product in the treatment of migraine: A preliminary report, Proc. Staff Meet Mayo Clin. 1945. xx:241-248.
Palmer, H. Migraine headache, Clinics. 1945. IV: 531-554.
Walton, RP and Preacher, CB, Toxicity of methylamino-iso-octene. Federation Proc. 1946. V, 211.
MacNeal, P. S., and Davis, D.: The Use of methyl-iso-octenylamine in migraine. Ann Intern Med. 1947 26(4):526-7.
Pantalone AL and Thomas GJ. Methyl-iso-octenylamine (octin) relief of headaches following spinal tap. Curr Res Anesth Analg. 1952 31(6):69-71.

Peters GA and Zeller WW. Evaluation of a new agent (methyl-iso-octenylamine) in the treatment of vasodilating headaches. Proc Staff Meet Mayo Clin. 1949 24(23):565-8.
Seltzer, A.: The use of methyl-iso-octenylamine (Octin) in migraine and related headaches: preliminary report. Med Ann Dist Columbia. 1948 17(7):395-6.
Blumenthal, L.S., and Fuchs, M.: Headache Clinics I. Am. Pract. and Digest Treat. 1950. 1: 1012.
Blumenthal, L.S., and Fuchs, M.: Headache Clinics II. Am. Pract. and Digest Treat. 1951. 2:163.
Ogden, HD., Headache Studies. Statistical Data. II. Headache Patterns. J. Allergy. 1952. 23:458.
Blumenthal, L.S. and Fuchs, M. Headache Clinics IV. Am. Pract. and Digest Treat. 1953. 4:31.
Brazeau, P.: Oxytocics, in Goodman L.S., Gilman, A. (eds): The Pharmacological Basis of Therapeutics, ed 4. New York, The Macmillan Co. 1970. 893-907.
Ogden, H.D.: Controlled studies of a new agent in vascular headache. Headache. 1963 3:29-31.
Young, H.: A study of a non-ergotamine agent in the office treatment of vascular headache. Ind Med Surg. 1966 35(2):127-9.
Johnson, D.E.: An alternative to ergotamines in the treatment of vascular headaches. Clin. Med. 1970. 77:33-36.
Yuill, G.M., et al. A double-blind crossover trial of Isometheptene mucate compound and ergotamine in migraine. Br J Clin Pract. 1972 26(2):76-9.
Diamond S. Treatment of migraine with Isometheptene, acetaminophen, and dichloralphenazone combination: A double-blind, crossover trial. Headache. 1976 15(4):282-7.
Valdivia, LF, et al. Pharmacological analysis of the mechanisms involved in the tachycardic and vasopressor responses to the antimigraine . . . Life Sciences 2004. 74:3223-3234.
Freitag, FG., et al. Comparative Study of a Combination of Isometheptene Mucate, Dichloralphenazone . . . Headache. 2001. 41(4): 391-8. PMID:11318886.
Gibbs TS. Health Care Utilization in Patients With Migraine: Demographics and Patterns of Care in the Ambulatory Setting. Headache. 2003 43(4):330-5.
Loder, E. Fixed Drug Combinations for the Acute Treatment of Migraine Place in Therapy CNS Drugs. 2005;19(9):769-84.
Chrousos, G. P. & Gold, P. W. The concepts of stress and stress system disorders: overview of physical and behavioral homeostasis. JAMA 1992: 267:1244-1252.
Moffett, Adrienne; et al. (1972). "Effect of tyramine in migraine: . . . ". Journal of Neurology, Neurosurgery and Psychiatry 35, 4: 496-499.
Borowsky B, et al.(2001). "Trace amines: identification of a family of mammalian G protein-coupled receptors." Proc Natl Acad Sci USA 98:8966-8971.
Kossel, Albrecht, 1910. Über das Agmatin. Zeitschrift fur Physiologische Chemie 66: 257-261.
Wang, C-C., et al., Beneficial effect of agmatine on brain apoptosis, astrogliosis, and edema after rat transient cerebral ischemia.BMC Pharmacol. 2010. 10:11.
Gong, Z-H., et al. Anxiolytic effect of agmatine in rats and mice. Eur. J. Pharmacol. 2006. 550:112-116.
Arteni NS, et al. Agmatine facilitates memory of an inhibitory avoidance task in adult rats. Neurobiol Learn Mem 2002;78:465-9.
Zomkowski, A.D., et al. Agmatine produces antidepressant-like effects in two models of depression in mice. NeuroReport 2002. 13:387-391.
Li, Y.F., et al. Antidepressant-like effect of agmatine and its possible mechanism. Eur. J. Pharmacol. 2003. 469:81-88.
Hwang SL, et al. Activation of imidazoline receptors in adrenal gland to lower plasma glucose in streptozotocin-induced diabetic rats. Diabetologia 2005;48:767-75.
Ozyazgan S, et al. The effect of agmatine on the vascular reactivity in streptozotocin-diabetic rats. Pharmacol Res 2003;48:133-8.
Demady D.R., et al. Agmatine enhances the NADPH oxidase activity of neuronal NO synthase and leads to oxidative inactivation of the enzyme. Mol Pharmacol 2001;59:24-9.

(56) References Cited

OTHER PUBLICATIONS

Mistry SK, et al. Cloning of human agmatinase. An alternate path for polyamine synthesis induced in liver . . . Am J Physiol Gastrointest Liver Physiol. 2002 282(2):G375-81.

McGuffin, P., et al. Whole genome linkage scan of recurrent depressive disorder from the depression network study. Hum. Mol. Genet., 2005. 14:3337-3345.

Demirhan, O., et al. The expression of folate sensitive fragile sites in patients with bipolar disorder. Yonsei Med. J. 2009. 50:137-141.

Kaneva, R., et al. Bipolar disorder in the Bulgarian Gypsies: genetic heterogeneity in a young founder population. Am J. Med. Genet. Neuropsychiatr. 2009. 150B: 191-201.

De Vos H., et al. "Imidazoline receptors, non-adrenergic idazoxan binding sites and α2-adrenoceptors in the human central nervous system." Neuroscience 1994; 59: 589-598.

Bousquet P et al. "Imidazoline receptors and cardiovascular regulations. A statement." Ann NY Acad Sci 1995; 763: 526-530.

Miralles A, et al. "Discrimination and Pharmacological Characterization of I2-Imidazoline Sites with [3H] Idazoxan and Alpha-2 . . ." J Phar. Exp Ther 1993;264,1187-1197.

Wikberg J.E.S., et al. Evidence that drug binding to non-adrenergic [3H]-Idazoxan binding sites (I-Receptors) occurs to interacting . . . Pharmacol Toxicol 1992; 70: 208-219.

Greney H, et al "Heterogeneity of imidazoline binding sites revealed by a cirazoline derivative." Eur J Pharmacol 1994; 271: 533-536.

Scheen A.J. Pharma-Clinics. "Medication of the month. Moxonidine (Moxon)". Rev Med Liege 2000; 55: 61-63.

Camilleri G., et al. "Comparison of the efficacy and the safety of two imidazoline receptors agonists: rilmenidine and moxonidine." Ann Cardiol Angeiol 2001; 50: 169-174.

Raddatz R., et al. "Imidazoline binding domains on MAO-B. Localization and accessibility." Ann NY Acad Sci 1999; 881: 26-31.

Molderings G.J., et al. "Imidazoline binding sites and receptors in cardiovascular tissue." Gen Pharmacol 1999; 32: 17-22.

Trendelenburg, A-U, et al."A re-investigation of questionable subclassifications of presynaptic α2-autoreceptors: . . . " Naunyn-Schmiedeberg's Arch Pharmacol 1997; 356:721-737.

Ei-Ayoubi R., et al."Imidazoline receptors in the heart: characterization, distribution and regulation." J Cardiovasc Pharmacol 2002; 39: 875-883.

Ei-Ayoubi, R., et al. Imidazoline receptors but not alpha2-adrenoceptors are regulated in spontaneously hypertensive rat heart . . . J Pharmacol Exp Ther 2004; 310: 446-451.

Bousquet P., et al. "Imidazoline receptors: a challenge." Pharm Acta Hely 2000; 74: 205-209.

Regunathan S., et al. "Imidazoline receptors and agmatine in blood vessels: a novel system inhibiting vascular smooth muscle . . . " J Pharmacol Exp Ther 1996; 276: 1272-1282.

Coupry I., et al. The imidazoline-guanidinium receptive site: a subtype of imidazoline receptors. Therapie 1992: 47: 519-524.

Macinnes N., et al. Autoradiographic localisation of [3H]2-BFI imidazoline I2 binding sites in mouse brain. Eur J Pharmacol 2005; 516: 139-44.

Raasch W., et al. Presynaptic release of noradrenaline is mediated not only through α2-adrenoceptors but also through imidazoline . . . Dtsch Med Wschr 1999; 124: S114.

Chan CKS, et al. Role of imidazoline receptors in . . . cardiovascular . . . moxonidine, rilmenidine and clonidine in conscious rabbits. J Pharmacol Exp Ther 1996; 276: 411-420.

Mukaddam-Daher S, et al. Receptors involved in moxonidine-stimulated atrial natriuretic peptide release from isolated normotensive . . . Eur J Pharmacol 2006; 541: 73-79.

Mehrotra, S., et al. Current and prospective pharmacological targets in relation to antimigraine action. Naunyn-Schmiedeberg's Arch Pharmacol (2008), 378(4):371-94.

* cited by examiner

CHIRAL HPLC ISOMER 2

| ■ | Iodo-clonidine | 104 |
| ▽ | Amino-clonidine | 227 |
| ● | Guanabenz | 1,410 |
| ○ | 2-BFI | 25,740 |
| ◆ | Idazoxan | 71,070 |

ISOMETHEPTENE ISOMER

This patent application claims priority from Provisional patent applications 61/926,739 filed Jan. 13, 2014; 61/814,664 filed Apr. 22, 2013; 61/793,456 filed Mar. 15, 2013; and 61/754,281 filed Jan. 18, 2013; which prior disclosures are incorporated in the present application.

All references cited in this specification, and their references, are incorporated by reference herein in their entirety where appropriate for teachings of additional or alternative details, features, and/or technical background.

FIELD OF THE INVENTION

The invention relates to synthesis, separation and purification of racemic Isometheptene (6-methylamino-2-methylheptene) or Isometheptene Mucate salt (in a 2:1 molar ratio) as well as enantiomers 1 and 2 thereof; moreover, the invention describes the use of each isomer alone or in combination with other ameliorative compounds for treatment of various painful conditions such as tension or migraine headaches and menstrual cramps and various cognitive disorders such as moderate cognitive impairment, presenile or senile dementia and cognitive disorders from drug treatments.

More particularly, the invention provides the preparation and structural characterization optical Isometheptene isomers 1 and 2, or (S)-enantiomer and (R)-enantiomer, respectively; in addition via x-ray of crystallized optical Isometheptene mucate (R)-isomer.

BACKGROUND

Isometheptene is a non-ergot vasoconstrictor agent that has been used in the treatment of tension headache, vascular headache and migraine headache either alone or as one or more than one active ingredients in various combination drug products (CDPs) (Horton, B T, Petes, G A and Blumenthal, L S. A new product in the treatment of migraine: A preliminary report, Proc. Staff Meet Mayo Clin. 1945.xx:241-248; Palmer, H. Toxicity of methylamino-iso-octene. Migraine headache, Clinics. 1945. Iv: 531-554; Walton, R P and Preacher, C B, Federation Proc. 1946. v, 211; MacNeal, P. S., and Davis, D.: The Use of methyl-iso-octenylamine in migraine. Ann Intern Med. 1947 26(4):526-7. PMID: 20292892; Pantalone A L and Thomas G J. Methyl-iso-octenylamine (octin) relief of headache following spinal tap. Curr Res Anesth Analg. 1952 31(1):69-71. PMID:14896702; Peters G A and Zeller W W. Evaluation of a new agent (methyl-iso-octenylamine) in the treatment of vasodilating headaches. Proc Staff Meet Mayo Clin. 1949 24(23):565-8. PMID:15396281; Seltzer, A.: The use of methyl-iso-octenylamine (Octin) in migraine and related headaches: preliminary report. Med Ann Dist Columbia. 1948 17(7):395-6. PMID: 18871972; Blumenthal, S., and Fuchs, M.: Headache Clinics I. Am. Pract. and Digest Treat. 1950. 10: 1012; Headache Clinics II. Am. Pract. and Digest Treat. 1951. 2:163; Ogden, H D., Headache Statistics II. Headache Patterns. J. Allergy. 1952 23:458; Headache Clinics IV. Am. Pract. and Digest Treat. 1953. 4:31; Brazeau, P.: Oxytocics, in Goodman L. S., Gilman, A. (eds): The Pharmacological Basis of Therapeutics, ed 4. New York, The Macmillan Co. 1970. 893-907; Ogden, H. D.: Controlled studies of a new agent in vascular headache. Headache. 1963 3:29-31. PMID:13939581; Young, H.: A study of a non-ergotamine agent in the office treatment of vascular headache. Ind Med. Surg. 1966 35(2): 127-9. PMID:5323440; Johnson, D. E.: An alternative to ergotamines in the treatment of vascular headaches. Clin. Med. 1970. 77:33-36; Yuill, G. M., et al. A double-blind crossover trial of Isometheptene mucate compound and ergotamine in migraine. Br J Clin Pract. 1972 26(2):76-9. PMID:4552744; Diamond, S. Treatment of migraine with Isometheptene, acetaminophen, and dichloralphenazone combination: A double-blind, crossover trial. Headache. 1976 15(4):282-7. PMID:1107267; Valdivia, L F. Pharmacological analysis of the mechanisms involved in the tachycardic and vasopressor responses to the antimigraine agent, Isometheptene, in pithed rats. Life Sciences 2004. 74:3223-3234; Freitag, F G. Comparative Study of a Combination of Isometheptene Mucate, Dichloralphenazone With Acetaminophen and Sumatriptan Succinate in the Treatment of Migraine Headache. 2001 41(4):391-8. PMID:11318886; Gibbs T S. Health Care Utilization in Patients With Migraine: Demographics and Patterns of Care in the Ambulatory Setting Headache. 2003 43(4):330-5. PMID:12656703; Loder, E. Fixed Drug Combinations for the Acute Treatment of Migraine Place in Therapy CNS Drugs. 2005; 19(9):769-84. PMID:16142992; de Souza C D, et al. Efficacy and tolerability of combined dipyrone, Isometheptene and caffeine in the treatment of mild-to-moderate primary headache episodes. Expert Rev Neurother. 2012. 12(2):159-67. doi: 10.1586/ern.11.193. PMID: 22288671).

Isometheptene (6-methylamino-2-methylheptene) was first prepared according to the process described in U.S. Pat. No. 2,230,753 (1941); and it is soluble in water in its hydrochloride or mucate salt form. "Isometheptene is a specified stimulant listed by the World Anti-doping Agency (WADA)" Br. J. Pharmacol. 2008 June; 154(3):606-622.

More particularly, racemic Isometheptene is a well-known aliphatic amine and includes its pharmacologically acceptable acid addition salts (i.e., 2:1 ratio of Isometheptene:mucate). It is a commercially available drug in its common racemic form as a combination drug product (CDP) with acetaminophen (APAP) and dichloralphenazone (DCP) or as a combination drug product with APAP and caffeine. In Brazil, and other countries particularly in South America, Isometheptene is available in combination with dipyrone (de Souza, C D, et al. Efficacy and tolerability of combined dipyrone, Isometheptene and caffeine in the treatment of mild-to-moderate primary headache episodes. Expert Rev Neurother. 2012 12(2):159-67. doi: 10.1586/ern.11.193. PMID: 22288671). It was available in Germany, among several European countries, under the trademark OCTIN from Knoll A. G. (now part of Abbott).

It is believed to be a cerebrovascular constrictor which action may reduce pressure on the pain producing areas surrounding blood vessels. Isometheptene is usually used in combination with other headache ameliorating drugs such as APAP, caffeine and/or dichloralphenazone.

Accordingly, the compositions containing Isometheptene and other active ingredients useful in this invention may be administered either intravenously, parenterally, orally, transdermally, transmucosally, or as a nasal spray. Isometheptene (6-methylamino-2-methylheptene) was first prepared according to the process described in U.S. Pat. No. 2,230,753 (1941); and it is soluble in water in its hydrochloride or mucate salt form. "Isometheptene is a specified stimulant listed by the World Anti-doping Agency (WADA)" Br. J. Pharmacol. 2008 June; 154(3):606-622.

More particularly, racemic Isometheptene is a well-known aliphatic amine and includes its pharmacologically acceptable acid addition salts (i.e., 2:1 ratio of Isometheptene:mucate). It is a commercially available drug in its common racemic form as a combination drug product (CDP) with acetaminophen (APAP) and dichloralphenazone (DCP) or as a combination drug product with APAP and caffeine. In Brazil, and other countries particularly in South America, Isometheptene is available in combination with dipyrone (de Souza, C D, et al. Efficacy and tolerability of combined dipyrone, Isometheptene and caffeine in the treatment of mild-to-moderate primary headache episodes. Expert Rev Neurother. 2012 12(2):159-67. doi: 10.1586/ern.11.193. PMID: 22288671). It was available in Germany, among several European countries, under the trademark OCTIN from Knoll A. G. (now part of Abbott).

It is believed to be a cerebrovascular constrictor which action may reduce pressure on the pain producing areas surrounding blood vessels. Isometheptene is usually used in combination with other headache ameliorating drugs such as APAP, caffeine and/or dichloralphenazone.

In the US, the IDA and ICA products are marketed as prescription drugs under the auspices of the Drug Efficacy Study Implementation (DESI), because they were available before the 1962 FDA reform (1938-1962), were evaluated by National Academy of Sciences/National Research Council to conduct Drug Efficacy Study and were deemed effective for tension and vascular headache and possibly effective for migraine headache.

One DESI ICA product marketed as MigraTen® contained:

It is believed to be a cerebrovascular constrictor which action may reduce pressure on the pain producing areas surrounding blood vessels. Isometheptene is usually used in combination with other headache ameliorating drugs such as APAP, caffeine and/or dichloralphenazone.

Accordingly, the compositions containing Isometheptene and other active ingredients useful in this invention may be administered either intravenously, parenterally, orally, transdermally, transmucosally, or as a nasal spray.

For example, the Isometheptene mucate is commonly administered as a mucate salt in a combination drug product (CDP) containing Isometheptene, dichloralphenazone (DCP), and acetaminophen (APAP) in which the combination product can be abbreviated IDA (IDA) or a different CDP containing Isometheptene, caffeine, and acetaminophen (APAP), which combination product can be abbreviated ICA (ICA).

In the US, the IDA and ICA products are marketed as prescription drugs under the auspices of the Drug Efficacy Study Implementation (DESI), because they were available before the 1962 FDA reform (1938-1962), were evaluated by National Academy of Sciences/National Research Council to conduct Drug Efficacy Study and were deemed effective for tension and vascular headache and possibly effective for migraine headache.

One DESI ICA product marketed as MigraTen® contained: Isometheptene mucate (65 mg); Caffeine (100 mg): acetaminophen (APAP) (325 mg) in a capsule formulation and was deemed possibly effective for relief of migraine headache in a regimen: 2 capsules at once; 1 capsule q1h (up to 5 caps/12 h period) and deemed effective for the relief of tension headache or vascular headache in a regimen of 1-2 capsules q4 h (up to 8 caps/day). Another ICA DESI product on the market is branded as Prodrin® and contains 130 mg of Isometheptene, 20 mg of caffeine, 500 mg of APAP in a tablet formulation with the same dosing instructions for migraine, tension and vascular headache as MigraTen.

One of the DESI IDA products marketed under the trademark Midrin®, contains Isometheptene Mucate (65 mg); Dichloralphenazone (100 mg) and Acetaminophen (325 mg) and is indicated for relief of migraine headache with a usual adult dosage of two capsules at once followed by one capsule every hour until relieved, administering up to 5 capsules within a twelve hour period. Midrin® is also indicated for relief of tension headache with a usual adult dosage of one or two capsules every four hours up to 8 capsules a day." While the FDA has recognized that Isometheptene is safe and effective by the standards of DESI, various administrative actions to compel DESI manufacturers to upgrade the status of DESI drugs to the level of NDA drugs have resulted in ending the US Midrin production by Curaco since 2011; however, numerous other manufacturers have continued to manufacture and distribute similar products.

Headache indications include several distinct and overlapping conditions including primary and secondary headaches as described in the International Headache Society (HIS) criteria ("Classification and diagnostic criteria for headache disorders, cranial neuralgias and facial pain. Headache Classification Committee of the International Headache Society". *Cephalalgia* 8 Suppl 7: 1-96. 1988. PMID 3048700.) In addition to the headaches classified by the HIS, headaches include vascular headache, which is not mentioned in the Headache classification of the International Headache Society (IHS), although it is still used by many physicians, the US Food and Drug Administration and certain medical classification systems. In the IHS classification, vascular headaches may be considered a cluster headache, migraine and toxic headache.

Headache may be considered a cluster headache, migraine and toxic headache.

Episodic tension-type headache (ETTH) is a subtype of tension-type headache. Tension-type headaches (TTH) are the most common type of headaches among adults, and as a result of high prevalence, imposes the greatest socioeconomic impact of any primary headache type (Bendtsen, 2011; Crystal, 2010). The pain may render a sufferer unable to attend activities, force them to stay home from work, or impair their ability to function at work. According to Mayo Clinic, tension headaches affect 90% of women and 70% of men. According to Vos et. al, (Vos, 2012) it is the most common form of headache and affects 1.4 B people worldwide, approximately 20.8% of the population and affect women more than men (23% to 18% respectively).

A tension-type headache is classified into subtypes based on how often it occurs: infrequent ETTH (<1 day/month on average), frequent ETTH (1-14 days/month on average), or chronic TTH or CTTH (≥15 days/month on average) (International Headache Society, 2013). An ETTH (infrequent or frequent) may be described as a mild to moderate constant band-like pain, tightness, or pressure around the forehead or back of the head and neck. ETTH may last from 30 minutes to several days. ETTH usually begins gradually, and often occurs in the middle of the day. The severity of a tension headache generally increases significantly with its frequency. Because the symptoms of ETTH overlap with other primary headache types, diagnosis is generally made, not only by inclusion, but also of exclusion of certain symptoms such as nausea, exacerbation by physical exercise and occurrence of both photophobia and phonophobia (Sacco, 2008). Once diagnosed and other conditions are ruled out, the primary goal of treatment for ETTH is acute, abortive therapy (Bendtsen, 2011; Lenaerts, 2009), such as would be provided with TNX-201.hronic TTH occurs more frequently, has been shown to be more refractory to successful treatment, and shares many characteristics of a group of headaches called Chronic Daily Headaches or CDH, including sometimes no more than one additional symptom of nausea, photophobia, or phonophobia (Crystal, 2010; International Headache Society, 2013). As a result, accurate diagnosis is imperative, and the primary goal of treatment is headache prophylaxis, including selected antidepressants, serotonin-specific reuptake inhibitors, benzodiazepines, other anxiolytics, and muscle relaxants (Bendtsen, 2011; Lenaerts, 2009).

Although the mechanism of action for any headache treatment is not yet fully understood, much work has been performed and analysis published. For example, several review articles (Solomon 1995, Gallagher 2002, Gibbs 2003, Mehrota 2008) provide information on the potential pharmacological mechanism of the medications that treat or prevent migraine.

Migraine is described as a paroxysmal disorder characterized by attacks of headache, nausea, vomiting, photophobia, and phonophobia.

Migraine without aura often has a strict menstrual relationship. In contrast to the first edition of The International Classification of Headache Disorders, the second edition gives criteria for A1.1.1 Pure menstrual migraine, and A1.1.2 Menstrually-related migraine, but lists these conditions in the appendix because of uncertainty over whether they should be regarded as separate entities.

Migraine pathophysiology is believed by genetic predisposition to involve leakage of ion channels in the brain stem such that the decreased blood flow in the brain leads to neuropeptide release from trigeminal nerves inducing dilatation of cranial extracerebral blood vessel. This condition stimulates the trigeminovascular system producing headache associated phonophobia and photophobia as well as nausea and vomiting. A. Maassen VanDenBrink and K. Y. Chan (2008) European J. Pharmacology, 585; 313-319.

Migraine affects people of all races and both sexes with women accounting for 79% (61% between 20 and 49 years of age) of physician visits for migraines and Caucasians for 91% of the physician visits. The pathogenesis of migraine headache involves a) the cranial blood vessels, b) the trigeminal innervation of these vessels, and c) the reflex connection of the trigeminovascular system in the cranial parasympathetic outflow.

In addition to Isometheptene, medications for treating headache that are approved by the Food and Drug Administration (FDA) include as single agents or in combination; acetaminophen (APAP), aspirin (ASA), caffeine, barbiturates (e.g., butalbital), non-steroidal anti-inflammatory drugs (NSAIDS) (e.g., diclofenac), ergot alkaloids (e.g. ergotamine, dihydroergotamine), triptans (e.g., sumatriptan, rizatriptan, naratriptan, zolmitriptan, eletriptan, almotriptan, frovatriptan, and avitriptan), anti-epileptics (e.g. topiramate) and toxins (ie, botulinum toxin). Some drugs that have been used for headache include neuroleptics (e.g., thorazine, haloperidol). Potential pharmacological targets for the treatment of migraine include medications that target 5-hydroxytryptamine (5-HT) or serotonin receptor subtypes (5-HT$_{1-7}$), adrenergic receptor subtypes ($\alpha$1, $\alpha$2, and $\beta$), calcitonin gene-related peptide (CGRP1 and CGRP2) receptors, adenosine (A1, A2, and A3) receptors, glutamate (NMDA, AMPA, kainate, and metabotropic) receptors, dopamine receptors, endothelin receptors, and female hormone (estrogen and progesterone) receptors, plus some miscellaneous receptors and ion channels. The anti-migraine pharmacological mechanism of action of Isometheptene is unknown, but Isometheptene is considered to be a sympathomimetic action leading to cranial vasoconstriction. As described above, Isometheptene mucate is formulated combined in Midrin with acetaminophen and dichloralphenazone (a mild non-barbiturate sedative) wherein Isometheptene is known as sympathomimetic agent acting as both an alpha and beta adrenoreceptor agonist and a vasoconstrictor. If two capsules are taken near the onset of a mild migraine attack followed within an hour by two or three capsules, the treatment consisting of may be satisfactory. Although well tolerated, the dosage is usually not given more than two or three times a week.

Cramps are unpleasant, sometimes painful sensations caused by involuntary muscle contraction or muscle overshortening. Cramps can be symptoms of muscle spasm. Cramps can be separated into smooth muscle cramps and skeletal muscle cramps. Cramps related to internal (or visceral) organs are related to spasm of smooth muscle or skeletal muscle or distension of organs by functional or pathological disorders. Cramps of internal organs can be associated with visceral pain. Smooth muscle cramps are commonly associated with menstruation or visceral disorders including gastrointestinal and urinary disorders. In the female, smooth muscle cramps that are associated with menstruation, are called menstrual cramps and may also occur before and during a female menstrual cycle. Severe or persistent smooth muscle cramps may also be symptomatic of endometriosis or other health problems. Moreover, smooth muscle cramps can be associated with gastrointestinal disorders, including infectious or autoimmune gastroenteritis and functional disorders such as irritable bowel syndrome (IBS). Thus, smooth muscle cramps are associated with visceral pain in many conditions, including interstitial cystitis. An ideal treatment for cramps would have both analgesic and antispastic properties.

Skeletal muscle cramps are associated with muscle fatigue, low sodium, low potassium and certain drugs, including statins. Skeletal muscle cramps also include nocturnal leg cramps which are involuntary muscle contractions that occur during the night or (less commonly) while resting. Nocturnal leg cramps are common in the elderly, teenagers or in women during the late stages of pregnancy, and can vary in intensity from mild to extremely painful.

Menopause

Menopause is an event that typically (but not always) occurs in women that can be defined as the permanent cessation of the primary functions of the ovaries and is functionally evident when there is a termination of periodic shedding of the uterine lining (known as menses).

Hot and Cold Flushes

Hot and cold flushes (or flashes) are unpleasant sensations associated with vascular events. Hot flashes (also known as hot flushes, or night sweats if they happen at night) are a symptom which may have several other causes, but which is often caused by the changing hormone levels that are characteristic of menopause.

Cognitive Disorders

Cognitive disorders are a category of mental health disorders that primarily affect learning, memory, perception, and problem solving, and include amnesia, dementia, and delirium. Causes vary between the different types of disorders but most include damage to the memory portions of the brain. Mild cognitive impairment (MCI, also known as incipient dementia, or isolated memory impairment) is a brain function syndrome involving the onset and evolution of cognitive impairments beyond those expected based on the age and education of the individual, but which are not significant enough to interfere with their daily activities. MCI can be a transitional stage between normal aging and dementia. Alzheimer's disease (AD) is the most common form of dementia. AD is commonly diagnosed in people over 65 years of age, although the less-prevalent early-onset Alzheimer's can occur much earlier. In the early stages, the most common symptom is difficulty in remembering recent events. As the disease advances, symptoms can include confusion, irritability and aggression, mood swings, trouble with language, and long-term memory loss. In later stages, AD patients often withdraw from family and society. Gradually, bodily functions are lost, ultimately leading to death.

Traumatic Brain Injury

Traumatic brain injury (TBI), also known as intracranial injury, occurs when an external force traumatically injures the brain. TBI can be classified based on severity, mechanism (closed or penetrating head injury), or other features (e.g., occurring in a specific location or over a widespread area). Head injury usually refers to TBI, but is a broader category because it can involve damage to structures other than the brain, such as the scalp and skull.

Neurotoxicity

Neurotoxicity: Neurotoxicity occurs when the exposure to natural or artificial toxic substances, which are called neurotoxins, alters the normal activity of the nervous system in such a way as to cause damage to nervous tissue. Neurotoxicity can result from exposure to substances used in chemotherapy, radiation treatment, drug therapies, certain drug abuse, and organ transplants, as well as exposure to heavy metals, certain foods and food additives, pesticides, industrial and/or cleaning solvents, cosmetics, and some naturally occurring substances. Symptoms may appear immediately after exposure or be delayed. They may include limb weakness or numbness, loss of memory, vision, and/or intellect, uncontrollable obsessive and/or compulsive behaviors, delusions, headache, cognitive and behavioral problems and sexual dysfunction.

Depression

Anti-depressant, clinical depression, major depression, unipolar depression, unipolar disorder or recurrent depression in the case of repeated episodes) is a psychiatric diagnosis for a mood disorder characterized by episodes of all-encompassing low mood accompanied by low self-esteem and loss of interest or pleasure in normally enjoyable activities (anhedonia) and disturbed sleep (typically early morning awakening). MDD is a syndrome described by a cluster of symptoms in the American Psychiatric Association's diagnostic manual, DSM-IV. The term "depression" is ambiguous and can be used to describe MDD, but is also used to describe other mood disorders or to lower mood states lacking clinical significance. Bipolar disorder or bipolar affective disorder (historically known as manic-depressive disorder or manic depression) is a psychiatric diagnosis for a mood disorder characterized by episodes of a frenzied state known as mania (or hypomania), typically alternating with episodes of depression described in DSM-IV.

Schizophrenia

Schizophrenia is a psychiatric diagnosis for a thought disorder characterized by a breakdown of thought processes and by a deficit of typical emotional responses. Common symptoms include auditory hallucinations, paranoid or bizarre delusions, or disorganized speech and thinking.

Anxiety

Anxiety disorder is a blanket term covering several different forms of a type of common psychiatric disorder characterized by excessive rumination, worrying, uneasiness, apprehension and fear about future uncertainties either based on real or imagined events, which may affect both physical and psychological health.

Epilepsy

Epilepsy is a common and diverse set of chronic neurological disorders characterized by seizures. In many cases a cause cannot be identified; however, factors that are associated include brain trauma, strokes, brain cancer, and drug and alcohol misuse among others.

Stress Disorders

Stress disorders are an increasingly recognized group of conditions relating to the body's reaction to stressful circumstances and in some cases to decompensated reactions. "Hypothalamic hypophysiotropic factors" were proposed by G. W. Harris in the 1940s and substantial body of evidence has confirmed that these factors may contribute to stress disorders (Chrousos, G. P. Stress and disorders of the stress system Nat. Rev. Endocrinol. 5, 374-381 (2009); published online 2 Jun. 2009; doi:10.1038/nrendo.2009.106; Raisman, G. An urge to explain the incomprehensible: Geoffrey Harris and the discovery of the neural control of the pituitary gland. Ann. Rev. Neurosci. 1997: 20:533-566; Chrousos, G. P. & Gold, P. W. The concepts of stress and stress system disorders: overview of physical and behavioral homeostasis. JAMA 1992: 267: 1244-1252. Charmandari, e., Tsigos, C. & Chrousos, G. P. Neuroendocrinology of stress. Ann. Rev. Physiol. 2005. 67: 259-284.)

Excess Sweating

Hyperhidrosis or excess sweating, can either be generalized or localized to specific parts of the body. Hands, feet, armpits, and the groin area are among the most active regions of perspiration due to the relatively high concentration of sweat glands. When excessive sweating is localized it is referred to as primary or focal hyperhidrosis. Generalized or secondary hyperhidrosis usually involves the body as a whole and is the result of an underlying condition. Hyperhidrosis can also be classified depending by onset, either congenital or acquired. Primary or focal hyperhidrosis must be distinguished from secondary hyperhidrosis, which can start at any point in life. The later form may be due to a disorder of the thyroid or pituitary glands, diabetes mellitus, tumors, gout, menopause, certain drugs, or mercury poisoning. Hyperhidrosis may also be divided into palmoplantar (symptomatic sweating of primarily the hands or feet), gustatory and generalized hyperhidrosis.

Symptoms Related to Drug Withdrawal

Withdrawal is the group of symptoms that occur upon the abrupt discontinuation or decrease in intake of medications or recreational drugs. In order to experience the symptoms of withdrawal, one must have first developed a physical or mental dependence (often referred to as chemical dependency). Withdrawal happens after consuming one or more substances for a certain period of time, which is both dose dependent and varies based upon the drug consumed.

In view of these various aspects of migraine a wide variety of prospective targets for migraine treatment exists.

As is presently understood, sympathomimetic drugs activate the sympathetic nervous system and mimic the effect of catecholamine substances that act directly as agonists of one or more receptors that include alpha ($\alpha 1$, $\alpha 2$) and beta ($\beta$) adrenergic receptors. Natural endogenous catecholamines include dopamine, norepinephrine (noradrenaline), and epinephrine (adrenaline). Of these catecholamine (or monoamine) substances, dopamine and norepinephrine are generally considered neurotransmitters, and adrenaline is generally considered a hormone, but these distinctions are vague in practice. Generally, sympathomimetic drugs act in several direct or indirect ways including: causing the release of catecholamines from synapses; inhibiting the reuptake of inhibiting the reuptake of catecholamines from synapses; inhibiting the metabolism or degradation of catcholamines; interacting with adrenergic receptors directly as agonists; and/or modulating the sensitivity or responsiveness of catecholamine responsive cells or systems.

Isometheptene has been shown to increase heart rate and diastolic blood pressure, which are properties associated with sympathomimetic agents. The heart rate increase has been shown to be blocked by propranolol, a non-selective beta (β) adrenergic receptor antagonist, while the diastolic blood pressure increase has been shown to be blocked by prazosin, an alpha-1 (α1) adrenergic receptor antagonist. Valdivia, L. F., Cenurion, D., Perusquia, M., Arulmani, U., Saxena, P. R., and Villalom, C. M. "Pharmacological Analysis of the Mechanisms Involved in the Tachycardic and Vasopressor Responses to the Antimigraine Agent, Isometheptene, in Pithed Rats" Life Sciences 74: 3223-3234 (2004). Together these findings suggest that racemic Isometheptene has sympathetic effects which are complex on heart rate and blood pressure. However, it is unknown whether Isometheptene interacts with alpha (α)- or beta (β)-adrenergic receptors as an agonist, and/or stimulates the release of catecholamines, and/or modulates the sensitivity of catecholamine responsive cells or systems.

Some comparisons have been made of the pressor effects of Isometheptene and those of tyramine (4-hydroxyphenethylamine; para-tyramine, mydrial or uteramin). Tyramine is a naturally occurring monoamine compound that acts as a catecholamine releasing agent. Tyramine is present in a plants and animals. But high levels of tyramine are typically found in the diet from the metabolism of microorganisms (decarboxylation of tyrosine) in cheese or wine. In humans, tyramine is metabolized by monoamine oxidase (MAO) and if MAO function is inhibited by the use of monoamine oxidase inhibitors (MAOIs), then dietary tyramine can raise blood pressure and in rare cases, precipitate a hypertensive crisis, which is also referred to as the "cheese effect". Tyramine may act on a group of G protein-coupled receptors, such as TA1 or TAAR1 that is expressed in brain as well as peripheral tissues, including the kidneys.

A literature search was conducted to obtain information on nonclinical pharmacology and safety (safety pharmacology, pharmacokinetic, and toxicology) of Isometheptene alone and in a CDP to support an IND on Isometheptene. The results of this literature search indicated that 35 papers that reference Isometheptene have been published since 1972. Upon review of the abstracts of these published papers, 12 of these 35 papers provided some information on the mechanism of action of Isometheptene for the treatment of migraine, the pharmacological profile of Isometheptene in animal models, and the pharmacokinetics and metabolism of Isometheptene in animals and humans. None of these publications provide information on the toxicological profile of Isometheptene in animals.

Moffett, Adrienne; Swash, M; Scott, D F (1972). "Effect of tyramine in migraine: a double-blind study". *Journal of Neurology, Neurosurgery, & Psychiatry with Practical Neurology* 35, 4: 496-499. doi:10.1136/jnnp.35.4.496.

D'Andrea, G; Nordera, G P; Perini, F; Allais, G; Granella, F (May 2007). "Biochemistry of neuromodulation in primary headaches: focus on anomalies of tyrosine metabolism". Neurological Sciences 28, Supplement 2: S94-S96. doi:10.1007/s10072-007-0758-4. PMID 17508188.

Borowsky B, Adham N, Jones K A, Raddatz R, Artymyshyn R, Ogozalek K L, Durkin M M, Lakhlani P P, Bonini J A, Pathirana S, et al. (2001). "Trace amines: identification of a family of mammalian G protein-coupled receptors." *Proc Natl Acad Sci USA* 98:8966-8971.

Imidazoline-I1 Receptors:

A receptor system that modulates sympathetic effects has been recently identified and termed the imidazoline receptors (I receptors). Three isoforms have been identified: I1, I2, and I3. A putative natural ligand is agmatine (see below).

Moxonidine is believed to be an agonist of the I1 receptor and the net effect of moxonidine is sympathoinhibitory (Schafer), so that agonists of the I1 receptor generally are sympathoinhibitory and antagonists are sympathomimetic. Schafer U, Burgdorf C, Engelhardt A, Raasch W, Kurz T, Richardt G. Moxonidine displays a presynaptic alpha-2-adrenoceptor-dependent synergistic sympathoinhibitory action at imidazoline-I1 receptors. *Ann NY Acad Sci* 2003; 1009: 265-269.

Clonidine is also a ligand of the I1/moxonidine receptor and is sympathoinhibitory. However, Clonidine is also a centrally acting alpha-2 agonist, which is believed to account for many of its effects on sympathetic tone and on treatment effects. Central alpha-2 receptors are believed to be pre-synaptic and agonists to central alpha-2 receptors decrease sympathetic outflow. Clonidine was developed and initially FDA approved and used for the treatment of hypertension but has since found other uses, including treatment of attention deficit hyperactivity disorder (ADHD) in an extended release form. Off-label uses, supported by less evidence, suggest effects on some types of neuropathic pain, opioid detoxification, sleep hyperhidrosis, anxiety and panic disorder, insomnia, menopausal symptoms and as an anaesthetic drug.

Clonidine is applied in conjunction with stimulants to treat ADHD because it may moderate ADHD-associated impulsive and oppositional behavior, and may reduce tics, which are involuntary movements in ADHD or Tourette syndrome. Clonidine is used to ease sympathetic withdrawal symptoms (tachycardia and hypertension) associated for example with the long-term use of narcotics, alcohol and nicotine (smoking). Moreover, Clonidine is applied to reduce sweating, hot and cold flushes, and general restlessness in drug withdrawal and also menopause.

Clonidine has also been studied to treat pain during heart attack, postoperative and intractable pain as an oral or epidural agent.

Agmatine [(4-aminobutyl)guanidine] is believed to be an endogenous ligand for I1 receptors and to function as an agonist. Agmatine was identified in herring sperm in 1910 by Albrecht Kossel. Kossel, Albrecht 1910. Über das Agmatin. *Zeitschaft für Physiologische Chemie* 66: 257-261

Agmatine has several properties of neurotransmitters: it is synthesized in the brain, stored in synaptic vesicles, accumulated by uptake, and released by membrane depolarization. Agmatine is the decarboxylation product of the amino acid arginine and inactivated by agmatinase. In addition to I1 receptors, agmatine binds to the $\alpha_2$-adrenergic receptor (where it has neither agonist nor antagonist effect) and blocks NMDA receptors and other cation ligand-gated channels. Functionally, agmatine inhibits nitric oxide synthase (NOS) and induces the release of some peptide hormones.

Exogenous agmatine treatment has been shown in animal studies to exert a variety of activities including: anti-convulsant (Aricioglu, F., et al. Effect of agmatine on electrically and chemically induced seizures in mice. Ann. N.Y. Acad. Sci., 2003. 1009:141-146), antineurotoxic (Halaris, A., Piletz, J. Agmatine: metabolic pathway and spectrum of activity in brain. CNS Drugs, 2007. 21:885-900), vasodilatory (Satriano, J. Agmatine: at the crossroads of the arginine pathways. Ann. N.Y. Acad. Sci., 2003. 1009:34-43), neuroprotective (Kuo, J. R., et al. Agmatine promoted angiogenesis, neurogenesis, and inhibition of gliosis-reduced traumatic brain injury in rats. J. Trauma 2011 71(4):E87-93. doi: 10.1097/TA.0b013e31820932e2; Lu W, et al. Agmatine inhibits morphine-induced memory impairment in the mouse step-down inhibitory avoidance task. Pharmacol Biochem Behav 2010; 97:256-61; McKay B E, et al. Learning and memory in agmatine-treated rats. Pharmacol Biochem Behavior 2002; 72:551-7; Zarifkar A, et al. Agmatine prevents LPS-induced spatial memory impairment and hippocampal apoptosis. Eur J Pharmacol 2010; 634:134-8; Bhutada, P et al Agmatine, an endogenous ligand of imidazoline receptor protects against memory impairment and biochemical alterations in streptozotocin-induced diabetic rats. Progress in Neuro-Psychopharmacology & Biological Psychiatry 37 (2012) 96-105), anti-apoptotic (Wang, C. C., et al., Beneficial effect of agmatine on brain apoptosis, astrogliosis, and edema after rat transient cerebral ischemia. BMC Pharmacol. 2010. 10:11), anxiolytic (Gong, Z. H., et al. Anxiolytic effect of agmatine in rats and mice. Eur. J. Pharmacol. 2006. 550:112-116), memory enhancing (Arteni N S, et al. Agmatine facilitates memory of an inhibitory avoidance task in adult rats. Neurobiol Learn Mem 2002; 78:465-9.; Liu P and Bergin D H. Differential effects of i.c.v. microinfusion of agmatine on spatial working and reference memory in the rat. Neuroscience 2009; 159: 951-61; Liu P and Collie N D. Behavioral effects of agmatine in naive rats are task- and delay dependent. Neuroscience 2009; 163:82-96), antidepressant (Zomkowski, A. D., et al. Agmatine produces antidepressant-like effects in two models of depression in mice. NeuroReport 2002. 13:387-391; Aricioglu, F. and Altunbas, H. Is agmatine an endogenous anxiolytic/antidepressant agent? Ann. N.Y. Acad. Sci. 2003. 1009: 136-140.; Li, Y. F., et al. Antidepressant-like effect of agmatine and its possible mechanism. Eur. J. Pharmacol. 2003. 469:81-88; Halaris and Piletz, 2007 (Ibid.); Taksande, B. G., et al. Antidepressant like effect of selective serotonin reuptake inhibitors involve modulation of imidazoline receptors by agmatine. Neuropharmacology 2009. 57: 415-424), anti-diabetic (Chang C H, et al. Increase of beta-endorphin secretion by agmatine is induced by activation of imidazoline I(2A) receptors in adrenal gland of rats. Neurosci Lett 2010; 468:297-9; Hwang S L, et al. Activation of imidazoline receptors in adrenal gland to lower plasma glucose in streptozotocin-induced diabetic rats. Diabetologia 2005; 48:767-75; Ozyazgan S, et al. The effect of agmatine on the vascular reactivity in streptozotocin-diabetic rats. Pharmacol Res 2003; 48:133-8) and anti-oxidant (Battaglia V, Grancara S, Satriano J, Saccoccio S, Agostinelli E, Toninello A. Agmatine prevents the Ca(2+)-dependent induction of permeability transition in rat brain mitochondria. Amino Acids 2010; 38:431-7.; Condello S, Curr M, Ferlazzo N, Caccamo D, Satriano J, Ientile R. Agmatine effects on mitochondrial membrane potential and NF-κB activation protect against rotenoneinduced cell damage in human neuronal-like SH-SY5Y cells. J Neurochem 2010; 116:67-75; Demady D R, Jianmongkol S, Vuletich J L, Bender A T, Osawa Y. Agmatine enhances the NADPH oxidase activity of neuronal NO synthase and leads to oxidative inactivation of the enzyme. Mol Pharmacol 2001; 59:24-9).

Agmatine is metabolized by agmatinase (Mistry S K, et al. Cloning of human agmatinase. An alternate path for polyamine synthesis induced in liver by hepatitis B virus. Am J Physiol Gastrointest Liver Physiol. 2002 282(2):G375-81), which is upregulated in hippocampal interneurons of subjects with mood disorders (Bernstein, H-G et al, Agmatinase, an inactivator of the putative endogenous antidepressant agmatine, is strongly upregulated in hippocampal interneurons of subjects with mood disorders. Neuropharmacology 62 (2012) 237e246).

Agmatinase is an enzyme encoded in human by a gene located on chromosome 1p36, a gene locus which has repeatedly been linked to bipolar disorder and major depression and in some cases to schizophrenia (Fanous A H, et al. Genetic overlap of schizophrenia and bipolar disorder in a high-density linkage survey in the Portuguese Island population. Am J Med Genet B Neuropsychiatr Genet. 2012 159B(4):383-91. doi: 10.1002/ajmg.b.32041. Epub 2012 Mar. 27. PMID: 22461138; McGuffin, P., et al. Whole genome linkage scan of recurrent depressive disorder from the depression network study. Hum. Mol. Genet., 2005. 14:3337-3345; Tatemir, D., et al. Chromosomal fragile site expression in Turkish psychiatric patients. Psychiatry Res. 2006. 144:197-203; Demirhan, O., et al. The expression of folate sensitive fragile sites in patients with bipolar disorder. Yonsei Med. J. 2009. 50:137-141; Diagnostic and Statistical Manual of Mental Disorders Revised 1987. DSM IIIR; American Psychiatric Association; Kaneva, R., et al. Bipolar disorder in the Bulgarian Gypsies: genetic heterogeneity in a young founder population. Am. J. Med. Genet. B Neuropsychiatr. Genet. 2009. 150B:191-201; Fullerton, J. M., et al. Two-dimensional genome scan identifies multiple genetic interactions in bipolar affective disorder. Biol. Psychiatry, 2010. 67:478-486).

Several agonists of the I1 receptor have been identified and studied. Moxonidine and Rilmenidine are considered selective agonists at the imidazoline receptor subtype 1 (I1). Moxonidine and Rilmenidine are prescription medications for the treatment of hypertension outside the U.S. Rilmenidine is marketed under the brand names HYPERIUM, Iterium and Tenaxum. The I1 receptor subtype is found in both the rostral ventro-lateral pressor and ventromedial depressor areas of the medulla oblongata. Moxonidine therefore causes a decrease in sympathetic nervous system activity and, therefore, a decrease in blood pressure. Compared to the older central-acting antihypertensives, moxonidine binds with much greater affinity to the I1-receptor than to the alpha-2-adrenergic receptor. In contrast, clonidine binds to both receptors with equal affinity. Selective I1 agonists may promote sodium excretion, improve insulin resistance and glucose tolerance and protect against hypertensive target organ damage, such as kidney disease and cardiac hypertrophy. However, Moxonidine may be associated with poor outcomes in heart failure (Cohn J et al. Adverse mortality effect of central sympathetic inhibition with sustained-release moxonidine in patients with heart failure (MOXCON) Eur J Heart Fail (2003). 5 (5): 659-67. doi:10.1016/S1388-9842(03)00163-6. PMID 14607206.

REFERENCES

Molderings G J. "Imidazoline receptors: basic knowledge, recent advances and future prospects for therapy and diagnosis." *Drugs Future* 1997; 22: 757-772.

De Vos H, Bricca G, De Keyser J, De Backer J-P, Bousquet P, Vauquelin G. "Imidazoline receptors, non-adrenergic idazoxan binding sites and α2 adrenoceptors in the human central nervous system." Neuroscience 1994; 59: 589-598.

Bousquet P, Greney H, Bennai F et al. "Imidazoline receptors and cardiovascular regulations. A statement." Ann NY Acad Sci 1995; 763: 526-530.

Ernsberger P. "Heterogeneity of imidazoline binding sites: proposed I1 and I2 subtypes." Fund Clin Pharmacol 1992; 6(Suppl.1): 55.

Miralles A, Olmos G, Sastre M, Barturen F, Martin J, Garcia-Sevilla J A. "Discrimination and pharmacological characterization of I2-imidazoline sites with [3H]idazoxan and α2-adrenoceptor with [3H]RX821002 (2-methoxyidazoxan) in the human and rat brains." J Pharmacol Exp Ther 1993; 264: 1187-1197.

Wikberg J E S, Uhlen S, Chjalari V. "Evidence that drug binding to non-adrenergic [3H]idazoxan binding sites (Ireceptors) occurs to interacting or interconvertible affinity forms of the receptor." Pharmacol Toxicol 1992; 70: 208-219.

Greney H, Molines D, Bousquet P, Dontenwill M. "Heterogeneity of imidazoline binding sites revealed by a cirazoline derivative." Eur J Pharmacol 1994; 271: 533-536.

Morgan N G, Chan S L F. "Imidazoline receptors and their ligands as potentiators of nutrient-induced insulin secretion." Drug Design Reviews 2004; 1: 185-193.

Scheen A J. Pharma Clinics. "Medication of the month. Moxonidine (Moxon)". Rev Med Liege 2000; 55: 61-63.

Camilleri G, Portal B, Quiniou G, Clerson P. "Comparison of the efficacy and the safety of two imidazoline receptors agonists: rilmenidine and moxonidine." Ann Cardiol Angiol 2001; 50: 169-174.

Raddatz R, Savic S L, Laniers S M. "Imidazoline binding domains on MAO-B. Localization and accessibility." Ann NY Acad Sci 1999; 881: 26-31

Molderings G J, Göthert M. "Imidazoline binding sites and receptors in cardiovascular tissue." Gen Pharmacol 1999; 32: 17-22.

Trendelenburg A-U, Sutej I, Wahl C A, Molderings G J, Rump L C, Starke K. "A re-investigation of questionable subclassifications of presynaptic a2-autoreceptors: rat vena cava, rat atria, human kidney and guinea-pig urethra." Naunyn-Schmiedeberg's Arch Pharmacol 1997; 356:721-737.

El-Ayoubi R, Gutkowska J, Regunathan S, Mukaddam-Daher S. "Imidazoline receptors in the heart: characterization, distribution and regulation." J Cardiovasc Pharmacol 2002; 39: 875-883.

Schafer U, Burgdorf C, Engelhardt A, Raasch W, Kurz T, Richardt G. "Moxonidine displays a presynaptic alpha-2-adrenoceptor-dependent synergistic sympathoinhibitory action at imidazoline-I1 receptors." Ann NY Acad Sci 2003; 1009: 265-269.

Mukaddam-Daher S, Gutkowska J. "Imidazoline receptors in the heart: a novel target and a novel mechanism of action that involves atrial natriuretic peptides." Braz J Med Biol Res 2004; 37: 1239-1245.

El-Ayoubi R, Menaouar A, Gutkowska J, Mukaddam-Daher S. "Imidazoline receptors, but not alpha2-adrenoceptors are regulated in SHR heart by chronic moxonidine treatment." J Pharmacol Exp Ther 2004; 310: 446-451.

Bousquet P, Bruban V, Schann S, Feldman J. "Imidazoline receptors: a challenge." Pharm Acta Helv 2000; 74: 205-209.

Regunathan S, Youngson C, Raasch W, Wang H, Reis D J. "Imidazoline receptors and agmatine in blood vessels: a novel system inhibiting vascular smooth muscle proliferation." J Pharmacol Exp Ther 1996; 276: 1272-1282.

Coupry I, Limon I, Tesson F, Lachaud V, Gargalidis-Moudanos C, Parini A. Imidazoline-guanidine site: a subtype of imidazoline receptors. Therapie 1992:47:519-524.

Holt A, Wieland B, Baker G B. Allosteric modulation of semicarbazide-sensitive amine oxidase activities in vitro by imidazoline receptor ligands. Br J Pharmacol 2004; 143: 495-507.

MacInnes N, Handley S. "Autoradiographic localization of [3H]2-BFI imidazoline I2 binding sites in mouse brain." Eur J Pharmacol 2005; 516: 139-44.

Romer L, Wurster S, Savola J-M, Raasmaja A. "Identification and characterization of the imidazoline I2-binding sites in the hamster brown adipose tissue as a study model for imidazoline receptors." Arch Physiol Biochem 2003; 111: 159-166.

Raasch W, List B, Hauser W, Schafer U, Dominiak P. "Presynaptic release of noradrenaline is mediated not only through α2-adrenoceptors but also through imidazoline binding sites." Dtsch Med Wschr 1999; 124: 5114.

Khan Z P, Ferguson C, Jones R M. "Alpha-2 and imidazoline receptor agonists. Their pharmacology and therapeutic role." Anaesthesia 1999; 54: 146-165.

Head G A, Mayorov D N. "Imidazoline receptors, novel agents and therapeutic potential." Cardiovasc Hematol Agents Med Chem 2006; 4: 17-32.

Chan C K S, Sannajust F, Head G A. "Role of imidazoline receptors in the cardiovascular actions of moxonidine, rilmenidine and clonidine in conscious rabbits." J Pharmacol Exp Ther 1996; 276: 411-420.

Mukaddam-Daher S, Menaouar A, Gutkowska J. "Receptors in moxonidine stimulated atrial natriuretic peptide release from isolated normotensive rat hearts." Eur J Pharmacol 2006; 541: 73-79.

Isometheptene (6-methylamino-2-methylheptene) was first prepared according to the process described in U.S. Pat. No. 2,230,753 (1941); and it is soluble in water in its hydrochloride or mucate salt form. "Isometheptene is a specified stimulant listed by the World Anti-doping Agency (WADA)" Br. J. Pharmacol. 2008 June; 154(3):606-622.

Accordingly, the compositions containing Isometheptene and other active ingredients useful in this invention may be administered either intravenously, parenterally, orally, transdermally, transmucosally, or as a nasal spray.

For example, the Isometheptene mucate is commonly administered as a mucate salt in a combination drug product (CDP) containing Isometheptene, dichloralphenazone (DCP), and acetaminophen (APAP) in which the combination product can be abbreviated IDA (IDA) or a different CDP containing Isometheptene, caffeine, and acetaminophen (APAP), which combination product can be abbreviated ICA (ICA).

In the US, the IDA and ICA products are marketed as prescription drugs under the auspices of the Drug Efficacy Study Implementation (DESI), because they were available before the 1962 FDA reform (1938-1962), were evaluated by National Academy of Sciences/National Research Council to conduct Drug Efficacy Study and were deemed effective for tension and vascular headache and possibly effective for migraine headache.

One DESI ICA product marketed as MigraTen® contained: Isometheptene mucate (65 mg); Caffeine (100 mg): acetaminophen (APAP) (325 mg) in a capsule formulation and was deemed possibly effective for relief of migraine headache in a regimen: 2 capsules at once; 1 capsule q1h (up to 5 caps/12 h period) and deemed effective for the relief of tension headache or vascular headache in a regimen of 1-2 capsules q4 h (up to 8 caps/day). Another ICA DESI product on the market is branded as Prodrin® and contains 130 mg of Isometheptene, 20 mg of caffeine, 500 mg of APAP in a tablet formulation with the same dosing instructions for migraine, tension and vascular headache as MigraTen.

One of the DESI IDA products marketed under the trademark Midrin®, contains Isometheptene Mucate (65 mg); Dichloralphenazone (100 mg) and Acetaminophen (325 mg) and is indicated for relief of migraine headache with a usual adult dosage of two capsules at once followed by one capsule every hour until relieved, administering up to 5 capsules within a twelve hour period. Midrin® is also indicated for relief of tension headache with a usual adult dosage of one or two capsules every four hours up to 8 capsules a day." While the FDA has recognized that Isometheptene is safe and effective by the standards of DESI, various administrative actions to compel DESI manufacturers to upgrade the status of DESI drugs to the level of NDA drugs have resulted in ending the US Midrin production by Curaco since 2011; however, numerous other manufacturers have continued to manufacture and distribute similar products.

In the pharmacological literature references, effects of medication and treatment of migraine have been reported.

Another publication (Willems 2001) relates to an investigation of the external carotid vascular effects of Isometheptene (administered as 1 minute intra-arterial [IA] infusions at 10, 30, 100, and 300 µg/min or about 1, 3, 10, and 30 µg/kg for a 10 kg dog) in vagosympathectomized dogs. At these dose levels, Isometheptene caused dose-dependent decreases in external carotid blood flow without affecting blood pressure or heart rate. The vasoconstrictor responses to Isometheptene were attenuated in dogs pretreated with reserpine at 5,000 µg/kg and were also attenuated by rauwolscine ([apha-2]-adrenoceptor antagonist) at 300 µg/kg in untreated dogs and were practically abolished in reserpine-pretreated dogs. Results using selective antagonists for specific [alpha-2]-adrenoceptor subtypes indicated that the Isometheptene-induced canine external carotid vasoconstriction appeared to be mediated by both indirect (a tyramine-like action) and direct (acting at receptors) mechanisms that mainly involved [alpha-2A-]- and [alpha-2C]-adrenoceptors while the involvement of [alpha-1]-adrenoceptors was rather limited for this effect.

A third publication (Mehrotra 2006) investigated the in vitro effects of current and prospective anti-migraine drugs on porcine meningeal artery segments. Porcine meningeal artery veins (n=5) were exposed to a single concentration response curve of Isometheptene (about 0.01 to 50 µM), either in the absence or presence of a particular antagonist concentration. Results indicated that Isometheptene (and other antimigraine drugs) failed to contract the meningeal artery while α-CGRP (calcitonin gene related peptide) produced concentration-dependent relaxations that were antagonized by olcegepant (a CGRP receptor antagonist). Thus, the porcine meningeal artery might not be involved in the vasoconstriction of the carotid vascular bed elicited by anti-migraine drugs in anaesthetized pigs.

Taken together, these nonclinical pharmacological results suggest that Isometheptene causes cranial vasoconstriction that may be effective in the treatment of migraine. Furthermore, the non-clinical state of the art is summarized from the following reviews.

Solomon G D. "The pharmacology of medications used in treating headache." Semin. Pediatr. Neurol. (1995), 2(2):165-177. This review article discussed the pathogenesis of migraine and the various pharmaceutical agents, including Isometheptene, used for treating migraine. Research on the trigeminovascular system, serotonin receptors, and substance P have provided clues to improving the pharmacotherapy of migraine, a common and disabling disease of uncertain pathogenesis.

Selective serotonin agonists, nonsteroidal anti-inflammatory drugs (NSAIDs), Isometheptene mucate, and phenothiazines were listed as being useful to treat acute migraine attacks. Prophylactic agents for migraine were listed to include beta-blockers, calcium channel blockers, NSAIDs, antidepressants, and valproate. Isometheptene mucate, a sympathomimetic agent, was listed as being useful for adults and adolescents with migraine. Actions involve indirect β- and α-andrenoreceptor activity and direct α-andrenoreceptor agonism (Valvidia et al. 2004). Available preparations listed were Isometheptene with a mild sedative and acetaminophen, or a CDP. The listed usual dosage and dosing regimen for adults and adolescents was 2 capsules at onset, then 1 capsule every hour to a total of 5 capsules per day. For children from 8 to 12 years of age, the listed dosage and dosing regimen was 1 capsule initially, followed by 1 capsule every hour to a limit of 3 capsules per day.

Gallagher R M and Cutrer F M. "Migraine: Diagnosis, Management, and New Treatment Options." Am J Managed Care (2002), 8(3):S58-S73. This review article summarized the safety and tolerability of medications used to treat acute migraine attacks, reviewed the classification of headaches and the causes of and diagnostic criteria for migraine, and discussed the clinical tolerability profiles and therapeutic benefits of second-generation triptans. Mild to moderate migraines were listed as being often treated with aspirin, acetaminophen, NSAIDs, antiemetic drugs, or Isometheptene (in combination with other active agents, such as caffeine and acetaminophen).

Gibbs T S, Fleischer A B Jr, Feldman S R, Sam M C, O'Donovan C A. Health care utilization in patients with migraine: demographics and patterns of care in the ambulatory setting. Headache (2003), 43(4):330-335.

Spierings 1980 reported that Isometheptene administered intravenously [IV] at 0.25 mg/kg for each of 4 treatments for a maximum dose of 1.0 mg/kg) was compared to saline (control) and shown to cause vasoconstriction in the arteriovenous anastomoses of anaesthetized cats (8/group). This review article indicated that migraine affects people of all races and both sexes. Women accounted for 79% (61% between 20 and 49 years of age) of physician visits for migraines and Caucasians for 91% of the physician visits. The prevalence of headaches in preschool- and school entry-age children varies from 5.9% to 37.7%. The most commonly used CDP for migraine over a 9-year study period (1990 to 1998) was butalbital/aspirin/caffeine with 2.3 million prescriptions and the second most commonly used CDP was acetaminophen/dichloralphenazone/Isometheptene mucate with 2.1 million prescriptions.

Mehrotra S, Gupta S, Chan K Y, Villalon C M, Centurion D, Saxena P R, MaassenVanDenBrink A. "Current and prospective pharmacological targets in relation to antimigraine action." Naunyn Schmiedebergs Arch Pharmacol (2008), 378 (4):371-94. This review article indicated that migraine is a recurrent, incapacitating, neurovascular disorder characterized by unilateral and throbbing headaches associated with photophobia, phonophobia, nausea, and vomiting. The pathogenesis of migraine headache was considered to involve three key factors, a) the cranial blood vessels, b) the trigeminal innervation of these vessels, and c) the reflex connection of the trigeminovascular system in the cranial parasympathetic outflow.

Specific drugs (ergotamine, and dihydroergotamine) used in the treatment of migraine interact with vascular receptors, a fact that has raised concerns about the cardiovascular safety of these pharmaceutical agents. The various potential pharmacological targets for the treatment of migraine were discussed. These targets included 5-hydroxytryptamine (5-HT) receptor subtypes (5-HT1-7), adrenergic receptor subtypes (α1, α2, and β), calcitonin gene-related peptide (CGRP1 and CGRP2) receptors, adenosine (A1, A2, and A3) receptors, glutamate (NMDA, AMPA, kainate, and metabotropic) receptors, dopamine receptors, endothelin receptors, and female hormone (estrogen and progesterone) receptors plus some miscellaneous receptors and ion channels.

Reference is also made to Isometheptene treatment for relieving symptoms of acute pancreatitis in the afflicted patient in U.S. Pat. No. 4,522,827 (Knoll A G).

In studying the effect of Isometheptene, as an indirectly acting non-ergot sympathomimetic with analgesic and antispastic properties, on secretin-cholecystokinin-stimulated pancreatic and biliary outputs, Gullo et al. Dig. Dis. Sci. (1985) reported that the drug inhibited only pancreatic outputs. Accordingly, the inhibitory effect on pancreatic secretion, coupled with the analgesic action, suggests a potential benefit of this drug in acute pancreatic pathology.

Moreover, as is known for many racemic compounds in medicine, the biology of only one single racemate isomer was often found to be pharmacologically effective with reduced significant side effects which may be due to the nonspecific binding of the opposite racemate.

There is an urgent need for new and safer prescription drugs for episodic tension-type headaches (ETTH). Although Isometheptene was approved as a DESI drug for migraine headaches (OCTIN®, Knoll) during the period of 1938 to 1962, FDA withdrew approval of the OCTIN® NDA 6-420 in 1981 citing a lack of substantial evidence of effectiveness; however, it has been widely marketed as a combination ingredient drug product. Since the combination the FDA considers combination drug products (CDPs) that contain Isometheptene to be "identical, related or similar" ("IRS") to the single-ingredient Isometheptene products reviewed under DESI Notice 3265, it has declared Isometheptene-containing drug products unapproved new drugs that cannot be marketed without approved NDA. Since (R)-Isometheptene binds $I_1$ with much stronger affinity than (S)-Isometheptene, delivering TNX-201 as a single (R)-isomer of Isometheptene may result in a better therapeutic than the racemate.

It is therefore an object of the present invention to develop a single isomeric form or enantiomer which can be identified on the basis of a specific receptor binding affinity.

In particular, it is an object of the present invention to isolate and characterize the enantiomer of Isometheptene indicating the greater potential of relief for the sufferer from headache, cramps, menopause, flushes, cognitive impairment, neurotoxins, TBI, anxiety disorders, depression, bipolar disorder, epilepsy, schizophrenia, stress disorders, excess sweating and withdrawal symptoms.

More specifically, it is an object of the present invention to treat episodic tension-type headaches (as more recently classified by the International Headaches Society, 2013) by administering a composition containing an Isometheptene enantiomer. (R) Isometheptene was found to bind more strongly to an Imidazoline Receptor Subtype 1 ($I_1$) than the opposite (S)-Isometheptene enantiomer.

LIST OF ACRONYMS AND ABBREVIATIONS

| | |
|---|---|
| AE | Adverse Event |
| API | Active Pharmaceutical Ingredient |
| CNS | Central Nervous System |
| CGRP | Calcitonin Gene Related Peptide |
| CDP | Combination Drug Product |
| CDH | Chronic Daily Headache |
| CFU | Colony Forming Units |
| CTTH | Chronic Tension-Type Headache |
| DESI | Drug Efficacy Study Implementation |
| FAERS | FDA Adverse Event Reporting System |
| FDA | Food and Drug Administration |
| GC, GLC | Gas Liquid Chromatography |
| GMP | Good Manufacturing Practice |
| HPLC | High Performance Liquid Chromatography |
| ICA | Formulation containing Isometheptene (65 or 130 mg), caffeine (20 or 100 mg) and acetaminophen (325 or 500 mg) |
| ICH | International Conference of Harmonization |
| ICH | Intracranial Hemorrhage |
| IDA | Formulation containing Isometheptene (65 mg), dichloralphenazone (100 mg) and acetaminophen (325 mg) |
| IHCD | International Headache Classification |
| IHS | International Headache Society |
| IMH | Isometheptene mucate |
| IND | Investigational New Drug |
| IRS | Identical, Related, or Similar |
| IV | Intravenous |
| NMDA | N-Methyl-D-aspartic acid |
| NLT | Not less than |
| NMT | Not more than |
| NOS | Nitric oxide synthase |
| PCV | Post-partum cerebral vasculopathy |
| PT | Preferred term |
| RRT | Relative retention time |
| SAE | Serious Adverse Event |
| SOC | System Organ Class |
| TDD | Total daily dose |
| TNX-201 | TONIX oral dosage form containing TBD mg of (R)-Isometheptene mucate |
| TTH | Tension-Type Headache |

SUMMARY

Aspects of the invention disclosed herein include synthesis and purification of the Isometheptene racemic compound, having a structure according to Formula (I),

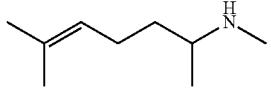

(6-methylamino-2-methylheptene)

or a hydrochloride, or a pharmaceutically acceptable addition salt thereof.

An aspect of the invention is found in the isolation and purification of Isometheptene stereoisomer 1 and stereoisomer 2 which are stereochemically characterized as being S-enantiomer and R-enantiomer, respectively.

A special aspect shows an S-enantiomeric Isometheptene compound comprising the structure according to Formula (Ia),

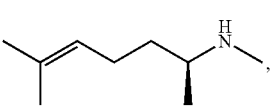

(S)-Isometheptene or a hydrochloride, or a pharmaceutically acceptable addition salt thereof; and an R-enantiomeric Isometheptene compound comprising the structure according to Formula (Ib),

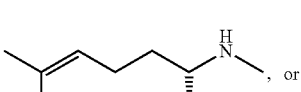

(R)-Isometheptene a hydrochloride, or a pharmaceutically acceptable addition salt thereof.

An aspect of the invention provides each Isometheptene isomer compound as a hydrochloride, a tartrate (1:1) or a mucate (2:1) salt.

An aspect of the invention now provides an (S)-Isometheptene mucate salt according to Formula (II):

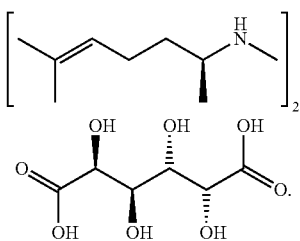

Another aspect of the invention provides an (R)-Isometheptene mucate salt according to Formula (III):

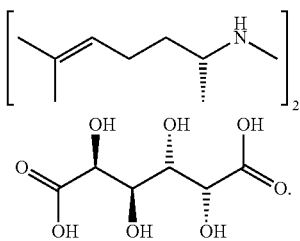

A special aspect of the invention provides a purified (R)-Isometheptene mucate salt in crystalline form.

Further aspects of the invention disclosed herein and copending reference applications include methods of synthesis and purification, isolation and characterization of comparative mechanism of action the Isometheptene.

An aspect of the invention also provides administering a therapeutic amount of a composition comprising an Isometheptene (S)-enantiomer or (R)-enantiomer compound; and a pharmaceutically acceptable carrier.

This aspect of the invention provides such a composition, further including a therapeutic effect on headaches, cramping or cognitive disorders; in a particular aspect, the Isometheptene compounds can ameliorate or extinguish symptoms of headaches, including tension, vascular or migraine headaches, cramping or cognitive disorders.

This aspect of the invention provides a compound or composition, administered alone or in combination with one or more additional therapeutics, chemotherapeutic drugs, anti-proliferative agents, anti-inflammatory agents, anti-asthmatic agents, anti-allergic agents, immunosuppressive agents, immunomodulatory agents, cardiovascular disease treatment agents, anti-diabetic agents, or blood disorder treatment agents.

An aspect of the invention provides a method, comprising administering to a patient an effective amount of a compound of Isometheptene (R)-enantiomer or (S)-enantiomer, or hydrochloride or addition salt thereof, or the composition of such compounds, so as to treat, reduce the severity or even prevent the pain associated with the disease or condition; wherein the disease or condition is one or more of inflammatory diseases or disorders, allergic diseases or disorders, metabolic diseases, cardiovascular disease or disorders, or a neurogenic vascular disease or painful condition associated therewith.

An aspect of the composition including (R)-Isometheptene addition salt provides an ameliorative effect on headaches or cramping due to a vascular, neurovascular or neurogenic disorder or dysfunction during migraine episodes.

An aspect of the composition including (R)-Isometheptene addition salt provides an ameliorative effect on headaches or cramping due to a vascular, neurovascular or neurogenic disorder or dysfunction during menstrual cycle episodes.

Another aspect of the (R)-Isometheptene treatment would ease hypertension alleviating composition comprising a therapeutic amount of the (R)-Isometheptene enantiomer compound or salt, and a pharmaceutically acceptable addition salt thereof, and a nontoxic carrier.

Another aspect is found in the effect of the composition of (S)-enantiomer of Isometheptene hydrochloride or pharmaceutically acceptable addition salt thereof, and one or more pharmaceutical substances selected from acetaminophen, ibuprofen, aspirin, caffeine, dichloralphenazone, naproxen, and sumatriptan succinate; and a nontoxic carrier.

Another aspect of the invention provides the selective I1 receptor binding effect in a composition, comprising the therapeutic amount of (R)-Isometheptene hydrochloride or pharmaceutically acceptable addition salt thereof, and one or more pharmaceutical substances selected from acetaminophen, ibuprofen, aspirin, caffeine, dichloralphenazone, naproxen, and sumatriptan succinate; and a nontoxic carrier.

The aforementioned ameliorative aspect of the invention further comprises a hypertension lowering effect.

An advantageous aspect of the invention provides a treatment wherein a single dosage of (R)-Isometheptene enantiomer hydrochloride or addition salt thereof is administered to a patient, optionally twice, three times or four times in a day, in capsules containing increasing amounts of 15 mg, 30 mg, 32.5 mg, 50 mg, 65 mg, 100 mg, 130 mg, 150 mg, 300 mg or 500 mg.

The pharmaceutical composition also including Isometheptene mucate, Isometheptene bitartrate, or Isometheptene hydrochloride can be administered in the treatment of migraines and tension headaches, its effectiveness believed based on its vasoconstricting properties.

Moreover, the pharmaceutical composition including an Isometheptene salt, and an inert pharmaceutically acceptable excipient, can be further combined with one or more anti-tension compounds including paracetamol, dichloralphenazone, sumatriptan succinate, caffeine and either acetaminophen, naproxen, aspirin or ibuprofen.

The following methods address the tension headaches, or migraine associated headaches, such as a method of treatment of migraine comprising administering a therapeutic composition containing (R)-Isometheptene enantiomer to a human in need of such treatment.

A method of treatment of migraine comprising administering to a human in need of such treatment a therapeutic composition containing the (S)-Isometheptene murate salt in combination with suitable pharmaceutical agents.

Furthermore, according to the advantageous aspects of the invention, a method of treatment of hypertension comprises administering a therapeutic amount of a composition comprising Isometheptene (R)-enantiomer mucate salt and a pharmaceutically acceptable carrier to a patient in need of such treatment.

In addition, a method of administering to a patient in need of treatment of hypertension, a therapeutic amount of a composition comprising Isometheptene (R)-isomer mucate salt combined with an active ingredient selected from acetaminophen, ibuprofen, aspirin, caffeine, dichloralphenazone, naproxen, and sumatriptan succinate; and a pharmaceutically acceptable nontoxic carrier.

Another separate aspect is found in the method of treatment of migraine by administering a therapeutic amount of a composition comprising Isomeptene (S)-enantiomer mucate salt and a pharmaceutically acceptable carrier to a patient in need of such treatment.

A further method of treatment of migraine comprises administering to a patient in need of such treatment, a therapeutic amount of a composition comprising Isomeptene (R)-enantiomer mucate salt combined with an active ingredient selected from acetaminophen, ibuprofen, aspirin, caffeine, dichloralphenazone, naproxen, and sumatriptan succinate; and a pharmaceutically acceptable carrier.

According to the present invention, a method of nitric oxidase inhibition includes administering a therapeutic amount of a composition comprising Isomeptene (R)-enantiomer mucate salt combined with an active ingredient selected from acetaminophen, ibuprofen, aspirin, caffeine, dichloralphenazone, naproxen, and sumatriptan succinate; and a pharmaceutically acceptable carrier.

The inventive methods of treatment with any of the Isomeptene compounds may include a composition comprising peroral, parenteral, IV, sublingual, inhalable, or transdermal formulations; such a method may include a gel, capsule, tablet, delayed release pellet or tablet coating formulation.

An inventive method of treating hypertension by administering to a patient in need of such treatment, a therapeutic amount of a composition comprising Isomeptene (R)-enantiomer mucate salt combined with an active ingredient selected from acetaminophen, ibuprofen, aspirin, caffeine, dichloralphenazone, naproxen, and sumatriptan succinate; and a pharmaceutically acceptable carrier.

Further aspects of the invention disclosed herein include methods of synthesis and purification, isolation and characterization of comparative mechanism of action the Isomeptene, as well as in vitro tests of the isolated Isomeptene racemates, as centrally acting agonists; in particular, the invention shows aspects of the different affinities of the (S)-enantiomer and (R)-enantiomer of Isomeptene to various CNS receptors.

Other advantageous aspects of the invention provide a preparation of purified Isomeptene stereoisomers 1 and 2 through chemical synthesis from chiral precursors, and further stereochemically characterize the Isomeptene stereoisomers 1 and 2 as being an (S)-enantiomer and (R)-enantiomer, respectively.

A particularly advantageous aspect of the invention is provided in that (R)-Isomeptene enantiomer is found to bind to the CNS moxonidine binding I1 about 60 fold more avidly than the (S)-Isomeptene enantiomer.

An alternative aspect of the invention provides the purified (S)-Isomeptene enantiomer which interacts with I1 about 60 fold less avidly than the R-Isomeptene enantiomer.

An advantageous aspect of the invention is found in the selective or specific (R)-Isomeptene enantiomer activity may be favorably effective for the treatment of mild, moderate, or severe heart failure.

An advantageous aspect of the invention is found in the selective or specific (R)-Isomeptene enantiomer activity may be favorably effective for the treatment of mild, moderate, or cognitive dysfunction.

One aspect of treatment includes providing the patient in need of the treatment with a therapeutic dose of about 10-30 mg (R)-Isomeptene enantiomer, once or twice daily.

Another aspect of the (R)-Isomeptene enantiomer may be provided by the therapeutic dose of about 30-40 mg, once or twice daily. One aspect of the (R)-Isomeptene enantiomer may be provided by the therapeutic dose of about 50-100 mg, once or twice daily. One aspect of the (R)-Isomeptene enantiomer may be provided by the therapeutic dose of about 50-500 mg, three or four doses every six to eight hours daily. One aspect of the (R)-Isomeptene enantiomer may be provided by the therapeutic dose, in controlled release preparations, of about 50-500 mg, once or twice daily.

Another aspect of the invention is found in the therapeutic use of CDP compositions including a combination of the (R)-Isomeptene enantiomer with other analgesic agents (FDC), such as caffeine, acetaminophen, sumatriptan succinate, aspirin, ibuprofen, naproxen and dichloralphenazone.

An alternate aspect of the invention is provided by a composition combining the (S)-Isomeptene enantiomer molecule with other analgesic agents (FDC), such as caffeine, acetaminophen, sumatriptan succinate, aspirin, ibuprofen, naproxen and dichloralphenazone.

The invention provides these useful aspects:
A method of treatment of hypertension including administering a therapeutic amount of a composition comprising Isomeptene (R)-enantiomer mucate salt and a pharmaceutically acceptable carrier to a patient in need of such treatment.

A method of treatment of hypertension including administering to a patient in need of such treatment, a therapeutic amount of a composition comprising an (R)-Isomeptene mucate salt combined with an active ingredient selected from acetaminophen, ibuprofen, aspirin, caffeine, dichloralphenazone, naproxen, and sumatriptan succinate; and a pharmaceutically acceptable carrier.

Further aspect includes a method to ameliorate or eliminate discomfort of a patient suffering from cramps, hot and cold flushes, cognitive disorders, TBI, neurotoxicity, depression, schizophrenia, anxiety, epilepsy, stress disorders, excess sweating, or symptoms related to drug withdrawal.

A method of treatment of migraine including administering a therapeutic amount of a composition comprising an (S)-Isomeptene mucate salt and a pharmaceutically acceptable carrier to a patient in need of such treatment.

A method of treatment of migraine including administering to a patient in need of such treatment, a therapeutic amount of a composition comprising Isomeptene (R)-enantiomer mucate salt combined with an active ingredient selected from acetaminophen, ibuprofen, aspirin, caffeine, dichloralphenazone, naproxen, and sumatriptan succinate; and a pharmaceutically acceptable carrier.

An aspect of the invention is provided by the use of (R)-Isomeptene enantiomer for inhibiting nitric oxidase (NO).

Such an aspect of the invention provides a method of treatment wherein the therapeutic composition comprises:
a tablet formulation comprising about 20 mg-150 mg of Isomeptene (R)-enantiomer, 20 mg of caffeine, and 325 or 500 mg of acetaminophen, (or 200 mg, 400 mg, or 800 mg ibuprofen).

Alternatively, the method of treatment of claim 7, wherein the therapeutic composition comprises:
a capsule formulation comprising about 30 to about 90 mg of Isomeptene (R)-enantiomer, about 100 mg of caffeine, and 325 mg of acetaminophen (or 200 mg, 400 mg, or 800 mg ibuprofen).

The method of treatment of neurogenic discomfort, wherein the therapeutic composition comprises:
an injectable solution comprising about 30 mg to about 100 mg of Isomeptene (R)-enantiomer, 20 mg of caffeine, and 150 mg of acetaminophen (or 200 mg, 400, or 800 mg ibuprofen), and physiological saline solution.

Another aspect of the invention provides a method for producing a composition which includes the steps of mixing a therapeutically effective amount of (R)-metheptene mucate salt with an anti-inflammatory substance selected from the group consisting of acetaminophen, ibuprofen, aspirin, dichloralphenazone, naproxen, and sumatriptan succinate; and a nontoxic carrier.

It is known that the chiral forms of methamphetamine, amphetamine and MMDA show that chirality in related molecules can have profound effects on their biological activity and disposition in the body.

In vitro tests of the isolated Isometheptene racemates, as centrally acting agonists, show aspects of the different affinities of the (S)-enantiomer and (R)-enantiomer of Isometheptene to various CNS receptors.

A distinct aspect of the invention includes the discovery that the (R)-Isometheptene enantiomer compound is capable of selectively or specifically binding to Imidazoline subtype 1 ($I_1$) receptor.

Another aspect includes a composition comprising an (R)-enantiomer of Isometheptene or pharmaceutically acceptable addition salt thereof, and a nontoxic carrier. Nontoxic carriers may include alpha-cyclodextrin, beta cyclodextrin, hydroxyethyl-beta-cyclodextrin, and hydroxyethyl-alpha-cyclodextrin.

An aspect of the invention also provides administering a therapeutic amount of a composition comprising an (R)-enantiomeric salt compound; and a pharmaceutically acceptable carrier.

An aspect of the invention provides (R)-Isometheptene mucate for treatment of episodic tension-type headaches (ETTH).

Another aspect of the invention provides a method for producing a composition which includes steps of mixing a therapeutically effective amount of (R)-Isometheptene mucate salt with an anti-inflammatory substance selected from the group consisting of acetaminophen, ibuprofen, aspirin, dichloralphenazone, naproxen, and sumatriptan succinate; and a nontoxic carrier.

Another aspect of the invention provides (R)-Isometheptene mucate for treatment of episodic tension-type headaches including infrequent ETTH, frequent ETTH, or chronic TTH or CTTH.

An aspect of the invention provides also a method of making the compound comprising the steps of:
(a) combining (S)-methyloxirane with 3-methyl-2-buten-1-yl magnesium chloride in THF in the presence of Copper iodide,
(b) neutralizing, extracting with ether, drying with magnesium sulfate, removing solvent, and distilling the (S)-6-Methyl-hept-5-en-2-ol
(c) reacting (S)-6-Methyl-hept-5-en-2-ol with methanesulfonyl chloride and DIEA in anhydrous DCM;
(d) cooling the reaction mixture to about 5° C.;
(e) adding mesyl chloride dropwise;
(f) diluting the reaction mixture after 18 hours at RT;
(g) washing said mixture with water, brine and drying over $MgSO_4$;
(h) concentrate to oily product, (S)-Methanesulfonic acid 1,5-dimethyl-hex-4-enyl ester, wherein the 1H NMR in $CDCl_3$ at 500 MHz identifies the parameters: 5.08 ppm 1 Hm, 4.80 ppm 1 Hm, 2.99 ppm 3 Hs, 2.08 ppm 2 Hm, 1.75 ppm 1 Hm, 1.69 ppm 3 Hs, 1.624 1 Hm, 1.61 3 Hs, 1.43 ppm 3 Hd;
(i) reacting (S)-Methanesulfonic acid 1,5-dimethyl-hex-4-enyl ester with N,N-dimethyl-acetamide (170 mL), and 40% methylamine in water in a sealed, heavy-walled reaction vessel at 50° C.;
(k) adding diethyl ether and washing said mixture with water and brine, drying over $MgSO_4$; and filtering to remove the solvent;
(l) removing the ether in vacuo (~25 mmHg) to yield (R)-Isometheptene in the free base form; and
(m) adding a pharmacologically acceptable acid (such as hydrochloric, mucic, tartaric) to form a pharmacologically acceptable salt.

A useful aspect of the present invention provides a method for producing a composition including the steps of mixing a therapeutically effective amount of (R)-metheptene mucate salt with an anti-inflammatory substance selected from the group consisting of acetaminophen, ibuprofen, aspirin, dichloralphenazone, naproxen, and sumatriptan succinate; and a nontoxic carrier.

BRIEF DESCRIPTION OF THE DRAWINGS

In the detailed description reference is made to the illustrative figures listed below.

DETAILED DESCRIPTION

Figure 1:
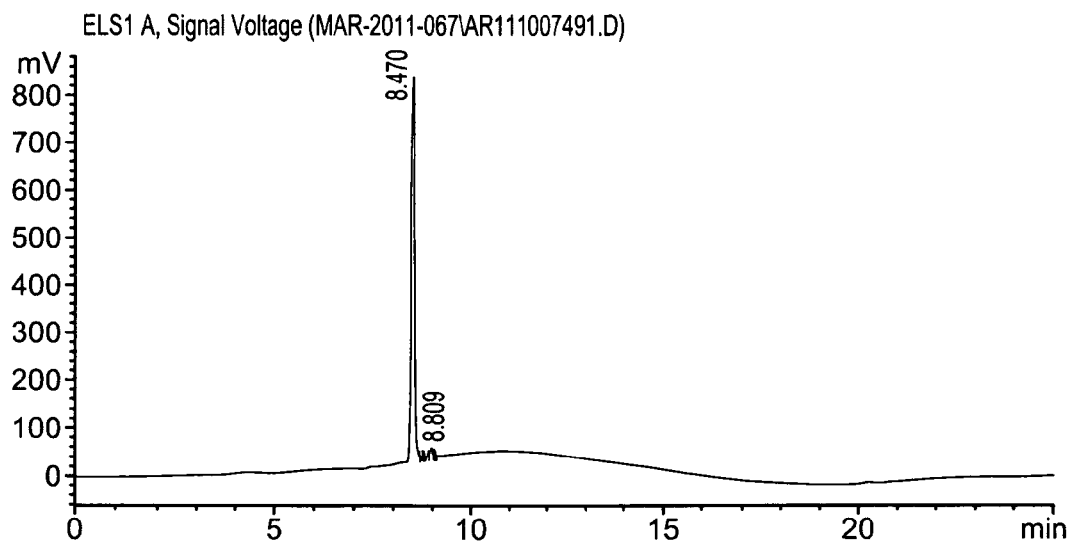
FIG. 1 illustrates high performance liquid chromatography (HPLC) elution of a purified Isometheptene isomer 2.

In general, Isometheptene is known as a sympathomimetic agent, often used in combination with dichloralphenazone and acetaminophen in the treatment of migraine and tension headache. However, in embodiments of this invention, there is illustrated the synthesis, purification and both structural and biological characterization, in addition to the racemic Isometheptene, of both (R)- and (S)-Isometheptene racemates.

Aspects of the invention provide distinct binding affinities of the twin enantiomers to CNS receptors. Certain examples of molecules with related structures show how the activity of enantiomers is unpredictable, including 3,4-methylenedioxy-N-methylamphetamine (MMDA). For example, (R)-amphetamine (which is optically Levo- or (−) amphetamine) has a chain of four contiguous carbons with a chiral carbon in an alpha position relative to a methyl-amino group that shares an absolute configuration with (R)-Isometheptene. (S)-amphetamine (which is optically Dextro- or (+) amphetamine) has a chain of four contiguous carbons with a chiral carbon in an alpha position relative to a methyl-amino group that shares an absolute configuration with (S)-Isometheptene.

As a background of similar activity, amphetamines are psychoactive stimulants of central nervous system (CNS) which as a mixture includes amphetamine, dextroamphetamine, and methamphetamine. Since amphetamine includes isomers called dextroamphetamine and levoamphetamine, wherein pure dextroamphetamine has been found more potent than the amphetamine mixture. Medications containing the amphetamines include Adderall©, Dexedrine©, DextroStat©, and Desoxyn© for treatment of narcolepsy, obesity, and attention deficit/hyperactivity disorder. Amphetamines can be modified to emphasize specific actions, which include CNS stimulation, cardiovascular actions, or appetite suppressant. Both methylphenidate and amphetamine compounds have been in Schedule II of the Controlled Substances Act since 1971. In medical use, there is controversy over whether the benefits of amphetamines for ADHD and weight loss outweigh the drug's harmful side effects. However, it is known that amphetamines appear successful in treating narcolepsy. Diethylproprion, fenfluramine, methylphenidate (commonly known as the prescription drugs Ritalin© or Concerta©), and phenmetrazine are drugs imitating amphetamines. Substances legally available over-the-counter include discovery that the intravenous injection of amphetamines (particularly methamphetamine) produced enhanced euphoric effects with a more rapid onset than oral administration. Although structurally similar to amphetamine, methamphetamine has more pronounced effects on the CNS.

As another example, (R)-methamphetamine (which is optically Levo- or (−) methamphetamine) has four contiguous carbons and a methylamino-group with a chiral alpha-carbon in the same absolute configuration as (R)-Isometheptene. In addition, (S)-methamphetamine (which is optically Dextro- or (+) methamphetamine) has four contiguous carbons and a methylamino-group with a chiral alpha-carbon in the same absolute configuration as (S)-Isometheptene. (R)-methamphetamine is a sympathomimetic vasoconstrictor which is the active ingredient used in some over-the-counter nasal decongestants including the US formulation of Vicks® Vapor Inhaler.

(S)-methamphetamine is a stimulant and addictive drug, street named "crystal meth", which is controlled by the US Drug Enforcement Administration (DEA). (S)-methamphetamine is a stimulant by virtue of interacting with the norepinephrine transporter and other receptors. As yet another example, (R)-3,4-methylenedioxy-N-methylamphetamine (R-MMDA)(which is optically Levo- or (−)MMDA) has four contiguous carbons and a methylamino-group with a chiral alpha-carbon in the same absolute configuration as (R)-Isometheptene. S-MMDA (which is optically Dextro- or (+) MMDA) has four contiguous carbons and a methylamino-group with a chiral alpha-carbon in the same absolute configuration as (S)-Isometheptene. Given as the racemate MDMA has a half-life of around 8 hours. For example, the area under the blood plasma concentration versus time curve (AUC) was two to four times higher for (R)-MDMA than the (S)-MDMA after a 40 mg oral dose in human volunteers. Likewise, the plasma half-life of (R)-MDMA was significantly longer than for (S)-MDMA (5.8±2.2 hours vs 3.6±0.9 hours). While (R)-MDMA has longer half-life, (S)-MDMA is more effective in eliciting 5-HT, NE, and DA release. (R)-MDMA is more selective for 5-HT and NE release and has only a small effect on DA release. [Chizh B A, Headley P M. NMDA antagonists and neuropathic pain—multiple drug targets and multiple uses. Curr Pharm Des. 2005; 11:2977-2994.]

It is known that the chiral forms of methamphetamine, amphetamine and MMDA show that chirality is related molecules can have profound effects on their biological activity and disposition in the body. An aspect of the invention includes the (R)-Isometheptene enantiomer compound being capable of selectively or specifically binding to the I1 receptor.

Another aspect includes a composition comprising an (S)- or (R)-enantiomer of Isometheptene or pharmaceutically acceptable addition salt thereof, and a nontoxic carrier. Nontoxic carriers may include alpha-cyclodextrin, beta cyclodextrin, hydroxyethyl-beta-cyclodextrin, and hydroxyethyl-alpha-cyclodextrin as possible nontoxic carriers here.

The Isometheptene can be solubilized by binding into the cyclodextrin cavity, which might improve rapidity of onset and bioavailability. An abstract for "Cyclodextrins as pharmaceutical solubilizers." Adv Drug Deliv Rev. 2007 Jul. 30; 59(7):645-66. Epub 2007 May 29. can be found at: http://www.ncbi.nlm.nih.gov/pubmed/17601630

The identification of the I1 receptor as the Isometheptene receptor reveals a new molecular target for ETTH therapeutics. In particular the data described below have shown that (R)-Isometheptene binds I1 with much stronger affinity than (S)-Isometheptene. Together, these data indicate that (R)-Isometheptene, as a single isomer may be an improved treatment for ETTH relative to racemic Isometheptene.

The structural formula (I) of racemic Isometheptene is disclosed:

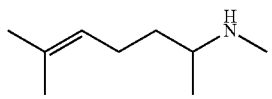

IUPAC name: 3,6-dimethylhept-5-en-2-amine.

Isometheptene is a monounsaturated aliphatic secondary amine. Alternatively named compound formulas include 6-methylamino-2-methylheptene, N,6-Dimethyl-5-hepten-2-amine, or 6-methylamino-2-methyl-heptene.

According to this invention, as shown below, the Isometheptene isomers have now been stereostructurally purified and their stereochemistry characterized. Thus, it has now been established that Isometheptene Isomer 1 is an (S)-enantiomer or (S)-Isometheptene, and Isometheptene Isomer 2 is an (R)-enantiomer, or (R)-Isometheptene.

More particularly, the purified Isometheptene racemic compound consists of approximately equal parts, isomer 1 and isomer 2, respectively, having the structural formulae (Ia) and (Ib) respectively;

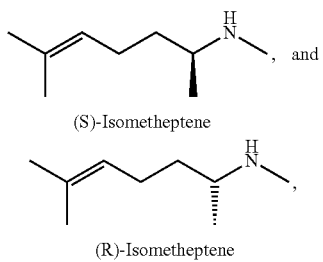

Disclosed in the embodiments of this invention are the (R) and (S) type enantiomers of the racemic compound, Isometheptene, or a pharmaceutical composition thereof, and a process of preparing it, for use in a method for treatment of patients suffering from migraine; in addition, the compound may be effectively combined with other suitable pharmaceutical agents.

Aspects of the invention provide distinct binding affinities of the twin enantiomers to CNS receptors.

Further aspects of the invention disclosed herein include methods of synthesis and purification, isolation and characterization of comparative mechanism of action the Isometheptene, as well as in vitro tests of the isolated Isometheptene racemates, as centrally acting agonists; in particular, the invention shows aspects of the different affinities of the (S)-enantiomer and (R)-enantiomer of Isometheptene to various CNS receptors.

Other advantageous aspects of the invention provide purified Isometheptene stereoisomers 1 and 2 through chemical synthesis from chiral precursors, and further stereochemically characterized the Isometheptene stereoisomers 1 and 2 as (S)-enantiomer and (R)-enantiomer, respectively.

A particularly advantageous aspect of the invention is provided in that (R)-Isometheptene enantiomer is found to bind to the CNS moxonidine binding I1 receptor about 60 fold more avidly than the (S)-Isometheptene enantiomer. The (R) Isometheptene binds to the I1 receptor with a 60-fold increase in potency to that of (S) isomentheptene. See Table 1.

The I1 receptor has been found to be the receptor for the central hypertensive agent moxonidine. Besides central hypertension, moxonidine has been efficacious in the treatment of metabolic syndrome, which includes dyslipidemia, insulin resistance, glucose intolerance, hypertension and central obesity. Moxonidine has also been considered as a treatment for heart failure. [Reference: Edwards, L. P., Brown-Bryan, T. A., McLean, L., and Ernsberger, P. "Pharmacological Properties of the Central Antihypertensive Agent, Moxonidine." Cardiovasc. Ther. 30: 199-208 (2012)].

Moxonidine is believed to function as an agonist of the I1 receptor. Known imidazoline drugs with a postulated high affinity to the I1 receptor are AGN192403, rilmenidine, moxonidine and clonidine. Specific ligands of the I1 receptor are 2-BFI, BU239. The putative natural ligand for imidazoline I(1), I(2) and I(3) receptors is agmatine. Idazoxan is believed to function as antagonist of the I1 and I2 receptors.

Radwanska A, Dlugokecka J, Wasilewski R, Kaliszan R. J Physiol Pharmacol. 2009 March; 60(1):131-42. Testing conception of engagement of imidazoline receptors in imidazoline drugs effects on isolated rat heart atria.

Idazoxan is believed to function as antagonist. Idazoxan (INN) is both a selective α2 adrenergic receptor antagonist, and an antagonist for the imidazoline receptor. Idoxane was investigated as an adjunctive treatment in schizophrenia because it may treat the "negative" symptoms of schizophrenia. These effects were associated with the α2 adrenergic receptor antagonist properties.

Bousquet, P; Bruban, V; Schann, S; Greney, H; Ehrhardt, J D; Dontenwill, M; Feldman, J (1999). "Participation of imidazoline receptors and alpha(2-)-adrenoceptors in the central hypotensive effects of imidazoline-like drugs". *Annals of the New York Academy of Sciences* 881: 272-8. doi:10.1111/j.1749-6632.1999.tb09369.x. PMID 10415925.

The potential human metabolic pathway for generation of 2-methyl-6-methylamino-2-hepten-1-ol from Isometheptene has been described (Lyris 2005).

Accordingly, Isometheptene is first demethylated to N-desmethyl-Isometheptene (which was also detected in urine samples collected during this study). Further, the N-desmethyl-Isometheptene metabolite undergoes acid hydrolysis to form 2-methyl-6-methylamino-2-hepten-1-ol. The major urinary metabolite of (+/−)-Isometheptene in the rat was identified as trans-2-methyl-6-methylamino-2-hepten-1-ol (Taylor 1977). Another metabolite, cis-2-Methyl-6-methylamino-2-hepten-1-ol, was identified as a minor urinary metabolite of Isometheptene in the rat.

According to this invention, Isometheptene is a racemic compound which has now been separated into its twin isomer racemates 1 and 2 and characterized as pure (S)-enantiomer and (R)-enantiomer, respectively.

Isometheptene isomers 1 and 2 can be produced according to either of two alternative synthetic schemes A and B, outlined below:

Scheme A:

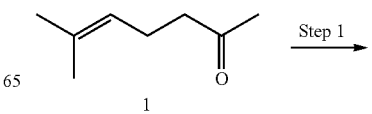

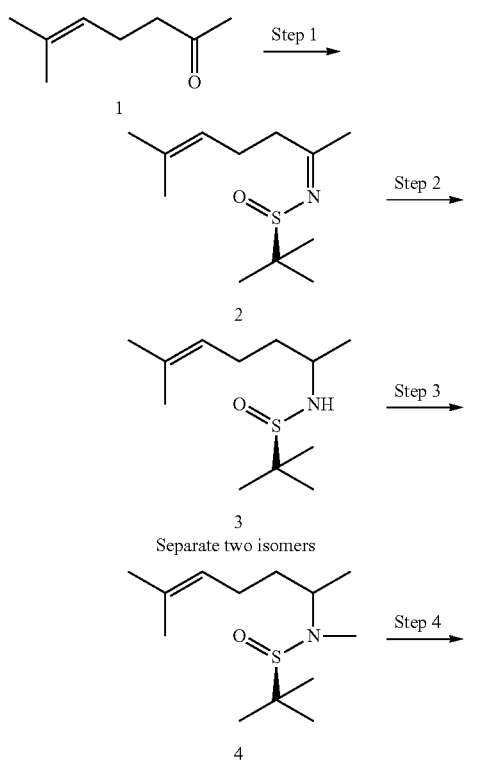

Scheme B:

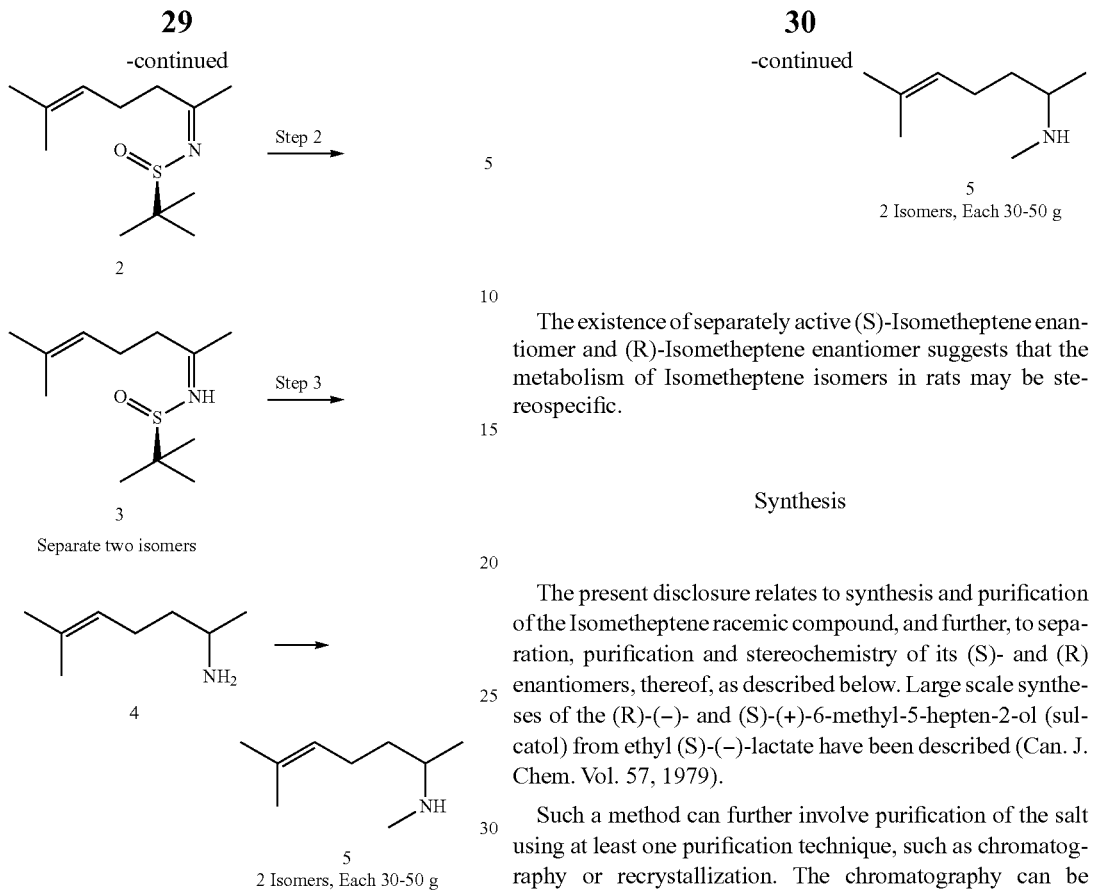

2 Isomers, Each 30-50 g

The existence of separately active (S)-Isometheptene enantiomer and (R)-Isometheptene enantiomer suggests that the metabolism of Isometheptene isomers in rats may be stereospecific.

Synthesis

The present disclosure relates to synthesis and purification of the Isometheptene racemic compound, and further, to separation, purification and stereochemistry of its (S)- and (R) enantiomers, thereof, as described below. Large scale syntheses of the (R)-(−)- and (S)-(+)-6-methyl-5-hepten-2-ol (sulcatol) from ethyl (S)-(−)-lactate have been described (Can. J. Chem. Vol. 57, 1979).

Such a method can further involve purification of the salt using at least one purification technique, such as chromatography or recrystallization. The chromatography can be reverse-phase chromatography or regular phase chromatography. In some embodiments, the regular phase chromatography can use alumina or silica gel. According to another embodiment of the invention, a method for synthesis, isolation and purification of the compounds is provided, including passing the crude reaction products through a chromatography column and collecting the particular compound which elutes at the appropriate retention time.

A method for isolation and purification of the novel compounds is provided, comprising passing the crude reaction products through a chromatography column and collecting the particular compound which elutes at the appropriate retention time.

According to another embodiment of the invention, a method for analyzing stereoisomers is provided. The method involves conducting high performance liquid chromatography (HPLC) and applying specific compounds of Formulae (Ia, Ib, and II-III) to the chromatography column as a standard. The method preferably involves applying both types of stereoisomers as standards to determine relative retention/elution times.

The foregoing HPLC can be used to determine the relative amount of stereoisomer and the intermediates of the synthesis thereof by determining the area under the respective curves in the chromatogram produced.

According to another aspect of the invention a method for isolation and purification of salt intermediate is provided, comprising recrystallizing the crude products or intermediates thereof from a solvent or a mixture of solvents. This process can be in addition to the method described above, and the anion exchange resin column step.

Stereoselective Synthesis of Isomeptheptene and Determination Of Isometheptene Stereochemistry by Use of Mosher's Amides

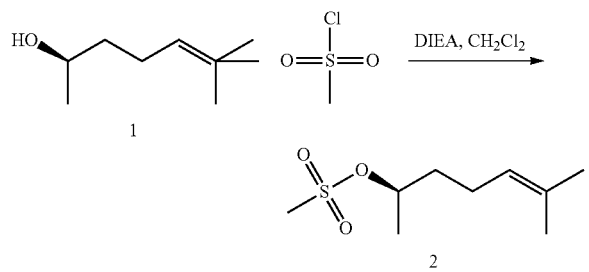

Formation of (R)-Methanesulfonic acid 1,5-dimethyl-hex-4-enyl ester from (R)-6-Methyl-hept-5-en-2-ol (1) and methanesulfonyl chloride (R)-Methanesulfonic acid 1,5-dimethyl-hex-4-enyl ester (2). (R)-6-Methyl-hept-5-en-2-ol (1) (2.26 g, 17.6 mmol) and DIEA (5.52 mL, 31.7 mmol) were dissolved in anhydrous DCM (24 mL), the reaction mixture was cooled to 5° C., mesyl chloride (1.64 mL, 21.1 mmol) was added dropwise, and the reaction mixture was allowed to slowly warm to RT. After 18 h at RT the reaction mixture was diluted with DCM (60 mL), washed with water (3×35 mL), brine (35 mL), dried with MgSO4, solvent was concentrated to give a dark oil which was purified by SiO2 flash chromatography using Hexane-EtOAc to give the title compound as an oil (3.225 g, 86%). H1 NMR: see supporting information. TLC, Hexane-DCM-EtOAc, 40:40:20, 2 Rf 0.70 (developed with KMnO4 stain). 1H NNMR in CDCl3 (500 MHz): 5.08 ppm 1 Hm, 4.80 ppm 1 Hm, 2.99 ppm 3 Hs, 2.08 ppm 2 Hm, 1.75 ppm 1 Hm, 1.69 ppm 3 Hs, 1.624 1 Hm, 1.61 3 Hs, 1.43 ppm 3 Hd.

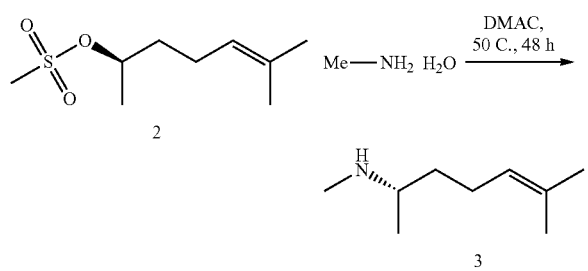

Formation of (5) Isometheptene from (R)-Methanesulfonic acid 1,5-dimethyl-hex-4-enyl ester and methylamine (S)-Isometheptene (3): (R)-Methanesulfonic acid 1,5-dimethyl-hex-4-enyl ester (2) (1.00 g, 4.85 mmol) was dissolved in N,N-dimethyl-acetamide (24 mL), 40% methylamine in water (17.11 mL, 194 mmol) was added at RT using a heavy-walled reaction vessel (150 mL) with teflon screw cap. The reaction vessel was sealed, stirred, and heated at 50 C for 66 h after which the reaction mixture was cooled to 5° C., and the system was opened to monitor the reaction by TLC. The reaction mixture was diluted with Et2O (200 mL), shaken, the organic layer was washed with water (4×50 mL), brine (50 mL), dried with MgSO4, and solvent was concentrated to give the titled compound as an oil (606 mg, 88%). H1 NMR in CDCl3 (500 mHz): 1H NNMR in CDCl3: 5.10 ppm 1 Ht (J=6.8 Hz), 2.53 ppm 1 Hm, 2.40 ppm 3 Hs, 2.00 ppm 2 Hm, 1.68 ppm 3 Hs, 1.61 ppm 3 Hs, 1.49 ppm 1 Hm, 1.31 ppm 1 Hm, 1.04 ppm 3 Hd (J=6.5 Hz).

TLC sample was prepared by taking an aliquot (100 uL) of reaction mixture, diluting with EtOAc (100 uL), washing with brine (500 uL), TLC organic layer. TLC, Hexane-EtOAc, 75:25, 2 Rf 0.35. DCM-7 N NH3-MeOH, 90:10, 3 Rf, 0.45 (developed with KMnO4 stain).

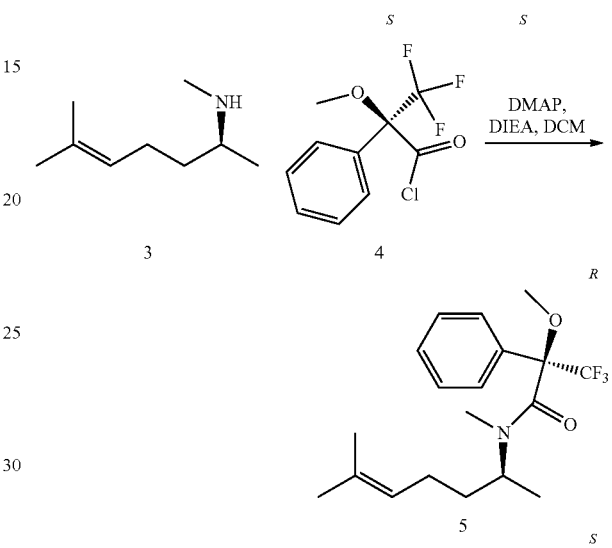

Formation of (S) Isometheptene (R)-Mosher amide

Synthesis of (S)-Isometheptene (R)-Mosher amide (5)

(S)-Isometheptene (3) (79 mg, 0.56 mmol) was dissolved in anhydrous DCM (5.6 mL), DMAP (10 mg, 0.082 mmol), DIEA (0.156 mL, 0.90 mmol) were added, and the reaction mixture was cooled to 5 C. Mosher's (S)-acid chloride (0.126 mL, 0.67 mmol) was added dropwise at 5 C and the reaction was allowed to warm to RT. After 16 h at RT additional DIEA (0.156 mL, 0.90 mmol), then Mosher's (S)-acid chloride (0.126 mL, 0.67 mmol) were added dropwise at RT and the reaction mixture was stirred at RT for 16 h. The reaction was quenched with saturated NH4Cl (28 mL), the mixture was extracted with Et2O (3×28 mL), the organic extracts were combined, dried with MgSO4, solvent was concentrated, to give an oil which was purified by SiO2 flash chromatography using Hexane-EtOAc to give the title compound as an oil (80 mg, 40%). H1 NMR in CDCl3 (500 mHz): 1H NMR in CDCl3: 7.54 ppm (2H m), 7.37 ppm (3 Hm), 5.08 ppm 1 Hm, 4.835 ppm 1 Hm, 3.68 ppm 3 Hs, 2.45 ppm 3 Hs, 1.82 ppm 1 Hm, 1.92 ppm 1 Hm, 1.68 ppm 3 Hs, 1.56 ppm 3 Hs, 1.41 ppm 2 Hm, 1.118 ppm 3 Hd (J=6.5 Hz). TLC, DCM-7 N NH3-MeOH, 90:10, 3 Rf, 0.45. Hexane-EtOAc, 85:15, 5 Rf 0.45 (developed with KMnO4 stain).

Determination of Isometheptene Stereochemistry by Use of Mosher's amides

The twin enantiomers of Isometheptene were assayed for their individual activities while the stereochemistry of the enantiomers were unknown. Therefore, the Mosher's amides of these Isomethepene enantiomers were prepared, then the H1 NMR were analyzed and compared to that of compound 5 with known stereochemistry. H1 NMR were taken of the individual compounds and of mixtures of compounds as well. Inspection of the chemical shifts for the alpha proton (approx. 4.8 ppm) (attached to chiral C of Isomeptene) and methyl protons (approx. 1.1 ppm) attached to chiral C revealed that isomer 1 has (S) stereochemistry and isomer 2 has (R) stereochemistry.

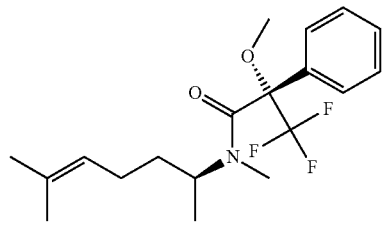

C = (S)-isomeptene-(R)-Mosher's amide
A = isomer 1 isomeptene-(R)-Mosher's amide

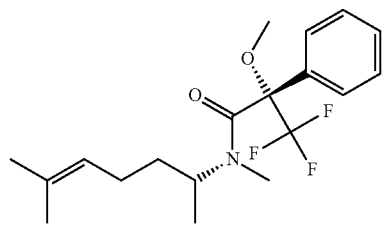

(R)-isomeptene-(R)-Mosher's amide
B = isomer 2 isomeptene-(R)-Mosher's amide

Structures of the Mosher's amides of Isomeptene used in the NMR assignment of stereochemistry (see Table A).

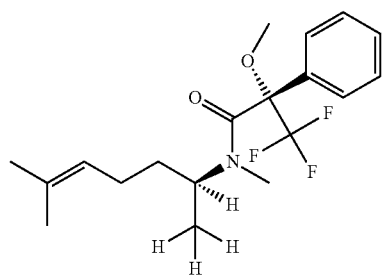

CHN alpha proton
c-methyl protons

TABLE A

| Amide | HNMR CHN alpha proton | HNMR C-methyl proton |
|---|---|---|
| A = isomeptene isomer 1 (R)-Mosher's amide | 4.838 ppm | 1.113 ppm |
| B = isomeptene isomer 2 (R)- Mosher's amide | 4.757 ppm | 1.028 ppm |
| C = (S)-isomeptene-(R)- Mosher's amide | 4.835 ppm | 1.118 ppm |

Location in Molecule and HNMR Chemical Shifts to Determine the Stereochemistry of Isomeptene Isomer 1-(R)-Mosher's Amide and Isomeptene Isomer 2-(R)-Mosher's Amide by Comparison to (S)-Isomeptene-(R)-Mosher's Amide

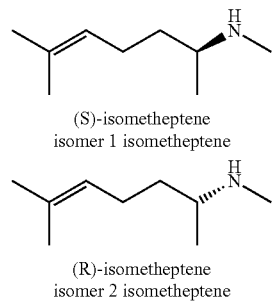

(S)-isomeptene
isomer 1 isomeptene (R)-isomeptene
isomer 2 isomeptene

Assignment of (S) and (R) Stereostructures of Isomeptene Isomer 1 and Isomeptene Isomer 2, Based on the HNMR Studies of Mosher's Amides.

The following description is directed to the method of stereospecific synthesis and structural characterization of Isomeptene Isomer 1 ((S)-enantiomer) and Isomeptene Isomer 2 ((R)-enantiomer).

Synthesis of Isomeptene Mucate-Isomer-1
(S-Isomer)

Mucic acid (840 mg, 4.0 mmol) was suspended in distilled water (40 mL) at RT. Isomeptene-isomer-1 (1.356 g, 9.6 mmol) was dissolved in $Et_2O$ (19 mL) and added dropwise via addition funnel to the mucic acid at RT while stirring to give dissolution of the mucic acid suspension. The biphasic solution was stirred at RT for 16 h, the aqueous layer was separated, extracted with toluene (5×80 mL) (the final extraction with toluene was stood for 30 min before the aqueous layer was separated), then the aqueous layer was evaporated in vacuo (1 mm Hg) at 35°-40° C. to give a white solid which was dissolved in MeOH (8 mL) by gently heating to give a solution. $CH_3CN$ (80 mL) was added slowly dropwise via addition funnel at RT to the stirred MeOH solution to give a suspension which was stirred at RT for about 30 min. The solids were filtered, washed with $CH_3CN$ thrice, air-dried, then dried in vacuo (0.1 mm Hg) at RT for 16 h to give the titled compound as a white solid (1.390 mg, 70%). The molar ratio of Isomeptene to mucic acid in the salt was 2:1, based on the NMR spectrum: 1H NMR (500 MHz), in $D_2O$: 1H NNMR in $CDCl_3$: 5.16 ppm 1 Ht (J=6.8 Hz), 4.25 ppm 1 Hs, 3.95 ppm 1 Hs, 3.2 ppm 1 Hm, 2.66 ppm 3 Hs, 2.09 ppm 2 Hm, 1.75 ppm 1 Hm, 1.69 ppm 3 Hs, 1.62 ppm 3 Hs, 1.58 ppm 1 Hm, 1.29 ppm 3 Hd (J=7 Hz). MS: mass calc for C9H19N, 141.15. Found: 142.4 (M+H).

Synthesis of Isomeptene Mucate-Isomer-2
(R-Isomer)

Mucic acid (628 mg, 3.0 mmol) was suspended in distilled water (40 mL) at RT. Isomeptene-isomer-2 (3.04 g, 21.5 mmol) was dissolved in $Et_2O$ (57 mL) and added dropwise via addition funnel to the mucic acid at RT while stirring to give dissolution of the mucic acid suspension. The biphasic solution was stirred at RT for 16 h, the aqueous layer was separated, extracted with toluene (5×80 mL) (the final extraction with toluene was stood for 30 min before the aqueous layer was separated), then the aqueous layer was evaporated in vacuo (1 mm Hg) at 35°-40° C. to give a white solid which was dissolved in MeOH (8 mL) by gently heating to give a solution. CH₃CN (80 mL) was added slowly dropwise via addition funnel at RT to the stirred MeOH solution to give a suspension which was stirred at RT for about 30 min. The solids were filtered, washed with CH₃CN thrice, air-dried, then dried in vacuo (0.1 mm Hg) at RT for 16 h to give the titled compound as a white (1.390 mg, 70%). The molar ratio of Isometheptene to mucic acid in the salt was 2:1, based on the NMR spectrum: 1H NMR (500 MHz, in D₂O), 1H NNMR in CDCl₃: 5.16 ppm 1 Ht (J=6.8 Hz), 4.25 ppm 1 Hs, 3.95 ppm 1 Hs, 3.2 ppm 1 Hm, 2.66 ppm 3 Hs, 2.09 ppm 2 Hm, 1.75 ppm 1 Hm, 1.69 ppm 3 Hs, 1.62 ppm 3 Hs, 1.58 ppm 1 Hm, 1.29 ppm 3 Hd (J=7 Hz). MS: mass calc for $C_9H_{19}N$, 141.15. Found: 142.4 (M+H).

(S)-6-Methyl-hept-5-en-2-ol

Synthesis of the (R)-Mosher Ester of (S)-Sulcatol

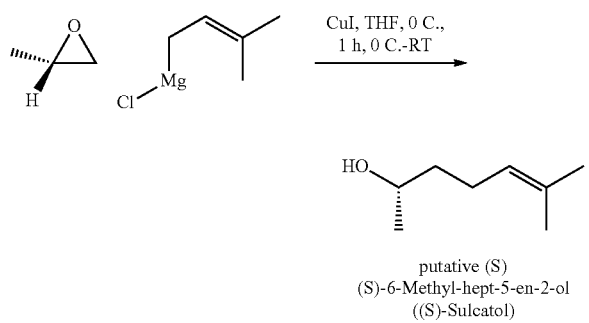

putative (S)
(S)-6-Methyl-hept-5-en-2-ol
((S)-Sulcatol)

3-Methylbut-2-enylmagnesium chloride, 0.50 M in THF (100 mL, 50 mmol) was cooled to 0° C., CuI (952 mg, 5.0 mmol), then (S)-2-Methyl-oxirane (1.752 mL, 25.0 mmol) in anhydrous THF (12 mL) was slowly added to the stirred reaction mixture via syringe pump at a rate of 16 mL/h over 45 min to give a dark suspension which was stirred at 0° C. under an Ar atm for 1 h, then allowed to slowly warm to RT over several h. After stirring at RT for 18 h the reaction mixture was poured into sat. aqueous NH₄Cl (75 mL), the mixture was extracted with Et₂O (3×100 mL), the organic extracts were combined, washed with water (100 mL), brine (100 mL), dried with MgSO₄, and solvent was evaporated in vacuo (30 mm Hg) at 25° C. to give an oil which was purified by SiO₂ flash chromatography to give the title compound as an oil in 2 fractions (1.6 g, 0.6 g, 69%). H¹ NMR (CDCl₃).

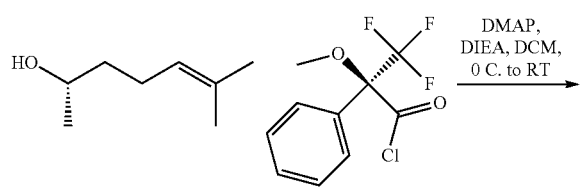

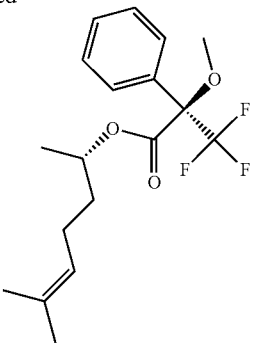

(R)-Mosher ester of (S)-Sulcatol. {(R)-3,3,3-Trifluoro-2-methoxy-2-phenyl-propionic acid (S)-1,5-dimethyl-hex-4-enyl ester.} and Determination of Chiral Purity of Synthesized (S)-Sulcatol Via (R)-Mosher Ester(S)-Sulcatol (S)-6-Methyl-hept-5-en-2-ol (0.088 mL, 0.58 mmol) was dissolved in anhydrous DCM (6 mL), DMAP (10.6 mg, 0.087 mmol), DIEA (0.192 mL, 1.10 mmol) were added, then (S)-3,3,3-Trifluoro-2-methoxy-2-phenyl-propionyl chloride (0.152 mL, 0.813 mmol) was added dropwise at RT while stirring. After 18 h at RT N,N-Dimethyl-1,3-propanediamine (0.146 mL, 1.16 mmol) was added at RT and the reaction mixture was stirred at RT for 20 min. The mixture was diluted with Et₂O (60 mL), washed with 1 N aqueous HCl (20 mL), 2 M Na₂CO₃ (20 mL), brine (20 mL), dried with MgSO₄, solvent was evaporated in vacuo at 30° C. to give an oil which was coevaporated with CCl₄ three times to remove residual Et₂O to give an oil which was further dried in vacuo (0.1 mm Hg) for 1 h to give an oil (242 mg). H¹ NMR (CDCl₃): see supporting information. LRMS: mass calculated for $C_{18}H_{23}F_3O_3$: 344.16. found: 366.8 (M+Na⁺)

Another useful method has been found as follows:

Stereoselective Synthesis of (R)-Isometheptene and (R)-Isometheptene Mucate

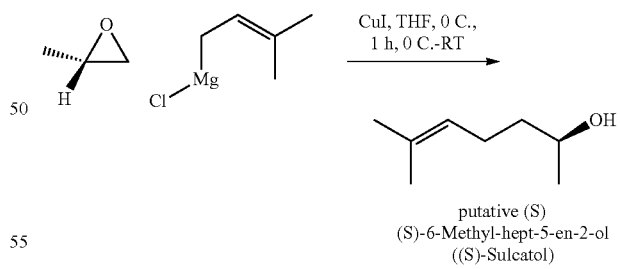

putative (S)
(S)-6-Methyl-hept-5-en-2-ol
((S)-Sulcatol)

(S)-6-Methyl-hept-5-en-2-ol. [Small Scale, e.g., ca. 1 g Final Product]

3-Methylbut-2-enylmagnesium chloride, 0.50 M in THF (100 mL, 50 mmol) was cooled to 0° C., CuI (952 mg, 5.0 mmol), then (S)-2-methyl-oxirane (1.752 mL, 25.0 mmol) in anhydrous THF (12 mL) was slowly added to the stirred reaction mixture via syringe pump at a rate of 16 mL/h over 45 min to give a dark suspension which was stirred at 0° C. under an Argon atm for 1 h, then allowed to slowly warm to RT over several h. After stirring at RT for 18 h the reaction mixture was poured into sat aqueous NH$_4$Cl (75 mL), the mixture was extracted with Et$_2$O (3×100 mL), the organic extracts were combined, washed with water (100 mL), brine (100 mL), dried with MgSO$_4$, and solvent was evaporated in vacuo (30 mm Hg) at 25° C. to give an oil which was purified by SiO$_2$ flash chromatography to give the title compound as an oil in 2 fractions (2.2 g, 69%). H$^1$ NMR (CDCl$_3$): • 5.14 (m, 1H), 3.82 (m, 1H), 3.08 (m, 1H), 1.69 (s, 3H), 1.62 (s, 2H), 1.48 (m, 2H), 1.19 (d, 3H, J=6 Hz).

Below is the description of a method of synthesis of a larger amount of S-sulcatol (i.e. 13.68 g).

3-Methylbut-2-enylmagnesium chloride, 0.50 M in THF (760 mL, 380 mmol) was transferred to a 2 liter, flame-dried round-bottom flask. After cooling to 4° C., CuI (7.62 g, 40 mmol) was added to give a dark suspension, and (S)-2-methyl-oxirane 99% (14 mL, 200 mmol) in anhydrous THF (12 mL) was slowly added to the stirred reaction mixture via syringe pump at a rate of 110 mL/h at 4° C. to give a dark suspension which was allowed to slowly warm to RT in the ice bath. After stirring at RT for 16 h, TLC and NMR showed (S)-sulcatol {(S)-6-Methyl-hept-5-en-2-ol} and a more polar, more volatile side product. The reaction mixture was poured into sat. aqueous NH$_4$Cl (600 mL) to give a blue aqueous suspension and an organic layer with pH 9. This mixture was stirred for 30 minutes, the mixture was extracted three times with Et$_2$O (800 mL, 400 mL, and 400 mL). The organic extracts were combined, washed with water (200 mL), brine (200 mL), dried with MgSO$_4$, and stripped of solvent in vacuo (30 mm Hg) at 35° C. to give 31.8 grams of a yellow oil which was purified three times by distillation in vacuo at 15-20 mm Hg. The higher boiling fractions, bp. 80° C., contained the (S)-sulcatol. The yield of (S)-sulcatol was 13.68 g. H$^1$ NMR (CDCl$_3$): • 5.14 (m, 1H), 3.81 (m, 1H), 2.08 (m, 1H), 1.69 (s, 3H), 1.62 (s, 2H), 1.48 (m, 2H), 1.19 (d, 3H, J=6 Hz). TLC in 3:1 hexane/ethyl acetate:sulcatol:Rf 0.35, impurity: Rf 0.3, visualized with KMnO$_4$ and charring.

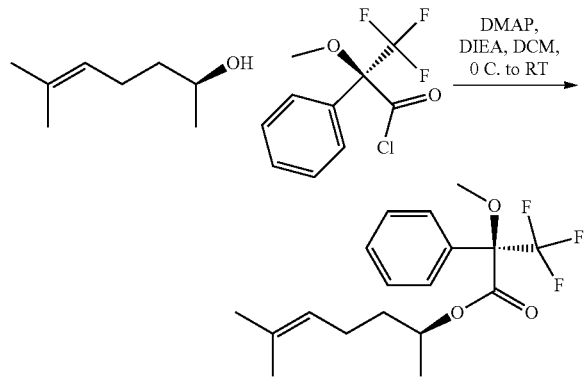

(R)-Mosher ester of (S)-Sulcatol. ((R)-3,3,3-Trifluoro-2-methoxy-2-phenyl-propionic acid (S)-1,5-dimethyl-hex-4-enyl ester (S)-6-Methyl-hept-5-en-2-ol (0.088 mL, 0.58 mmol) was dissolved in anhydrous DCM (6 mL), DMAP (10.6 mg, 0.087 mmol), DIEA (0.192 mL, 1.10 mmol) were added, then (S)-3,3,3-Trifluoro-2-methoxy-2-phenyl-propionyl chloride (0.152 mL, 0.813 mmol) was added dropwise at RT while stirring. After 18 h at RT, N,N-Dimethyl-1,3-propanediamine (0.146 mL, 1.16 mmol) was added at RT; and the reaction mixture was stirred at RT for 20 min. The mixture was diluted with Et$_2$O (60 mL), washed with 1 N aqueous HCl (20 mL), 2 M Na$_2$CO$_3$ (20 mL), brine (20 mL), dried with MgSO$_4$, solvent was evaporated in vacuo at 30° C. to give an oil which was coevaporated with CCl$_4$ three times to remove residual Et$_2$O to give an oil which was further dried in vacuo (0.1 mm Hg) for 1 h to give the title compound as a crude oil (242 mg). H$^1$ NMR (CDCl$_3$): • 7.55 (m, 2H), 7.40 (m, 3H), 5.15 (m, 1H), 5.03 (m, 1H), 3.57 (s, 3H), 1.92 (m, 2H), 1.70 (m, 1H), 1.65 (s, 3H), 1.55 (m, 1H), 1.51 (s, 3H), 1.34 (d, 3H, J=6.5 Hz). LRMS: mass calculated for C$_{18}$H$_{23}$F$_3$O$_3$: 344.16. found: 366.8 (M+Na$^+$).

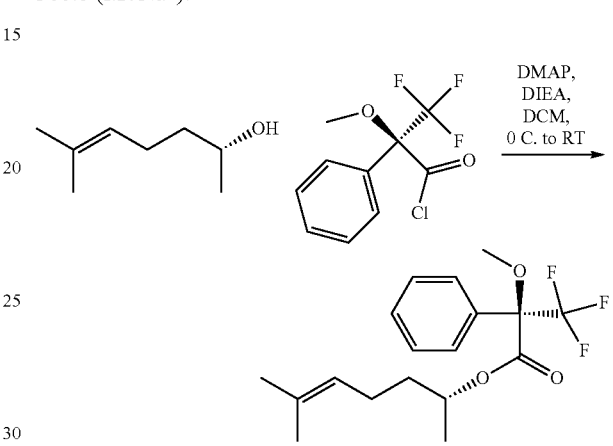

(R)-Mosher ester of (R)-Sulcatol. {(R)-3,3,3-Trifluoro-2-methoxy-2-phenyl-propionic acid (R)-1,5-dimethyl-hex-4-enyl ester.}

The title compound was prepared using the procedure described for the preparation of (R)-Mosher ester of (S)-Sulcatol to give the title compound as a crude oil (241 mg). H$^1$ NMR (CDCl$_3$): • 7.54 (m, 2H), 7.40 (m, 3H), 5.14 (m, 1H), 5.08 (m, 1H), 3.55 (s, 3H), 2.02 (m, 2H), 1.74 (m, 1H), 1.68 (s, 3H), 1.60 (m, 1H), 1.57 (s, 3H), 1.27 (d, 3H, J=6.5 Hz).

Determination of Chiral Purity of Synthesized (S)-Sulcatol Via (R)-Mosher Ester of (S)-Sulcatol Inspection of regions 5.02-5.08 ppm (chemical shifts of protons bonded to chiral carbon) for (R)-Mosher ester of (S)-Sulcatol and (R)-Mosher ester of (R)-Sulcatol indicated chiral purity of (S)-6-Methyl-hept-5-en-2-ol to be >95%.

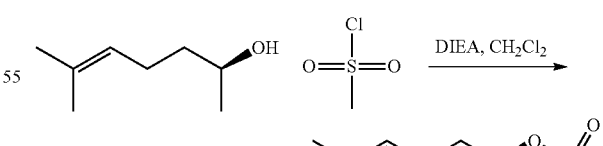

(S)-Methanesulfonic acid 1,5-dimethyl-hex-4-enyl ester (S)-6-Methyl-hept-5-en-2-ol (2.64 g, 20.58 mmol) and DIEA (6.45 mL, 37.0 mmol) were dissolved in anhydrous DCM (28 mL), the reaction mixture was cooled to 5° C., mesyl chloride (1.91 mL, 24.7 mmol) was added dropwise, and the reaction mixture was allowed to slowly warm to RT. After 18 h at RT the reaction mixture was diluted with DCM (100 mL), washed with water (3×35 mL), brine (35 mL), dried with MgSO4, solvent was concentrated to give a dark oil which was purified by SiO2 flash chromatography using Hexane-EtOAc to give the title compound as an oil (3.213 g, 76%). TLC, Hexane-DCM-EtOAc, 40:40:20, 2 $R_f$ 0.70 (developed with KMnO4 stain). $H^1$ NMR (CDCl$_3$): • 5.08 (m, 1H), 4.80 (m, 1H), 2.99 (s, 3H), 2.10 (m, 2H), 1.75 (m, 1H), 1.69 (s, 3H), 1.62 (m, 1H), 1.61 (s, 3H), 1.43 (d, 3H, J=6.5 Hz).

Optionally, for larger scale preparations, the dark oil may be used in the next step (reaction with methylamine) without silica chromatography, or dissolved in Hexane-DCM-EtOAc, 40:40:20, filtered through silica to remove baseline impurities, and stripped of solvent.

Below is the description of a method of synthesis of a larger amount of (S)-Methanesulfonic acid 1,5-dimethyl-hexyl-enyl ester (19.8 g).

The (S)-sulcatol (13.68 g) from the aforegoing section was converted to (S) Methanesulfonic acid 1,5-dimethyl-hexyl-4-enyl ester as described above. However, instead of by chromatography the product was purified by filtering a methylene chloride solution through silica gel in a filtration funnel (6 cm height×9.5 cm inside diameter, 60 A 220-240 mesh slica) and removing under vacuum. The yield of (S)-Methanesulfonic acid 1,5-dimethyl-hexyl-4-enyl ester was 19.8 g. This material showed no side products by NMR.

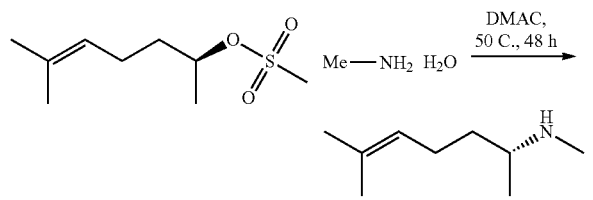

Optionally, the (R)-Isometheptene free base could be further purified by distillation. Thus, the chemical and optical purity of the product could optionally be further improved by recrystallization of the salt formed with a chiral carboxylic acid (e.g. D-tartaric acid, mandelic acid, O,O-dibenzoyl-D-tartaric acid, N-acetyl-L-phenylalanine) followed by treatment with aqueous NaOH and extraction with ether to re-isolate the (R)-Isometheptene free base.

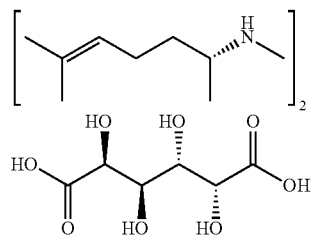

(R)-Isometheptene Mucate Salt, See Table A (R)-Isometheptene Mucate

Mucic acid (1.224 g, 5.82 mmol) was suspended in distilled water (58 mL) at RT. (R)-Isometheptene (1.974 g, 13.98 mmol) was dissolved in Et$_2$O (28 mL) and added dropwise via addition funnel to the mucic acid at RT while stirring to give dissolution of the mucic acid suspension. The biphasic solution was stirred at RT for 16 h, the aqueous layer was separated, extracted with toluene (3×50 mL) (the final extraction with toluene was stood for 30 min before the aqueous layer was separated), then the aqueous layer was evaporated in vacuo (1 mm Hg) at 35-40° C. to give a white solid which was dissolved in MeOH (12 mL) by gently heating to give a solution which was allowed to cool to RT. CH3CN (65 mL) was added slowly dropwise via addition funnel at RT to the stirred MeOH solution to give a white suspension which was stirred at RT for about 30 min. The solids were filtered, washed with CH3CN thrice, air-dried, then dried in vacuo (0.1 mm Hg) at RT for 16 h to give the titled compound as a white solid (2.531 g, 88%). $H^1$ NMR (D$_2$O) • 5.17 (m, 1H), 4.24 (s, 1H), 3.93 (s, 1H), 3.21 (m, 1H), 2.66 (s, 3H), 2.09 (m, 1H), 1.76 (m, 1H), 1.69 (s, 3H), 1.62 (s, 3H), 1.57 (m, 1H), 1.29 (d, 3H, J=6.5 Hz). $C^{13}$ NMR (D$_2$O) • 178.4, 133.8, 121.4, 70.86, 70.57, 54.2, 31.3, 28.8, 23.9, 22.3, 16.0, 14.1. LRMS: mass calculated for C$_9$H$_{19}$N, 141.15. found: 142.3 (M+H)$^+$. Elemental analyses calculated for C$_9$H$_{19}$N: C %, 58.51; H %, 9.82; N %, 5.69. found: C %, 58.21; H %, 9.95; N %, 5.54.

Optionally, the Isometheptene mucate can be further purified by recrystallization from solvents and solvent combinations such as acetone/methanol, acetone/DMSO, acetonitrile/DMSO, acetonitrile/MeOH, DMSO, n-butanol, or isopropanol.

(R)-Isometheptene (S)-Methanesulfonic acid 1,5-dimethyl-hex-4-enyl ester (2) (3.21 g, 15.56 mmol) was dissolved in N,N-dimethyl-acetamide (55 mL), 40% methylamine in water (54.9 mL, 622 mmol) was added at RT using a heavy-walled reaction vessel (150 mL) with teflon screw cap. The reaction vessel was sealed, stirred, and heated at 50° C. for 64 h after which the reaction mixture was cooled to 5° C., and the system was opened to monitor the reaction by TLC. The reaction mixture was diluted with Et$_2$O (320 mL), shaken, the organic layer was washed with water (4×100 mL), brine (100 mL), dried with MgSO4, and solvent was concentrated to give the titled compound as an oil (1.974 g, 90%). TLC sample was prepared by taking an aliquot (100 uL) of reaction mixture, diluting with EtOAc (100 uL), washing with brine (500 uL), TLC organic layer. TLC, Hexane-EtOAc, 75:25, product, $R_f$ 0.35. DCM-7 N NH$_3$-MeOH, 90:10, 3 $R_f$, 0.45 (developed with KMnO$_4$ stain). $H^1$ NMR (CDCl$_3$): • 5.10 (m, 1H), 2.52 (m, 1H), 2.40 (s, 3H), 1.99 (m, 2H), 1.68 (s, 3H), 1.61 (s, 3H), 1.49 (m, 2H), 1.31 (m, 1H), 1.04 (d, 3H, J=6.0 z).

TABLE A

| (R)-Isometheptene Mucate Drug Substance | |
|---|---|
| Common API name: | (R)-Isometheptene mucate |
| Chemical name: | (R)-N,6-dimethylhept-5-en-2-amine hemi((2R,3S,4R,5S)-2,3,4,5-tetrahydroxyhexanedioate) |
| Physical state: | Crystalline solid |
| Molecular weight: | 464.59 |
| Molecular formula: | C$_{22}$H$_{44}$N$_2$O$_8$ |

TABLE A-continued

(R)-Isometheptene Mucate Drug Substance

Structure:

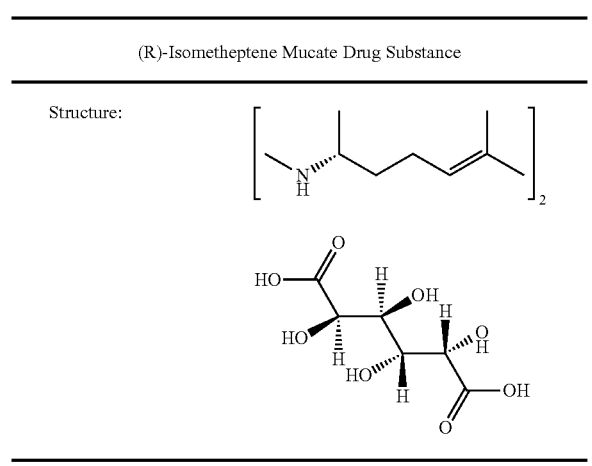

Synthetic Scheme for (R)-Isometheptene Mucate

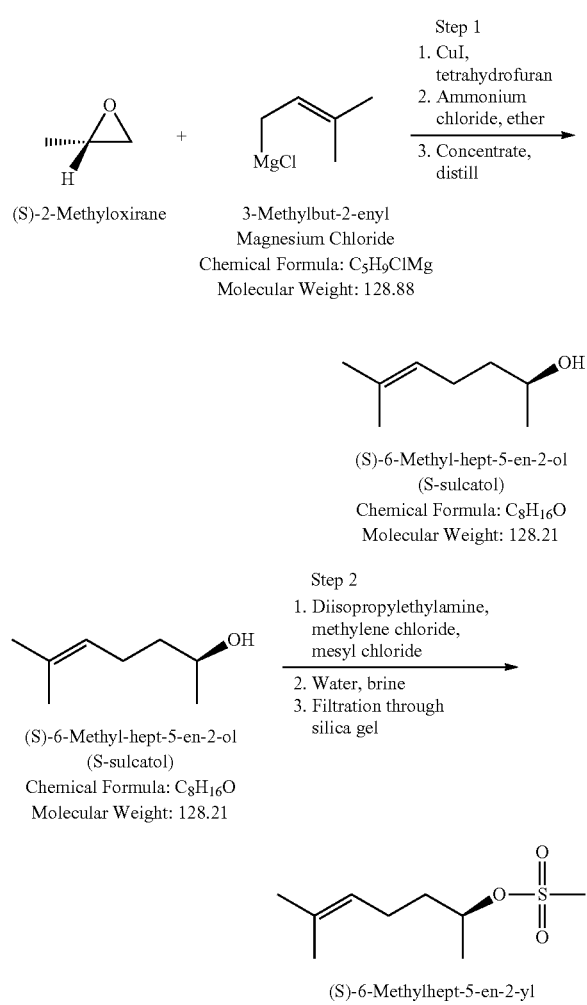

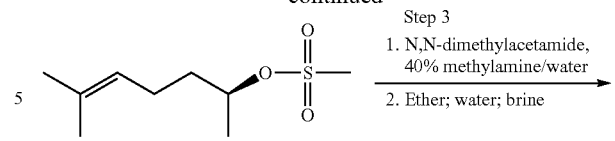

(S)-6-Methylhept-5-en-2-yl
Methanesulfonate
Chemical Formula: $C_9H_{18}O_3S$
Molecular Weight: 206.30

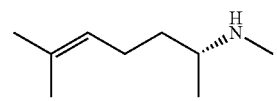

(R)-Isometheptene
Chemical Formula: $C_9H_{19}N$
Molecular Weight: 141.25

Mucic Acid
Chemical Formula: $C_6H_{10}O_8$
Molecular Weight: 210.14

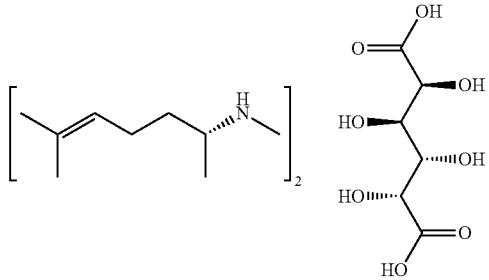

(R)-Isometheptene Mucate
Chemical Formula: $C_{24}H_{48}N_2O_8$
Molecular Weight: 492.65

Synthesis of (R)-Enantiomeric Isometheptene Salt

A method of making the compound of claim 3, comprising the steps of:
(a) combining (S)-methyloxirane with 3-methyl-2-buten-1-ylmagnesium chloride in THF in the presence of Copper iodide;
(b) neutralizing, extracting with ether, drying with magnesium sulfate, removing solvent, and distilling the (S)-6-Methyl-hept-5-en-2-ol;
(c) reacting (S)-6-Methyl-hept-5-en-2-ol with methanesulfonyl chloride and DIEA in anhydrous DCM;
(d) cooling the reaction mixture to about 5° C.;
(e) adding mesyl chloride dropwise;
(f) diluting the reaction mixture after 18 hours at RT;
(g) washing said mixture with water, brine and drying over $MgSO_4$;

(h) concentrate to oily product, (S)-Methanesulfonic acid 1,5-dimethyl-hex-4-enyl ester, wherein the 1H NMR in CDCl₃ at 500 MHz identifies the parameters: 5.08 ppm 1 Hm, 4.80 ppm 1 Hm, 2.99 ppm 3 Hs, 2.08 ppm 2 Hm, 1.75 ppm 1 Hm, 1.69 ppm 3 Hs, 1.624 1 Hm, 1.61 3 Hs, 1.43 ppm 3 Hd.;
(i) reacting (S)-Methanesulfonic acid 1,5-dimethyl-hex-4-enyl ester with N,N-dimethyl-acetamide (170 mL), and 40% methylamine in water in a sealed, heavy-walled reaction vessel at 50° C.;
(k) adding diethyl ether and washing said mixture with water and brine, drying over MgSO₄; and filtering to remove the solvent;
(l) removing the ether in vacuo (~25 mmHg) to yield (R)-Isometheptene in the free base form; and
(m) adding a pharmacologically acceptable acid, comprising hydrochloric, mucic, or tartaric, to form a pharmacologically acceptable salt.

Synthesis of Isometheptene Mucate-Isomer-2 ((R) Isomer)

Mucic acid (628 mg, 3.0 mmol) was suspended in distilled water (40 mL) at room temperature (RT). Isometheptene-isomer-2 (3.04 g, 21.5 mmol) was dissolved in Et₂O (57 mL) and added dropwise via addition funnel to the mucic acid at RT while stirring to give dissolution of the mucic acid suspension. The biphasic solution was stirred at RT for 16 h, the aqueous layer was separated, extracted with toluene (5×80 mL) (the final extraction with toluene was stood for 30 min before the aqueous layer was separated), then the aqueous layer was evaporated in vacuo (1 mm Hg) at 35°-40° C. to give a white solid which was dissolved in MeOH (8 mL) by gently heating to give a solution. CH₃CN (80 mL) was added slowly dropwise via addition funnel at RT to the stirred MeOH solution to give a suspension which was stirred at RT for about 30 min. The solids were filtered, washed with CH₃CN thrice, air-dried, then dried in vacuo (0.1 mm Hg) at RT for 16 h to give the titled compound as a white (1.390 mg, 70%). The molar ratio of Isometheptene to mucic acid in the salt was 2:1, based on the NMR spectrum: 1H NMR (500 MHz, in D₂O), 1H NNMR in CDCl₃: 5.16 ppm 1 Ht (J=6.8 Hz), 4.25 ppm 1 Hs, 3.95 ppm 1 Hs, 3.2 ppm 1 Hm, 2.66 ppm 3 Hs, 2.09 ppm 2 Hm, 1.75 ppm 1 Hm, 1.69 ppm 3 Hs, 1.62 ppm 3 Hs, 1.58 ppm 1 Hm, 1.29 ppm 3 Hd (J=7 Hz). MS: mass calc for C₉H₁₉N, 141.15. Found: 142.4 (M+H).

Another useful method has been found as follows:

Stereoselective Synthesis of (R)-Isometheptene and (R)-Isometheptene Mucate

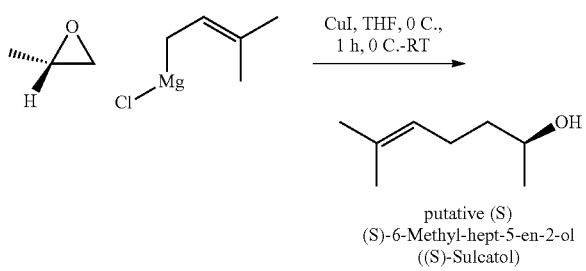

putative (S)
(S)-6-Methyl-hept-5-en-2-ol
((S)-Sulcatol)

(R)-Isometheptene (R)-Mosher Amide (R)-Isometheptene (76 mg, 0.54 mmol) (derived from (R)-Isometheptene mucate) was dissolved in anhydrous DCM (5.4 mL), DMAP (10 mg, 0.082 mmol), DIEA (0.178 mL, 1.02 mmol) were added, and Mosher's (S)-acid chloride (0.141 mL, 0.753 mmol) was added dropwise at RT while stirring. After 18 h at RT N,N-Dimethyl-1,3-propanediamine (0.135 mL, 1.08 mmol) was added at RT and the reaction mixture was stirred at RT for 20 min. The mixture was diluted with Et₂O (27 mL), washed with 1 N aqueous HCl (10 mL), sat NaHCO₃ (10 mL), brine (10 mL), dried with MgSO₄, solvent was evaporated in vacuo at 30° C. to give an oil which was coevaporated with CCl₄ 3 times to remove residual Et₂O to give an oil which was further dried in vacuo (0.1 mm Hg) for 1 h to give the title compound as a crude oil (212 mg). TLC, DCM-7 N NH3-MeOH, 90:10, (R)-Isometheptene, $R_f$, 0.45. TLC, Hexane-EtOAc, 85:15, (R)-Isometheptene (R)-Mosher amide, $R_f$ 0.45 (developed with KMnO₄ stain). H¹ NMR (CDCl₃): ••7.51 (m, 2H), 7.38 (m, 3H), 5.10 (m, 1H), 4.76 (m, 1H), 3.71 (s, 3H), 2.43 (s, 3H), 1.95 (m, 2H), 1.68 (s, 3H), 1.58 (s, 3H), 1.50 (m, 1H), 1.45 (m, 1H), 1.03 (d, 3H, J=7 Hz).

Determination of Chiral Purity of Synthesized (R)-Isometheptene Via (R)-Mosher Amide of (R)-Isometheptene Inspection of regions 4.9-4.7 ppm (chemical shifts of protons bonded to chiral carbon) for (R)-Mosher amide of (S)-Isometheptene (4.84 ppm) and (R)-Mosher amide of (R)-Isometheptene (4.76 ppm) indicated chiral purity of (R)-Isometheptene to be >98%.

Polarimetry (R) Isometheptene mucate (synthesized as described) has an optical rotation [α]D=+6.0 in water at room temperature, and isomer 1 Isometheptene mucate has an [α]D=−6.6 in water at room temperature. This is consistent with isomer 1 being the S isomer, and provides further support for the contention that isomer 1 is (S) and isomer 2 is (R). The experimental procedure of the above summarized evidence is as follows:

Polarimeter was calibrated with glucose (2.845 g in 100 ml, 1 dm path length, reading=+1.50) [α]=+52.7, Temperature=ambient;

199.3 mg of (R) Isometheptene mucate (isomer 2) dissolved in 10 ml water.

Readings=+0.10 and +0.14 (average=+0.12), path length=1 dm,

[α]=+6.0

205.6 mg of (S) Isometheptene mucate (isomer 1) dissolved in 10 ml water.

Readings=−0.15 and −0.12 (average=−0.135), path length=1 dm,

[α]=−6.6.

X-Ray Crystal Structure of (R)-Isomentheptene Mucate Hemi-Hydrate

According to the invention a crystals of (R)-Isometheptene mucate anhydrous were obtained by evaporation of a solution in water at ambient temperature and tested by x-ray diffraction. The x-ray structure was consistent with the R stereochemistry assigned to Isomer 2 through the afordescribed NMR experiment.

Moreover, elemental analysis of (R)-Isometheptene mucate precipitated from methanol through addition of acetonitrile showed presence of 0.5 equivalent of H₂O in the crystal. By contrast, however, x-ray crystallography found no water molecule present in the crystals grown in water.

According to further analysis the x-ray crystal of (R)-Isometheptene mucate revealed that the two different conformations of the (R)-Isometheptene cation in Isometheptene mucate salt overlap. In fact, the analysis showed a substantially disordered (poor overlap) hydrophobic dimethylalkene part of the molecule but highly ordered (good overlap) near the cation where the mucate anion appears to dock.

Method of X-Ray Diffraction Experiment:

All reflection intensities were measured at 100(2) K using a SuperNova diffractometer (equipped with Atlas detector) with Mo Kα radiation (λ=0.71073 Å) under the program CrysAlisPro (Version 1.171.36.24 Agilent Technologies, 2012). The program CrysAlisPro (Version 1.171.36.24 Agilent Technologies, 2012) was used to refine the cell dimensions. Data reduction was done using the program CrysAlisPro (Version 1.171.36.24 Agilent Technologies, 2012). The structure was solved with the program SHELXS-2013 (Sheldrick, 2013) and was refined on $P^2$ with SHELXL-2013 (Sheldrick, 2013). Analytical numeric absorption corrections based on a multifaceted crystal model were applied using CrysAlisPro (Version 1.171.36.24 Agilent Technologies, 2012).

The temperature of the data collection was controlled using the system Cryojet (manufactured by Oxford Instruments). The H atoms were placed at calculated positions using the instructions AFIX 13, AFIX 23, AFIX 43 or AFIX 137 with isotropic displacement parameters having values 1.2 or 1.5 times Ueq of the attached C or N atoms.

Figure 16:
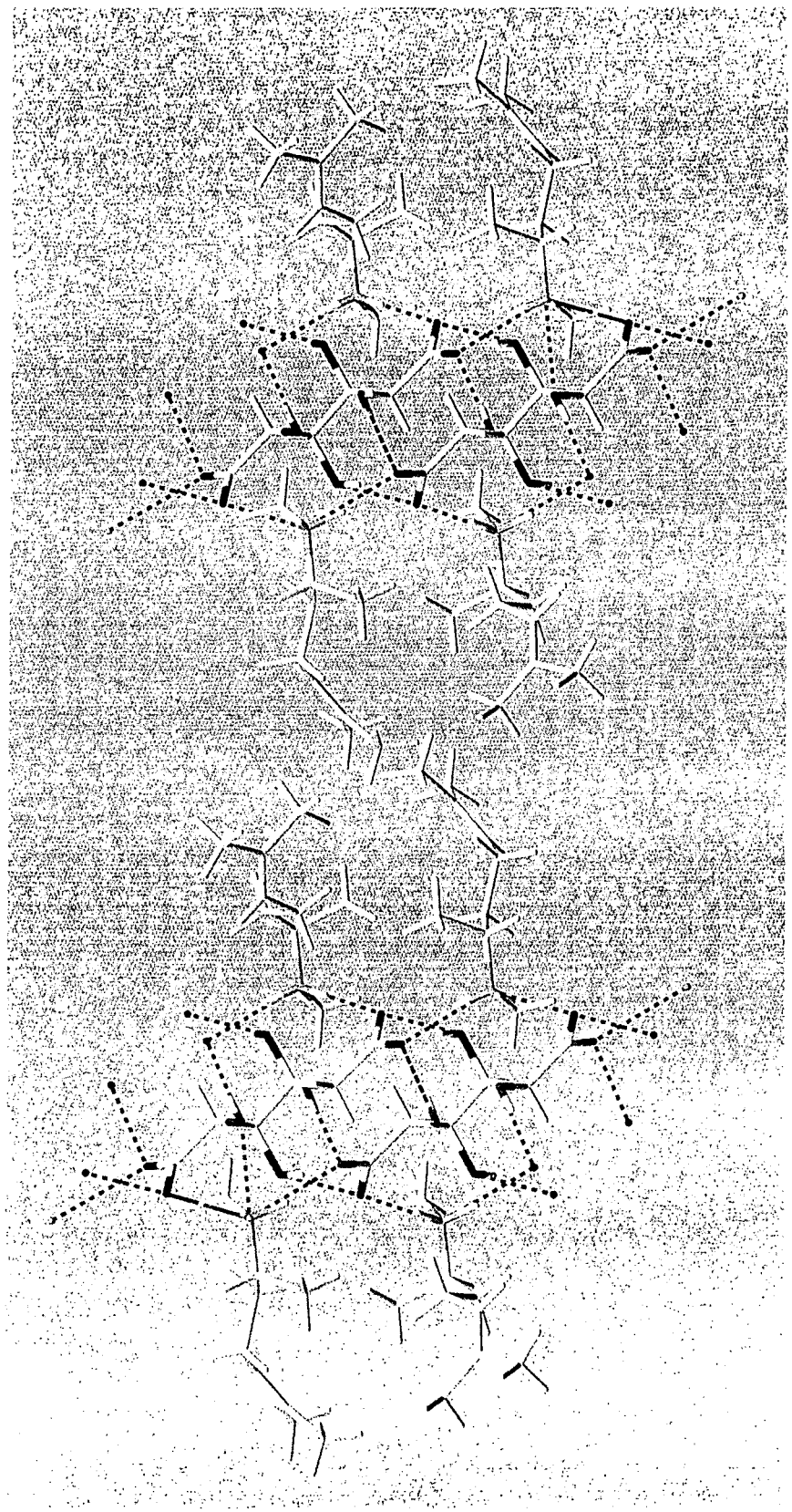
FIG. 16 illustrates (R)-Isometheptene mucate crystal structure showing intermolecular hydrogen bonds.

As shown in FIG. 16, the Isometheptene species are H-bond donors via two N—H . . . O(mucate) to two mucate species. The mucate species form 2-D H-bonded plane that are parallel to (1 0 0); those intermolecular hydrogen bond interactions are most likely found along the largest crystal faces. Each Isometheptene species are H-bond donors via two N—H . . . O (mucate) to two mucate species. The mucate species form 2-D H-bonded plane that are parallel to (1 0 0) (those intermolecular hydrogen bond interactions are most likely found along the largest crystal faces).

Figure 17:
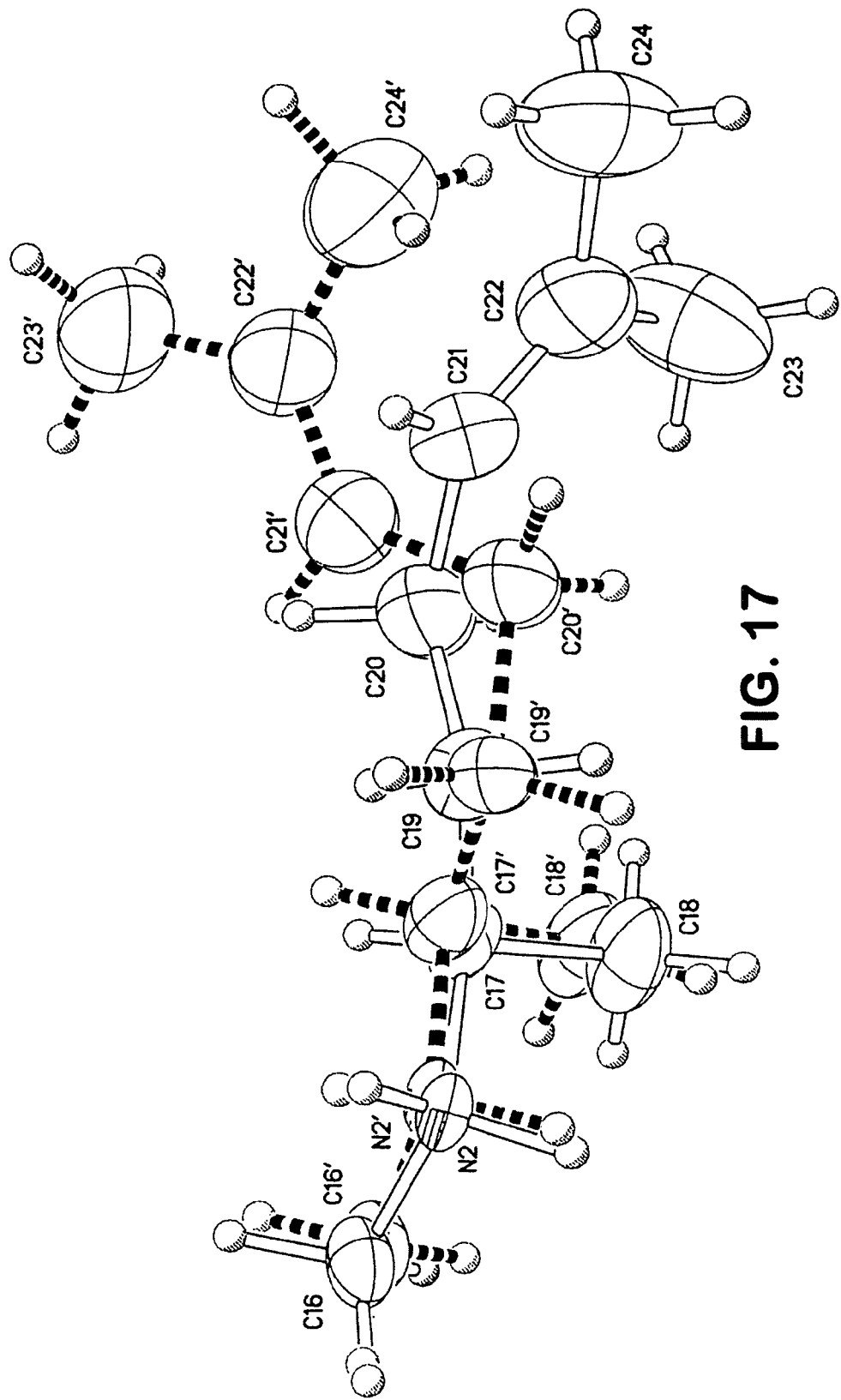
FIG. 17 illustrates the twofold crystal structure of (R)-Isometheptene mucate salt x-ray, demonstrating a greater amount of disorder at the dimethyl end than at the amine end.

The (R)-Isometheptene mucate crystal structure is partly disordered (FIG. 17). One of the two crystallographically independent Isometheptene cations is found to be disordered over two orientations (the occupancy factor of the major component of the disorder refines to 0.520(4)). The absolute configuration was established by the structure determination of a compound containing a chiral reference molecule of known absolute configuration and was confirmed by anomalous-dispersion effects in diffraction measurements on the crystal. Although the Flack parameter refines to 0.1(3), both Hooft and Parsons parameters refine to −0.08(4) and −0.05(4), respectively.

Figure 18:
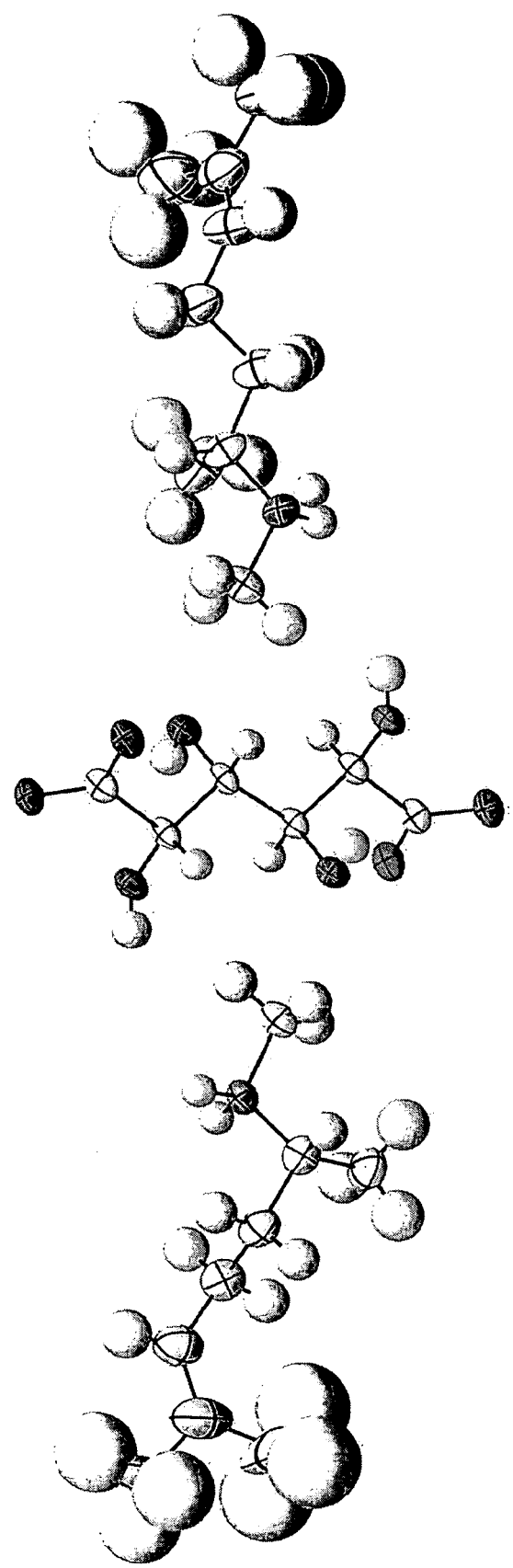
FIG. 18 illustrates the crystal structure of (R)-Isometheptene mucate x-ray, including hydrogen atoms.

Taking reference to FIG. 18, the (R)-Isometheptene Mucate X-ray structure is illustrated by displacement plot for (R)-Isometheptenemucate (with hydrogen atoms). The structure refines to about R1 equal to 5%. The chiral atoms of the Isometheptene species are in the (R)-configuration, consistent with Mosher's amide NMR data.

Figure 19:
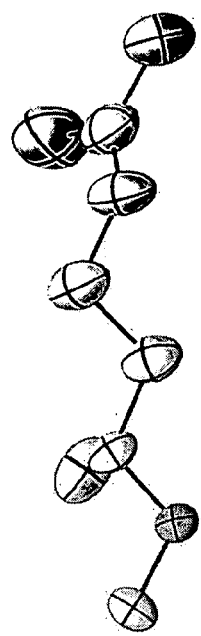
FIG. 19 illustrates the crystal structure of (R)-Isometheptene mucate x-ray, not including hydrogen atoms.
Figure 19:
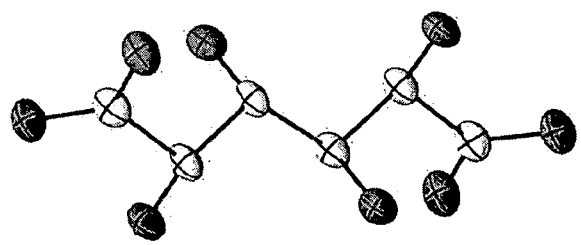
Figure 19:
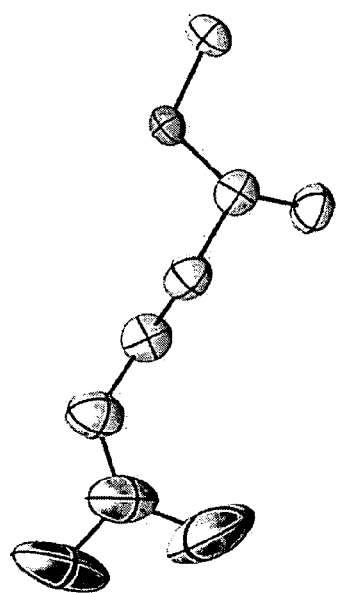

FIG. 19 represents a displacement plot for (R)-Isometheptene mucate (showing only C, N, and O, no hydrogen atoms). The structure refines to about R1 equal to 5%. The chiral atoms of the Isometheptene species are in the (R)-configuration, consistent with the Mosher's amide NMR data.

Fw=492.64, colorless plate, 0.56×0.26×0.08 mm$^3$, monoclinic, C2 (no. 5), a=36.3410(7), b=7.88266(12), c=9.82344(18) Å, β=94.0983(17)°, V=2806.86(9) Å$^3$, Z=4, $D_x$=1.166 g cm$^{-3}$, μ=0.708 mm$^{-1}$, abs. corr. range: 0.764-0.955. 31114 Reflections were measured up to a resolution of (sin θ/λ)$_{max}$=0.62 Å$^{-1}$. 5499 Reflections were unique ($R_{int}$=0.0287), of which 5295 were observed [I>2σ(I)]. 403 Parameters were refined using 304 restraints. R1/wR2 [I>2σ(1)]: 0.0498/0.1458. R1/wR2 [all refl.]: 0.0522/0.1486. S=1.054. Residual electron density found between −0.28 and 0.38 e Å$^{-3}$ Biological Activity As presently described, the racemic, enantiomer (S) and (R)-Isometheptene compound has now been purified and tested. All molecules were found having distinctly different affinities for certain CNS target receptors, e.g., imidazoline-1 subtype 1 (I1) and Imidazoline-2 subtype (I2) (Table 1). The receptor I1 is presently known to bind the drug, moxonidine, which is a centrally acting antihypertensive therapeutic compound with low activation of adrenergic receptors. As evidenced in recent assays, Isomer 1 and Isomer 2 bind differently to Imidazoline receptor 2 (I2).

It has now been discovered that the purified Isometheptene isomer 2 (or (R)-Isometheptene enantiomer) has a significant binding affinity for the I1-Imidazoline sites (Table 1), which is also the selective receptor of moxonidine, a centrally acting antihypertensive agent. Present understanding of the I1-imidazoline receptor is that of a cell-surface receptor mediating cellular responses, participating in cardiovascular control by the CNS, and providing a potential therapeutic target for multiple cardiovascular and metabolic disorders. The antihypertensive agents with an imidazoline or related structure, all show high affinity for I1-imidazoline sites (affinity constant Ki<10 nM). The second-generation agents, moxonidine and rilmenidine have reduced sedative side-effects, and show lower affinity (higher Ki) at α2-adrenergic receptors relative to the first-generation agents with pronounced sedative side-effects, including clonidine, guanabenz, guanfacine, and α-methylnorepinephrine (the active metabolite of α-methyldopa).

Screening at 10 uM with racemic Isometheptene did not show meaningful binding (i.e, >70% inhibition) at several receptors on screening which include α1-, α2A- or β-adrenergic receptors, serotonin receptors. Of the receptors that were positive on screening, racemic Isometheptene at 10 μM inhibited ligand binding to the α2B-adrenergic receptor of 76%. Further testing the purified S-Isometheptene and R-Isometheptene isomers at 10 μM in this assay, showed they inhibited ligand binding to the α2B-adrenergic receptor by 29% and 57%, respectively. Further testing of (S)-Isometheptene and (R)-Isometheptene by equilibrium binding showed similar binding of α2B-adrenergic receptor with Ki's of 2700 nM and 2300 nM, respectively.

For pharmacologic effects on α2B-adrenergic receptor, we focus on ligands that interact with Ki's<100 nM, so this level of interaction is low. Of the receptors that were positive on screening, racemic Isometheptene at 10 μM inhibited ligand binding to the Sigma receptor (non-selective, meaning either Sigma 1 or Sigma 2 receptor) of 62%. Further testing the purified (S)-Isometheptene and (R)-Isometheptene isomers at 10 μM in this assay, showed they inhibited ligand binding to the non-selective Sigma receptor by 87% and 86%, respectively. Further testing of (S)-Isometheptene and R-Isometheptene by equilibrium binding showed they bound Sigma-1 receptor with Ki's of only 2100 nM and 1900 nM, respectively; and the Sigma-2 receptor with Ki's of only 5200 nM and 5600 nM, respectively. For pharmacologic effects on Sigma receptors, we focus on ligands that interact with Ki's 2500 nM, so this level of interaction for both isomers of Isometheptene on Sigma-2 is of potential biological interest. Of the receptors that were positive on screening, racemic Isometheptene at 10 μM inhibited ligand binding to the Imidazoline 1 (I1) receptor of 95%. Further testing of S-Isometheptene and R-Isometheptene by equilibrium binding showed they bound I1 receptor with Ki's of 1100 nM and 18 nM, respectively. For pharmacologic effects, we focus on ligands that interact with Ki's <100 nM, so the binding of R-Isometheptene to I2 is physiologically significant. Note that Imidazoline-I1 and Imidazoline-I2 binding have not been associated with headache treatments to our knowledge.

Many racemic compounds consist of individual (R)- or (S)-enantiomers which exhibit different binding activities. It has now been discovered that as shown in the affinity measurements of the isolated Isometheptene isomers at Table 1, the (R)-enantiomer of Isometheptene may have a structural domain better suited for binding with greater affinity or avidity to a specific CNS target receptor than the opposite racemate or (S)-enantiomer. The purified racemic Isometheptene compound has been tested as two racemate molecules with different affinities for certain CNS acceptors, e.g., imidazoline-1 (I1) and imidazoline-2 (I2) (see Table 1). As mentioned above, the I1 receptor is described particularly to bind the drug, moxonidine, which is a centrally acting antihypertensive therapeutic compound.

TABLE 1

BINDING AFFINITIES OF ISOMETHEPTENE IN VARIOUS CNS RECEPTORS

| | Inhibition @ 10 μM(%) | | | Ki(nM) | |
|---|---|---|---|---|---|
| | Racemic | Isomer 1 | Isomer 2 | Isomer 1 | Isomer 2 |
| 5-HT 1A | 37 | | | | |
| 5-HT7 | 46 | 13 | 31 | | |
| Adrenergic a2B | 76 | 29 | 57 | 2700 | 2300 |
| Adrenergic a2C | 41 | 0 | 0 | | |
| Imidazoline-1 (I1) | 95 | | | 1100 | 18 |
| Imidazoline-2 (I2) | | 84 | 86 | 1100 | 1500 |
| Sigma (non-select) | 62 | 87 | 86 | | |
| Sigma 1 | | | | 2100 | 1900 |
| Sigma 2 | | | | 5200 | 5600 |

In view of the ambiguous physiological effects of tests involving the racemic Isometheptene compound or composition thereof, it is believed that the effect of its single active (R)-Isometheptene enantiomer mucate (Isomer 2) will be more specific with fewer side effects. Accordingly, a single (R)-isomer of Isometheptene will result in a better therapeutic than the racemate. This will eliminate the potential cardiovascular effect from the (S)-isomer without affecting the anti-ETTH activity that predominantly resides in (R)-Isometheptene.

Therefore, treatment of patients suffering from ETTH (migraine) may be studied by applying increasing doses of Isometheptene (R)-enantiomer in order to determine the efficacy of the composition in a pharmacological profile of the induced cardiovascular responses and side effects on heart rates.

For example, (R)-Isometheptene mucate isomer as an active ingredient of a CDP with caffeine and acetaminophen as the other active ingredients is due to be evaluated for the treatment of migraine.

The (R)-Isometheptene isomer mucate can be administered in the form of hard gelatin capsules without excipients added.

In order to determine the relieving effect of the single (R)-Isometheptene mucate isomer, a patient in need of such treatment is administered, optionally twice or four times daily, capsules containing increasing amounts of 15 mg, 30 mg, 50 mg, 100 mg, 150 mg, 300 mg or 500 mg.

Figure 20:
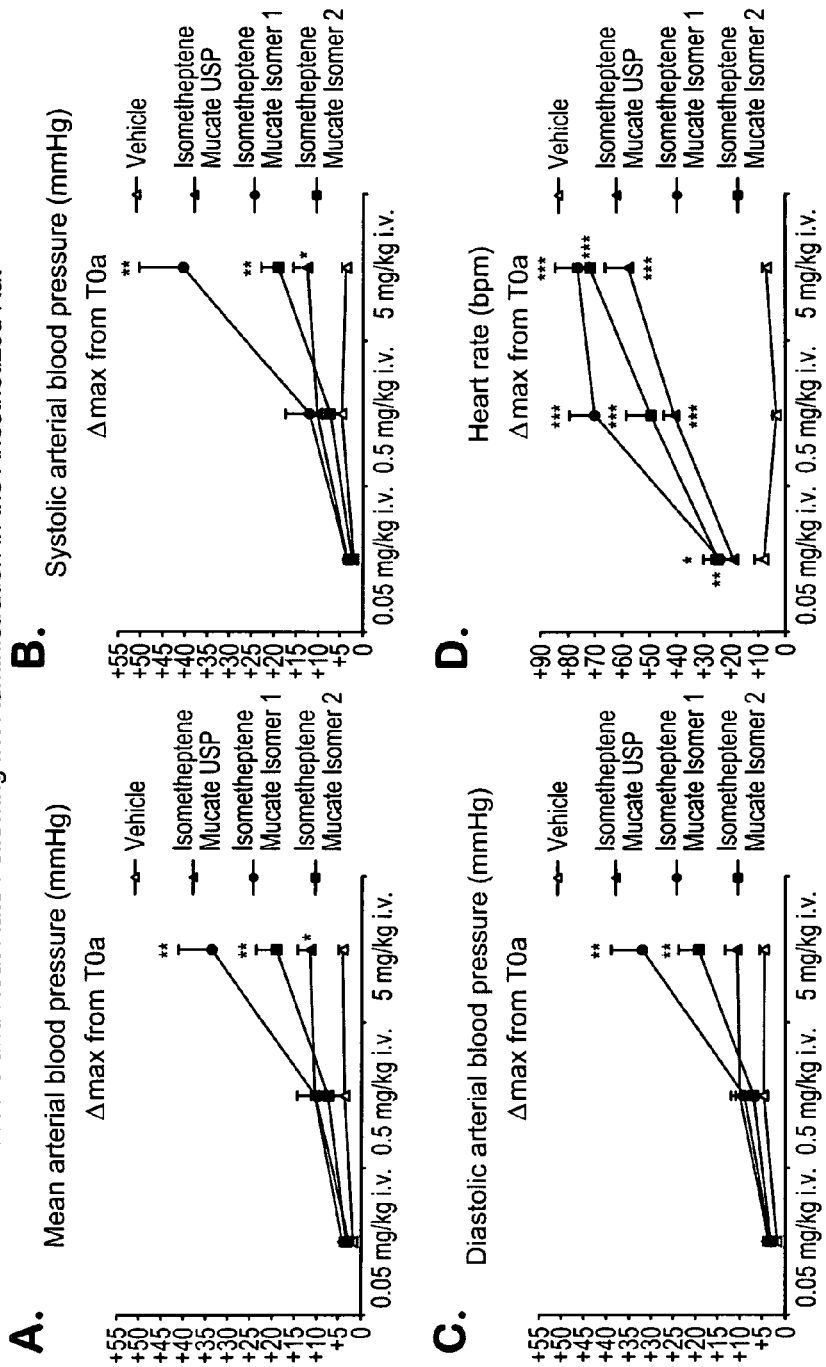
FIG. 20 illustrates the effects of Isometheptene mucate and its Isomers 1 and 2 on (A) mean, (B) systolic, (C) diastolic arterial blood pressure and (D) heart rate, following i.v. administration in the rat.

Arterial Blood Pressure (BP) and Heart Rate Effects In Vivo (FIG. 20)

A study in rat described below shows a comparison of the effects of Isometheptene Mucate USP and its Isomers on arterial blood pressure and heart rate following i.v. administration in the anesthetized rat.

Rats were anesthetized with Inactin® (sodium thiobutabarbital 100 to 150 mg/kg i.p.) and prepared for the recording of the following parameters:
(A) Mean, (B) systolic and (C) diastolic arterial blood pressure (mmHg), via a pressure transducer introduced into the left carotid artery;
(D) Heart rate (beats/min), derived from pulse blood pressure.

The parameters measured were allowed to stabilize for a period of at least 20 minutes before the test substance was administered.

Measurements were performed before and then 30 seconds, 1, 2, 5, 10 and 15 minutes after the end of each i.v. bolus administration.

Results are expressed in absolute values and as maximal change from pre-dose.

Six (6) rats were studied per group.

Each test substance was evaluated at 3 doses (0.05, 0.5 and 5 mg/kg), administered i.v. as a 30-second bolus, at intervals of 15 minutes, and compared with a time-matched vehicle control group.

The experiment therefore included 4 groups.

Inter-group comparison on maximal absolute changes from pre-dose (each test substance versus vehicle, and each isomer versus racemate) was performed using an Unpaired Student's t test.

The results are illustrated in the diagrams, FIG. 20 A-D.

Results:

Isometheptene Mucate USP (0.05, 0.5 and 5 mg/kg), administered as a 30-second i.v. bolus to anesthetized rats, only induced a slight but dose-dependent hypertension from 0.5 mg/kg when comparing the amplitude of the response to that observed in the time-matched vehicle control group. The increase occurred shortly following the administration and reached a maximum of 4.0±0.6 mmHg from pre-dose for mean BP at 0.05 mg/kg (NS), 10.5±0.9 mmHg from pre-dose at 0.5 mg/kg (NS) and 11.7±2.8 mmHg from pre-dose at 5 mg/kg (p<0.05). Isometheptene Mucate USP induced a clear and rapid dose-dependent tachycardia that reached a maximum of 19.0±4.3 bpm from respective pre-dose at 0.05 mg/kg (NS), 40.8±4.0 bpm at 0.5 mg/kg (p<0.001) and 57.8±8.6 bpm at 5 mg/kg (p<0.001).

Isometheptene Mucate Isomer 1 (0.05, 0.5 and 5 mg/kg), administered as a 30-second i.v. bolus to anesthetized rats, induced a dose-dependent hypertension, but also only from 0.5 mg/kg when comparing the amplitude of the response to that observed in the time-matched vehicle control group. The increase occurred shortly following the administration and reached a maximum of 2.7±0.8 mmHg max from pre-dose for mean BP at 0.05 mg/kg (NS), 10.3±4.0 mmHg max from pre-dose at 0.5 mg/kg (NS) and 34.7±7.6 mmHg max from pre-dose at 5 mg/kg (p<0.01). Isometheptene Mucate Isomer 1 also caused a clear and rapid dose-dependent tachycardia that reached a maximum of 23.8±3.2 bpm from respective pre-dose at 0.05 mg/kg (p<0.01), 70.3±9.1 bpm at 0.5 mg/kg (p<0.001) and 76.5±8.2 bpm at 5 mg/kg (p<0.001).

Isometheptene Mucate Isomer 2 (0.05, 0.5 and 5 mg/kg), administered as a 30-second i.v. bolus to anesthetized rats, induced a slight but dose-dependent hypertension, but only from 0.5 mg/kg when comparing the amplitude of the response to that observed in the time-matched vehicle control group. The increase occurred shortly following the administration and reached a maximum of 3.0±0.9 mmHg max from pre-dose for mean BP at 0.05 mg/kg (NS), 7.5±1.5 mmHg max from pre-dose for mean BP at 0.5 mg/kg (NS) and 19.2±4.4 mmHg max from pre-dose at 5 mg/kg (p<0.01). Isometheptene Mucate Isomer 2 also caused a clear and rapid dose-dependent tachycardia that reached a maximum of 24.7±5.6 bpm from respective pre-dose at 0.05 mg/kg (p<0.05), 49.5±9.2 bpm at 0.5 mg/kg (p<0.001) and 72.2±5.9 bpm at 5 mg/kg (p<0.001).

Although the maximum increase in arterial blood pressure observed following the administration of Isometheptene Mucate Isomer 1 at 5 mg/kg was higher than that observed with Isometheptene mucate Isomer 2 (34.7±7.6 mm Hg versus 19.2±4.4 mmHg), there was no statistical difference between the two isomers. A trend for systolic blood pressure was however observed (p=0.0762). The tachycardia observed following Isometheptene Mucate Isomer 1 and Isomer 2 administration was not statistically different.

These results suggest that Isometheptene Mucate (the racemate), Isometheptene Mucate Isomer 1, and Isometheptene Mucate Isomer 2 (0.05, 0.5 and 5 mg/kg), administered as a bolus of 30-second i.v. bolus to anesthetized rats, induced a dose-dependent hypertension. Both Isomer 1 and Isomer 2 induced a more pronounced hypertension than that induced by the racemate, and Isomer 1 clearly induced (although not statistically significant) a more pronounced hypertension than Isomer 2. The racemate and the two isomers induced a dose-dependent tachycardia that was not statistically different, although that observed following the administration of 0.5 mg/kg was slightly higher with isomer 1.

Safety of the Isometheptene (R)-Enantiomer

The pharmacology, pharmacokinetics, and toxicology of Isometheptene enantiomer alone or as a CDP containing, e.g., Isometheptene (R)-enantiomer, caffeine, and acetaminophen are important aspects for characterizing the efficacy of the inventive compound.

No published papers were identified that provided information on the safety pharmacology profiles of racemic Isometheptene alone or as an active ingredient in a CDP.

Treatment with (R)-Isometheptene includes a daily oral dose or twice daily ranging from about 10 mg to about 50 mg, taken alone, or combined with other active ingredients such as a mild sedative, and a decongestant or proton pump inhibitor, such as Ibuprofen or Celebrex, at a dosage of about 100 mg to about 900 mg.

One published report (Valdivia 2004) investigated the cardiovascular responses induced by Isometheptene (IV at consecutive doses of 0.03, 0.1, 0.3, 1, and 3 mg/kg with 5 to 15 minutes between doses) in male Wistar rats. Isometheptene alone produced dose-dependent increases in heart rate and diastolic blood pressure. Using co-administration of various receptor antagonists, the Isometheptene-induced tachycardic responses in rats apparently involved only an indirect (tyramine-like action) mechanism mediated by α-adrenoceptors and the corresponding vasopressor responses were mediated by a predominantly indirect (tyramine-like action) as well as a minor direct (α-adrenoceptors) sympathomimetic mechanism.

We suggest that Isometheptene (R)-enantiomer treatment, administered orally either alone or in a CDP, may have a lower potential adverse effects to the cardiovascular system. Thus, we set out to determine the molecular target of Isometheptene by screening for binding to a broad set of targets, which included receptors, enzymes, channels and transporters.

Isometheptene does not display significant binding to any of the adrenergic receptors studied. Of the targets studied, Isometheptene bound the I1 receptor. On screening, 10 μM racemic Isometheptene showed >95% inhibition of ligand binding. A full binding profile of Isometheptene mucate and the (R)- and (S)-Isometheptene mucate enantiomers on the I1 receptor is shown below. As shown in the figure below, (R)-Isometheptene showed strong binding ($K_i$=18 nM), while (S)-Isometheptene showed very weak binding ($K_i$=1100 nM) (Molderings, 1993). Consistent with the approximately 50:50 ratios of the isomers in racemic Isometheptene mucate, binding studies showed racemic Isometheptene possessed approximately half the potency of the pure (R)-isomer ($K_i$=42 nM), see Table 1.

The identification of I1 as the Isometheptene receptor reveals a new molecular target for ETTH therapeutics and also indicates that (R)-Isometheptene as a single isomer is an improved treatment for ETTH relative to racemic Isometheptene. The I1 receptor was not previously known to be a target for ETTH therapeutics. The putative natural ligand for I1 is agmatine and pharmacologic ligands of I1 include monoxidine and clonidine (Head, 2006; Molderings, 1997). The activities of agmatine, moxonidine and clonidine can be used to understand the function of the I1 receptor. The I1 receptor subtype is found in both the rostral ventro-lateral pressor and ventromedial depressor areas of the medulla oblongata. The discovery that (R)-Isometheptene binds the I1 receptor is the first known link of this receptor to therapeutics for ETTH.

Many racemic compounds consist of (R)- or (S)-enantiomers which are mirror images of each other exhibiting different binding activities. In fact, the receptor binding affinity measurements differ between the two isolated Isometheptene enantiomers as shown at Table 1, suggesting perhaps that the two enantiomers of the racemic compound have different structural domains. Initial measurements revealed for example, that Isomer 2 (which is now identified as the (R)-Isometheptene enantiomer) appears to bind with greater (about 60 fold) affinity or avidity to a specific CNS target receptor than its opposite racemate isomer 1 or (S)-Isometheptene enantiomer.

As presently described, the racemic Isometheptene compound has now been purified and tested as two racemate molecules with distinctly different affinities for certain CNS target receptors, e.g., imidazoline-1 (I1) and imidazoline-2 (I2) (see Table 1). The I1 receptor is presently known to bind the drug, moxonidine, which is a centrally acting antihypertensive therapeutic compound with low activation of adrenergic receptors. As evidenced in the above assays, Isomer 1 and Isomer 2 bind differently to the I2 receptor.

It has now been discovered that the purified Isometheptene isomer 2 (or (R) Isometheptene enantiomer) has a significant binding affinity for I1 (Table 1), which is also the selective receptor of moxonidine, a centrally acting antihypertensive agent. Present understanding of the I1 receptor is that of a cell-surface receptor mediating cellular responses, participating in cardiovascular control by the CNS, and providing a potential therapeutic target for multiple cardiovascular and metabolic disorders. The antihypertensive agents with an imidazoline or related structure, all show high affinity for the I1 receptor (affinity constant Ki<10 nM). The second-generation agents, moxonidine and rilmenidine have reduced sedative side-effects, and show lower affinity (higher Ki) at α2-adrenergic receptors relative to the first-generation agents with pronounced sedative side-effects, including clonidine, guanabenz, guanfacine, and α-methylnorepinephrine (the active metabolite of α-methyldopa).

Screening at 10 µM with racemic Isometheptene did not show meaningful binding (i.e, >70% inhibition) at several receptors on screening which include α1-, α2A- or β-adrenergic receptors, serotonin receptors. Of the receptors that were positive on screening, racemic Isometheptene at 10 µM inhibited ligand binding to the α2B-adrenergic receptor of 76%. Further testing the purified (S)-Isometheptene and (R)-Isometheptene isomers at 10 µM in this assay, showed they inhibited ligand binding to the α2B-adrenergic receptor by 29% and 57%, respectively. Further testing of (S)-Isometheptene and (R)-Isometheptene by equilibrium binding showed similar binding of α2B-adrenergic receptor with Ki's of 2700 nM and 2300 nM, respectively.

For pharmacologic effects on α2B-adrenergic receptor, we focus on ligands that interact with Ki's<100 nM, so this level of interaction is low. Of the receptors that were positive on screening, racemic Isometheptene at 10 µM inhibited ligand binding to the Sigma receptor (non-selective, meaning either Sigma 1 or Sigma 2 receptor) of 62%. Further testing the purified (S)-Isometheptene and (R)-Isometheptene isomers at 10 µM in this assay, showed they inhibited ligand binding to the non-selective Sigma receptor by 87% and 86%, respectively. Further testing of (S)-Isometheptene and (R)-Isometheptene by equilibrium binding showed they bound Sigma-1 receptor with Ki's of only 2100 nM and 1900 nM, respectively; and the Sigma-2 receptor with Ki's of only 5200 nM and 5600 nM, respectively. For pharmacologic effects on Sigma receptors, we focus on ligands that interact with Ki's 2500 nM, so this level of interaction for both isomers of Isometheptene on Sigma-2 is of potential biological interest. Of the receptors that were positive on screening, racemic Isometheptene at 10 µM inhibited ligand binding to the Imidazoline 1 (I1) receptor of 95%. Further testing of (S)-Isometheptene and (R)-Isometheptene by equilibrium binding showed they bound I1 receptor with Ki's of 1100 nM and 18 nM, respectively. For pharmacologic effects, we focus on ligands that interact with Ki's<100 nM, so the binding of (R)-Isometheptene to I1 is physiologically significant. Note that I1- and I2-receptor binding have not been associated with headache treatments to our knowledge.

Many racemic compounds consist of individual (R)- or (S)-enantiomers which exhibit different binding activities. It has now been discovered that as shown in the affinity measurements of the isolated Isometheptene isomers at Table 1, the (R)-enantiomer of Isometheptene may have a structural domain best suited for binding with greater affinity or avidity to a specific CNS target receptor than the opposite racemate or enantiomer. The presently described racemic compound, Isometheptene, has now been purified and tested as two isomeric molecules with different affinities for certain CNS acceptors, e.g., and I2-receptor (see Table 1). As mentioned above, the I1 receptor is described particularly to bind the drug, moxonidine, which is a centrally acting antihypertensive therapeutic compound.

Figure 21:
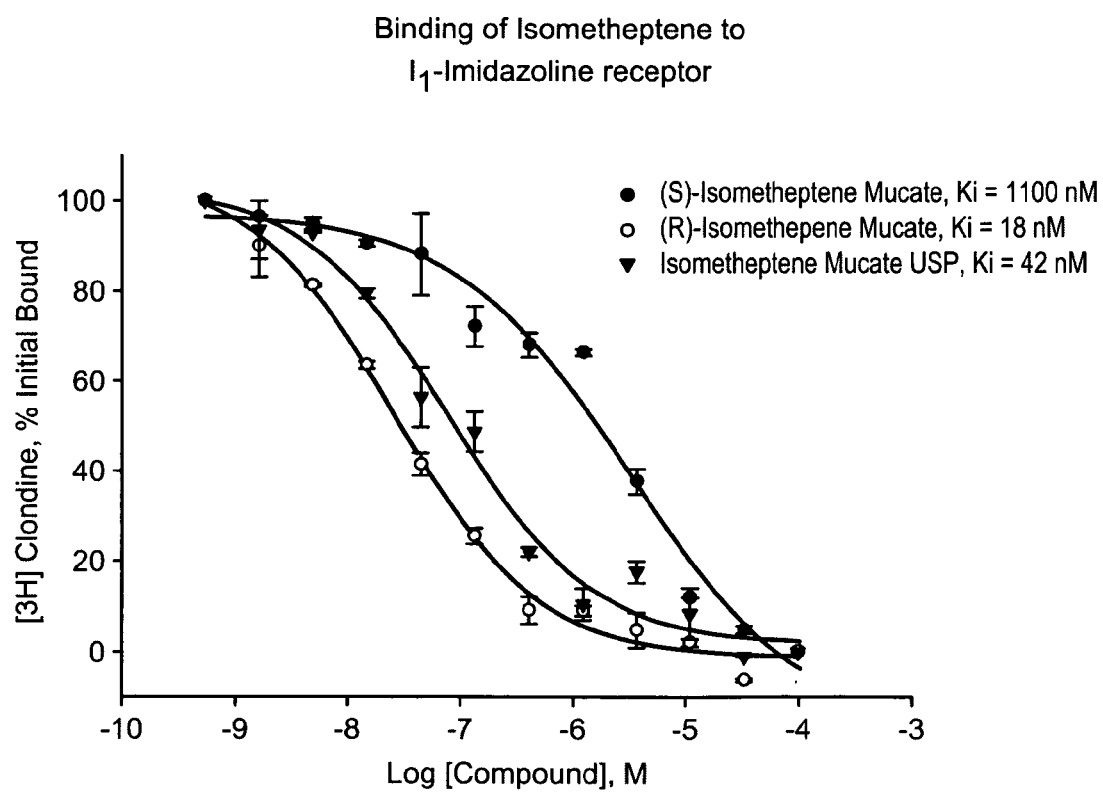
FIG. 21 illustrates the $I_1$ Imidazoline receptor binding of (S)-Isometheptene Mucate, (R) Isomentheptene Mucate, and Isometheptene Mucate.

The diagram shown in FIG. 21, the results of an experiment in which (S)-Isometheptene Mucate salt, (R)-Isometheptene Mucate salt, and Isometheptene Mucate salt USP (racemic) were studied for binding to the I1 receptor.

Figure 22:
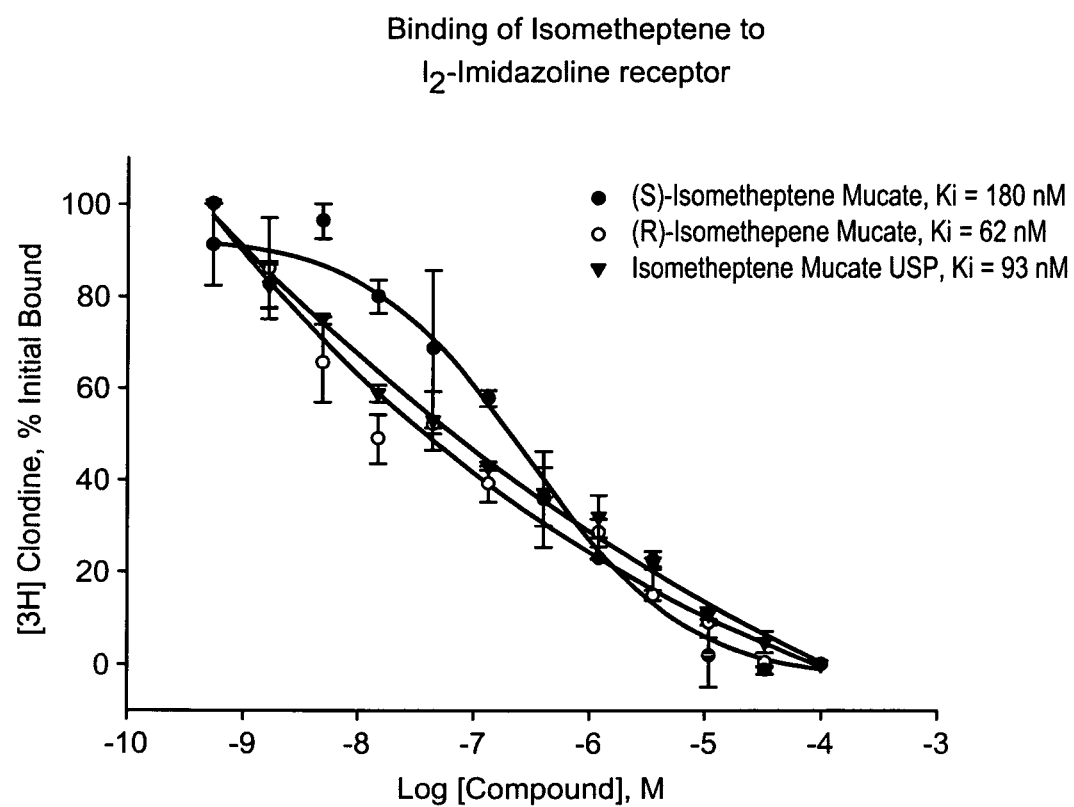
FIG. 22 illustrates the $I_2$ Imidazoline receptor binding of (S)-Isometheptene Mucate, (R) Isomentheptene Mucate, and Isometheptene Mucate.

The diagram in FIG. 22 shows the results of an experiment in which (S)-Isometheptene Mucate salt, (R)-Isometheptene Mucate salt, and Isometheptene Mucate salt USP (racemic) were studied for binding to the I2 receptor.

Surprisingly, further activities of the optical Isometheptene isomers have been found directed to the TAAR1 (trace amine associated receptor) receptor which is expressed in the CNS and belongs to the G-Protein Coupled Receptor (GPCR) receptor family. TAAR1 is activated by biogenic amines such as tyramine, a molecule found in trace levels in the CNS [Borowsky et al, PNAS 98: 8966-8971 (2001)]. Biogenic amines present in food have been shown to result in hypertensive crisis when taken with MAO inhibitors [Maguire et al, Pharmacol. Rev. 61: 1-8 (2009)].

To measure interactions with TAAR1, cell line stably expressing a recombinant human TAAR1 receptor were studied in the cAMP Biosensor Assay (DiscoveRx, Freemont, Calif.) since TAAR1 is coupled to G-proteins that signal through cAMP. The (S)- and (R)-Isometheptene isomers at a final concentration of 10 µM activate TAAR1 differentially, as shown on the table below, wherein (S)-Isometheptene activates more effectively than the R-Isometheptene. These activities may be linked to side-effects of racemic Isometheptene, due to the interaction of S-Isometheptene to the TAAR1 tyramine receptor.

| Compound | Efficacy |
| --- | --- |
| (S)-Isometheptene free base | 49.4% |
| (R)-Isometheptene free base | 25.6% |

Therefore, the lower TAAR1 activation of the Isometheptene (R)-enantiomer indicates lower side effects with its use.

Figure 23:
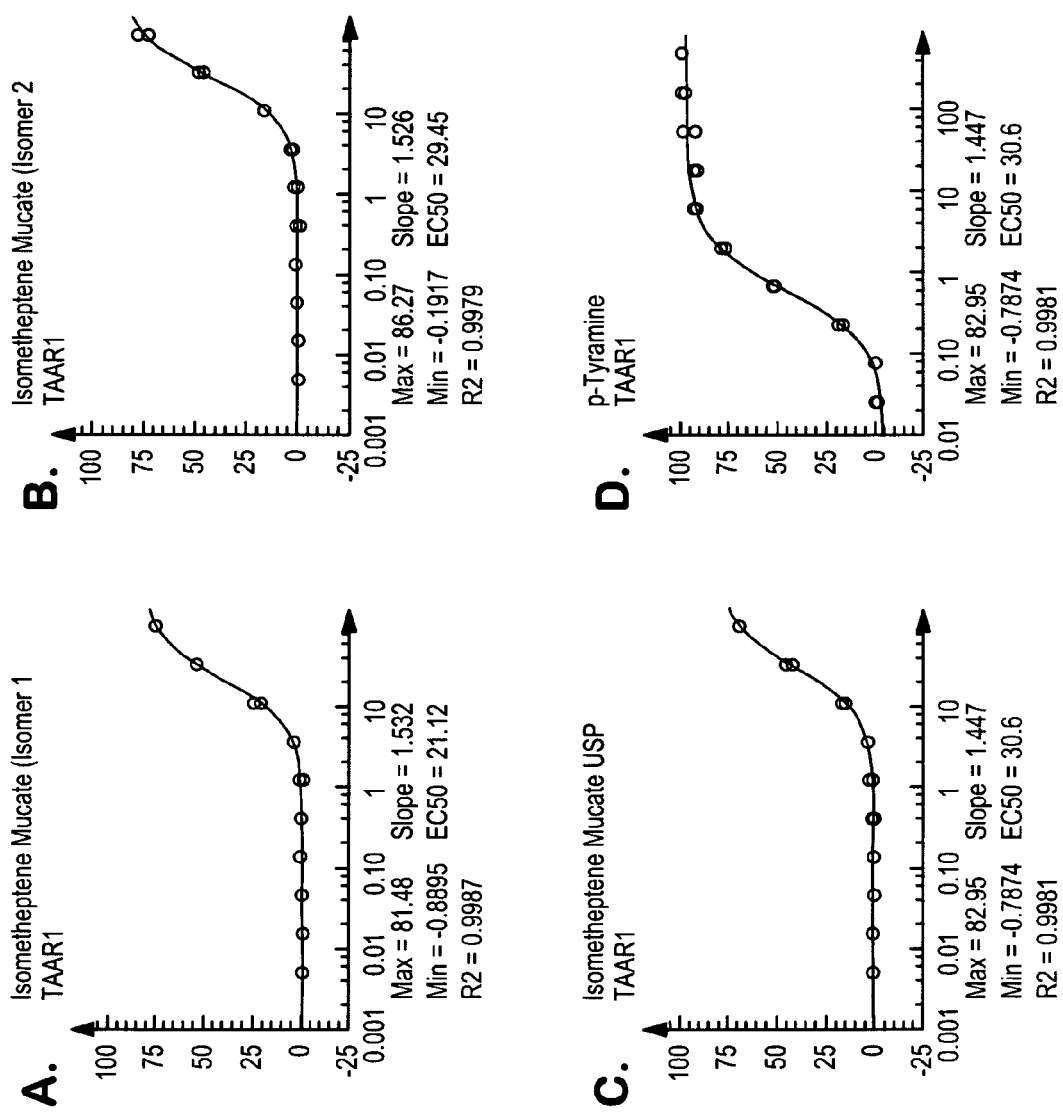
FIG. 23 illustrates the TAAR1 cAMP Biosensor Assay of (A) Isometheptene Mucate Isomer 1, (B) Isometheptene Mucate Isomer 2, (C) Isometheptene Mucate USP, (D) p-Tyramine.

Isometheptene Mucate USP, Isometheptene Mucate isomer 1, Isometheptene Mucate isomer 2 and p-Tyramine (control) in the TAAR1 cAMP Biosensor Assay of FIG. 23 as shown by the following diagrams (A), (B), (C), and (D). The data is shown as an agonist dose response curve, normalized to the maximal and minimal response observed in the presence of control ligand and vehicle respectively The TAAR1 cAMP accumulation assay was also used to study the activity of (S)- and (R)-Isometheptene as mucate salts. In the figure shown (FIG. 23), (A) Isomer 1 is (S) and (B) Isomer 2 is (R) Isometheptene. The S Isometheptene mucate salt ($EC_{50}$ 21.12 µM) activates TAAR1 more potently than R-Isometheptene mucate salt ($EC_{50}$ 29.45 µM), which is consistent with the Isometheptene isomer free base activation of TAAR1 described above.

Mechanism of Action:

The (R)-enantiomer of Isometheptene (Isomer 2) is found to bind to the CNS I1 receptor, with comparatively high affinity (Table 1); with its binding avidity being about 60 fold greater than that of Isometheptene S-enantiomer (Isomer 1). However, the compound appears to bind only weakly to the adrenergic alpha-2B receptor.

This neuronal I1 receptor, is found in both the rostral ventrolateral pressor and ventromedial depressor areas of the medulla oblongata. The same receptor also binds a selective agonist, moxonidine, which is a centrally-acting antihypertensive causing a decrease in sympathetic nervous system activity and blood pressure. Therefore, like moxonidine, on the basis of its specific binding to the ($I_1$) I1 receptor, the Isometheptene (R)-enantiomer (Isomer 2) may similarly promote sodium excretion, improve insulin resistance and glucose tolerance and protect against hypertensive target organ damage, such as kidney disease and cardiac hypertrophy. A further aspect may be found in beta blockers inhibiting the metastatic cascade of tumor cells. Further activities of the optical Isometheptene isomers have been found directed to the TAAR1 (trace amine associated receptor) receptor which is expressed in the CNS and belongs in the GPCR receptor family. TAAR1 is activated by biogenic amines such as tyramine, a molecule found in trace levels in the CNS [Borowsky et al, PNAS 98: 8966-8971 (2001)]. Biogenic amines present in food have been shown to result in hypertensive crisis when taken with MAO inhibitors [Maguire et al, Pharmacol. Rev. 61: 1-8 (2009)].

Therefore, the lower TAAR1 activation of the (R)-Isometheptene enantiomer indicates lower side effects with its use.

Several comparative studies of acute migraine treatment using pharmaceutical compositions of Isometheptene alone, and Isometheptene containing fixed drug combinations (FDCs) have been reported (E. Loder Review, CNS DRUGS 2005: 19(9):780).

Simultaneous administration of more than one drug in acute treatment of migraine is common because, in general, treatment with only one the agent has not been as successful. This observation holds true mostly for Isometheptene or combinations with other drugs regardless of the type of administration such as parenteral or i.v.

Considering the several stages and processes involved in migraine pathophysiology, adjustable polytherapy is preferred for the treatment of dopamine antagonist, an anti-inflammatory agent plus a serotonin agonist, a dopamine antagonist plus a serotonin agonist, a dopamine antagonist plus an anti-inflammatory agent plus a serotonin agonist. Such fixed combinations (FDCs) contain standard quantities of the combined drugs in a tablet, injectable solution, nasal spray or suppository.

Taking reference to the appended figures which depict comparative chromatography of the twin Isometheptene enantiomer forms as illustrative examples that are not deemed in any way as limiting the present invention:

The HPLC Isomer 2 (or (R)-Enantiomer) of Isometheptene is shown in FIG. 1 as eluted from a reverse phase Zorbax SB-CN column: 25 mm×4.6 mm, 5 microM; at a flow of 1.0 ml/minute with a solvent of MPB-CAN MPA-0.1% TFA in water. Max Plot. The signal voltage is recorded at 8.470-8.809 minutes RT.

Figure 3:
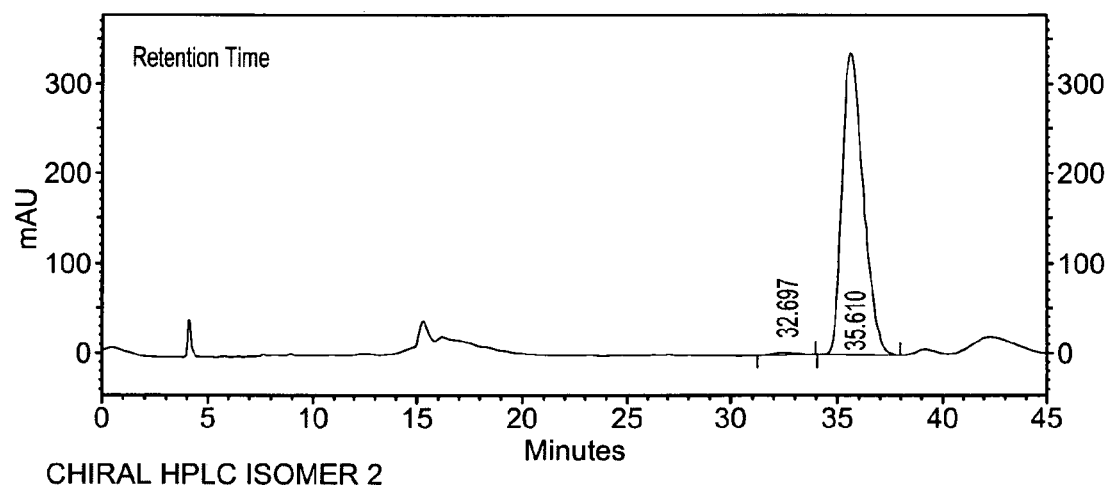
FIG. 3 illustrates a chiral HPLC sample elution of purified Isometheptene isomer 2.

The chromatogram of purified Isometheptene Isomer 2 is shown in FIG. 3 as eluted from the chiral pack IC 250×4.6 mm, 5 microns, with a solvent gradient of MPA-nHexane:MPB-IPA::90:10, at a flow rate of about 0.8 ml/min., and observed at a wavelength of 205 nm with column temperature of 30° C. Accordingly, the Isometheptene peak 2 eluted at 35.610 minutes.

Figure 4:
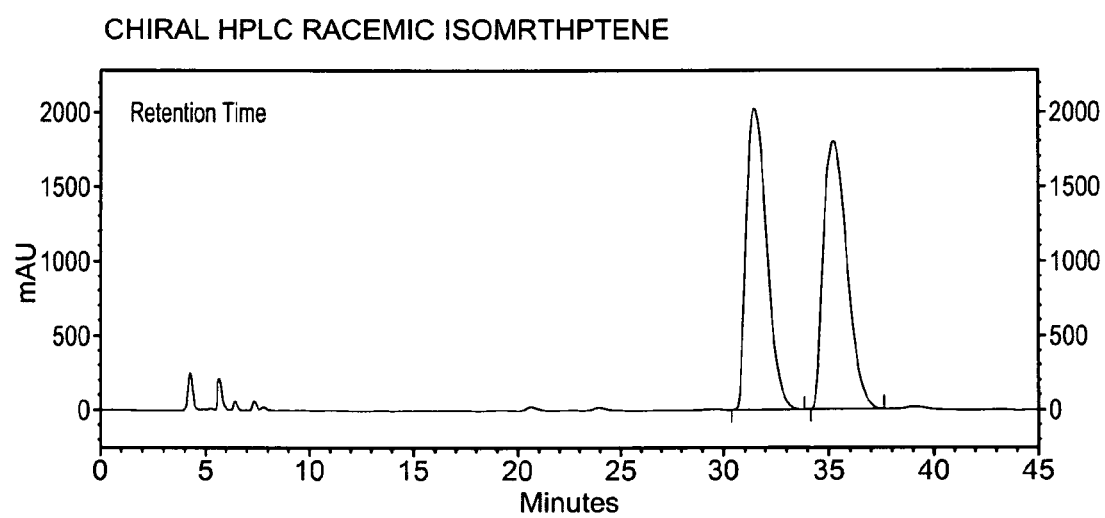
FIG. 4 illustrates a chiral pack HPLC eluting a racemic mixture of Isometheptene into peak 1 and peak 2 peak.

The Chiral HPLC Racemic Isometheptene mixture is shown at FIG. 4 as resolved in Peak 1 (31.370 minutes retention time) and Peak 2 (35.100 retention time) using the chiral pack IC 250×4.6 mm, 5 microns, with a solvent gradient of MPA-nHexane:MPB-IPA::90:10, at a flow rate of about 0.8 ml/min., and observed at a wavelength of 205 nm with column temperature of 30 C. Peak 2 is designated as containing the Isometheptene enantiomer 2 and Peak 1 is believed to contain Isometheptene enantiomer 1.

Figure 12:
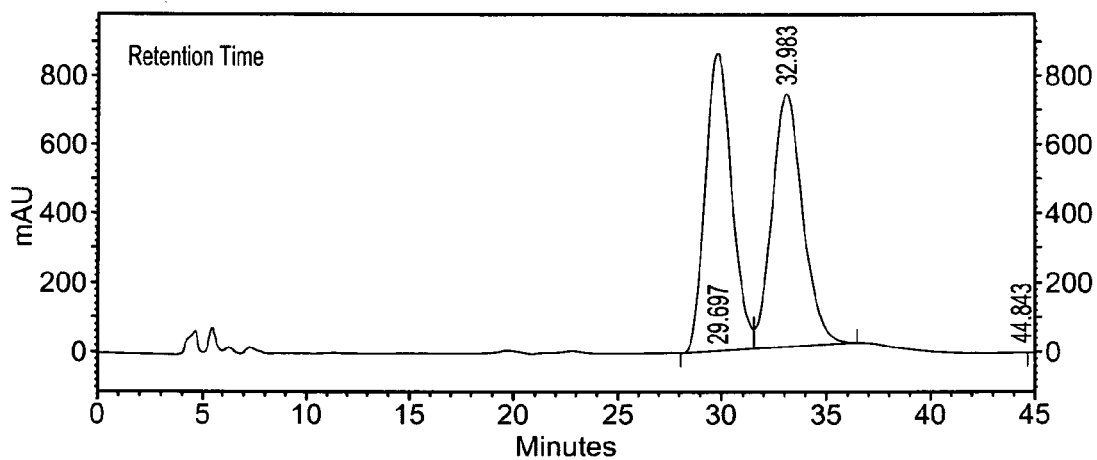
FIG. 12 illustrates a second Chiral HPLC of Isometheptene racemic mixture resolved in Peak 1 and Peak 2.

Similarly, the racemic mixture was resolved by chiral HPLC at FIG. 12 on the same chiral Pack IC as described above.

Figure 5:
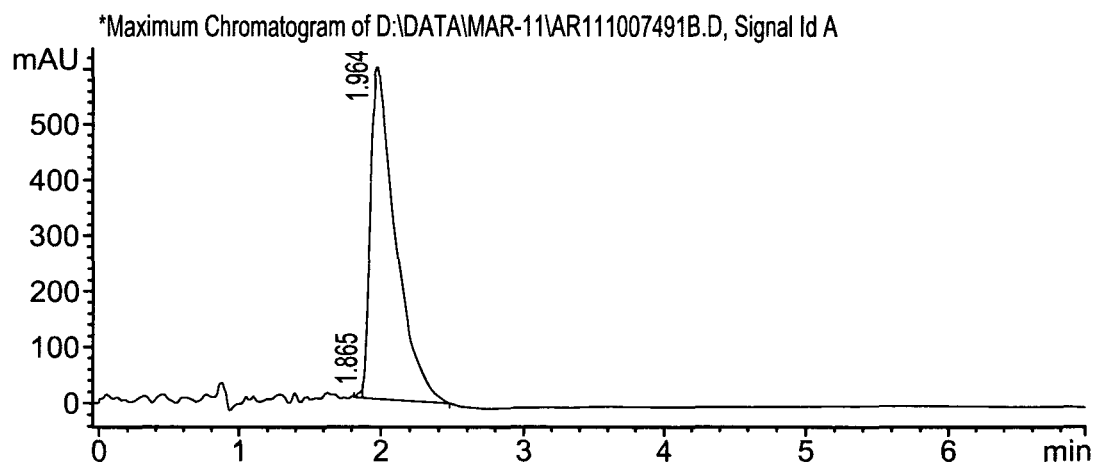
FIG. 5 illustrates a liquid chromatogram of the Isometheptene (R)-enantiomer.

FIG. 5 shows a chromatogram of LC-Isomer 2 wherein the purified enantiomer 2 occupies 99.639% of the eluted peak.

Figure 6:
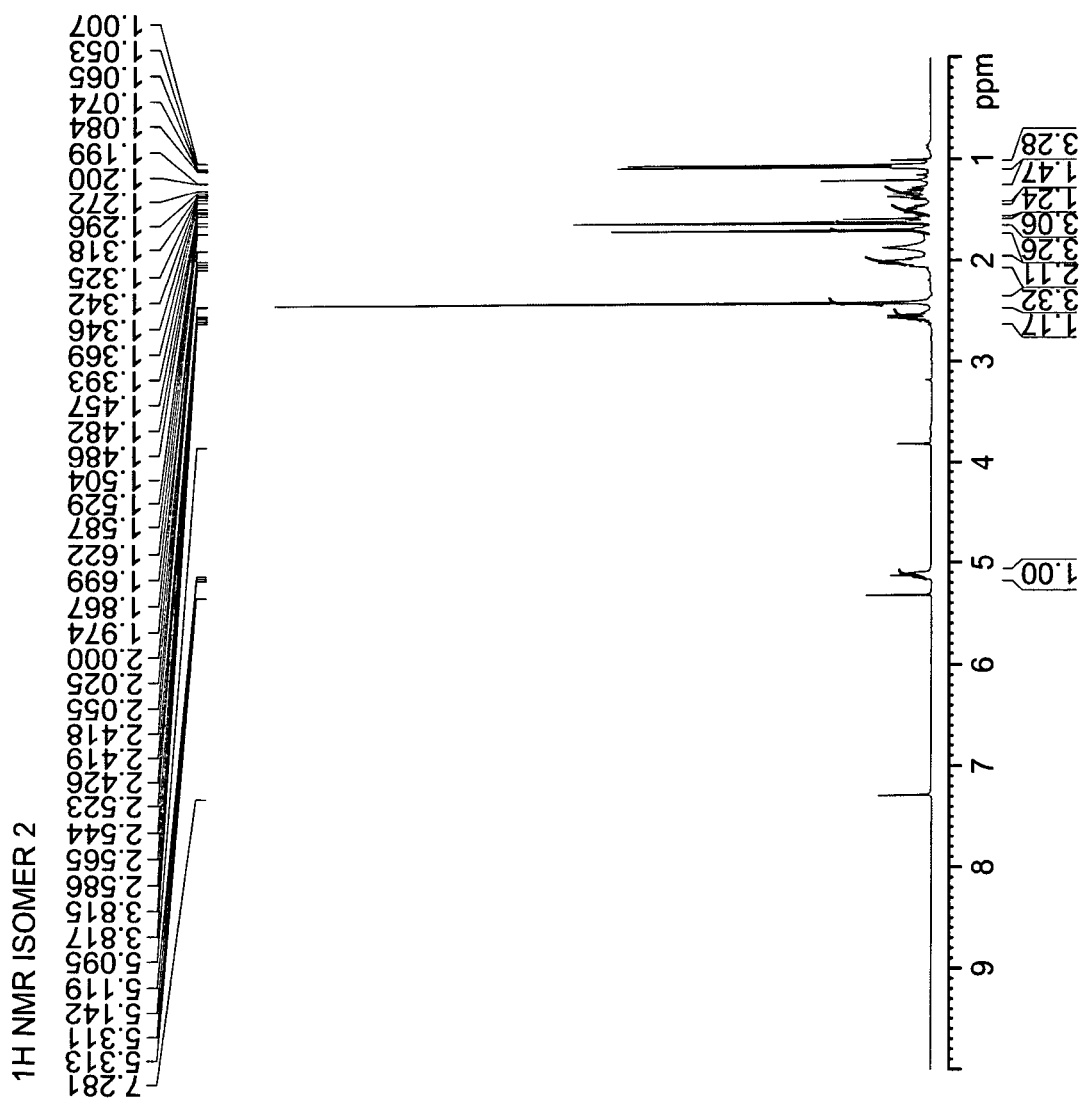
FIG. 6 illustrates an 1H NMR of the Isometheptene (R)-enantiomer.

FIG. 6 shows 1H NMR of Isomer 2 demonstrating the purity of the molecule.

Figure 7:
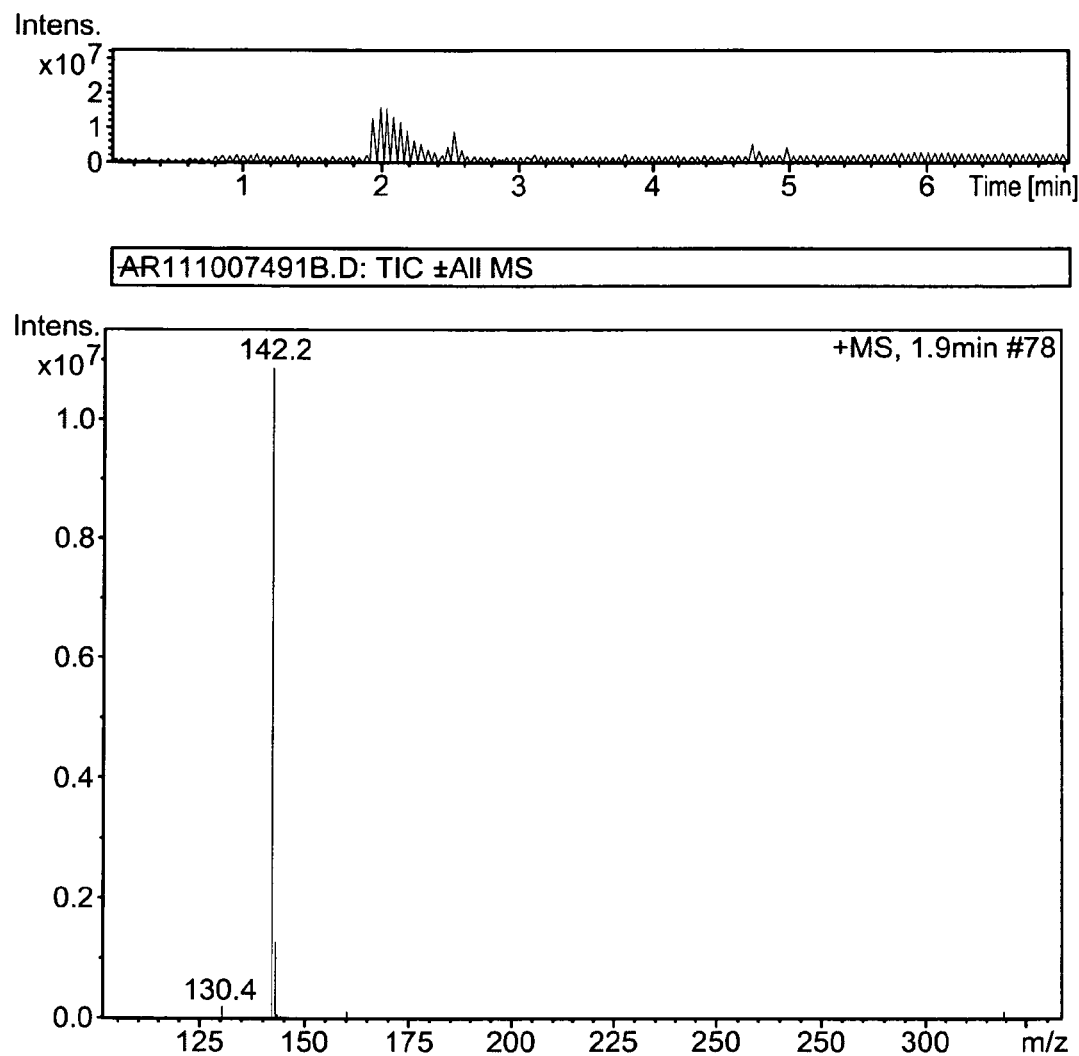
FIG. 7 illustrates mass spectrum (MS) of Isometheptene (R)-enantiomer.

FIG. 7 depicts a mass spectrum analysis of Isomer 2 indicating the purity of the sample.

Figure 8:
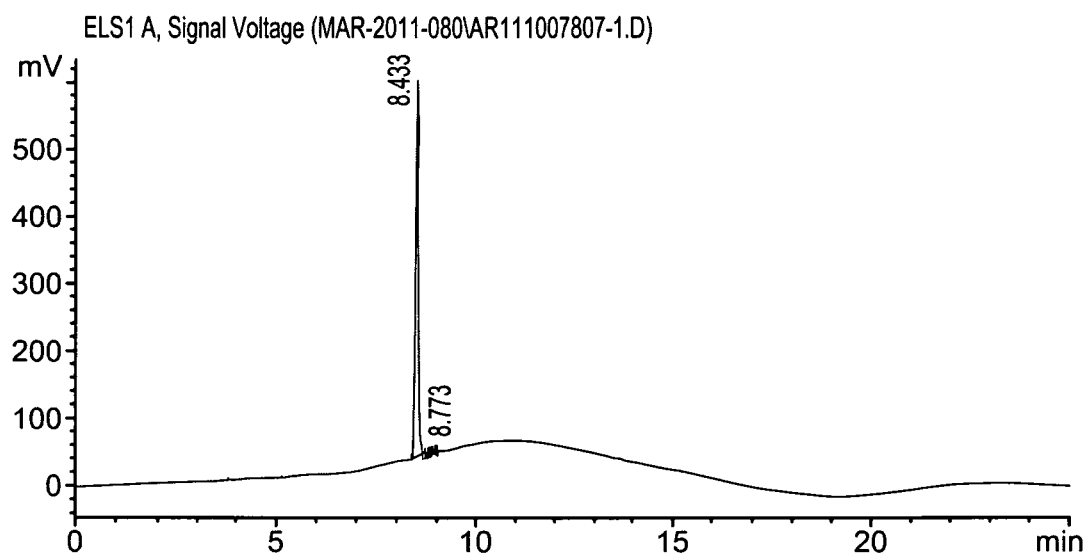
FIG. 8 illustrates an HPLC of Isometheptene (S)-enantiomer.

The HPLC Isomer 1 (or enantiomer 1) of the purified Isometheptene isomer shown in FIG. 8 was eluted from a reverse phase Zorbax SB-CN column: 25 mm×4.6 mm, 5 microM; at a flow of 1.0 ml/minute with a solvent of MPB-CAN MPA-0.1% TFA in water. Max Plot. The Signal voltage is 8.433-8.773 minutes RT.

Figure 11:
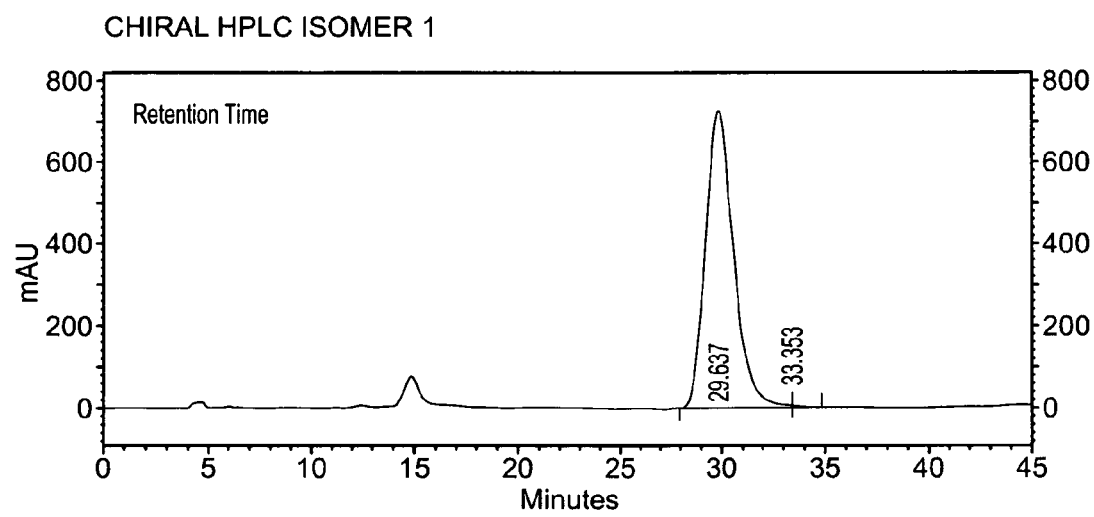
FIG. 11 illustrates a Chiral HPLC of (S)-enantiomer.

The chromatogram of purified Isometheptene Isomer 1 is shown in FIG. 11, as eluted from the chiral pack IC 250×4.6 mm, 5 microns, with a solvent gradient of MPA-nHexane:MPB-IPA::90:10, at a flow rate of about 0.8 ml/min., and observed at a wavelength of 205 nm with column temperature of 30 C. The Isometheptene Peak 1 eluted at 29.637 minutes, distinct from a putative Peak 2 time of 33.353 minutes.

Figure 13:
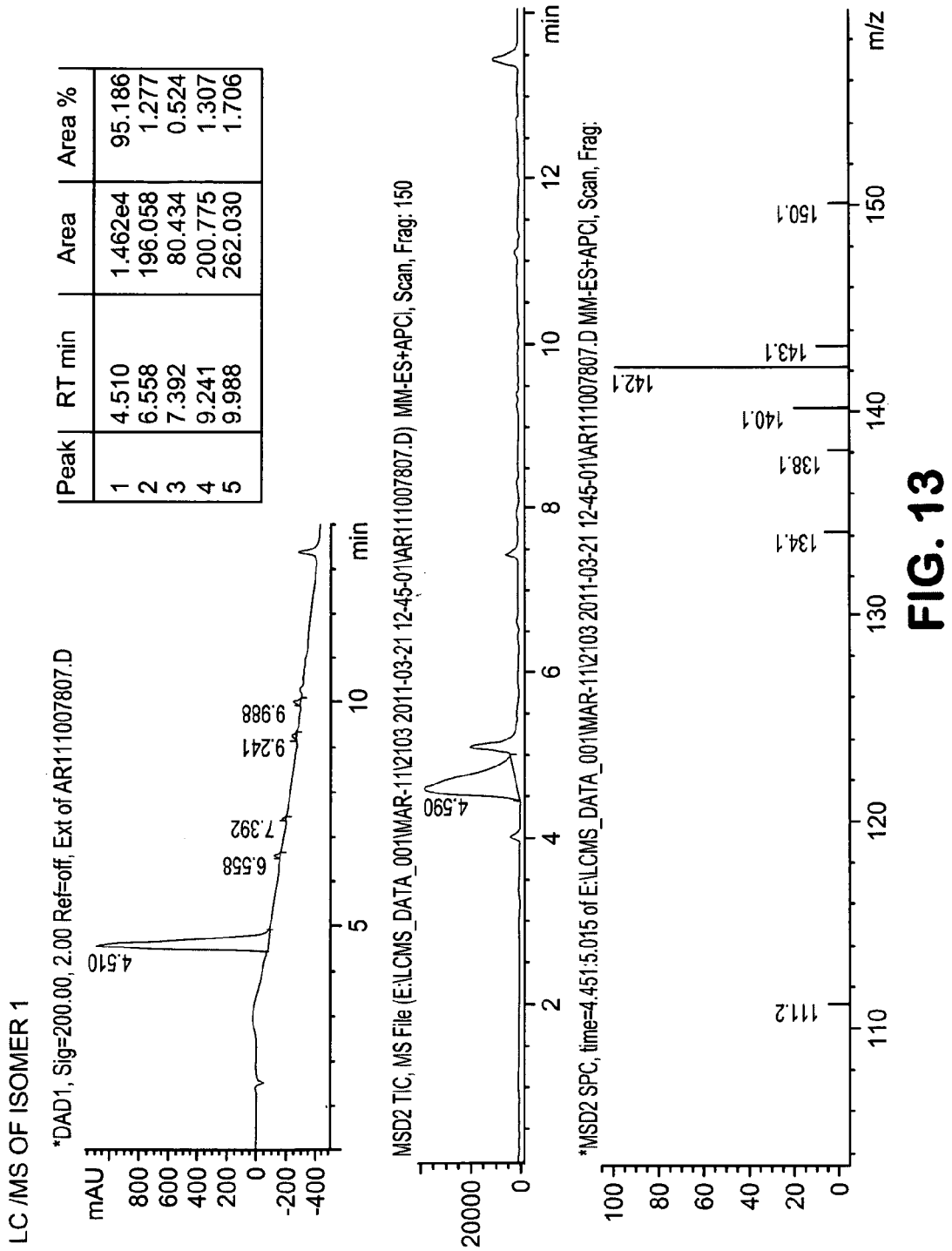
FIG. 13 illustrates a LC/MS data of Isometheptene (S)-enantiomer.
Figure 14:
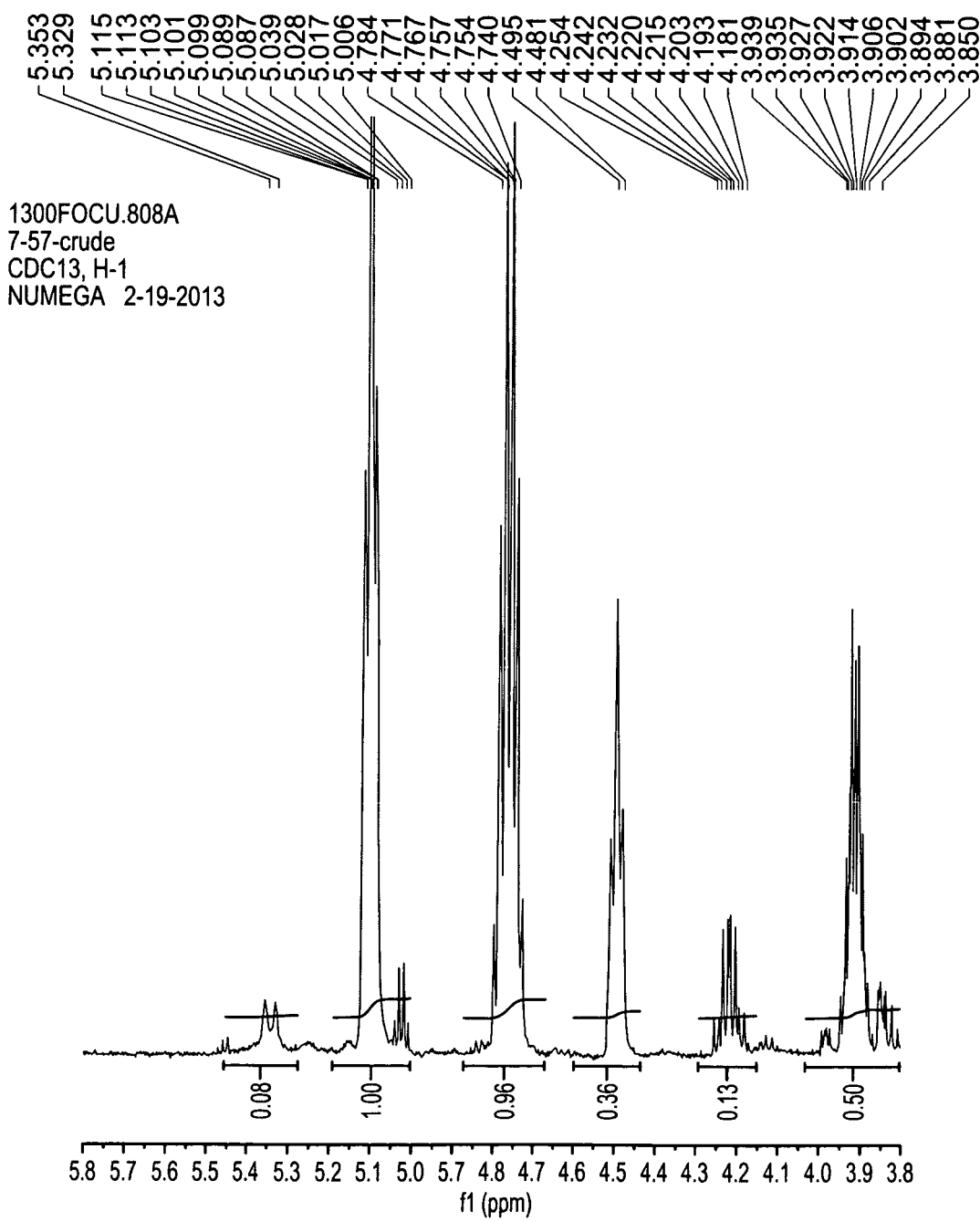
FIG. 14 illustrates an H1 NMR of (R)-Isometheptene (R)-Mosher amide, showing no (S)-peak at 4.84 ppm.
Figure 15:
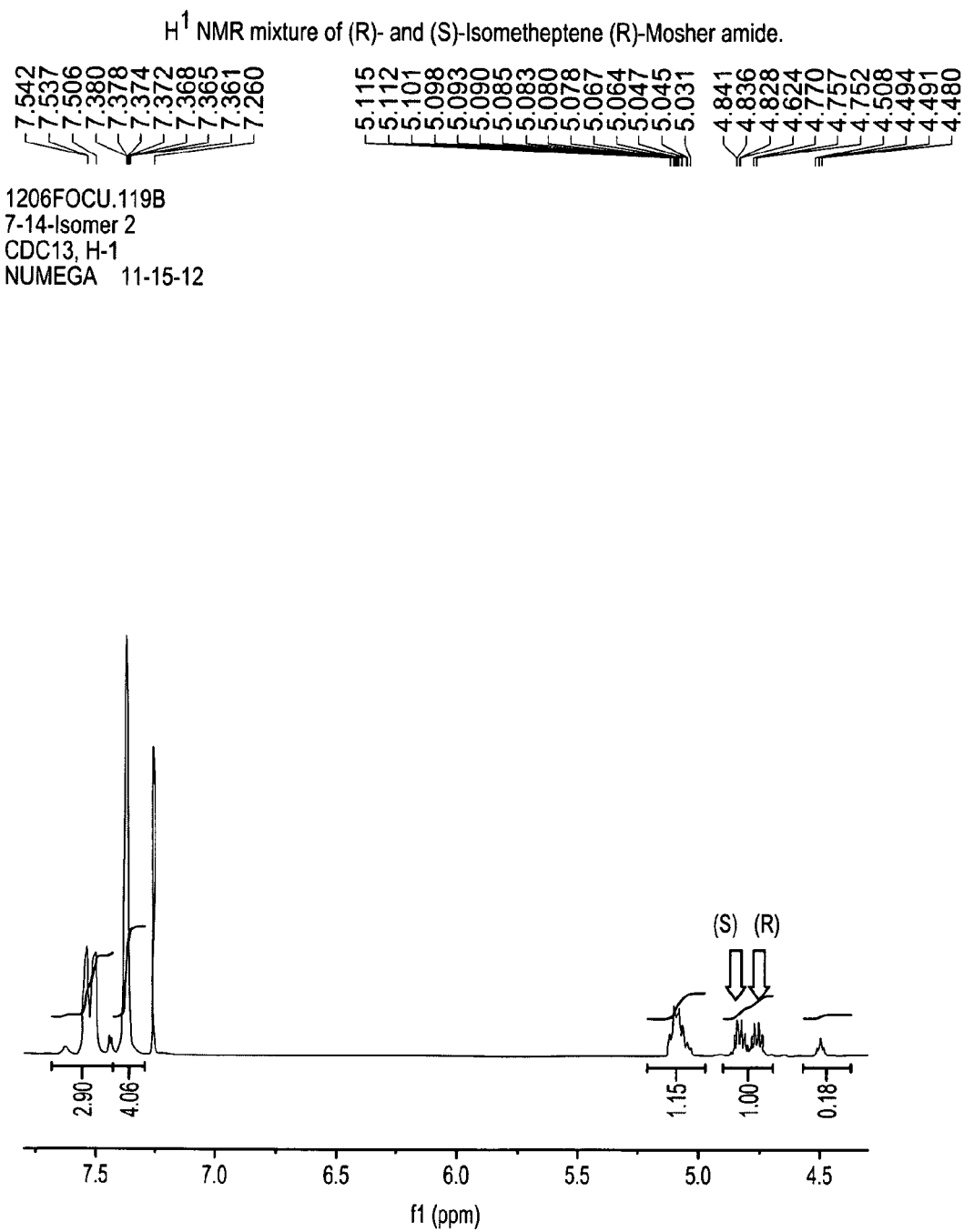
FIG. 15 illustrates separation of H1 NMR mixture of (R)- and (S)-Isometheptene (R)-Mosher amide.

FIG. 13 discloses a liquid chromatography/mass spectroscopy analysis (LC/MS) of purified Isomer 1 wherein the chromatogram of Isomer 1 indicates an area of 95.186%.

Figure 2:
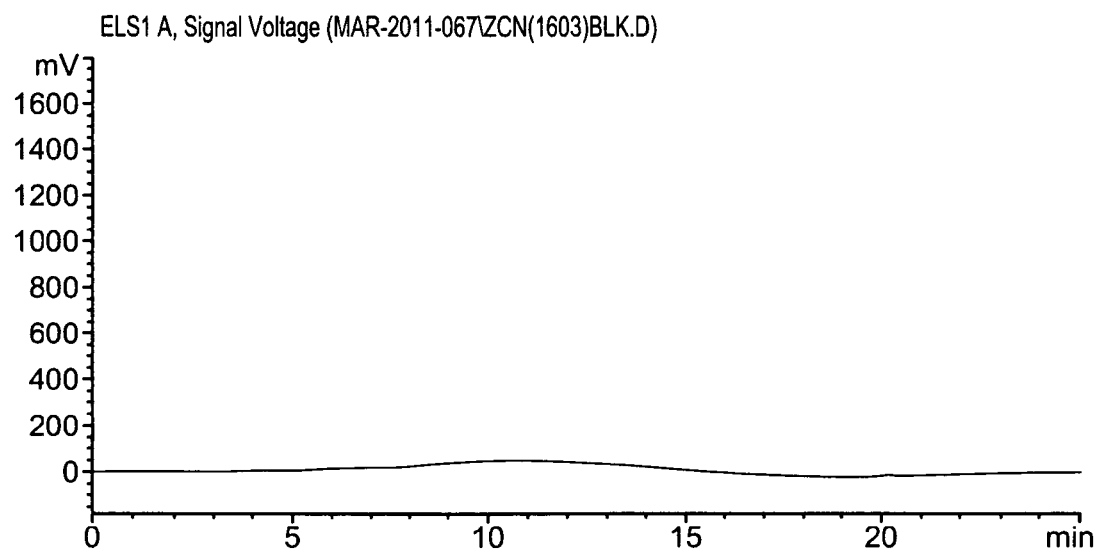
FIG. 2 illustrates an HPLC sample elution of a blank from a chiral pack column.
Figure 9:
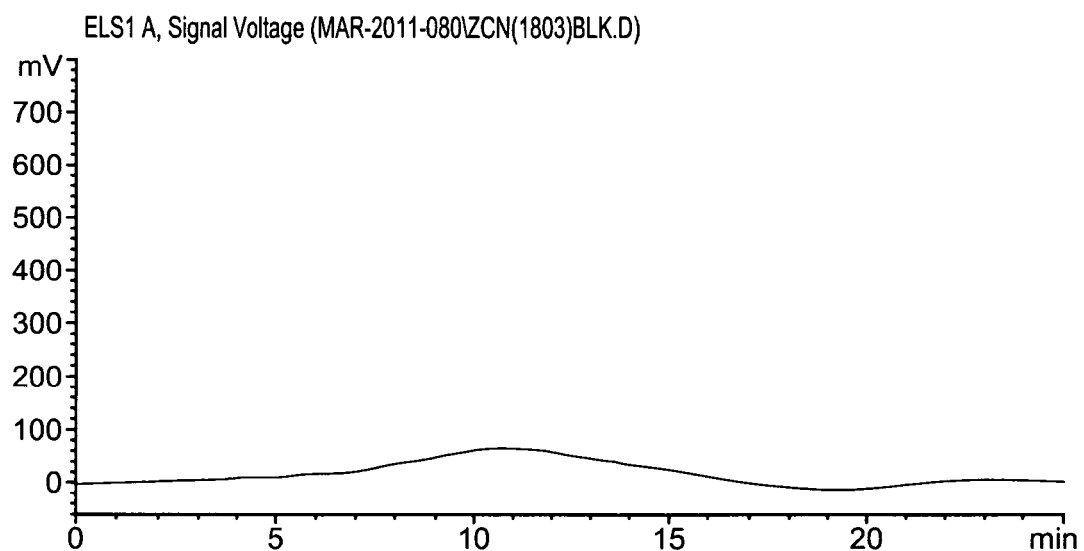
FIG. 9 illustrates an HPLC of a blank of Isometheptene isomer.
Figure 10:
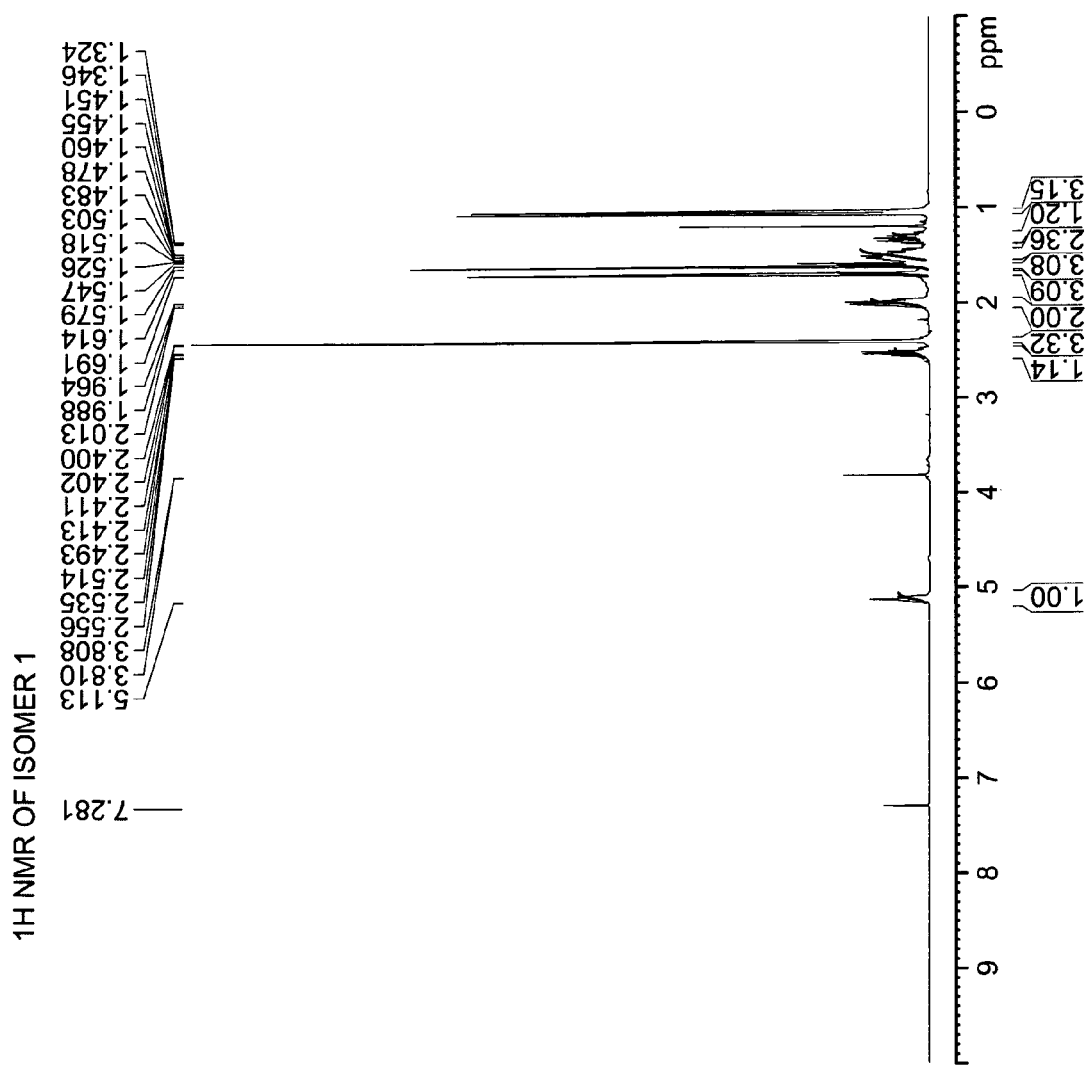
FIG. 10 illustrates a 1H NMR of (S)-enantiomer.

Finally, the HPLC RT blank of Isomer 2 on Zorbax column (FIG. 2), and similarly the HPLC RT of the blank of Isomer 1 at FIG. 9 show absence of any distinct isomer material.

Pharmaceutical Preparations.

The pharmaceutical preparations of the invention embrace a variety of forms, including, but not limited to, a composition that is enteric coated, a composition that is a controlled release or sustained release formulation, a composition that is a solution, a composition that is a topical formulation, a composition that is a suppository, a composition that is a transdermal patch, a composition that is lyophilized, a composition that is in an inhaler, a compositions that is in a prefilled syringe, a composition that is in a nasal spray device, and the like. The composition can be for oral administration, parenteral administration, mucosal administration, nasal administration, topical administration, ocular administration, local administration, rectal, intrathecal, etc. If parenteral, the administration can be subcutaneous, intravenous, intradermal, intraperitoneal, intrathecal, etc. The pharmaceutical preparation may be in a packaged unit dosage or multi-unit dosage. Routes of administration of the compounds in a pharmaceutically acceptable form may include, without limitation, parenteral, subcutaneous, intramuscular, intravenous, intrarticular, intrabronchial, intraabdominal, intracapsular, intracartilaginous, intracavitary, intracelial, intracerebellar, intracerebroventricular, intracolic, intracervical, intragastric, intrahepatic, intramyocardial, intraosteal, intrapelvic, intrapericardiac, intraperitoneal, intrapleural, intraprostatic, intrapulmonary, intrarectal, intrarenal, intraretinal, intraspinal, intrasynovial, intrathoracic, intrauterine, intravesical, bolus, vaginal, rectal, buccal, sublingual, intranasal, and transdermal.

According to yet another embodiment of the invention, a pharmaceutical preparation containing a compound of the present invention, additive salt or intermediate, in a lyophilized formulation is prepared by combining a cryoprotective agent, such as mannitol, with the same. The resulting preparation may also contain any one of, any combination of, or all of a buffering agent, an antioxidant, and an isotonicity agent.

In various embodiments, the pharmaceutical agent is an antispasmodic agent, a steroidal or non-steroidal anti-inflammatory agent, a $5HT_1$ agonist, a $5HT_3$ antagonist, a $5HT_4$ antagonist, a $5HT_4$ agonist, a bulk-forming agent, an alpha2-adrenergic agonist, a mineral oil, a fiber or a hematopoietic stimulating agent.

More particularly, depending on the disease or condition to be treated or prevented, one or more additional therapeutic drugs, compounds, reagents, or agents, which are normally or typically administered to treat or prevent the disease or condition, may also be administered with the compounds of this invention, or may also be present in the compositions of this invention. It will be appreciated that additional therapeutic agents that are normally or typically administered to treat or prevent a given disease or condition are termed "appropriate for the disease or condition being treated".

In another embodiment, other agents, compounds, drugs, or reagents are suitable for administering in combination with the compounds of the present invention, including without limitation, anti-inflammatory agents, e.g., non-steroidal anti-inflammatory drugs (NSAIDs), corticosteroids, TNF blockers or inhibitors, IL-RA, azathioprine, cyclophosphamide, sulfasalazine; agents; cardiovascular disease treatment agents, e.g., ACE inhibitors, beta-blockers, diuretics, nitrates, calcium channel blockers, statins; diabetes treatment agents, e.g., insulin, glitazones, sulfonyl ureas. The amount of additional therapeutic agent, compound, drug, or reagent present in the compositions of the invention, or administered in conjunction with the compounds of the invention, are no more than the amount which would normally be administered in a composition comprising that therapeutic agent, compound, drug, or reagent as the only active agent. As a guide, the amount of additional therapeutic agent, compound, drug, or reagent in a composition according to the present invention will range from about 40%-100% of the amount normally present in a composition comprising that agent, compound, drug, or reagent as the only therapeutically active agent.

The pharmaceutical preparations of the present invention may include, or be diluted into, a pharmaceutically-acceptable carrier. The term "pharmaceutically-acceptable carrier" as used herein means one or more compatible solid, gel, or liquid fillers, diluents or encapsulating substances which are suitable for administration to a human or other mammal such as a non-human primate, a dog, cat, horse, cow, sheep, pig, or goat. The term "carrier" denotes an organic or inorganic ingredient, natural or synthetic, with which the active ingredient is combined to facilitate the application. The carriers are capable of being commingled with the compositions, compounds and preparations of the present invention, and with each other, in a manner such that there is no interaction which would substantially impair the desired pharmaceutical efficacy or stability. Carrier formulations suitable for oral administration, for suppositories, and for parenteral administration, etc., can be found in Remington's Pharmaceutical Sciences, Mack Publishing Company, Easton, Pa.

Aqueous formulations may include a chelating agent, a buffering agent, an anti-oxidant and, optionally, an isotonicity agent. In an embodiment, the formulation is pH adjusted to between 3.0 and 3.5.

Chelating agents include, for example, but are not limited to ethylenediaminetetraacetic acid (EDTA) as a free acid, salt or various combinations and derivatives thereof, citric acid and derivatives thereof, niacinamide and derivatives thereof, sodium desoxycholate and derivatives thereof, and L-glutamic acid, N,N-diacetic acid and derivatives thereof.

Buffering agents include but are not limited to, citric acid, sodium citrate, sodium acetate, acetic acid, sodium phosphate and phosphoric acid, sodium ascorbate, tartaric acid, maleic acid, glycine, sodium lactate, lactic acid, ascorbic acid, Imidazoline, sodium bicarbonate and carbonic acid, sodium succinate and succinic acid, histidine, and sodium benzoate and benzoic acid, or combinations thereof.

Antioxidants include, for example, an ascorbic acid derivative, butylated hydroxy anisole, butylated hydroxy toluene, alkyl gallate, sodium meta-bisulfite, sodium bisulfite, sodium dithionite, sodium thioglycollate acid, sodium formaldehyde sulfoxylate, tocopheral and derivatives thereof, monothioglycerol, or sodium sulfite or combinations thereof. In one embodiment, the antioxidant is monothioglycerol.

Illustrative isotonicity agents include, but are not limited to, sodium chloride, mannitol, lactose, dextrose, glycerol, or sorbitol, or combinations thereof.

Preservatives that can be used with the present compositions include without limitation benzyl alcohol, parabens, thimerosal, chlorobutanol and preferably benzalkonium chloride. Typically, the preservative will be present in a composition in a concentration of up to about 2% by weight. The exact concentration of the preservative, however, will vary depending upon the intended use and can be easily ascertained by one skilled in the art.

The compounds of the invention can be prepared in lyophilized compositions, typically in the presence of a cryoprotecting agent such as mannitol, or lactose, sucrose, polyethylene glycol, and polyvinyl pyrrolidines. Cryoprotecting agents which result in a reconstitution pH of 6.0 or less are desired. The invention therefore provides a lyophilized preparation of the therapeutic agent(s) of the invention. The preparation can contain a cryoprotecting agent, such as mannitol or lactose, which is preferably neutral or acidic in water.

Oral, parenteral and suppository formulations of agents are well known and commercially available. The therapeutic compound(s) of the invention can be added to such well known formulations. One or more compounds of the invention can be mixed together in solution or semi-solid solution in such formulations, provided in a suspension within such formulations, or contained in particles within such formulations.

As used herein, "pharmaceutically acceptable" refers to those compounds, materials, compositions, and/or dosage forms that are, within the scope of sound medical judgment, suitable for contact with the tissues of human beings and animals without a resulting or excessive toxicity, irritation, allergic response, or other problem complications commensurate with a reasonable benefit/risk ratio. As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues, such as amines, alkali or organic salts of acidic residues, such as carboxylic acids, and the like. The pharmaceutically acceptable salts include the conventional non-toxic salts or the quaternary ammonium salts of the parent compound formed, for example, from non-toxic inorganic or organic acids. For example, such conventional non-toxic salts include those derived from inorganic acids such as hydrochloric, hydrobromic, sulfuric, sulfamic, phosphoric, nitric and the like; and the salts prepared from organic acids such as acetic, propionic, succinic, glycolic, stearic, lactic, malic, tartaric, citric, ascorbic, pamoic, maleic, hydroxymaleic, phenylacetic, glutamic, benzoic, salicylic, sulfanilic, 2-acetoxybenzoic, fumaric, toluenesulfonic, methanesulfonic, ethane disulfonic, oxalic, isethionic, and the like. These physiologically acceptable salts are prepared by methods known in the art, e.g., by dissolving the free amine bases with an excess of the acid in aqueous alcohol, or neutralizing a free carboxylic acid with an alkali metal base such as a hydroxide, or with an amine. Certain acidic or basic compounds of the present invention may exist as zwitterions. All forms of the compounds, including free acid, free base and zwitterions, are contemplated to be within the scope of the present invention. It is well known in the art that compounds containing both amino and carboxyl groups often exist in equilibrium with their zwitterionic forms. Thus, any of the compounds described herein that contain, for example, both amino and carboxyl groups, also include reference to their corresponding zwitterions.

A product containing therapeutic compound(s) of the invention and, optionally, one or more other active agents can be configured as an oral dosage. The oral dosage may be a liquid, a semisolid or a solid. The oral dosage may be configured to release the therapeutic compound(s) of the invention before, after or simultaneously with the other agent. The oral dosage may be configured to have the therapeutic compound(s) of the invention and the other agents release completely in the stomach, release partially in the stomach and partially in the intestine, in the intestine, in the colon, partially in the stomach, or wholly in the colon. The oral dosage also may be configured whereby the release of the therapeutic compound(s) of the invention is confined to the stomach or intestine while the release of the other active agent is not so confined or is confined differently from the therapeutic compound(s) of the invention. For example, the therapeutic compound(s) of the invention may be an enterically coated core or pellets contained within a pill or capsule that releases the other agent first and releases the therapeutic compound(s) of the invention only after the therapeutic compound(s) of the invention passes through the stomach and into the intestine. The therapeutic compound(s) of the invention also can be in a sustained release material, whereby the therapeutic compound(s) of the invention is released throughout the gastrointestinal tract and the other agent is released on the same or a different schedule. The same objective for therapeutic compound(s) of the invention release can be achieved with immediate release of therapeutic compound(s) of the invention combined with enteric coated therapeutic compound(s) of the invention. In these instances, the other compound or agent could be released immediately in the stomach, throughout the gastrointestinal tract or only in the intestine.

The materials useful for achieving these different release profiles are well known to those of ordinary skill in the art. Immediate release is obtainable by conventional tablets with binders which dissolve in the stomach. Coatings which dissolve at the pH of the stomach, or which dissolve at elevated temperatures, will achieve the same purpose. Release only in the intestine is achieved using conventional enteric coatings such as pH sensitive coatings which dissolve in the pH environment of the intestine (but not the stomach), or coatings that dissolve over time. Release throughout the gastrointestinal tract is achieved by using sustained-release materials and/or combinations of the immediate release systems and sustained and/or delayed intentional release systems (e.g., pellets which dissolve at different pHs).

In the event that it is desirable to release the therapeutic compound(s) of the invention first, the therapeutic compound(s) of the invention could be coated on the surface of the controlled release formulation in any pharmaceutically acceptable carrier suitable for such coatings and for permitting the release of the therapeutic compound(s) of the invention, such as in a temperature sensitive pharmaceutically acceptable carrier routinely used for controlled release. Other coatings, which dissolve when placed in the body, are well known to those of ordinary skill in the art.

The therapeutic compound(s) of the invention also may be mixed throughout a controlled release formulation, whereby it is released before, after, or simultaneously with another agent. The therapeutic compound(s) of the invention may be free, that is, solubilized within the material of the formulation. The therapeutic compound(s) of the invention also may be in the form of vesicles, such as wax-coated micropellets dispersed throughout the material of the formulation. The coated pellets can be fashioned to immediately release the therapeutic compound(s) of the invention based on temperature, pH, or the like. The pellets also can be configured so as to delay the release of the therapeutic compound(s) of the invention, allowing the other agent a period of time to act before the therapeutic compound(s) of the invention exerts its effects. The therapeutic compound(s) of the invention also can be configured, e.g., as pellets, to release the therapeutic compound(s) of the invention in virtually any sustained release pattern, including patterns exhibiting first order release kinetics or sigmoidal order release kinetics using materials of the prior art and well known to those of ordinary skill in the art.

The therapeutic compound(s) of the invention also can be contained within a core within the controlled release formulation. The core may have any one or any combination of the properties described above in connection with the pellets. The therapeutic compound(s) of the invention may be, for example, in a core coated with a material, dispersed throughout a material, coated onto a material or adsorbed into or throughout a material.

It should be understood that the pellets or core may be of virtually any type. They may be drug coated with a release material, drug interspersed throughout material, drug adsorbed into a material, and so on. The material may be erodible or nonerodible.

The therapeutic compound(s) of the invention may be provided in particles. Particles as used herein means nano or microparticles (or in some instances larger) which can consist in whole or in part of the therapeutic compound(s) of the invention or the other agents as described herein. The particles may contain the therapeutic compound(s)/agent(s) in a core surrounded by a coating, including, but not limited to, an enteric coating. The therapeutic agent(s) also may be dispersed throughout the particles. The therapeutic agent(s) also may be adsorbed into the particles. The particles may be of any order release kinetics, including zero order release, first order release, second order release, delayed release, sustained release, immediate release, and any combination thereof, etc. The particle may include, in addition to the therapeutic agent(s), any of those materials routinely used in the art of pharmacy and medicine, including, but not limited to, erodible, nonerodible, biodegradable, or nonbiodegradable material or combinations thereof. The particles may be microcapsules which contain the antagonist in a solution or in a semisolid state. The particles may be of virtually any shape.

Both non-biodegradable and biodegradable polymeric materials can be used in the manufacture of particles for delivering the therapeutic agent(s). Such polymers may be natural or synthetic polymers. The polymer is selected based on the period of time over which release is desired. Bioadhesive polymers of particular interest include bioerodible hydrogels described by H. S. Sawhney, C. P. Pathak and J. A. Hubell in *Macromolecules*, (1993) 26:581-587, the teachings of which are incorporated herein. These include polyhyaluronic acids, casein, gelatin, glutin, polyanhydrides, polyacrylic acid, alginate, chitosan, poly(methyl methacrylates), poly(ethyl methacrylates), poly(butylmethacrylate), poly(isobutyl methacrylate), poly(hexylmethacrylate), poly(isodecyl methacrylate), poly(lauryl methacrylate), poly(phenyl methacrylate), poly(methyl acrylate), poly(isopropyl acrylate), poly(isobutyl acrylate), and poly(octadecyl acrylate).

The therapeutic agent(s) may be contained in a controlled release formulation or controlled release systems. The term "controlled release" is intended to refer to any drug-containing formulation in which the manner and profile of drug release from the formulation are controlled. This refers to immediate as well as nonimmediate release formulations, with nonimmediate release formulations including but not limited to sustained release and delayed release formulations. The term "sustained release" (also referred to as "extended release") is used in its conventional sense to refer to a drug formulation that provides for gradual release of a drug over an extended period of time, and that preferably, although not necessarily, results in substantially constant blood levels of a drug over an extended time period. The term "delayed release" is used in its conventional sense to refer to a drug formulation in which there is a time delay between administration of the formulation and the release of the drug therefrom. "Delayed release" may or may not involve gradual release of drug over an extended period of time, and thus may or may not be "sustained release." These formulations may be for any mode of administration.

Delivery systems specific for the gastrointestinal tract are roughly divided into three types: the first is a delayed release system designed to release a drug in response to, for example, a change in pH; the second is a timed-release system designed to release a drug after a predetermined time; and the third is a microflora enzyme system making use of the abundant enterobacteria in the lower part of the gastrointestinal tract (e.g., in a colonic site-directed release formulation).

An example of a delayed release system is one that uses, for example, an acrylic or cellulosic coating material and dissolves on pH change. Because of ease of preparation, many reports on such "enteric coatings" have been made. In general, an enteric coating is one which passes through the stomach without releasing substantial amounts of drug in the stomach (i.e., less than 10% release, 5% release and even 1% release in the stomach) and sufficiently disintegrating in the intestinal tract (by contact with approximately neutral or alkaline intestine juices) to allow the transport (active or passive) of the active agent through the walls of the intestinal tract.

Various in vitro tests for determining whether or not a coating is classified as an enteric coating have been published in the pharmacopoeia of various countries. A coating which remains intact for at least 2 hours, in contact with artificial gastric juices such as HCl of pH 1 at 36 to 38° C. and thereafter disintegrates within 30 minutes in artificial intestinal juices such as a $KH_2PO_4$ buffered solution of pH 6.8 is one example. One such well known system is EUDRAGIT material, commercially available and reported on by Boehringer, Manchester University, Saale Co., and the like. Enteric coatings are discussed further below.

A timed release system is represented by Time Erosion System (TES) by Fujisawa Pharmaceutical Co., Ltd. and Pulsincap by R. P. Scherer. According to these systems, the site of drug release is decided by the time of transit of a preparation in the gastrointestinal tract. Since the transit of a preparation in the gastrointestinal tract is largely influenced by the gastric emptying time, some time release systems are also enterically coated.

Systems making use of the enterobacteria can be classified into those utilizing degradation of azoaromatic polymers by an azo reductase produced from enterobacteria as reported by a group at Ohio University (M. Saffran, et al., Science, Vol. 233: 1081 (1986)) and a group at Utah University (J. Kopecek, et al., Pharmaceutical Research, 9(12), 1540-1545 (1992)); and those utilizing degradation of polysaccharides by beta-galactosidase of enterobacteria as reported by a group a Hebrew University (unexamined published Japanese patent application No. 5-50863 based on a PCT application) and a group at Freiberg University (K. H. Bauer et al., Pharmaceutical Research, 10(10), S218 (1993)). In addition, the system using chitosan degradable by chitosanase by Teikoku Seiyaku K. K. (unexamined published Japanese patent application No. 4-217924 and unexamined published Japanese patent application No. 4-225922) is also included.

The enteric coating is typically, although not necessarily, a polymeric material. Preferred enteric coating materials comprise bioerodible, gradually hydrolyzable and/or gradually water-soluble polymers. The "coating weight," or relative amount of coating material per capsule, generally dictates the time interval between ingestion and drug release. Any coating should be applied to a sufficient thickness such that the entire coating does not dissolve in the gastrointestinal fluids at pH below about 5, but does dissolve at pH about 5 and above. It is expected that any anionic polymer exhibiting a pH-dependent solubility profile can be used as an enteric coating in the practice of the present invention. The selection of the specific enteric coating material will depend on the following properties: resistance to dissolution and disintegration in the stomach; impermeability to gastric fluids and drug/carrier/enzyme while in the stomach; ability to dissolve or disintegrate rapidly at the target intestine site; physical and chemical stability during storage; non-toxicity; ease of application as a coating (substrate friendly); and economical practicality.

Suitable enteric coating materials include, but are not limited to: cellulosic polymers such as cellulose acetate phthalate, cellulose acetate trimellitate, hydroxypropylmethyl cellulose phthalate, hydroxypropylmethyl cellulose succinate and carboxymethylcellulose sodium; acrylic acid polymers and copolymers, preferably formed from acrylic acid, methacrylic acid, methyl acrylate, ammonium methylacrylate, ethyl acrylate, methyl methacrylate and/or ethyl methacrylate (e.g., those copolymers sold under the trade name EUDRAGIT); vinyl polymers and copolymers such as polyvinyl acetate, polyvinylacetate phthalate, vinylacetate crotonic acid copolymer, and ethylene-vinyl acetate copolymers; and shellac (purified lac). Combinations of different coating materials may also be used. Well known enteric coating material for use herein are those acrylic acid polymers and copolymers available under the trade name EUDRAGIT from Rohm Pharma (Germany). The EUDRAGIT series E, L, S, RL, RS and NE copolymers are available as solubilized in organic solvent, as an aqueous dispersion, or as a dry powder. The EUDRAGIT series RL, NE, and RS copolymers are insoluble in the gastrointestinal tract but are permeable and are used primarily for extended release. The EUDRAGIT series E copolymers dissolve in the stomach. The EUDRAGIT series L, L-30D and (S) copolymers are insoluble in stomach and dissolve in the intestine, and are thus most preferred herein.

A particular methacrylic copolymer is EUDRAGIT L, particularly L-30D and EUDRAGIT L 100-55. In EUDRAGIT L-30D, the ratio of free carboxyl groups to ester groups is approximately 1:1. Further, the copolymer is known to be insoluble in gastrointestinal fluids having pH below 5.5, generally 1.5-5.5, i.e., the pH generally present in the fluid of the upper gastrointestinal tract, but readily soluble or partially soluble at pH above 5.5, i.e., the pH generally present in the fluid of lower gastrointestinal tract. Another particular methacrylic acid polymer is EUDRAGIT S, which differs from EUDRAGIT L-30D in that the ratio of free carboxyl groups to ester groups is approximately 1:2. EUDRAGIT (S) is insoluble at pH below 5.5, but unlike EUDRAGIT L-30D, is poorly soluble in gastrointestinal fluids having a pH in the range of 5.5 to 7.0, such as in the small intestine. This copolymer is soluble at pH 7.0 and above, i.e., the pH generally found in the colon. EUDRAGIT (S) can be used alone as a coating to provide drug delivery in the large intestine. Alternatively, EUDRAGIT S, being poorly soluble in intestinal fluids below pH 7, can be used in combination with EUDRAGIT L-30D, soluble in intestinal fluids above pH 5.5, in order to provide a delayed release composition which can be formulated to deliver the active agent to various segments of the intestinal tract. The more EUDRAGIT L-30D used, the more proximal release and delivery begins, and the more EUDRAGIT (S) used, the more distal release and delivery begins. It will be appreciated by those skilled in the art that both EUDRAGIT L-30D and EUDRAGIT (S) can be replaced with other pharmaceutically acceptable polymers having similar pH solubility characteristics. In certain embodiments of the invention, the preferred enteric coating is ACRYL-EZE™ (methacrylic acid co-polymer type C; Colorcon, West Point, Pa.).

The enteric coating provides for controlled release of the active agent, such that drug release can be accomplished at some generally predictable location. The enteric coating also prevents exposure of the therapeutic agent and carrier to the epithelial and mucosal tissue of the buccal cavity, pharynx, esophagus, and stomach, and to the enzymes associated with these tissues. The enteric coating therefore helps to protect the active agent, carrier and a patient's internal tissue from any adverse event prior to drug release at the desired site of delivery. Furthermore, the coated material of the present invention allows optimization of drug absorption, active agent protection, and safety. Multiple enteric coatings targeted to release the active agent at various regions in the gastrointestinal tract would enable even more effective and sustained improved delivery throughout the gastrointestinal tract.

The coating can, and usually does, contain a plasticizer to prevent the formation of pores and cracks that would permit the penetration of the gastric fluids. Suitable plasticizers include, but are not limited to, triethyl citrate (Citroflex 2), triacetin (glyceryl triacetate), acetyl triethyl citrate (Citroflec A2), Carbowax 400 (polyethylene glycol 400), diethyl phthalate, tributyl citrate, acetylated monoglycerides, glycerol, fatty acid esters, propylene glycol, and dibutyl phthalate. In particular, a coating comprised of an anionic carboxylic acrylic polymer will usually contain approximately 10% to 25% by weight of a plasticizer, particularly dibutyl phthalate, polyethylene glycol, triethyl citrate and triacetin. The coating can also contain other coating excipients such as detackifiers, antifoaming agents, lubricants (e.g., magnesium stearate), and stabilizers (e.g., hydroxypropylcellulose, acids and bases) to solubilize or disperse the coating material, and to improve coating performance and the coated product.

The coating can be applied to particles of the therapeutic agent(s), tablets of the therapeutic agent(s), capsules containing the therapeutic agent(s) and the like, using conventional coating methods and equipment. For example, an enteric coating can be applied to a capsule using a coating pan, an airless spray technique, fluidized bed coating equipment, or the like. Detailed information concerning materials, equipment and processes for preparing coated dosage forms may be found in Pharmaceutical Dosage Forms: Tablets, eds. Lieberman et al. (New York: Marcel Dekker, Inc., 1989), and in Ansel et al., Pharmaceutical Dosage Forms and Drug Delivery Systems, 6th Ed. (Media, PA: Williams & Wilkins, 1995). The coating thickness, as noted above, must be sufficient to ensure that the oral dosage form remains intact until the desired site of topical delivery in the lower intestinal tract is reached.

In another embodiment, drug dosage forms are provided that comprise an enterically coated, osmotically activated device housing a formulation of the invention. In this embodiment, the drug-containing formulation is encapsulated in a semipermeable membrane or barrier containing a small orifice. As known in the art with respect to so-called "osmotic pump" drug delivery devices, the semipermeable membrane allows passage of water in either direction, but not drug. Therefore, when the device is exposed to aqueous fluids, water will flow into the device due to the osmotic pressure differential between the interior and exterior of the device. As water flows into the device, the drug-containing formulation in the interior will be "pumped" out through the orifice. The rate of drug release will be equivalent to the inflow rate of water times the drug concentration. The rate of water influx and drug efflux can be controlled by the composition and size of the orifice of the device. Suitable materials for the semipermeable membrane include, but are not limited to, polyvinyl alcohol, polyvinyl chloride, semipermeable polyethylene glycols, semipermeable polyurethanes, semipermeable polyamides, semipermeable sulfonated polystyrenes and polystyrene derivatives; semipermeable poly(sodium styrenesulfonate), semipermeable poly(vinylbenzyltrimethylammonium chloride), and cellulosic polymers such as cellulose acetate, cellulose diacetate, cellulose triacetate, cellulose propionate, cellulose acetate propionate, cellulose acetate butyrate, cellulose trivalerate, cellulose trilmate, cellulose tripalmitate, cellulose trioctanoate, cellulose tripropionate, cellulose disuccinate, cellulose dipalmitate, cellulose dicylate, cellulose acetate succinate, cellulose propionate succinate, cellulose acetate octanoate, cellulose valerate palmitate, cellulose acetate heptanate, cellulose acetaldehyde dimethyl acetal, cellulose acetate ethylcarbamate, cellulose acetate methylcarbamate, cellulose dimethylaminoacetate and ethylcellulose.

In another embodiment, drug dosage forms are provided that comprise a sustained release coated device housing a formulation of the invention. In this embodiment, the drug-containing formulation is encapsulated in a sustained release membrane or film. The membrane may be semipermeable, as described above. A semipermeable membrane allows for the passage of water inside the coated device to dissolve the drug. The dissolved drug solution diffuses out through the semipermeable membrane. The rate of drug release depends upon the thickness of the coated film and the release of drug can begin in any part of the GI tract. Suitable membrane materials for such a membrane include ethylcellulose.

In another embodiment, drug dosage forms are provided that comprise a sustained release device housing a formulation of the invention. In this embodiment, the drug-containing formulation is uniformly mixed with a sustained release polymer. These sustained release polymers are high molecular weight water-soluble polymers, which when in contact with water, swell and create channels for water to diffuse inside and dissolve the drug. As the polymers swell and dissolve in water, more of drug is exposed to water for dissolution. Such a system is generally referred to as sustained release matrix. Suitable materials for such a device include hydropropyl methylcellulose, hydroxypropyl cellulose, hydroxyethyl cellulose and methyl cellulose.

In another embodiment, drug dosage forms are provided that comprise an enteric coated device housing a sustained release formulation of the invention. In this embodiment, the drug containing product described above is coated with an enteric polymer. Such a device would not release any drug in the stomach and when the device reaches the intestine, the enteric polymer is first dissolved and only then would the drug release begin. The drug release would take place in a sustained release fashion.

Enterically coated, osmotically activated devices can be manufactured using conventional materials, methods and equipment. For example, osmotically activated devices may be made by first encapsulating, in a pharmaceutically acceptable soft capsule, a liquid or semi-solid formulation of the compounds of the invention as described previously. This interior capsule is then coated with a semipermeable membrane composition (comprising, for example, cellulose acetate and polyethylene glycol 4000 in a suitable solvent such as a methylene chloride-methanol admixture), for example using an air suspension machine, until a sufficiently thick laminate is formed, e.g., around 0.05 mm. The semipermeable laminated capsule is then dried using conventional techniques. Then, an orifice having a desired diameter (e.g., about 0.99 mm) is provided through the semipermeable laminated capsule wall, using, for example, mechanical drilling, laser drilling, mechanical rupturing, or erosion of an erodible element such as a gelatin plug. The osmotically activated device may then be enterically coated as previously described. For osmotically activated devices containing a solid carrier rather than a liquid or semi-solid carrier, the interior capsule is optional; that is, the semipermeable membrane may be formed directly around the carrier-drug composition. However, preferred carriers for use in the drug-containing formulation of the osmotically activated device are solutions, suspensions, liquids, immiscible liquids, emulsions, sols, colloids, and oils. Particularly preferred carriers include, but are not limited to, those used for enterically coated capsules containing liquid or semisolid drug formulations.

Cellulose coatings include those of cellulose acetate phthalate and trimellitate; methacrylic acid copolymers, e.g. copolymers derived from methylacrylic acid and esters thereof, containing at least 40% methylacrylic acid; and especially hydroxypropyl methylcellulose phthalate. Methylacrylates include those of molecular weight above 100,000 daltons based on, e.g. methylacrylate and methyl or ethyl methylacrylate in a ratio of about 1:1. Typical products include Eudragit L, e.g. L 100-55, marketed by Rohm GmbH, Darmstadt, Germany. Typical cellulose acetate phthalates have an acetyl content of 17-26% and a phthalate content of from 30-40% with a viscosity of ca. 45-90 cP. Typical cellulose acetate trimellitates have an acetyl content of 17-26%, a trimellityl content from 25-35% with a viscosity of ca. 15-20 cS. An example of a cellulose acetate trimellitate is the marketed product CAT (Eastman Kodak Company, USA). Hydroxypropyl methylcellulose phthalates typically have a molecular weight of from 20,000 to 130,000 daltons, a hydroxypropyl content of from 5 to 10%, a methoxy content of from 18 to 24% and a phthalyl content from 21 to 35%. An example of a cellulose acetate phthalate is the marketed product CAP (Eastman Kodak, Rochester N.Y., USA). Examples of hydroxypropyl methylcellulose phthalates are the marketed products having a hydroxypropyl content of from 6-10%, a methoxy content of from 20-24%, a phthalyl content of from 21-27%, a molecular weight of about 84,000 daltons, sold under the trademark HP50 and available from Shin-Etsu Chemical Co. Ltd., Tokyo, Japan, and having a hydroxypropyl content, a methoxyl content, and a phthalyl content of 5-9%, 18-22% and 27-35%, respectively, and a molecular weight of 78,000 daltons, known under the trademark HP55 and available from the same supplier.

The therapeutic agents may be provided in coated or uncoated capsules. The capsule material may be either hard or soft, and as will be appreciated by those skilled in the art, typically comprises a tasteless, easily administered and water soluble compound such as gelatin, starch or a cellulosic material. The capsules are preferably sealed, such as with gelatin bands or other biologically amenable sealant material. See, for example, Remington: The Science and Practice of Pharmacy, Nineteenth Edition (Easton, Pa.: Mack Publishing Co., 1995), which describes materials and methods for preparing encapsulated pharmaceuticals.

A product containing therapeutic compound(s) of the invention can be configured as a suppository. The therapeutic compound(s) of the invention can be placed anywhere within or on the suppository to favorably affect the relative release of the therapeutic compound(s). The nature of the release can be zero order, first order, or sigmoidal, as desired.

Suppositories are solid dosage forms of medicine intended for administration via the rectum. Suppositories are compounded so as to melt, soften, or dissolve in the body cavity (around 98.6° F.) thereby releasing the medication contained therein. Suppository bases should be stable, nonirritating, chemically inert, and physiologically inert. Many commercially available suppositories contain oily or fatty base materials, such as cocoa butter, coconut oil, palm kernel oil, and palm oil, which often melt or deform at room temperature necessitating cool storage or other storage limitations. U.S. Pat. No. 4,837,214 to Tanaka et al. describes a suppository base comprised of 80 to 99 percent by weight of a lauric-type fat having a hydroxyl value of 20 or smaller and containing glycerides of fatty acids having 8 to 18 carbon atoms combined with 1 to 20 percent by weight diglycerides of fatty acids (which erucic acid is an example of). The shelf life of these type of suppositories is limited due to degradation. Other suppository bases contain alcohols, surfactants, and such diluents which raise the melting temperature but also can lead to poor absorption of the medicine and side effects due to irritation of the local mucous membranes (see for example, U.S. Pat. No. 6,099,853 to Hartelendy et al., U.S. Pat. No. 4,999,342 to Ahmad et al., and U.S. Pat. No. 4,765,978 to Abidi et al.).

The base used in the pharmaceutical suppository composition of this invention includes, in general, oils and fats comprising triglycerides as main components such as cacao butter, palm fat, palm kernel oil, coconut oil, fractionated coconut oil, lard and WITEPSOL®, waxes such as lanolin and reduced lanolin; hydrocarbons such as VASELINE®, squalene, squalane and liquid paraffin; long to medium chain fatty acids such as caprylic acid, lauric acid, stearic acid and oleic acid; higher alcohols such as lauryl alcohol, cetanol and stearyl alcohol; fatty acid esters such as butyl stearate and dilauryl malonate; medium to long chain carboxylic acid esters of glycerin such as triolein and tristearin; glycerin-substituted carboxylic acid esters such as glycerin acetoacetate; and polyethylene glycols and its derivatives, such as macrogols and cetomacrogol. They may be used either singly or in combination of two or more. If desired, the composition of this invention may further include a surface-active agent, a coloring agent, etc., which are ordinarily used in suppositories.

The pharmaceutical compositions of this invention may be prepared by uniformly mixing predetermined amounts of the active ingredient, the absorption aid and optionally the base, etc. in a stirrer or a grinding mill, at an elevated temperature if required. The resulting composition may be formed into a suppository in unit dosage form by, for example, casting the mixture in a mold, or by forming it into a gelatin capsule using a capsule filling machine.

The compositions according to the present invention also can be administered as a nasal spray, nasal drop, suspension, gel, ointment, cream or powder. The administration of a composition can also include using a nasal tampon or a nasal sponge containing or impregnated with a composition of the present invention.

The nasal delivery systems that can be used with the present invention can take various forms including aqueous preparations, non-aqueous preparations and combinations thereof. Aqueous preparations include, for example, aqueous gels, aqueous suspensions, aqueous liposomal dispersions, aqueous emulsions, aqueous microemulsions and combinations thereof. Non-aqueous preparations include, for example, non-aqueous gels, non-aqueous suspensions, non-aqueous liposomal dispersions, non-aqueous emulsions, non-aqueous microemulsions and combinations thereof. The various forms of the nasal delivery systems can include a buffer to maintain pH, a pharmaceutically acceptable thickening agent and a humectant. The pH of the buffer can be selected to optimize the absorption of the therapeutic agent(s) across the nasal mucosa.

With respect to the non-aqueous nasal formulations, suitable forms of buffering agents can be selected such that when the formulation is delivered into the nasal cavity of a mammal, selected pH ranges are achieved therein upon contact with, e.g., a nasal mucosa. In the present invention, the pH of the compositions should be maintained from about 2.0 to about 6.0. It is desirable that the pH of the compositions is one which does not cause significant irritation to the nasal mucosa of a recipient upon administration. An aerosol or spray device may be used in conjunction with the nasal delivery systems of the invention.

The viscosity of the compositions of the present invention can be maintained at a desired level using a pharmaceutically acceptable thickening agent. Thickening agents that can be used in accordance with the present invention include methyl cellulose, xanthan gum, carboxymethyl cellulose, hydroxypropyl cellulose, carbomer, polyvinyl alcohol, alginates, acacia, chitosans and combinations thereof. The concentration of the thickening agent will depend upon the agent selected and the viscosity desired. Such agents can also be used in a powder formulation discussed above.

The compositions of the present invention can also include a humectant to reduce or prevent drying of the mucus membrane and to prevent irritation thereof. Illustratively, suitable humectants that can be used in the present invention include sorbitol, mineral oil, vegetable oil and glycerol; soothing agents; membrane conditioners; sweeteners; and combinations thereof. The concentration of the humectant in the present compositions will vary depending upon the agent selected.

One or more therapeutic agents may be incorporated into the nasal delivery system or any other delivery system described herein.

A composition formulated for topical administration may be liquid or semi-solid (including, for example, a gel, lotion, emulsion, cream, ointment, spray or aerosol) or may be provided in combination with a "finite" carrier, for example, a non-spreading material that retains its form, including, for example, a patch, bioadhesive, dressing or bandage. It may be aqueous or non-aqueous; it may be formulated as a solution, emulsion, dispersion, a suspension or any other mixture.

Some modes of administration include topical application to the skin, eyes or mucosa. Thus, typical vehicles are those suitable for pharmaceutical or cosmetic application to body surfaces. The compositions provided herein may be applied topically or locally to various areas in the body of a patient. As noted above, topical application is intended to refer to application to the tissue of an accessible body surface, such as, for example, the skin (the outer integument or covering) and the mucosa (the mucous-producing, secreting and/or containing surfaces). Exemplary mucosal surfaces include the mucosal surfaces of the eyes, mouth (such as the lips, tongue, gums, cheeks, sublingual and roof of the mouth), larynx, esophagus, bronchial, nasal passages, vagina and rectum/anus; in some embodiments, preferably the mouth, larynx, esophagus, vagina and rectum/anus; in other embodiments, preferably the eyes, larynx, esophagus, bronchial, nasal passages, and vagina and rectum/anus. As noted above, local application herein refers to application to a discrete internal area of the body, such as, for example, a joint, soft tissue area (such as muscle, tendon, ligaments, intraocular or other fleshy internal areas), or other internal area of the body. Thus, as used herein, local application refers to applications to discrete areas of the body.

Also in certain embodiments, including embodiments that involve aqueous vehicles, the compositions may also contain a glycol, that is, a compound containing two or more hydroxy groups. A glycol which is particularly preferred for use in the compositions is propylene glycol. In these embodiments, the glycol is preferably included in the compositions in a concentration of from greater than 0 to about 5 wt. %, based on the total weight of the composition. More preferably, the compositions contain from about 0.1 to less than about 5 wt. % of a glycol, with from about 0.5 to about 2 wt. % being even more preferred. Still more preferably, the compositions contain about 1 wt. % of a glycol.

For local internal administration, such as intra-articular administration, the compositions are preferably formulated as a solution or a suspension in an aqueous-based medium, such as isotonically buffered saline or are combined with a biocompatible support or bioadhesive intended for internal administration.

Lotions, which, for example, may be in the form of a suspension, dispersion or emulsion, contain an effective concentration of one or more of the compounds. The effective concentration is preferably to deliver an effective amount, typically at a concentration of between about 0.1-50%, by weight, or more of one or more of the compounds provided herein. The lotions also contain by weight from 1% to 50% of an emollient and the balance water, a suitable buffer, and other agents as described above. Any emollients known to those of skill in the art as suitable for application to human skin may be used. These include, but are not limited to, the following: (a) Hydrocarbon oils and waxes, including mineral oil, petrolatum, paraffin, ceresin, ozokerite, microcrystalline wax, polyethylene, and perhydrosqualene. b) Silicone oils, including dimethylpolysiloxanes, methyl phenylpolysiloxanes, water-soluble and alcohol-soluble silicone-glycol copolymers. (c) Triglyceride fats and oils, including those derived from vegetable, animal and marine sources. Examples include, but are not limited to, castor oil, safflower oil, cotton seed oil, corn oil, olive oil, cod liver oil, almond oil, avocado oil, palm oil, sesame oil, and soybean oil. (d) Acetoglyceride esters, such as acetylated monoglycerides. (e) Ethoxylated glycerides, such as ethoxylated glyceryl monostearate. (f) Alkyl esters of fatty acids having 10 to 20 carbon atoms. Methyl, isopropyl and butyl esters of fatty acids are useful herein. Examples include, but are not limited to, hexyl laurate, isohexyl laurate, isohexyl palmitate, isopropyl palmitate, isopropyl myristate, decyl oleate, isodecyl oleate, hexadecyl stearate, decyl stearate, isopropyl isostearate, diisopropyl adipate, diisohexyl adipate, dihexyldecyl adipate, diisopropyl sebacate, lauryl lactate, myristyl lactate, and cetyl lactate. (g) Alkenyl esters of fatty acids having 10 to 20 carbon atoms. Examples thereof include, but are not limited to, oleyl myristate, oleyl stearate, and oleyl oleate. (h) Fatty acids having 9 to 22 carbon atoms. Suitable examples include, but are not limited to, pelargonic, lauric, myristic, palmitic, stearic, isostearic, hydroxystearic, oleic, linoleic, ricinoleic, arachidonic, behenic, and erucic acids. (i) Fatty alcohols having 10 to 22 carbon atoms, such as, but not limited to, lauryl, myristyl, cetyl, hexadecyl, stearyl, isostearyl, hydroxystearyl, oleyl, ricinoleyl, behenyl, erucyl, and 2-octyl dodecyl alcohols. (j) Fatty alcohol ethers, including, but not limited to ethoxylated fatty alcohols of 10 to 20 carbon atoms, such as, but are not limited to, the lauryl, cetyl, stearyl, isostearyl, oleyl, and cholesterol alcohols having attached thereto from 1 to 50 ethylene oxide groups or 1 to 50 propylene oxide groups or mixtures thereof. (k) Ether-esters, such as fatty acid esters of ethoxylated fatty alcohols. (l) Lanolin and derivatives, including, but not limited to, lanolin, lanolin oil, lanolin wax, lanolin alcohols, lanolin fatty acids, isopropyl lanolate, ethoxylated lanolin, ethoxylated lanolin alcohols, ethoxylated cholesterol, propoxylated lanolin alcohols, acetylated lanolin, acetylated lanolin alcohols, lanolin alcohols linoleate, lanolin alcohols ricinoleate, acetate of lanolin alcohols ricinoleate, acetate of ethoxylated alcohol(S)-esters, hydrogenolysis of lanolin, ethoxylated hydrogenated lanolin, ethoxylated sorbitol lanolin, and liquid and semisolid lanolin absorption bases. (m) polyhydric alcohols and polyether derivatives, including, but not limited to, propylene glycol, dipropylene glycol, polypropylene glycol [M.W. 2000-4000], polyoxyethylene polyoxypropylene glycols, polyoxypropylene polyoxyethylene glycols, glycerol, ethoxylated glycerol, propoxylated glycerol, sorbitol, ethoxylated sorbitol, hydroxypropyl sorbitol, polyethylene glycol [M.W. 200-6000], methoxy polyethylene glycols 350, 550, 750, 2000, 5000, poly(ethylene oxide) homopolymers [M.W. 100,000-5,000,000], polyalkylene glycols and derivatives, hexylene glycol (2-methyl-2,4-pentanediol), 1,3-butylene glycol, 1,2,6,-hexanetriol, ethohexadiol USP (2-ethyl-1,3-hexanediol), $C_{15}$-$C_{18}$ vicinal glycol and polyoxypropylene derivatives of trimethylolpropane. (n) polyhydric alcohol esters, including, but not limited to, ethylene glycol mono- and di-fatty acid esters, diethylene glycol mono- and di-fatty acid esters, polyethylene glycol [M.W. 200-6000], mono- and di-fatty esters, propylene glycol mono- and di-fatty acid esters, polypropylene glycol 2000 monooleate, polypropylene glycol 2000 monostearate, ethoxylated propylene glycol monostearate, glyceryl mono- and di-fatty acid esters, polyglycerol poly-fatty acid esters, ethoxylated glyceryl monostearate, 1,3-butylene glycol monostearate, 1,3-butylene glycol distearate, polyoxyethylene polyol fatty acid ester, sorbitan fatty acid esters, and polyoxyethylene sorbitan fatty acid esters. (o) Wax esters, including, but not limited to, beeswax, spermaceti, myristyl myristate, and stearyl stearate and beeswax derivatives, including, but not limited to, polyoxyethylene sorbitol beeswax, which are reaction products of beeswax with ethoxylated sorbitol of varying ethylene oxide content that form a mixture of ether-esters. (p) Vegetable waxes, including, but not limited to, carnauba and candelilla waxes. (q) phospholipids, such as lecithin and derivatives. (r) Sterols, including, but not limited to, cholesterol and cholesterol fatty acid esters. (s) Amides, such as fatty acid amides, ethoxylated fatty acid amides, and solid fatty acid alkanolamides.

The lotions further preferably contain, by weight, from 1% to 10%, or preferably from 2% to 5%, of an emulsifier. The emulsifiers can be nonionic, anionic or cationic. Examples of satisfactory nonionic emulsifiers include, but are not limited to, fatty alcohols having 10 to 20 carbon atoms, fatty alcohols having 10 to 20 carbon atoms condensed with 2 to 20 moles of ethylene oxide or propylene oxide, alkyl phenols with 6 to 12 carbon atoms in the alkyl chain condensed with 2 to 20 moles of ethylene oxide, mono- and di-fatty acid esters of ethylene oxide, mono- and di-fatty acid esters of ethylene glycol where the fatty acid moiety contains from 10 to 20 carbon atoms, diethylene glycol, polyethylene glycols of molecular weight 200 to 6000, propylene glycols of molecular weight 200 to 3000, glycerol, sorbitol, sorbitan, polyoxyethylene sorbitol, polyoxyethylene sorbitan and hydrophilic wax esters. Suitable anionic emulsifiers include, but are not limited to, the fatty acid soaps, e.g., sodium, potassium and triethanolamine soaps, where the fatty acid moiety contains from 10 to 20 carbon atoms. Other suitable anionic emulsifiers include, but are not limited to, the alkali metal, ammonium or substituted ammonium alkyl sulfates, alkyl arylsulfonates, and alkyl ethoxy ether sulfonates having 10 to 30 carbon atoms in the alkyl moiety. The alkyl ethoxy ether sulfonates contain from 1 to 50 ethylene oxide units. Among satisfactory cationic emulsifiers are quaternary ammonium, morpholinium and pyridinium compounds. Certain of the emollients described in preceding paragraphs also have emulsifying properties. When a lotion is formulated containing such an emollient, an additional emulsifier is not needed, though it can be included in the composition.

The balance of the lotion is water or a $C_2$ or $C_3$ alcohol, or a mixture of water and the alcohol. The lotions are formulated by simply admixing all of the components together. Preferably the compound, such as loperamide, is dissolved, suspended or otherwise uniformly dispersed in the mixture.

Other conventional components of such lotions may be included. One such additive is a thickening agent at a level from 1% to 10% by weight of the composition. Examples of suitable thickening agents include, but are not limited to: cross-linked carboxypolymethylene polymers, ethyl cellulose, polyethylene glycols, gum tragacanth, gum kharaya, xanthan gums and bentonite, hydroxyethyl cellulose, and hydroxypropyl cellulose.

Creams can be formulated to contain a concentration effective to deliver an effective amount of therapeutic agent(s) of the invention to the treated tissue, typically at between about 0.1%, preferably at greater than 1% up to and greater than 50%, preferably between about 3% and 50%, more preferably between about 5% and 15% therapeutic agent(s) of the invention. The creams also contain from 5% to 50%, preferably from 10% to 25%, of an emollient and the remainder is water or other suitable non-toxic carrier, such as an isotonic buffer. The emollients, as described above for the lotions, can also be used in the cream compositions. The cream may also contain a suitable emulsifier, as described above. The emulsifier is included in the composition at a level from 3% to 50%, preferably from 5% to 20%.

These compositions that are formulated as solutions or suspensions may be applied to the skin, or, may be formulated as an aerosol or foam and applied to the skin as a spray-on. The aerosol compositions typically contain, by weight, from 25% to 80%, preferably from 30% to 50%, of a suitable propellant. Examples of such propellants are the chlorinated, fluorinated and chlorofluorinated lower molecular weight hydrocarbons. Nitrous oxide, carbon dioxide, butane, and propane are also used as propellant gases. These propellants are used as understood in the art in a quantity and under a pressure suitable to expel the contents of the container.

Suitably prepared solutions and suspensions may also be topically applied to the eyes and mucosa. Solutions, particularly those intended for ophthalmic use, may be formulated as 0.01%-10% isotonic solutions, pH about 5-7, with appropriate salts, and preferably containing one or more of the compounds herein at a concentration of about 0.1%, preferably greater than 1%, up to 50% or more. Suitable ophthalmic solutions are known [see, e.g., U.S. Pat. No. 5,116,868, which describes typical compositions of ophthalmic irrigation solutions and solutions for topical application]. Such solutions, which have a pH adjusted to about 7.4, contain, for example, 90-100 mM sodium chloride, 4-6 mM dibasic potassium phosphate, 4-6 mM dibasic sodium phosphate, 8-12 mM sodium citrate, 0.5-1.5 mM magnesium chloride, 1.5-2.5 mM calcium chloride, 15-25 mM sodium acetate, 10-20 mM D.L.-sodium, β-hydroxybutyrate and 5-5.5 mM glucose.

Gel compositions can be formulated by simply admixing a suitable thickening agent to the previously described solution or suspension compositions. Examples of suitable thickening agents have been previously described with respect to the lotions.

The gelled compositions contain an effective amount of therapeutic agent(s) of the invention, typically at a concentration of between about 0.1-50% by weight or more of one or more of the compounds provided herein; from 5% to 75%, preferably from 10% to 50%, of an organic solvent as previously described; from 0.5% to 20%, preferably from 1% to 10% of the thickening agent; the balance being water or other aqueous or non-aqueous carrier; such as, for example, an organic liquid, or a mixture of carriers.

The formulations can be constructed and designed to create steady state plasma levels. Steady state plasma concentrations can be measured using HPLC techniques, as are known to those of skill in the art. Steady state is achieved when the rate of drug availability is equal to the rate of drug elimination from the circulation. In typical therapeutic settings, the therapeutic agent(s) of the invention will be administered to patients either on a periodic dosing regimen or with a constant infusion regimen. The concentration of drug in the plasma will tend to rise immediately after the onset of administration and will tend to fall over time as the drug is eliminated from the circulation by means of distribution into cells and tissues, by metabolism, or by excretion. Steady state will be obtained when the mean drug concentration remains constant over time. In the case of intermittent dosing, the pattern of the drug concentration cycle is repeated identically in each interval between doses with the mean concentration remaining constant. In the case of constant infusion, the mean drug concentration will remain constant with very little oscillation. The achievement of steady state is determined by means of measuring the concentration of drug in plasma over at least one cycle of dosing such that one can verify that the cycle is being repeated identically from dose to dose. Typically, in an intermittent dosing regimen, maintenance of steady state can be verified by determining drug concentrations at the consecutive troughs of a cycle, just prior to administration of another dose. In a constant infusion regimen where oscillation in the concentration is low, steady state can be verified by any two consecutive measurements of drug concentration.

Accordingly, the invention herein is suited for chronic, acute, symptomatic, therapeutic, or prophylactic treatment of human or animal diseases or disorders comprising maladies of malignant or benign growth; disorders of metabolism; exaggerated inflammation and allergic responses; cardiovascular diseases; and complications associated with transplantation. Additionally, in an embodiment, the compounds of this invention act as potent and selective anti-pain or tension agents. In a further embodiment, the compounds of this invention act as potent and selective inhibitors of neurogenic spasmodic muscle contractions.

In an embodiment, the compounds and compositions of the invention are provided for use in treating or reducing the severity of organ transplantation rejection.

A compound of the invention may also be therapeutic for diseases of inflammation and allergy as manifested in cells required to mount an inflammatory response, such as neutrophils, macrophage, mast cells, T-cells, B-cells, plasma cells, dendritic cells and eosinophils. The pain and tension associated with inflammatory diseases or conditions which may be treatable by the invention include, but are not limited to, autoimmune diseases and common arthritis types, including rheumatoid arthritis, osteoarthritis, ankyolsing spondylitis, psoriatic arthritis; psoriasis, systemic lupus erythematosus, glomerulonephritis, scleroderma, general renal failure, inflammatory bowel disease, ulcerative colitis, Crohn's disease, pancreatitis, multiple sclerosis; inflammation due to hyper-responsiveness to cytokine production, chronic obstructive pulmonary, airway or lung disease (COPD, COAD or COLD), acute respiratory distress syndrome (ARDS) and occupation-related diseases such as aluminosis, anthracosis, asbestosis, chalicosis, ptilosis, siderosis, silicosis, tabacosis and byssinosis. Additionally, a compound of the present invention encompasses treatment of parasite-related diseases involving hypereosinophilia. A compound of the invention is also therapeutic for diseases and conditions related to immediate-type hypersensitivity, also referred to as allergic responses, conditions and diseases. These diseases and conditions include, but are not limited to, asthma (extrinsic or intrinsic), asthma related sequelae including small and large airway hyperactivity, bronanaphylaxis, aspirin-induced asthma, allergic airway inflammation, urticaria, Steven-Johnson syndrome, atopic dermatitis, bolus pemphigoid and the like. A compound of the invention is therapeutic for diseases involving neutrophils, macrophages, mast cells, T-cells, B-cells, plasma-cells, basophiles, eosinophiles and mast cells.

A compound of the present invention may also be used in treatment or therapy for discomfort and pain due to inflammation associated with metabolic diseases, such as diabetes and obesity.

Cardiovascular diseases, acute heart failure, enlargement of the heart, and atherosclerosis are also diseases that are suitable for ameliorating treatment or therapy using a compound of the invention described herein. Nonlimiting examples of cardiovascular diseases also include pulmonary hypertension, deep venous thrombosis, stroke, myocardial infarction, myocardial contractility diseases or disorders, ischemia, thromboembolism, pulmonary embolism, acute arterial ischemia, peripheral thrombotic occlusions, coronary artery disease and acute coronary syndrome (ACS). In an embodiment, the cardiovascular disease treated or lessened by a compound of this invention is artherosclerosis. In an embodiment, the neurovascular effect on cardiovascular disease treated or lessened by a compound of this invention is a myocardial contractility disease or disorder or an acute coronary syndrome.

In addition to the monotherapies described above, a compound of the invention is also therapeutic in combination with existing therapies directed to hypertension and tissue swelling. In this context, a combination is defined as a fixed proportion of the compound of the invention and another non-imidazoline type compound or compounds to be administered to the patient simultaneously, as in a kit, or at separate and distinct, or predetermined time periods or time intervals. The inhibitor compound or compounds need not be restricted to small molecular compounds such as those of this invention. The non-Imidazoline inhibitor compound may be a biologic such as an antibody, receptor, binding protein, lipid, sugar or the like. Furthermore, the other component or components of the combination may also represent energy in the form of radiation, or sources from the full range of the electromagnetic spectrum such heat, sound, X-ray or the like. Sources of irradiation, which may be externally or internally applied, include cobalt, gold, tritium, and radioisotopes capable of supplying effective translational energy for killing pain causing malignant tumors and tumorivasculary tissues.

By analogy, the compounds of this invention maybe combined with existing non-Isometheptene effective anti-pain and anti-cramping therapies for patients suffering from metabolic diseases, inflammatory and allergic disorders, atherosclerosis, cardiovascular disease, as described above for monotherapeutic uses.

Accordingly, the invention also provides compounds and pharmaceutical compositions thereof, which are useful as pain inhibitors, as well as methods for using such compounds to treat, ameliorate, reduce, eliminate, or prevent a painful condition, disease, or pathology, associated with neurovascular spasms. In some embodiments, the invention provides methods for using the compounds of the invention to treat, ameliorate, reduce the severity of, or prevent diseases or disorders, e.g., inflammatory diseases, allergic diseases, etc.

A biological sample refers to an in vitro or ex vivo sample and includes, without limitation, cell cultures or extracts thereof; cell, tissue or organ samples, or extracts thereof; biopsied material obtained from a subject, i.e., an animal or mammalian subject, including humans, or extracts thereof; and blood, plasma, serum, urine, saliva, feces, semen, tears, body cavity lavage material, or other body fluids or extracts thereof.

In another embodiment, one or more of the neurovascular spasm ameliorating compounds of the present invention, or pharmaceutically acceptable compositions containing such compounds, are employed for coating or lining an implantable medical device, e.g., stents, catheters, grafts, vascular grafts, prostheses and artificial valves. As will be appreciated by one having skill in the art, vascular grafts have been used to overcome restenosis, or a re-narrowing of a vessel wall following injury or surgery. In some patients, the implantation of a stent or another type of implantable device may be associated with a risk of clot formation (embolism) or platelet activation. To overcome or mitigate this risk, the stent or device can be coated (pre-coated) with a compound of the invention or a pharmaceutically acceptable composition thereof. In accordance with the invention, such coating (or pre-coating) may reduce or prevent inflammation reactions or undesirable cell proliferation with concomitant pain and muscle pain following implantation.

General description of suitable coatings and coated implantable devices may be found in U.S. Pat. Nos. 6,099,562; 5,886,026 and 5,304,121. The coatings are typically biocompatible polymeric materials such as a hydrogel polymer, polymethyldisiloxane, polycaprolactone, polyethylene glycol, polylactic acid, ethylene vinyl acetate and mixtures or combinations thereof. Optionally, the coatings may be covered with a suitable topcoat of a material such as fluorosilicone, polysaccharides, polyethylene glycol, phospholipid, or a combination thereof, to impart controlled release characteristics for the coated compounds or compositions. An implantable medical device coated or lined with a compound or composition according to the present invention is a further embodiment embraced by the invention. Additionally, the compounds may be coated on an implantable medical device through the use of beads or particles or through co-formulation with a polymer or other molecule to provide a drug depot, which allows the compound (drug) to be released over a longer time period relative to the administration of an aqueous formulation of the compound (drug).

The combination drug product (CDP) preparations for the treatment of migraine may include injectable solutions for epidermal, parenteral, peroral, or intravenous administration, or crystalline powders encapsulated in capsules or compressed in tablets for oral or sublingual administration.

Thus, Isometheptene may be one of the active ingredients in a combination drug product (CDP) containing Isometheptene, caffeine, and acetaminophen. The proposed clinical indication is migraine and 2 formulations (a tablet and a capsule formulation) of the CDP will be evaluated.

The CDP tablet formulation is to be same as Prodrin, which contains 135 mg of Isometheptene, 20 mg of caffeine, and 500 mg of acetaminophen (about 1.93 mg/kg of Isometheptene, 0.29 mg/kg of caffeine, and 7.14 mg/kg of acetaminophen for a 70 kg human).

The CDP capsule formulation is to be same as MigraLam or MigraTen, both of which contains 65 mg of Isometheptene, 100 mg of caffeine, and 325 mg of acetaminophen (about 0.92 mg/kg of Isometheptene, 1.43 mg/kg of caffeine, and 4.64 mg/kg of acetaminophen for a 70 kg human).

According to information on the Internet (WebMD Professional), the recommended oral dosing regimen for a CDP containing Isometheptene (racemic compound), acetaminophen, and dichloralphenazone for the symptomatic relief of migraine headache in adults is 2 capsules (each containing 65 mg of Isometheptene mucate, 325 mg acetaminophen, and 100 mg of dichloralphenazone) initially, followed by 1 capsule every hour until the headache is relieved. The dosage should not exceed 5 capsules in 12 hours. Based on information obtainable on the Internet, a similar dosing regimen is recommended for CDPs containing Isometheptene (racemic), caffeine, and acetaminophen. While no clinical trials on CDPs containing Isometheptene U.S.P. in children from 8 to 12 years of age have been reported in the published literature, a publication (Solomon, 1995) indicated the recommended dosing regimen for this age group is 1 capsule initially, followed by 1 capsule every hour to a limit of 3 capsules per day. The above dosage regimens for a CDP containing Isomethepene, caffeine, and acetaminophen are for the acute management of migraine. In humans, migraine headaches are recurring events that may require frequent (more than once a month) acute treatment and chronic (over years) treatment. Thus, migraine headache is considered a chronic condition that requires multiple acute treatments.

Metabolism:

Based on the published results of the completed nonclinical pharmacokinetic and drug metabolism studies on Isometheptene, the following is an overview of the key findings:

1. Isometheptene is metabolized to 6-amino-2-methyl-heptan-2-ol (heptaminol) in rats and humans and this metabolite is excreted in the urine.

2. Other human metabolites of Isometheptene include N-desmethyl-Isometheptene, which metabolite undergoes acid hydrolysis to form 2-methyl-6-methylamino-2-hepten-1-ol.

3. Based on results in rats, the metabolism of Isometheptene and urinary excretion of formed metabolites that may be stereospecific.

Isometheptene is usually administered as pharmaceutically acceptable salt such as Isometheptene mucate, bitartrate, or hydrochloride.

Isometheptene (or Isometheptene mucate salt) is a sympathomimetic amine known to cause to constrict blood vessels of both arteries and veins.

Drug Description

Each red capsule contains Isometheptene Mucate USP, 65 mg, Dichloralphenazone USP, 100 mg, and Acetaminophen USP, 325 mg.

Isometheptene Mucate is a white crystalline powder having a characteristic aromatic odor and bitter taste. It is an unsaturated aliphatic amine with sympathomimetic properties.

Dichloralphenazone is a white, microcrystalline powder, with slight odor and tastes saline at first, becoming acrid. It is a mild sedative.

Acetaminophen, a non-salicylate, occurs as a white, odorless, crystalline powder, possessing a slightly bitter taste.

Midrin (acetaminophen, Isometheptene and dichloralphenazone) capsules contain FD&C Yellow No. 6 as a color additive.

Since CDPs containing, e.g., Isometheptene, caffeine, and acetaminophen have been used for years (i.e., have substantial clinical experience) for the treatment of migraine, the proposed use of the Isometheptene R-enantiomer (isomer 2), taken alone or in combination compositions, is not believed to have toxic or other undesirable side effects upon use.

Isometheptene R-enantiomer as an active ingredient in a CDP with caffeine and acetaminophen as the other active ingredients is to be further evaluated for the treatment of migraine. The proposed clinical route and frequency of dosing for the CDP are oral and as needed (dosing no more than once an hour with no more than doses during a 12-hour period). To support the clinical development of Isometheptene as a CDP, the literature search identified 4 papers that provided some information on pharmacokinetics of Isometheptene alone but none for combinations with other agents. No pharmacokinetic papers were found on the CDPs to be evaluated during the proposed clinical trials on Isometheptene to be administered orally as one of the active agents in the CDP.

Alternatively, the treatment with S-Isometheptene follows similar procedures.

Safety of the Isometheptene R-Enantiomer

The pharmacology, pharmacokinetics, and toxicology of Isometheptene enantiomer alone or as a CDP containing, e.g., Isometheptene R-enantiomer, caffeine, and acetaminophen are important aspects for characterizing the efficacy of the inventive compound.

No published papers were identified that provided information on the safety pharmacology profiles of racemic Isometheptene alone or as an active ingredient in a CDP.

Treatment with R-Isometheptene includes a daily oral dose or twice daily ranging from about 10 mg to about 50 mg, taken alone, or combined with other active ingredients such as a mild sedative, and a decongestant or proton pump inhibitor, such as Ibuprofen or Celebrex, at a dosage of about 100 mg to about 900 mg.

One published report (Valdivia 2004) investigated the cardiovascular responses induced by Isometheptene (IV at consecutive doses of 0.03, 0.1, 0.3, 1, and 3 mg/kg with 5 to 15 minutes between doses) in male Wistar rats. Isometheptene alone produced dose-dependent increases in heart rate and diastolic blood pressure. Using co-administration of various receptor antagonists, the Isometheptene-induced tachycardic responses in rats apparently involved only an indirect (tyramine-like action) mechanism mediated by α-adrenoceptors and the corresponding vasopressor responses were mediated by a predominantly indirect (tyramine-like action) as well as a minor direct (α-adrenoceptors) sympathomimetic mechanism.

These findings suggest that Isometheptene (R)-enantiomer treatment, administered orally either alone or in a CDP, may have a lower potential adverse effects to the cardiovascular system.

In view of the ambiguous physiological effects of tests involving the racemic Isometheptene compound or composition thereof, it is believed that the effect of its single active (R)-Isometheptene enantiomer (isomer 2) will be more specific with fewer side effects. Therefore, treatment of patients suffering from migraine may be studied by applying increasing doses of Isometheptene (R)-enantiomer in order to determine the efficacy of the composition in a pharmacological profile of the induced cardiovascular responses and side effects on heart rates.

For example, Isometheptene (R)-enantiomer as an active ingredient of a CDP with caffeine and acetaminophen as the other active ingredients is due to be evaluated for the treatment of migraine.

Example 1

Variable Dosage

Isometheptene mucate (racemic mixture): 50 mg, 100 mg, 150 mg, 200 mg, 500 mg.

Example 2

Variable Dosage

Isometheptene R-enantiomer mucate: 15 mg, 0 mg, 50 mg, 100 mg, 150 mg, 200 mg or 500 mg.

Example 3

FDC

| | |
|---|---|
| R-Isometheptene enantiomer mucate: | 50 mg |
| Acetaminophen | 325 mg, (or |
| Ibuprofen | 200 mg) |
| Dichloralphenazone (DCP) | 100 mg |

Example 4

FDC

| | |
|---|---|
| R-Isometheptene enantiomer mucate | 32.5 mg |
| Dichloralphenazone | 100 mg, and |
| Acetaminophen | 325 mg, (or |
| Ibuprofen | 200, 400 or 800 mg) |

The CDP tablet formulation is to contain 135 mg of (R)-Isometheptene enantiomer, 20 mg of caffeine, and 500 mg of acetaminophen, (or Ibuprofen 800 mg). The CDP capsule formulation is to contain 65 mg of Isometheptene isomer ((R)-enantiomer), 100 mg of caffeine, and preferably 325 mg of acetaminophen (or Ibuprofen, 200 mg, 400 mg, or 800 mg).

Injectable CDP solution may contain 50 mg Isometheptene isomer 2 ((R)-enantiomer), combined with 30 mg caffeine, and 125 mg of acetaminophen in 0.50 ml phosphate buffered water or saline.

APPENDIX I

Assays of Compounds Affinity with Imidazoline I1 Receptor

Figure 24:
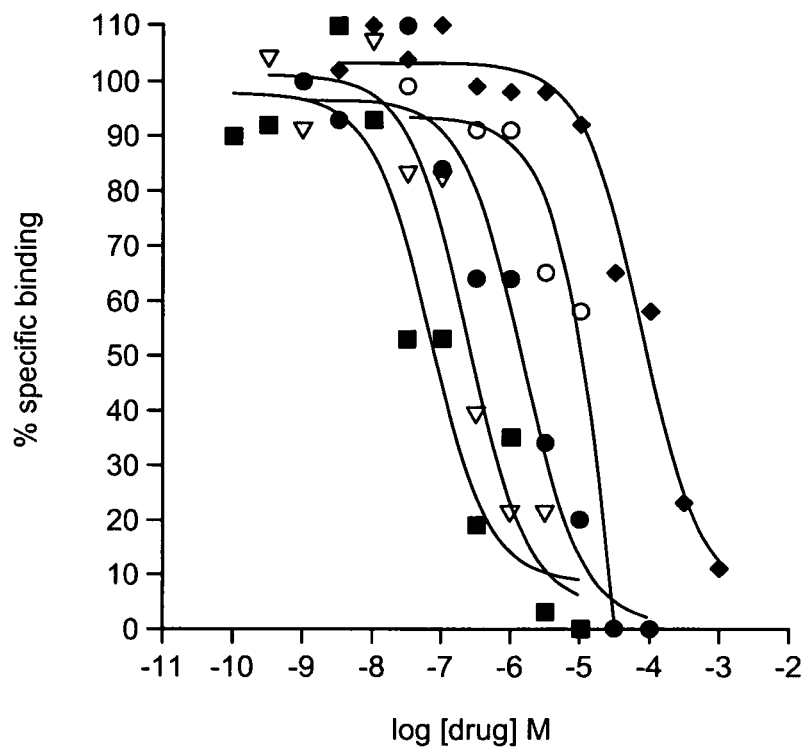
FIG. 24 illustrates the $I_1$ receptor binding assay comparison of several reference drugs.

The following experiment shows a reference drug binding assay of Imidazoline receptor, see FIG. 24:

Assay Characteristics:
  $K_D$ (binding affinity): 10 nM
  $B_{max}$ (receptor number): 50 fmol/mg protein
Materials and Methods:
  Receptor Source: PC12 cell membranes
  Radioligand: [$^{125}$I]-Iodoclonidine (1100 Ci/mmol)
  Final ligand concentration—[2.0 nM]
  Non-specific Determinant: Iodoclonidine [10.0 μM]

Reference Compound: Iodoclonidine
Positive Control: Iodoclonidine
Incubation Conditions: Reactions were carried out in 50 mM TRIS-HCl (pH 7.4) containing 5 mM EDTA, 5 mM EGTA, 5 mM MgCl$_2$ and 30 µM norepinephrine at room temperature for 60 minutes. The reaction was terminated by rapid vacuum filtration onto glass fiber filters. Radioactivity trapped onto the filters was determined and compared to control values in order to ascertain any interactions of test compound with the Imidazoline$_1$ binding site.

LITERATURE REFERENCE

Steffen, G., Dendorfer, A., and Dominiak, P. Imidazoline binding sites on PC12 cells and bovine chromaffin cells. *Ann. N.Y. Acad. Sci.* 763: 157-162 (1995), with modifications.

Piletz, J. E., Zhu, H. E., and Chikkala, D. N., Comparison of Ligand Binding Affinities at Human I$_1$-Imidazoline Binding Sites and the High Affinity State of Alpha-2 Adrenergic Subtypes. *JPET*: 279: 694-7002 (1996).

Evaluation of the Affinity of Compounds for the Peripheral Imidazoline Receptor in Bovine Adrenal Medulla Glands Determined in a Radioligand Binding Assay.

Experimental Protocol

Membrane homogenates of adrenal medulla glands (200 µg protein) are incubated for 60 min at 22° C. with 15 nM [$^3$H]clonidine in the absence or presence of the test compound in a buffer containing 137 mM NaCl, 2.68 mM KCl, 0.5 mM MgCl$_2$, 8.1 mM Na$_2$HPO$_4$, 1.47 mM KH$_2$PO$_4$, 0.5 mM EGTA, 0.5 mM EDTA, 0.5% ascorbic acid and 0.1% BSA (pH 7.4). It also contains 10 µM RX821002 to block the α$_2$-adrenergic receptors.

Nonspecific binding is determined in the presence of 10 µM rilmenidine.

Following incubation, the samples are filtered rapidly under vacuum through glass fiber filters (GF/B, Packard) presoaked with 0.3% PEI and rinsed several times with ice-cold 50 mM Tris-HCl using a 96-sample cell harvester (Unifilter, Packard). The filters are dried then counted for radioactivity in a scintillation counter (Topcount, Packard) using a scintillation cocktail (Microscint 0, Packard).

The results are expressed as a percent inhibition of the control radioligand specific binding.

The standard reference compound is rilmenidine, which is tested in each experiment at several concentrations to obtain a competition curve from which its IC$_{50}$ is calculated.

Bibliographic reference: MOLDERINGS, G. J., MOURA, D., FINK, K., BONISCH, H. and GOTHERT, M. (1993), Binding of [3H]clonidine to I1-imidazoline sites in bovine adrenal medullary membranes, Naun.-Sch. Arch. Pharm., 348: 70.

| General information: | |
|---|---|
| Assay volume and format: | 200 µl in 96-well plate: |
| Compound addition: | [100x] solution in solvent |
| Maximum tolerable DMSO concentration: | 1% |
| ExpresScreen compatible: | Yes ☒  No ☐ |
| HTS compatible: | Yes ☐  No ☒ |

Evaluation of the Affinity of Compounds for the Central Imidazoline I2 Receptor in the Rat Cerebral Cortex Determined in a Radioligand Binding Assay.

Experimental Protocol:

Membrane homogenates of cerebral cortex (1 mg protein) are incubated for 30 min at 22° C. with 2 nM [$^3$H]idazoxan in the absence or presence of the test compound in a buffer containing 50 mM Tris-HCl (pH 7.4), 0.5 mM EDTA and 3 µM yohimbine.

Nonspecific binding is determined in the presence of 10 µM cirazoline.

Following incubation, the samples are filtered rapidly under vacuum through glass fiber filters (Filtermat B, Wallac) presoaked with 0.3% PEI and rinsed several times with an ice-cold buffer containing 50 mM Tris-HCl and 150 mM NaCl using a 48-sample cell harvester (Mach II, Tomtec). The filters are dried then counted for radioactivity in a scintillation counter (Betaplate 1204, Wallac) using a solid scintillator (Meltilex B/HS, Wallac).

The results are expressed as a percent inhibition of the control radioligand specific binding. The standard reference compound is idazoxan, which is tested in each experiment at several concentrations to obtain a competition curve from which its IC$_{50}$ is calculated.

Bibliographic reference: BROWN, C. M., MAC KINNON, A. C., McGRATH, J. C., SPEDDING, M. and KILPATRICK A. T. (1990), α$_2$-adrenoceptor subtypes and imidazoline-like binding sites in the rat brain, Brit. J. Pharmacol, 99: 803.

| General information | |
|---|---|
| Assay volume and format: | 1 ml in 48-well plate |
| Compound addition: | [100x] solution in solvent |
| Maximum tolerable DMSO concentration: | 1% |
| ExpresScreen compatible: | Yes ☒  No ☐ |
| HTS compatible: | Yes ☐  No ☒ |

TAAR1 cAMP Assay

The cAMP Hunter cell line expressing human TAAR1 was expanded from freezer stocks according to standard procedures. Cells were seeded in a total volume of 20 µL into white walled, 384-well microplates and incubated at 37° C. for the appropriate time prior to testing. cAMP modulation was determined using the DiscoveRx HitHunter cAMP XS+ assay. For agonist determination, cells were incubated with sample to induce response. Media was aspirated from cells and replaced with 15 µL 2:1 HBSS/10 mM Hepes:cAMP XS+ Ab reagent. Intermediate dilution of sample stocks was performed to generate 4× sample in assay buffer. 4.5 µL of 4× sample was added to cells and incubated at 37° C. or room temperature for 30 or 60 minutes. Final assay vehicle concentration was 1%. After appropriate compound incubation, assay signal was generated through incubation with 20 µL cAMP XS+ ED/CL lysis cocktail for one hour followed by incubation with 20 µL cAMP XS+ EA reagent for three hours at room temperature. Microplates were read following signal generation with a PerkinElmer Envision™ instrument for chemiluminescent signal detection. Compound activity was analyzed using CBIS data analysis suite (ChemInnovation, CA). For Gs agonist mode assays, percentage activity was calculated using the following formula: % Activity=100%×(mean RLU of test sample−mean RLU of vehicle control)/(mean RLU of MAX control−mean RLU of vehicle control).

X-ray Data of (R)-Isometheptene Crystal

```
++++++++++++++++++++++++++++++++++++++++++++++++++++++++++++++++++
+ SHELXTL XLMP CRYSTAL STRUCTURE REFINEMENT -  MULTI-CPU VERSION  +
+ Copyright(c) Bruker AXS Inc. 1993-2013           Version 2013/2 +
+ xs0061a                       started at 14:26:54 on 19-Apr-2013 +
++++++++++++++++++++++++++++++++++++++++++++++++++++++++++++++++++

Command line parameters: xs0061a -a50000 -b3000 -c624 -t4

-a sets the approximate maximum number of atoms including hydrogens.
-b sets the maximum number of full-matrix parameters (leave unchanged for
CGLS). For example -b9000 allows refinement of 1000 anisotropic atoms or
3000 with BLOC 1. For a 32-bit version, -b times the square root of the
number of threads should not exceed about 65500. -c sets the reflection
buffer size. This depends on the CPU cache size but will rarely need
changing. -t sets the number of threads, otherwise the multi-CPU version
sets this equal to the number of available CPUs. For optimal performance
on systems with hyperthreading, usually the hyperthreading should be
switched off or -t used to halve the number of threads; e.g. -t4 rather
than -t8 for an Intel i7 processor.

Running  4 threads on  4 processors

TITL xs0061 in C2
CELL   1.54178    36.3410    7.88266    9.82344    90.000    94.0983   90.000
```

```
ZERR    4       0.0007    0.00012   0.00018   0.000     0.0017
0.000
LATT  -7
SYMM            - X ,               Y ,       - Z
SFAC  C   H   N   O
UNIT  96  192  8  32

V =    2806.86    F(000) =    1080.0    Mu =    0.71 mm-1    Cell
Wt =   1970.56    Rho =       1.166

TEMP -173

ACTA
HTAB
BOND
BOND $H
CONF
WPDB

L.S. 6
FMAP 2
PLAN 10
OMIT -2 143.8
OMIT -5 1 12
OMIT -7 3 11
OMIT -16 2 11

TWIN

WGHT    0.103900    1.128800
BASF    0.05322
FVAR        3.98836    0.51966
PART 0
rem anion
```

```
C1    1    0.706163    0.429292    0.997366    11.00000    0.04257
0.02979 =
          0.01397    0.00280    0.00441    0.00080
C2    1    0.737196    0.416578    0.899224    11.00000    0.03906
0.02217 =
          0.01755    0.00256    0.00469    -0.00129
AFIX  13
H2    2    0.761413    0.428392    0.953460    11.00000    -1.20000
AFIX  0
C3    1    0.733519    0.561090    0.796035    11.00000    0.03842
0.02105 =
          0.01577    0.00147    0.00572    -0.00054
AFIX  13
H3    2    0.734400    0.669777    0.848669    11.00000    -1.20000
AFIX  0
C4    1    0.765848    0.563035    0.704206    11.00000    0.03669
0.02269 =
          0.01495    0.00103    0.00358    0.00112
AFIX  13
H4    2    0.764812    0.455267    0.650362    11.00000    -1.20000
AFIX  0
C5    1    0.762613    0.710609    0.602455    11.00000    0.03771
0.02507 =
          0.01690    0.00232    0.00290    0.00001
AFIX  13
H5    2    0.738153    0.702683    0.549339    11.00000    -1.20000
AFIX  0
C6    1    0.793051    0.694567    0.502852    11.00000    0.03931
0.02949 =
          0.01338    0.00339    0.00197    -0.00255
O1    4    0.684903    0.304810    1.007669    11.00000    0.04330
0.03127 =
          0.01836    0.00140    0.00736    -0.00533
O2    4    0.704492    0.565405    1.063210    11.00000    0.05187
0.02985 =
```

```
                0.01987   -0.00213    0.01012   -0.00404
O3     4     0.736861    0.259152    0.829142   11.00000    0.04407
0.02391 =
                0.02421    0.00147    0.00824    0.00177
AFIX 147
H3A    2     0.753630    0.196468    0.864450   11.00000   -1.50000
AFIX   0
O4     4     0.698945    0.555610    0.718080   11.00000    0.03859
0.02625 =
                0.02065   -0.00120    0.00333    0.00254
AFIX 147
H4A    2     0.698511    0.471816    0.665161   11.00000   -1.50000
AFIX   0
O5     4     0.800339    0.566849    0.782267   11.00000    0.03729
0.02654 =
                0.01801    0.00002    0.00172    0.00194
AFIX 147
H5A    2     0.801469    0.653978    0.831620   11.00000   -1.50000
AFIX   0
O6     4     0.764202    0.866703    0.674143   11.00000    0.04269
0.02118 =
                0.02590    0.00153    0.00527    0.00206
AFIX 147
H6     2     0.746633    0.928953    0.644724   11.00000   -1.50000
AFIX   0
O7     4     0.815560    0.814816    0.492163   11.00000    0.04407
0.03204 =
                0.01724    0.00210    0.00381   -0.00749
O8     4     0.793526    0.558252    0.434976   11.00000    0.04958
0.03276 =
                0.01735   -0.00154    0.00882   -0.00683 rem cation 1
C7     1     0.819348    0.202910    0.650323   11.00000    0.04950
0.03230 =
```

```
              0.02744    0.00098    0.00141    0.00067
     AFIX 137
     H7A    2    0.828867    0.297389    0.707347    11.00000    -1.50000
     H7B    2    0.792381    0.199838    0.649884    11.00000    -1.50000
     H7C    2    0.826562    0.218425    0.556896    11.00000    -1.50000
     AFIX   0
     N1     3    0.834990    0.039478    0.706639    11.00000     0.03931
  0.03017 =
              0.01935    0.00134    0.00444   -0.00193
     AFIX  23
     H1A    2    0.828464   -0.052741    0.640877    11.00000    -1.20000
     H1B    2    0.823466    0.012955    0.792449    11.00000    -1.20000
     AFIX   0
     C8     1    0.876082    0.043222    0.734758    11.00000     0.03982
  0.04674 =
              0.03289   -0.00464    0.00022   -0.00285
     AFIX  13
     H8     2    0.881746    0.141568    0.797068    11.00000    -1.20000
     AFIX   0
     C9     1    0.895090    0.078200    0.605151    11.00000     0.04557
  0.06564 =
              0.05385    0.01229    0.01295   -0.00205
     AFIX 137
     H9A    2    0.884468    0.005389    0.531613    11.00000    -1.50000
     H9B    2    0.921519    0.054340    0.620819    11.00000    -1.50000
     H9C    2    0.891565    0.197476    0.579266    11.00000    -1.50000
     AFIX   0
     C10    1    0.889482   -0.114596    0.811526    11.00000     0.04077
  0.05675 =
              0.04016    0.00107    0.00061    0.00232
     AFIX  23
     H10A   2    0.874505   -0.129428    0.890996    11.00000    -1.20000
     H10B   2    0.915311   -0.095442    0.847279    11.00000    -1.20000
     AFIX   0
```

```
C11    1   0.887981   -0.279556   0.729606   11.00000    0.05079
0.05548 =
           0.04590    -0.00371    0.00106    0.00148
AFIX   23
H11A   2   0.862621   -0.297923   0.688522   11.00000   -1.20000
H11B   2   0.904765   -0.271591   0.654796   11.00000   -1.20000
AFIX    0
C12    1   0.899169   -0.425602   0.820456   11.00000    0.05925
0.05858 =
           0.06679    -0.00308   -0.01167    0.00706
AFIX   43
H12    2   0.880945   -0.465923   0.877147   11.00000   -1.20000
AFIX    0
C13    1   0.930887   -0.505015   0.831839   11.00000    0.07218
0.06479 =
           0.12357    -0.02518   -0.02976    0.01849
C14    1   0.937543   -0.645845   0.938741   11.00000    0.13726
0.06373 =
           0.18150    -0.02967   -0.10210    0.03701
AFIX  137
H14A   2   0.955775   -0.607385   1.010448   11.00000   -1.50000
H14B   2   0.946774   -0.747519   0.894967   11.00000   -1.50000
H14C   2   0.914329   -0.672521   0.979041   11.00000   -1.50000
AFIX    0
C15    1   0.961569   -0.466204   0.744866   11.00000    0.07420
0.15932 =
           0.29645    -0.03694    0.04293    0.03960
AFIX  137
H15A   2   0.969859   -0.571080   0.703075   11.00000   -1.50000
H15B   2   0.982111   -0.415748   0.800970   11.00000   -1.50000
H15C   2   0.952996   -0.386159   0.673130   11.00000   -1.50000
AFIX    0

EADP C16 C16'
EADP N2 N2'
```

```
SIMU 0.01 C16 > C24'

PART -1
SAME C7 > C15
C16    1    0.817876   -0.575492    1.145028   21.00000    0.05879
0.03379 =
            0.02613    0.00387   -0.00301   -0.00301
AFIX 137
H16A   2    0.824783   -0.577631    1.050419   21.00000   -1.50000
H16B   2    0.790934   -0.577668    1.146063   21.00000   -1.50000
H16C   2    0.828322   -0.674800    1.193796   21.00000   -1.50000
AFIX   0
N2     3    0.832394   -0.418590    1.212875   21.00000    0.03675
0.03922 =
            0.01831    0.00444    0.00551   -0.00412
AFIX  23
H2A    2    0.824418   -0.320208    1.155467   21.00000   -1.20000
H2B    2    0.821089   -0.406530    1.301116   21.00000   -1.20000
AFIX   0
C17    1    0.873014   -0.411688    1.238798   21.00000    0.04098
0.05984 =
            0.03281    0.00981    0.01325   -0.00784
AFIX  13
H17    2    0.883981   -0.467369    1.159670   21.00000   -1.20000
AFIX   0
C18    1    0.885252   -0.514419    1.367056   21.00000    0.05376
0.10799 =
            0.03830    0.03039   -0.00215    0.01548
AFIX 137
H18A   2    0.874314   -0.465184    1.446397   21.00000   -1.50000
H18B   2    0.912208   -0.511356    1.381479   21.00000   -1.50000
H18C   2    0.877041   -0.632240    1.355094   21.00000   -1.50000
AFIX   0
C19    1    0.886726   -0.230538    1.245134   21.00000    0.05783
0.08011 =
```

```
                0.04446   0.00148   0.00847  -0.01746
AFIX   23
H19A   2   0.881834  -0.181452   1.334831   21.00000  -1.20000
H19B   2   0.872764  -0.163246   1.173719   21.00000  -1.20000
AFIX    0
C20    1   0.927940  -0.216222   1.225018   21.00000   0.06125
0.09971 =
                0.05744  -0.01526   0.01160  -0.02412
AFIX   23
H20A   2   0.941704  -0.299118   1.284802   21.00000  -1.20000
H20B   2   0.932335  -0.243875   1.129221   21.00000  -1.20000
AFIX    0
C21    1   0.941852  -0.040835   1.257853   21.00000   0.06898
0.09165 =
                0.06506   0.00085   0.00994  -0.03485
AFIX   43
H21    2   0.929850   0.048653   1.207409   21.00000  -1.20000
AFIX    0
C22    1   0.968782   0.004998   1.348389   21.00000   0.05593
0.09469 =
                0.08296  -0.00832   0.01894  -0.01592
C23    1   0.990770  -0.116243   1.445192   21.00000   0.09515
0.11136 =
                0.13723  -0.01484  -0.03882  -0.00986
AFIX  137
H23A   2   0.981281  -0.231853   1.431714   21.00000  -1.50000
H23B   2   0.988239  -0.081326   1.539812   21.00000  -1.50000
H23C   2   1.016854  -0.113099   1.425966   21.00000  -1.50000
AFIX    0
C24    1   0.978993   0.188866   1.365377   21.00000   0.07487
0.09986 =
                0.14217  -0.01248   0.01156  -0.02779
AFIX  137
H24A   2   0.966749   0.254831   1.290662   21.00000  -1.50000
H24B   2   1.005789   0.201401   1.363821   21.00000  -1.50000
```

```
H24C   2    0.971102     0.230298    1.452729    21.00000   -1.50000
AFIX   0

PART  -2
SAME  C7 > C15
C16'   1    0.822474    -0.582154    1.157335   -21.00000    0.05879
0.03379 =
            0.02613     0.00387    -0.00301    -0.00301
AFIX 137
H16D   2    0.833363    -0.609037    1.071487   -21.00000   -1.50000
H16E   2    0.795514    -0.583338    1.142778   -21.00000   -1.50000
H16F   2    0.830331    -0.666839    1.226451   -21.00000   -1.50000
AFIX   0
N2'    3    0.834865    -0.412062    1.204537   -21.00000    0.03675
0.03922 =
            0.01831     0.00444     0.00551    -0.00412
AFIX  23
H2'1   2    0.823993    -0.387542    1.291995   -21.00000   -1.20000
H2'2   2    0.825077    -0.327009    1.137188   -21.00000   -1.20000
AFIX   0
C17'   1    0.875937    -0.390422    1.224743   -21.00000    0.03429
0.06551 =
            0.04099     0.01648     0.00156     0.00092
AFIX  13
H17'   2    0.887276    -0.415521    1.137154   -21.00000   -1.20000
AFIX   0
C18'   1    0.889488    -0.522456    1.333484   -21.00000    0.04897
0.11025 =
            0.04485     0.03451     0.00059     0.00325
AFIX 137
H18D   2    0.877147    -0.502778    1.417567   -21.00000   -1.50000
H18E   2    0.916224    -0.511358    1.352396   -21.00000   -1.50000
H18F   2    0.883681    -0.636901    1.299397   -21.00000   -1.50000
AFIX   0
```

```
C19'  1    0.882397   -0.205886    1.261806  -21.00000    0.04804
0.07212 =
           0.04329    -0.01175     0.00994   -0.02480
AFIX  23
H19C  2    0.869473   -0.181479    1.344983  -21.00000   -1.20000
H19D  2    0.870717   -0.135389    1.187312  -21.00000   -1.20000
AFIX   0
C20'  1    0.922566   -0.149044    1.287409  -21.00000    0.05260
0.09441 =
           0.05457    -0.01613     0.00976   -0.02394
AFIX  23
H20C  2    0.922930   -0.027174    1.311822  -21.00000   -1.20000
H20D  2    0.933911   -0.212512    1.366632  -21.00000   -1.20000
AFIX   0
C21'  1    0.945346   -0.174157    1.170077  -21.00000    0.06350
0.10756 =
           0.06153    -0.01127     0.01457   -0.01850
AFIX  43
H21'  2    0.939904   -0.272660    1.116663  -21.00000   -1.20000
AFIX   0
C22'  1    0.972093   -0.078333    1.129969  -21.00000    0.06251
0.13060 =
           0.06460     0.00888    -0.00025   -0.02631
C23'  1    0.991673   -0.118703    1.003156  -21.00000    0.07933
0.19500 =
           0.08515     0.02434     0.00025   -0.03709
AFIX 137
H23D  2    1.017376   -0.149016    1.029059  -21.00000   -1.50000
H23E  2    0.991005   -0.019171    0.943252  -21.00000   -1.50000
H23F  2    0.979327   -0.214088    0.954963  -21.00000   -1.50000
AFIX   0
C24'  1    0.982867    0.080901    1.201647  -21.00000    0.12470
0.12670 =
           0.09922     0.02656     0.00427   -0.03189
AFIX 137
```

| | | | | | | |
|---|---|---|---|---|---|---|
| H24D | 2 | 0.960708 | 0.139962 | 1.227738 | -21.00000 | -1.50000 |
| H24E | 2 | 0.996238 | 0.153625 | 1.141054 | -21.00000 | -1.50000 |
| H24F | 2 | 0.998797 | 0.054679 | 1.283669 | -21.00000 | -1.50000 |

AFIX   0
HKLF   4

Covalent radii and connectivity table for   xs0061 in C2
C    0.770
H    0.320
N    0.700
O    0.660

C1  -  O2  O1  C2
C2  -  O3  C3  C1
C3  -  O4  C2  C4
C4  -  O5  C3  C5
C5  -  O6  C4  C6
C6  -  O7  O8  C5
O1  -  C1
O2  -  C1
O3  -  C2
O4  -  C3
O5  -  C4
O6  -  C5
O7  -  C6
O8  -  C6
C7  -  N1
N1  -  C7  C8
C8  -  N1  C9  C10
C9  -  C8
C10 -  C8  C11
C11 -  C12 C10
C12 -  C13 C11
C13 -  C12 C15 C14

C14 - C13
C15 - C13
C16 - N2
N2 - C17 C16
C17 - N2 C19 C18
C18 - C17
C19 - C17 C20
C20 - C21 C19
C21 - C22 C20
C22 - C21 C24 C23
C23 - C22
C24 - C22
C16' - N2'
N2' - C16' C17'
C17' - N2' C19' C18'
C18' - C17'
C19' - C17' C20'
C20' - C21' C19'
C21' - C22' C20'
C22' - C21' C24' C23'
C23' - C22'
C24' - C22'

Floating origin restraints generated

31163 Reflections read, of which   49  rejected

-44 =< h =< 44,    -9 =< k =< 9,    -10 =< l =< 12,   Max. 2-theta = 143.79

·0 Systematic absence violations

Inconsistent equivalents etc.

| h | k | l | Fo^2 | Sigma(Fo^2) | N | Esd of mean(Fo^2) |
|---|---|---|---|---|---|---|
| 0 | -8 | 0 | 37612.37 | 356.11 | 2 | 2506.95 |
| 3 | -1 | 0 | 129724.34 | 664.44 | 2 | 3581.50 |
| 3 | 1 | 0 | 127969.05 | 585.70 | 2 | 3802.50 |
| 0 | 2 | 0 | 253497.31 | 1019.99 | 2 | 10841.00 |
| -5 | 1 | 1 | 226222.55 | 848.73 | 2 | 5212.00 |
| 37 | -5 | 2 | 2320.71 | 50.47 | 2 | 318.39 |
| -16 | 0 | 2 | 242097.92 | 553.34 | 9 | 3632.76 |
| -8 | 0 | 2 | 198360.67 | 594.36 | 4 | 3814.55 |
| 5 | 1 | 2 | 890483.38 | 1884.13 | 5 | 11280.84 |
| -1 | -9 | 3 | 6005.21 | 65.54 | 4 | 399.23 |
| 1 | -9 | 4 | 4688.19 | 69.62 | 2 | 565.54 |
| -12 | -8 | 6 | 3060.60 | 70.89 | 2 | 415.45 |
| -6 | -8 | 6 | 9264.09 | 115.16 | 2 | 698.19 |
| 8 | -6 | 6 | 11183.06 | 171.69 | 4 | 867.37 |
| 16 | -6 | 6 | 14121.38 | 183.43 | 2 | 988.75 |
| 9 | -5 | 7 | 9292.60 | 157.89 | 4 | 912.85 |
| -3 | -7 | 8 | 5566.82 | 104.30 | 2 | 597.72 |
| -14 | -6 | 8 | 10692.13 | 161.21 | 2 | 1028.60 |
| 17 | -5 | 8 | 2610.52 | 68.71 | 2 | 360.35 |
| 19 | -5 | 8 | 3072.10 | 70.44 | 2 | 401.68 |
| -30 | -4 | 8 | 9274.25 | 111.27 | 2 | 623.44 |
| -2 | -4 | 8 | 21511.16 | 216.40 | 5 | 1146.35 |
| 0 | -2 | 8 | 23586.72 | 213.84 | 5 | 1150.57 |
| -26 | 2 | 8 | 775.24 | 47.93 | 2 | 251.68 |
| -7 | 5 | 8 | 5725.96 | 135.60 | 2 | 2553.40 |
| -6 | 6 | 8 | 5955.66 | 126.86 | 2 | 651.50 |
| 0 | 6 | 8 | 10722.69 | 179.33 | 2 | 1021.63 |
| 8 | -6 | 9 | 949.98 | 34.98 | 2 | 251.73 |
| -3 | -3 | 9 | 30996.34 | 250.00 | 4 | 1403.31 |

| | | | | | | |
|---|---|---|---|---|---|---|
| -21 | -1 | 9 | 9260.13 | 54.25 | 2 | 7485.53 |
| -19 | -1 | 9 | 6100.72 | 108.51 | 2 | 3369.77 |
| -24 | 0 | 9 | 1233.71 | 48.50 | 2 | 849.58 |
| -30 | 2 | 9 | 729.83 | 36.95 | 2 | 248.40 |
| -23 | 3 | 9 | 4981.32 | 93.33 | 2 | 2175.87 |
| -3 | 3 | 9 | 31239.06 | 230.54 | 5 | 1239.20 |
| -10 | 4 | 9 | 5190.47 | 138.84 | 2 | 880.10 |
| -3 | 5 | 9 | 11887.99 | 182.78 | 2 | 1603.00 |
| -21 | -1 | 10 | 1736.59 | 48.23 | 2 | 1379.01 |
| -19 | -1 | 10 | 6749.07 | 184.77 | 2 | 2977.34 |
| -22 | 0 | 10 | 5822.31 | 162.13 | 2 | 1863.76 |
| -20 | 0 | 10 | 8987.51 | 216.19 | 2 | 3429.31 |
| -18 | 0 | 10 | 2977.96 | 139.45 | 2 | 1058.78 |
| -16 | 0 | 10 | 4113.75 | 97.81 | 2 | 3778.91 |
| -19 | 1 | 10 | 5232.78 | 171.84 | 2 | 1601.98 |
| -17 | 1 | 10 | 2745.86 | 98.92 | 2 | 1678.76 |
| -18 | 2 | 10 | 2565.30 | 52.30 | 2 | 2728.76 |
| -16 | 2 | 10 | 7615.25 | 36.94 | 2 | 8254.07 |
| 18 | 2 | 10 | 6130.45 | 96.49 | 2 | 525.71 |
| -17 | 3 | 10 | 959.46 | 50.73 | 2 | 457.43 |
| -15 | 3 | 10 | 318.21 | 32.13 | 2 | 254.96 | etc.

66 Inconsistent equivalents

5499 Unique reflections, of which    0 suppressed

R(int) = 0.0287    R(sigma) = 0.0154    Friedel opposites not merged

Maximum memory for data reduction =    5898 /    65132

Number of data for d > 0.811A (CIF: max) and d > 0.833A (CIF: full)

(ignoring systematic absences):

| | | |
|---|---|---|
| Unique reflections found (point group) | 5513 | 5076 |
| Unique reflections possible (point group) | 5514 | 5078 |
| Unique reflections found (Laue group) | 2969 | 2737 |
| Unique reflections possible (Laue group) | 2970 | 2739 |
| Unique Friedel pairs found | 2544 | 2339 |
| Unique Friedel pairs possible | 2544 | 2339 |

Default effective X-H and X-D distances for T = -173.0C
AFIX m =    1    2    3    4   4[N]  3[N]  15[B]  8[O]   9   9[N] 16
d(X-H) = 1.00 0.99 0.98 0.95 0.88 0.91 1.12 0.84 0.95 0.88 0.95

Note that these distances are chosen to give the best fit to the X-ray data
and so avoid the introduction of systematic error. The true internuclear
distances are longer and do not vary with temperature! The apparent
variation with temperature is caused by libration.

Least-squares cycle   1   Maximum vector length =  623   Memory required =    7228 /   612385 wR2 = 0.1486 before cycle   1 for   5499 data and    403 /   403 parameters

Disagreeable restraints before cycle   1

Observed   Target   Error   Sigma   Restraint

-0.0389  0.0100  SIMU U22 C21 C22'

```
              -0.0688    0.0200    SIMU U11 C22 C24'
              -0.0644    0.0200    SIMU U22 C22' C23'
              -0.0622    0.0200    SIMU U11 C22' C24'
```

Summary of restraints applied in cycle    1

|         | ANTIBUMP | DFIX | DANG | SAME/SADI | CHIV/Z | CHIV/NZ | FLAT |
|---------|----------|------|------|-----------|--------|---------|------|
| DELU | RIGU | SIMU | ISOR | SUMP | | | |

Number         0        0       0      57        0        0       0
   0      0     246      0       0 rms sigma      0.0000   0.0000  0.0000  0.0321   0.0000   0.0000  0.0000
0.0000  0.0000  0.0150  0.0000  0.0000 rms deviation  0.0000   0.0000  0.0000  0.0290   0.0000   0.0000  0.0000
0.0000  0.0000  0.0180  0.0000  0.0000

GooF = S =    1.054;    Restrained GooF =       1.060 for     304 restraints

Weight = 1 / [ sigma^2(Fo^2) + ( 0.1039 * P )^2 +  1.13 * P ]
where  P = ( Max ( Fo^2, 0 ) + 2 * Fc^2 ) / 3

|  N  |  value   |  esd    | shift/esd | parameter |
|-----|----------|---------|-----------|-----------|
|  1  | 3.98836  | 0.01343 |  0.000    | OSF       |
|  2  | 0.51966  | 0.00401 |  0.001    | FVAR  2   |
|  3  | 0.05322  | 0.27877 |  0.000    | BASF  1   |

Mean shift/esd =   0.001 Maximum =    -0.005 for   x C3

Max. shift = 0.000 A for H15B        Max. dU = 0.000 for C1

Least-squares cycle   2   Maximum vector length =   623   Memory required =      7228 /   612385 wR2 = 0.1486 before cycle   2 for    5499 data and    403 /    403 parameters

Disagreeable restraints before cycle    2

| Observed | Target | Error | Sigma | Restraint |
|---|---|---|---|---|
| | | -0.0389 | 0.0100 | SIMU U22 C21 C22' |
| | | -0.0688 | 0.0200 | SIMU U11 C22 C24' |
| | | -0.0644 | 0.0200 | SIMU U22 C22' C23' |
| | | -0.0622 | 0.0200 | SIMU U11 C22' C24' |

Summary of restraints applied in cycle    2

| | ANTIBUMP | DFIX | DANG | SAME/SADI | CHIV/Z | CHIV/NZ | FLAT | DELU | RIGU | SIMU | ISOR | SUMP |
|---|---|---|---|---|---|---|---|---|---|---|---|---|
| Number | 0 | 0 | 0 | 57 | 0 | 0 | 0 | 0 | 0 | 246 | 0 | 0 |
| rms sigma | 0.0000 | 0.0000 | 0.0000 | 0.0321 | 0.0000 | 0.0000 | 0.0000 | 0.0000 | 0.0000 | 0.0150 | 0.0000 | 0.0000 |
| rms deviation | 0.0000 | 0.0000 | 0.0000 | 0.0290 | 0.0000 | 0.0000 | 0.0000 | 0.0000 | 0.0000 | 0.0180 | 0.0000 | 0.0000 |

GooF = S =     1.054;    Restrained GooF =     1.060 for      304 restraints

Weight = 1 / [ sigma^2(Fo^2) + ( 0.1039 * P )^2 +   1.13 * P ] where   P = ( Max ( Fo^2, 0 ) + 2 * Fc^2 ) / 3

| N | value | esd | shift/esd | parameter |
|---|-------|-----|-----------|-----------|
| 1 | 3.98836 | 0.01343 | 0.000 | OSF |
| 2 | 0.51966 | 0.00401 | 0.000 | FVAR 2 |
| 3 | 0.05322 | 0.27877 | 0.000 | BASF 1 |

Mean shift/esd =   0.000  Maximum =    -0.002 for  U12 O3

Max. shift = 0.000 A for H15A    Max. dU = 0.000 for O4

Least-squares cycle   3   Maximum vector length =   623   Memory required =     7228 /    612385 wR2 = 0.1486 before cycle   3 for    5499 data and    403 /    403 parameters

Disagreeable restraints before cycle    3

| Observed | Target | Error | Sigma | Restraint |
|----------|--------|-------|-------|-----------|
|  |  | -0.0389 | 0.0100 | SIMU U22 C21 C22' |
|  |  | -0.0688 | 0.0200 | SIMU U11 C22 C24' |
|  |  | -0.0644 | 0.0200 | SIMU U22 C22' C23' |
|  |  | -0.0622 | 0.0200 | SIMU U11 C22' C24' |

Summary of restraints applied in cycle    3

|  | ANTIBUMP | DFIX | DANG | SAME/SADI | CHIV/Z | CHIV/NZ | FLAT |
|---|---|---|---|---|---|---|---|
| DELU | RIGU | SIMU | ISOR | SUMP | | | |
| Number | 0 | 0 | 0 | 57 | 0 | 0 | 0 |
| 0 | 0 | 246 | 0 | 0 | | | |
| rms sigma | 0.0000 | 0.0000 | 0.0000 | 0.0321 | 0.0000 | 0.0000 | 0.0000 |
| 0.0000 | 0.0000 | 0.0150 | 0.0000 | 0.0000 | | | |
| rms deviation | 0.0000 | 0.0000 | 0.0000 | 0.0290 | 0.0000 | 0.0000 | 0.0000 |
| 0.0000 | 0.0000 | 0.0180 | 0.0000 | 0.0000 | | | |

GooF = S =    1.054;    Restrained GooF =    1.060 for    304 restraints

Weight = 1 / [ sigma^2(Fo^2) + ( 0.1039 * P )^2 +    1.13 * P ]
where   P = ( Max ( Fo^2, 0 ) + 2 * Fc^2 ) / 3

| N | value | esd | shift/esd | parameter |
|---|---|---|---|---|
| 1 | 3.98836 | 0.01343 | 0.000 | OSF |
| 2 | 0.51966 | 0.00401 | 0.000 | FVAR  2 |
| 3 | 0.05323 | 0.27876 | 0.000 | BASF  1 |

Mean shift/esd =    0.000  Maximum =    -0.001 for   x  O8

Max. shift = 0.000 A for H16D     Max. dU = 0.000 for C15

Least-squares cycle    4   Maximum vector length =    623   Memory required =       7228 /    612385 wR2 = 0.1486 before cycle   4 for     5499 data and      403 /    403 parameters Disagreeable restraints before cycle    4

| Observed | Target | Error | Sigma | Restraint |
|---|---|---|---|---|
| | | -0.0389 | 0.0100 | SIMU U22 C21 C22' |
| | | -0.0688 | 0.0200 | SIMU U11 C22 C24' |
| | | -0.0644 | 0.0200 | SIMU U22 C22' C23' |
| | | -0.0622 | 0.0200 | SIMU U11 C22' C24' |

Summary of restraints applied in cycle    4

| | ANTIBUMP | DFIX | DANG | SAME/SADI | CHIV/Z | CHIV/NZ | FLAT | DELU | RIGU | SIMU | ISOR | SUMP |
|---|---|---|---|---|---|---|---|---|---|---|---|---|
| Number | 0 | 0 | 0 | 57 | 0 | 0 | 0 | 0 | 0 | 246 | 0 | 0 |
| rms sigma | 0.0000 | 0.0000 | 0.0000 | 0.0321 | 0.0000 | 0.0000 | 0.0000 | 0.0000 | 0.0000 | 0.0150 | 0.0000 | 0.0000 |
| rms deviation | 0.0000 | 0.0000 | 0.0000 | 0.0290 | 0.0000 | 0.0000 | 0.0000 | 0.0000 | 0.0000 | 0.0180 | 0.0000 | 0.0000 |

GooF = S =    1.054;    Restrained GooF =      1.060 for     304 restraints

Weight = 1 / [ sigma^2(Fo^2) + ( 0.1039 * P )^2 +   1.13 * P ]
where  P = ( Max ( Fo^2, 0 ) + 2 * Fc^2 ) / 3

```
  N      value       esd      shift/esd   parameter 1     3.98836    0.01343     0.000      OSF
  2     0.51966    0.00401     0.000      FVAR  2
  3     0.05323    0.27875     0.000      BASF  1
```

Mean shift/esd =  0.000  Maximum =  0.000 for  x  C6

Max. shift = 0.000 A for H16F    Max. dU = 0.000 for C23'

Least-squares cycle  5  Maximum vector length = 623  Memory required =  7228 / 612385 wR2 = 0.1486 before cycle  5 for  5499 data and  403 / 403 parameters

Disagreeable restraints before cycle  5

```
  Observed   Target    Error    Sigma    Restraint

-0.0389   0.0100   SIMU U22 C21 C22'
                      -0.0688   0.0200   SIMU U11 C22 C24'
                      -0.0644   0.0200   SIMU U22 C22' C23'
                      -0.0622   0.0200   SIMU U11 C22' C24'
```

Summary of restraints applied in cycle  5

```
          ANTIBUMP  DFIX   DANG  SAME/SADI  CHIV/Z  CHIV/NZ   FLAT
DELU   RIGU   SIMU   ISOR   SUMP
```

```
      Number       0        0        0       57        0        0        0
   0       0      246       0        0 rms sigma      0.0000  0.0000  0.0000  0.0321  0.0000  0.0000  0.0000
 0.0000  0.0000  0.0150  0.0000  0.0000 rms deviation  0.0000  0.0000  0.0000  0.0290  0.0000  0.0000  0.0000
 0.0000  0.0000  0.0180  0.0000  0.0000
```

GooF = S =    1.054;    Restrained GooF =      1.060 for     304 restraints

Weight = 1 / [ sigma^2(Fo^2) + ( 0.1039 * P )^2 +  1.13 * P ]
where   P = ( Max ( Fo^2, 0 ) + 2 * Fc^2 ) / 3

```
   N      value       esd    shift/esd  parameter 1    3.98836    0.01343    0.000    OSF
   2    0.51966    0.00401    0.000    FVAR  2
   3    0.05323    0.27875    0.000    BASF  1
```

Mean shift/esd =   0.000  Maximum =    0.000  for   x  O8

Max. shift = 0.000 A for H16E    Max. dU = 0.000 for C18'

Least-squares cycle   6   Maximum vector length =  623   Memory required =    7228 /   612385 wR2 = 0.1486 before cycle   6 for   5499 data and    403 /   403 parameters

Disagreeable restraints before cycle 6

| Observed | Target | Error | Sigma | Restraint |
|---|---|---|---|---|
| | | -0.0389 | 0.0100 | SIMU U22 C21 C22' |
| | | -0.0688 | 0.0200 | SIMU U11 C22 C24' |
| | | -0.0644 | 0.0200 | SIMU U22 C22' C23' |
| | | -0.0622 | 0.0200 | SIMU U11 C22' C24' |

Summary of restraints applied in cycle 6

| | ANTIBUMP | DFIX | DANG | SAME/SADI | CHIV/Z | CHIV/NZ | FLAT |
|---|---|---|---|---|---|---|---|
| DELU | RIGU | SIMU | ISOR | SUMP | | | |
| Number | 0 | 0 | 0 | 57 | 0 | 0 | 0 |
| 0 | 0 | 246 | 0 | 0 | | | |
| rms sigma | 0.0000 | 0.0000 | 0.0000 | 0.0321 | 0.0000 | 0.0000 | 0.0000 |
| 0.0000 | 0.0000 | 0.0150 | 0.0000 | 0.0000 | | | |
| rms deviation | 0.0000 | 0.0000 | 0.0000 | 0.0290 | 0.0000 | 0.0000 | 0.0000 |
| 0.0000 | 0.0000 | 0.0180 | 0.0000 | 0.0000 | | | |

GooF = S = 1.054;   Restrained GooF = 1.060 for 304 restraints

Weight = 1 / [ sigma^2(Fo^2) + ( 0.1039 * P )^2 + 1.13 * P ]
where   P = ( Max ( Fo^2, 0 ) + 2 * Fc^2 ) / 3

| N | value | esd | shift/esd | parameter |
|---|---|---|---|---|
| 1 | 3.98836 | 0.01343 | 0.000 | OSF |

```
   2     0.51966     0.00401     0.000    FVAR   2
   3     0.05323     0.27875     0.000    BASF   1
```

Mean shift/esd =   0.000  Maximum =    0.000 for    x  C6

Max. shift = 0.000 A for H23F     Max. dU = 0.000 for C18'

Largest correlation matrix elements

```
   -0.993  z N2'  / z N2              -0.950  U33 N2  / z N2
-0.895 z C17' / z C17
   -0.990  z C16' / z C16              0.950  z N2'  / U33 N2
-0.891 U33 C18' / z C18
   -0.983  y N2'  / y N2              -0.947  x C16' / U11 C16
 0.881 z C18' / U33 C18
   -0.981  y C16' / y C16              0.944  U11 C16 / x C16
-0.874 z C19' / z C19
   -0.977  x N2'  / x N2              -0.910  x C17' / x C17
-0.864 x N2'  / U11 N2
   -0.977  x C16' / x C16             -0.909  x C18' / x C18
 0.862 U11 N2 / x N2
   -0.964  z C16' / U33 C16           -0.897  y C16' / U12 C16
-0.858 z N2'  / U13 N2
    0.962  U33 C16 / z C16             0.896  U12 C16 / y C16
 0.853 U13 N2 / z N2
```

Idealized hydrogen atom generation before cycle   7

Name      x        y        z    AFIX  d(X-H)  shift  Bonded to
Conformation determined by

| | | | | | | | |
|---|---|---|---|---|---|---|---|
| H2 | 0.7614 | 0.4284 | 0.9535 | 13 | 1.000 | 0.000 | C2 |
| O3 C3 C1 | | | | | | | |
| H3 | 0.7344 | 0.6698 | 0.8487 | 13 | 1.000 | 0.000 | C3 |
| O4 C2 C4 | | | | | | | |
| H4 | 0.7648 | 0.4553 | 0.6504 | 13 | 1.000 | 0.000 | C4 |
| O5 C3 C5 | | | | | | | |
| H5 | 0.7382 | 0.7027 | 0.5493 | 13 | 1.000 | 0.000 | C5 |
| O6 C4 C6 | | | | | | | |
| H3A | 0.7536 | 0.1965 | 0.8644 | 147 | 0.840 | 0.000 | O3 |
| C2 H3A | | | | | | | |
| H4A | 0.6985 | 0.4718 | 0.6652 | 147 | 0.840 | 0.000 | O4 |
| C3 H4A | | | | | | | |
| H5A | 0.8015 | 0.6540 | 0.8316 | 147 | 0.840 | 0.000 | O5 |
| C4 H5A | | | | | | | |
| H6 | 0.7466 | 0.9290 | 0.6447 | 147 | 0.840 | 0.000 | O6 |
| C5 H6 | | | | | | | |
| H7A | 0.8289 | 0.2974 | 0.7073 | 137 | 0.980 | 0.000 | C7 |
| N1 H7A | | | | | | | |
| H7B | 0.7924 | 0.1998 | 0.6499 | 137 | 0.980 | 0.000 | C7 |
| N1 H7A | | | | | | | |
| H7C | 0.8266 | 0.2184 | 0.5569 | 137 | 0.980 | 0.000 | C7 |
| N1 H7A | | | | | | | |
| H1A | 0.8285 | −0.0527 | 0.6409 | 23 | 0.990 | 0.000 | N1 |
| C7 C8 | | | | | | | |
| H1B | 0.8235 | 0.0130 | 0.7924 | 23 | 0.990 | 0.000 | N1 |
| C7 C8 | | | | | | | |
| H8 | 0.8817 | 0.1416 | 0.7971 | 13 | 1.000 | 0.000 | C8 |
| N1 C9 C10 | | | | | | | |
| H9A | 0.8845 | 0.0054 | 0.5316 | 137 | 0.980 | 0.000 | C9 |
| C8 H9A | | | | | | | |
| H9B | 0.9215 | 0.0543 | 0.6208 | 137 | 0.980 | 0.000 | C9 |
| C8 H9A | | | | | | | |
| H9C | 0.8916 | 0.1975 | 0.5793 | 137 | 0.980 | 0.000 | C9 |
| C8 H9A | | | | | | | |

| | | | | | | | |
|---|---|---|---|---|---|---|---|
| H10A | 0.8745 | -0.1294 | 0.8910 | 23 | 0.990 | 0.000 | C10 |
| C8 | C11 | | | | | | |
| H10B | 0.9153 | -0.0954 | 0.8473 | 23 | 0.990 | 0.000 | C10 |
| C8 | C11 | | | | | | |
| H11A | 0.8626 | -0.2979 | 0.6885 | 23 | 0.990 | 0.000 | C11 |
| C12 | C10 | | | | | | |
| H11B | 0.9048 | -0.2716 | 0.6548 | 23 | 0.990 | 0.000 | C11 |
| C12 | C10 | | | | | | |
| H12 | 0.8809 | -0.4659 | 0.8771 | 43 | 0.950 | 0.000 | C12 |
| C13 | C11 | | | | | | |
| H14A | 0.9558 | -0.6074 | 1.0104 | 137 | 0.980 | 0.000 | C14 |
| C13 | H14A | | | | | | |
| H14B | 0.9468 | -0.7475 | 0.8950 | 137 | 0.980 | 0.000 | C14 |
| C13 | H14A | | | | | | |
| H14C | 0.9143 | -0.6725 | 0.9790 | 137 | 0.980 | 0.000 | C14 |
| C13 | H14A | | | | | | |
| H15A | 0.9699 | -0.5711 | 0.7031 | 137 | 0.980 | 0.000 | C15 |
| C13 | H15A | | | | | | |
| H15B | 0.9821 | -0.4157 | 0.8010 | 137 | 0.980 | 0.000 | C15 |
| C13 | H15A | | | | | | |
| H15C | 0.9530 | -0.3862 | 0.6731 | 137 | 0.980 | 0.000 | C15 |
| C13 | H15A | | | | | | |
| H16A | 0.8248 | -0.5776 | 1.0504 | 137 | 0.980 | 0.000 | C16 |
| N2 | H16A | | | | | | |
| H16B | 0.7909 | -0.5777 | 1.1461 | 137 | 0.980 | 0.000 | C16 |
| N2 | H16A | | | | | | |
| H16C | 0.8283 | -0.6748 | 1.1938 | 137 | 0.980 | 0.000 | C16 |
| N2 | H16A | | | | | | |
| H2A | 0.8244 | -0.3202 | 1.1555 | 23 | 0.990 | 0.000 | N2 |
| C17 | C16 | | | | | | |
| H2B | 0.8211 | -0.4065 | 1.3011 | 23 | 0.990 | 0.000 | N2 |
| C17 | C16 | | | | | | |
| H17 | 0.8840 | -0.4674 | 1.1597 | 13 | 1.000 | 0.000 | C17 |
| N2 | C19 | C18 | | | | | |

| | | | | | | | |
|---|---|---|---|---|---|---|---|
| H18A | 0.8743 | −0.4652 | 1.4464 | 137 | 0.980 | 0.000 | C18 |
| C17 | H18A | | | | | | |
| H18B | 0.9122 | −0.5114 | 1.3815 | 137 | 0.980 | 0.000 | C18 |
| C17 | H18A | | | | | | |
| H18C | 0.8770 | −0.6322 | 1.3551 | 137 | 0.980 | 0.000 | C18 |
| C17 | H18A | | | | | | |
| H19A | 0.8818 | −0.1815 | 1.3348 | 23 | 0.990 | 0.000 | C19 |
| C17 | C20 | | | | | | |
| H19B | 0.8728 | −0.1632 | 1.1737 | 23 | 0.990 | 0.000 | C19 |
| C17 | C20 | | | | | | |
| H20A | 0.9417 | −0.2991 | 1.2848 | 23 | 0.990 | 0.000 | C20 |
| C21 | C19 | | | | | | |
| H20B | 0.9323 | −0.2439 | 1.1292 | 23 | 0.990 | 0.000 | C20 |
| C21 | C19 | | | | | | |
| H21 | 0.9298 | 0.0487 | 1.2074 | 43 | 0.950 | 0.000 | C21 |
| C22 | C20 | | | | | | |
| H23A | 0.9813 | −0.2319 | 1.4317 | 137 | 0.980 | 0.000 | C23 |
| C22 | H23A | | | | | | |
| H23B | 0.9882 | −0.0813 | 1.5398 | 137 | 0.980 | 0.000 | C23 |
| C22 | H23A | | | | | | |
| H23C | 1.0169 | −0.1131 | 1.4260 | 137 | 0.980 | 0.000 | C23 |
| C22 | H23A | | | | | | |
| H24A | 0.9667 | 0.2548 | 1.2907 | 137 | 0.980 | 0.000 | C24 |
| C22 | H24A | | | | | | |
| H24B | 1.0058 | 0.2014 | 1.3638 | 137 | 0.980 | 0.000 | C24 |
| C22 | H24A | | | | | | |
| H24C | 0.9711 | 0.2303 | 1.4527 | 137 | 0.980 | 0.000 | C24 |
| C22 | H24A | | | | | | |
| H16D | 0.8334 | −0.6090 | 1.0715 | 137 | 0.980 | 0.000 | C16' |
| N2' | H16D | | | | | | |
| H16E | 0.7955 | −0.5833 | 1.1428 | 137 | 0.980 | 0.000 | C16' |
| N2' | H16D | | | | | | |
| H16F | 0.8303 | −0.6668 | 1.2265 | 137 | 0.980 | 0.000 | C16' |
| N2' | H16D | | | | | | |

| | | | | | | | | | |
|---|---|---|---|---|---|---|---|---|---|
| H2'1 | 0.8240 | -0.3875 | 1.2920 | 23 | 0.990 | 0.000 | N2' | C16' | C17' |
| H2'2 | 0.8251 | -0.3270 | 1.1372 | 23 | 0.990 | 0.000 | N2' | C16' | C17' |
| H17' | 0.8873 | -0.4155 | 1.1372 | 13 | 1.000 | 0.000 | C17' | N2' C19' | C18' |
| H18D | 0.8771 | -0.5028 | 1.4176 | 137 | 0.980 | 0.000 | C18' | C17' | H18D |
| H18E | 0.9162 | -0.5114 | 1.3524 | 137 | 0.980 | 0.000 | C18' | C17' | H18D |
| H18F | 0.8837 | -0.6369 | 1.2994 | 137 | 0.980 | 0.000 | C18' | C17' | H18D |
| H19C | 0.8695 | -0.1815 | 1.3450 | 23 | 0.990 | 0.000 | C19' | C17' | C20' |
| H19D | 0.8707 | -0.1354 | 1.1873 | 23 | 0.990 | 0.000 | C19' | C17' | C20' |
| H20C | 0.9229 | -0.0272 | 1.3118 | 23 | 0.990 | 0.000 | C20' | C21' | C19' |
| H20D | 0.9339 | -0.2125 | 1.3666 | 23 | 0.990 | 0.000 | C20' | C21' | C19' |
| H21' | 0.9399 | -0.2727 | 1.1167 | 43 | 0.950 | 0.000 | C21' | C22' | C20' |
| H23D | 1.0174 | -0.1490 | 1.0291 | 137 | 0.980 | 0.000 | C23' | C22' | H23D |
| H23E | 0.9910 | -0.0192 | 0.9433 | 137 | 0.980 | 0.000 | C23' | C22' | H23D |
| H23F | 0.9793 | -0.2141 | 0.9550 | 137 | 0.980 | 0.000 | C23' | C22' | H23D |
| H24D | 0.9607 | 0.1400 | 1.2277 | 137 | 0.980 | 0.000 | C24' | C22' | H24D |
| H24E | 0.9962 | 0.1536 | 1.1411 | 137 | 0.980 | 0.000 | C24' | C22' | H24D |
| H24F | 0.9988 | 0.0547 | 1.2837 | 137 | 0.980 | 0.000 | C24' | C22' | H24D | xs0061 in C2

| ATOM | x | y | z | sof | U11 |
|------|---|---|---|-----|-----|
| U22 | U33 | U23 | U13 | U12 | Ueq |

| C1 | 0.70616 | 0.42929 | 0.99737 | 1.00000 | 0.04257 |
|----|---------|---------|---------|---------|---------|
| 0.02979 | 0.01397 | 0.00280 | 0.00441 | 0.00080 | 0.02866 |
| 0.00480 | 0.00007 | 0.00037 | 0.00024 | 0.00000 | 0.00130 |
| 0.00151 | 0.00108 | 0.00105 | 0.00094 | 0.00111 | 0.00058 |

| C2 | 0.73720 | 0.41658 | 0.89922 | 1.00000 | 0.03906 |
|----|---------|---------|---------|---------|---------|
| 0.02217 | 0.01755 | 0.00256 | 0.00469 | −0.00129 | 0.02613 |
| 0.00467 | 0.00007 | 0.00036 | 0.00024 | 0.00000 | 0.00122 |
| 0.00126 | 0.00110 | 0.00104 | 0.00091 | 0.00103 | 0.00053 |

| H2 | 0.76141 | 0.42839 | 0.95346 | 1.00000 | 0.03136 |
|----|---------|---------|---------|---------|---------|
|    |         |         |         | 0.00000 | 0.00000 |

| C3 | 0.73352 | 0.56109 | 0.79604 | 1.00000 | 0.03842 |
|----|---------|---------|---------|---------|---------|
| 0.02105 | 0.01577 | 0.00147 | 0.00572 | −0.00054 | 0.02490 |
| 0.00462 | 0.00007 | 0.00038 | 0.00024 | 0.00000 | 0.00119 |
| 0.00113 | 0.00102 | 0.00111 | 0.00085 | 0.00108 | 0.00049 |

| H3 | 0.73440 | 0.66978 | 0.84867 | 1.00000 | 0.02988 |
|----|---------|---------|---------|---------|---------|
|    |         |         |         | 0.00000 | 0.00000 |

| C4 | 0.76585 | 0.56304 | 0.70421 | 1.00000 | 0.03669 |
|----|---------|---------|---------|---------|---------|
| 0.02269 | 0.01495 | 0.00103 | 0.00358 | 0.00112 | 0.02469 |
| 0.00464 | 0.00007 | 0.00038 | 0.00024 | 0.00000 | 0.00117 |
| 0.00116 | 0.00102 | 0.00112 | 0.00084 | 0.00107 | 0.00049 |

| H4 | 0.76481 | 0.45527 | 0.65036 | 1.00000 | 0.02963 |
|----|---------|---------|---------|---------|---------|
|    |         |         |         | 0.00000 | 0.00000 |

```
C5      0.76261   0.71061   0.60246   1.00000   0.03771
0.02507 0.01690   0.00232   0.00290   0.00001   0.02652
        0.00461   0.00007   0.00037   0.00023   0.00000   0.00121
0.00137 0.00106   0.00108   0.00089   0.00105   0.00055

H5      0.73815   0.70268   0.54934   1.00000   0.03182
                                      0.00000   0.00000

C6      0.79305   0.69457   0.50285   1.00000   0.03931
0.02949 0.01338   0.00339   0.00197  -0.00255   0.02739
        0.00456   0.00007   0.00038   0.00023   0.00000   0.00125
0.00144 0.00103   0.00105   0.00090   0.00107   0.00056

O1      0.68490   0.30481   1.00767   1.00000   0.04330
0.03127 0.01836   0.00140   0.00736  -0.00533   0.03073
        0.00335   0.00005   0.00028   0.00017   0.00000   0.00098
0.00103 0.00084   0.00078   0.00071   0.00084   0.00043

O2      0.70449   0.56540   1.06321   1.00000   0.05187
0.02985 0.01987  -0.00213   0.01012  -0.00404   0.03350
        0.00349   0.00005   0.00029   0.00018   0.00000   0.00105
0.00105 0.00084   0.00092   0.00073   0.00090   0.00045

O3      0.73686   0.25915   0.82914   1.00000   0.04407
0.02391 0.02421   0.00147   0.00824   0.00177   0.03045
        0.00329   0.00005   0.00024   0.00018   0.00000   0.00101
0.00108 0.00093   0.00077   0.00075   0.00074   0.00045

H3A     0.75363   0.19647   0.86445   1.00000   0.04568
                                      0.00000   0.00000

O4      0.69895   0.55561   0.71808   1.00000   0.03859
0.02625 0.02065  -0.00120   0.00333   0.00254   0.02844
```

```
     0.00322   0.00005   0.00027   0.00017   0.00000   0.00088
  0.00094   0.00082   0.00088   0.00065   0.00082   0.00040

H4A       0.69851   0.47182   0.66516   1.00000   0.04266
                                                      0.00000   0.00000

O5        0.80034   0.56685   0.78227   1.00000   0.03729
  0.02654   0.01801   0.00002   0.00172   0.00194   0.02729
     0.00319   0.00005   0.00027   0.00016   0.00000   0.00086
  0.00096   0.00078   0.00085   0.00064   0.00080   0.00040

H5A       0.80147   0.65398   0.83162   1.00000   0.04094
                                                      0.00000   0.00000

O6        0.76420   0.86670   0.67414   1.00000   0.04269
  0.02118   0.02590   0.00153   0.00527   0.00206   0.02979
     0.00332   0.00005   0.00024   0.00018   0.00000   0.00096
  0.00100   0.00095   0.00077   0.00073   0.00074   0.00044

H6        0.74663   0.92895   0.64472   1.00000   0.04468
                                                      0.00000   0.00000

O7        0.81556   0.81482   0.49216   1.00000   0.04407
  0.03204   0.01724   0.00210   0.00381  -0.00749   0.03104
     0.00322   0.00005   0.00027   0.00017   0.00000   0.00097
  0.00108   0.00084   0.00076   0.00071   0.00085   0.00044

O8        0.79353   0.55825   0.43498   1.00000   0.04958
  0.03276   0.01735  -0.00154   0.00882  -0.00683   0.03292
     0.00342   0.00005   0.00030   0.00017   0.00000   0.00102
  0.00105   0.00080   0.00092   0.00070   0.00092   0.00044

C7        0.81935   0.20291   0.65032   1.00000   0.04950
  0.03230   0.02744   0.00098   0.00141   0.00067   0.03648
```

```
   0.00526    0.00008    0.00040    0.00028    0.00000    0.00150
0.00163    0.00130    0.00130    0.00108    0.00129    0.00065

H7A       0.82887    0.29739    0.70735    1.00000    0.05472
                                              0.00000    0.00000

H7B       0.79238    0.19984    0.64988    1.00000    0.05472
                                              0.00000    0.00000

H7C       0.82656    0.21843    0.55690    1.00000    0.05472
                                              0.00000    0.00000

N1        0.83499    0.03948    0.70664    1.00000    0.03931
0.03017    0.01935    0.00134    0.00444   -0.00193    0.02950
   0.00402    0.00006    0.00033    0.00021    0.00000    0.00107
0.00126    0.00096    0.00098    0.00079    0.00097    0.00050

H1A       0.82846   -0.05274    0.64088    1.00000    0.03540
                                              0.00000    0.00000

H1B       0.82347    0.01296    0.79245    1.00000    0.03540
                                              0.00000    0.00000

C8        0.87608    0.04322    0.73476    1.00000    0.03982
0.04674    0.03289   -0.00464    0.00022   -0.00285    0.03993
   0.00559    0.00008    0.00049    0.00030    0.00000    0.00138
0.00173    0.00143    0.00149    0.00108    0.00131    0.00068

H8        0.88175    0.14157    0.79707    1.00000    0.04792
                                              0.00000    0.00000

C9        0.89509    0.07820    0.60515    1.00000    0.04557
0.06564    0.05385    0.01229    0.01295   -0.00205    0.05457
   0.00712    0.00009    0.00054    0.00037    0.00000    0.00156
0.00220    0.00193    0.00168    0.00136    0.00150    0.00084
```

|       |         |          |         |         |         |
|-------|---------|----------|---------|---------|---------|
| H9A   | 0.88447 | 0.00539  | 0.53161 | 1.00000 | 0.08185 |
|       |         |          |         | 0.00000 | 0.00000 |
| H9B   | 0.92152 | 0.05434  | 0.62082 | 1.00000 | 0.08185 |
|       |         |          |         | 0.00000 | 0.00000 |
| H9C   | 0.89157 | 0.19748  | 0.57927 | 1.00000 | 0.08185 |
|       |         |          |         | 0.00000 | 0.00000 |

C10     0.88948  -0.11460   0.81153   1.00000    0.04077
0.05675   0.04016   0.00107   0.00061   0.00232   0.04600
   0.00617   0.00009   0.00049   0.00033   0.00000   0.00141
0.00185   0.00158   0.00154   0.00118   0.00136   0.00071

|       |         |          |         |         |         |
|-------|---------|----------|---------|---------|---------|
| H10A  | 0.87450 | -0.12943 | 0.89100 | 1.00000 | 0.05520 |
|       |         |          |         | 0.00000 | 0.00000 |
| H10B  | 0.91531 | -0.09544 | 0.84728 | 1.00000 | 0.05520 |
|       |         |          |         | 0.00000 | 0.00000 |

C11     0.88798  -0.27956   0.72961   1.00000    0.05079
0.05548   0.04590  -0.00371   0.00106   0.00148   0.05084
   0.00619   0.00009   0.00049   0.00036   0.00000   0.00166
0.00194   0.00171   0.00156   0.00132   0.00150   0.00076

|       |         |          |         |         |         |
|-------|---------|----------|---------|---------|---------|
| H11A  | 0.86262 | -0.29792 | 0.68852 | 1.00000 | 0.06100 |
|       |         |          |         | 0.00000 | 0.00000 |
| H11B  | 0.90477 | -0.27159 | 0.65480 | 1.00000 | 0.06100 |
|       |         |          |         | 0.00000 | 0.00000 |

C12     0.89917  -0.42560   0.82046   1.00000    0.05925
0.05858   0.06679  -0.00308  -0.01167   0.00706   0.06231

|      |          |          |         |         |         |
|------|----------|----------|---------|---------|---------|
|      | 0.00707  | 0.00011  | 0.00054 | 0.00044 | 0.00000 | 0.00202 |
|      | 0.00216  | 0.00238  | 0.00183 | 0.00171 | 0.00168 | 0.00097 |

| H12 | 0.88094 | -0.46592 | 0.87715 | 1.00000 | 0.07478 |
|-----|---------|----------|---------|---------|---------|
|     |         |          |         | 0.00000 | 0.00000 |

| C13 | 0.93089 | -0.50501 | 0.83184 | 1.00000 | 0.07218 |
|-----|---------|----------|---------|---------|---------|
| 0.06479 | 0.12357 | -0.02518 | -0.02976 | 0.01849 | 0.08861 |
| 0.00858 | 0.00013 | 0.00066 | 0.00065 | 0.00000 | 0.00267 |
| 0.00264 | 0.00433 | 0.00277 | 0.00268 | 0.00216 | 0.00165 |

| C14 | 0.93754 | -0.64585 | 0.93874 | 1.00000 | 0.13726 |
|-----|---------|----------|---------|---------|---------|
| 0.06373 | 0.18150 | -0.02967 | -0.10210 | 0.03701 | 0.13293 |
| 0.00961 | 0.00020 | 0.00073 | 0.00080 | 0.00000 | 0.00537 |
| 0.00319 | 0.00710 | 0.00380 | 0.00547 | 0.00329 | 0.00348 |

| H14A | 0.95578 | -0.60739 | 1.01045 | 1.00000 | 0.19940 |
|------|---------|----------|---------|---------|---------|
|      |         |          |         | 0.00000 | 0.00000 |

| H14B | 0.94677 | -0.74752 | 0.89497 | 1.00000 | 0.19940 |
|------|---------|----------|---------|---------|---------|
|      |         |          |         | 0.00000 | 0.00000 |

| H14C | 0.91433 | -0.67252 | 0.97904 | 1.00000 | 0.19940 |
|------|---------|----------|---------|---------|---------|
|      |         |          |         | 0.00000 | 0.00000 |

| C15 | 0.96157 | -0.46620 | 0.74487 | 1.00000 | 0.07420 |
|-----|---------|----------|---------|---------|---------|
| 0.15932 | 0.29645 | -0.03694 | 0.04293 | 0.03960 | 0.17524 |
| 0.02039 | 0.00019 | 0.00142 | 0.00126 | 0.00000 | 0.00385 |
| 0.00844 | 0.01347 | 0.00899 | 0.00574 | 0.00464 | 0.00471 |

| H15A | 0.96986 | -0.57108 | 0.70307 | 1.00000 | 0.26285 |
|------|---------|----------|---------|---------|---------|
|      |         |          |         | 0.00000 | 0.00000 |

| H15B | 0.98211 | -0.41575 | 0.80097 | 1.00000 | 0.26285 |
|------|---------|----------|---------|---------|---------|
|      |         |          |         | 0.00000 | 0.00000 |

| | | | | | |
|---|---|---|---|---|---|
| H15C | 0.95300 | -0.38616 | 0.67313 | 1.00000 | 0.26285 |
| | | | | 0.00000 | 0.00000 |

| | | | | | |
|---|---|---|---|---|---|
| C16 | 0.81788 | -0.57549 | 1.14503 | 0.51966 | 0.05879 |
| 0.03379 | 0.02613 | 0.00387 | -0.00301 | -0.00301 | 0.03986 |
| | 0.04311 | 0.00089 | 0.00432 | 0.00433 | 0.00401 | 0.00621 |
| 0.00268 | 0.00561 | 0.00318 | 0.00425 | 0.00386 | 0.00279 |

| | | | | | |
|---|---|---|---|---|---|
| H16A | 0.82478 | -0.57763 | 1.05042 | 0.51966 | 0.05979 |
| | | | | 0.00401 | 0.00000 |

| | | | | | |
|---|---|---|---|---|---|
| H16B | 0.79093 | -0.57767 | 1.14606 | 0.51966 | 0.05979 |
| | | | | 0.00401 | 0.00000 |

| | | | | | |
|---|---|---|---|---|---|
| H16C | 0.82832 | -0.67480 | 1.19380 | 0.51966 | 0.05979 |
| | | | | 0.00401 | 0.00000 |

| | | | | | |
|---|---|---|---|---|---|
| N2 | 0.83239 | -0.41859 | 1.21288 | 0.51966 | 0.03675 |
| 0.03922 | 0.01831 | 0.00444 | 0.00551 | -0.00412 | 0.03126 |
| | 0.04262 | 0.00056 | 0.00364 | 0.00367 | 0.00401 | 0.00224 |
| 0.00219 | 0.00323 | 0.00189 | 0.00230 | 0.00166 | 0.00160 |

| | | | | | |
|---|---|---|---|---|---|
| H2A | 0.82442 | -0.32021 | 1.15547 | 0.51966 | 0.03751 |
| | | | | 0.00401 | 0.00000 |

| | | | | | |
|---|---|---|---|---|---|
| H2B | 0.82109 | -0.40653 | 1.30112 | 0.51966 | 0.03751 |
| | | | | 0.00401 | 0.00000 |

| | | | | | |
|---|---|---|---|---|---|
| C17 | 0.87301 | -0.41169 | 1.23880 | 0.51966 | 0.04098 |
| 0.05984 | 0.03281 | 0.00981 | 0.01325 | -0.00784 | 0.04403 |
| | 0.02910 | 0.00052 | 0.00216 | 0.00194 | 0.00401 | 0.00388 |
| 0.00472 | 0.00415 | 0.00366 | 0.00297 | 0.00330 | 0.00244 |

| | | | | | |
|---|---|---|---|---|---|
| H17 | 0.88398 | -0.46737 | 1.15967 | 0.51966 | 0.05284 |

|      |          |          |         |         |         |
|------|----------|----------|---------|---------|---------|
|      |          |          |         | 0.00401 | 0.00000 |

| C18  | 0.88525 | -0.51442 | 1.36706 | 0.51966 | 0.05376 |
|------|---------|----------|---------|---------|---------|
| 0.10799 | 0.03830 | 0.03039 | -0.00215 | 0.01548 | 0.06694 |
| 0.05132 | 0.00072 | 0.00327 | 0.00185 | 0.00401 | 0.00721 |
| 0.00739 | 0.00777 | 0.00606 | 0.00558 | 0.00515 | 0.00411 |

| H18A | 0.87431 | -0.46518 | 1.44640 | 0.51966 | 0.10042 |
|------|---------|----------|---------|---------|---------|
|      |         |          |         | 0.00401 | 0.00000 |

| H18B | 0.91221 | -0.51136 | 1.38148 | 0.51966 | 0.10042 |
|------|---------|----------|---------|---------|---------|
|      |         |          |         | 0.00401 | 0.00000 |

| H18C | 0.87704 | -0.63224 | 1.35509 | 0.51966 | 0.10042 |
|------|---------|----------|---------|---------|---------|
|      |         |          |         | 0.00401 | 0.00000 |

| C19  | 0.88673 | -0.23054 | 1.24513 | 0.51966 | 0.05783 |
|------|---------|----------|---------|---------|---------|
| 0.08011 | 0.04446 | 0.00148 | 0.00847 | -0.01746 | 0.06057 |
| 0.02923 | 0.00037 | 0.00218 | 0.00222 | 0.00401 | 0.00449 |
| 0.00566 | 0.00508 | 0.00441 | 0.00374 | 0.00414 | 0.00288 |

| H19A | 0.88183 | -0.18145 | 1.33483 | 0.51966 | 0.07268 |
|------|---------|----------|---------|---------|---------|
|      |         |          |         | 0.00401 | 0.00000 |

| H19B | 0.87276 | -0.16325 | 1.17372 | 0.51966 | 0.07268 |
|------|---------|----------|---------|---------|---------|
|      |         |          |         | 0.00401 | 0.00000 |

| C20  | 0.92794 | -0.21622 | 1.22502 | 0.51966 | 0.06125 |
|------|---------|----------|---------|---------|---------|
| 0.09971 | 0.05744 | -0.01526 | 0.01160 | -0.02412 | 0.07245 |
| 0.01505 | 0.00024 | 0.00138 | 0.00105 | 0.00401 | 0.00388 |
| 0.00506 | 0.00422 | 0.00397 | 0.00348 | 0.00384 | 0.00201 |

| H20A | 0.94170 | -0.29912 | 1.28480 | 0.51966 | 0.08694 |
|------|---------|----------|---------|---------|---------|
|      |         |          |         | 0.00401 | 0.00000 |

| | | | | | |
|---|---|---|---|---|---|
| H20B | 0.93234 | -0.24387 | 1.12922 | 0.51966 | 0.08694 |
| | | | | 0.00401 | 0.00000 |

| | | | | | |
|---|---|---|---|---|---|
| C21 | 0.94185 | -0.04083 | 1.25785 | 0.51966 | 0.06898 |
| 0.09165 | 0.06506 | 0.00085 | 0.00994 | -0.03485 | 0.07498 |
| | 0.01360 | 0.00023 | 0.00130 | 0.00088 | 0.00401 | 0.00378 |
| 0.00463 | 0.00389 | 0.00370 | 0.00315 | 0.00370 | 0.00199 |

| | | | | | |
|---|---|---|---|---|---|
| H21 | 0.92985 | 0.04865 | 1.20741 | 0.51966 | 0.08998 |
| | | | | 0.00401 | 0.00000 |

| | | | | | |
|---|---|---|---|---|---|
| C22 | 0.96878 | 0.00500 | 1.34839 | 0.51966 | 0.05593 |
| 0.09469 | 0.08296 | -0.00832 | 0.01894 | -0.01592 | 0.07719 |
| | 0.01557 | 0.00022 | 0.00129 | 0.00097 | 0.00401 | 0.00371 |
| 0.00592 | 0.00507 | 0.00463 | 0.00353 | 0.00394 | 0.00235 |

| | | | | | |
|---|---|---|---|---|---|
| C23 | 0.99077 | -0.11624 | 1.44519 | 0.51966 | 0.09515 |
| 0.11136 | 0.13723 | -0.01484 | -0.03882 | -0.00986 | 0.11684 |
| | 0.02117 | 0.00036 | 0.00186 | 0.00148 | 0.00401 | 0.00733 |
| 0.00896 | 0.01038 | 0.00878 | 0.00665 | 0.00689 | 0.00437 |

| | | | | | |
|---|---|---|---|---|---|
| H23A | 0.98128 | -0.23185 | 1.43171 | 0.51966 | 0.17526 |
| | | | | 0.00401 | 0.00000 |

| | | | | | |
|---|---|---|---|---|---|
| H23B | 0.98824 | -0.08133 | 1.53981 | 0.51966 | 0.17526 |
| | | | | 0.00401 | 0.00000 |

| | | | | | |
|---|---|---|---|---|---|
| H23C | 1.01685 | -0.11310 | 1.42597 | 0.51966 | 0.17526 |
| | | | | 0.00401 | 0.00000 |

| | | | | | |
|---|---|---|---|---|---|
| C24 | 0.97899 | 0.18887 | 1.36538 | 0.51966 | 0.07487 |
| 0.09986 | 0.14217 | -0.01248 | 0.01156 | -0.02779 | 0.10545 |
| | 0.02003 | 0.00029 | 0.00155 | 0.00150 | 0.00401 | 0.00577 |
| 0.00768 | 0.00936 | 0.00737 | 0.00608 | 0.00555 | 0.00366 |

| | | | | | |
|---|---|---|---|---|---|
| H24A | 0.96675 | 0.25483 | 1.29066 | 0.51966 | 0.15818 |
| | | | | 0.00401 | 0.00000 |
| H24B | 1.00579 | 0.20140 | 1.36382 | 0.51966 | 0.15818 |
| | | | | 0.00401 | 0.00000 |
| H24C | 0.97110 | 0.23030 | 1.45273 | 0.51966 | 0.15818 |
| | | | | 0.00401 | 0.00000 |
| C16' | 0.82247 | −0.58215 | 1.15734 | 0.48034 | 0.05879 |
| 0.03379 | 0.02613 | 0.00387 | −0.00301 | −0.00301 | 0.03986 |
| 0.04748 | 0.00100 | 0.00462 | 0.00475 | 0.00401 | 0.00621 |
| 0.00268 | 0.00561 | 0.00318 | 0.00425 | 0.00386 | 0.00279 |
| H16D | 0.83336 | −0.60904 | 1.07149 | 0.48034 | 0.05979 |
| | | | | 0.00401 | 0.00000 |
| H16E | 0.79551 | −0.58334 | 1.14278 | 0.48034 | 0.05979 |
| | | | | 0.00401 | 0.00000 |
| H16F | 0.83033 | −0.66684 | 1.22645 | 0.48034 | 0.05979 |
| | | | | 0.00401 | 0.00000 |
| N2' | 0.83487 | −0.41206 | 1.20454 | 0.48034 | 0.03675 |
| 0.03922 | 0.01831 | 0.00444 | 0.00551 | −0.00412 | 0.03126 |
| 0.04682 | 0.00061 | 0.00395 | 0.00404 | 0.00401 | 0.00224 |
| 0.00219 | 0.00323 | 0.00189 | 0.00230 | 0.00166 | 0.00160 |
| H2'1 | 0.82399 | −0.38754 | 1.29199 | 0.48034 | 0.03751 |
| | | | | 0.00401 | 0.00000 |
| H2'2 | 0.82508 | −0.32701 | 1.13719 | 0.48034 | 0.03751 |
| | | | | 0.00401 | 0.00000 |

```
C17'      0.87594   -0.39042    1.22474    0.48034    0.03429
0.06551   0.04099    0.01648    0.00156    0.00092    0.04698
   0.03177   0.00053    0.00229    0.00226    0.00401    0.00418
0.00520   0.00485    0.00399    0.00392    0.00374    0.00269

H17'      0.88728   -0.41552    1.13715    0.48034    0.05638
                                            0.00401    0.00000

C18'      0.88949   -0.52246    1.33348    0.48034    0.04897
0.11025   0.04485    0.03451    0.00059    0.00325    0.06816
   0.05364   0.00075    0.00346    0.00216    0.00401    0.00604
0.00831   0.00967    0.00743    0.00679    0.00565    0.00454

H18D      0.87715   -0.50278    1.41757    0.48034    0.10223
                                            0.00401    0.00000

H18E      0.91622   -0.51136    1.35240    0.48034    0.10223
                                            0.00401    0.00000

H18F      0.88368   -0.63690    1.29940    0.48034    0.10223
                                            0.00401    0.00000

C19'      0.88240   -0.20589    1.26181    0.48034    0.04804
0.07212   0.04329   -0.01175    0.00994   -0.02480    0.05416
   0.02630   0.00038    0.00226    0.00225    0.00401    0.00406
0.00522   0.00499    0.00399    0.00352    0.00396    0.00262

H19C      0.86947   -0.18148    1.34498    0.48034    0.06500
                                            0.00401    0.00000

H19D      0.87072   -0.13539    1.18731    0.48034    0.06500
                                            0.00401    0.00000

C20'      0.92257   -0.14904    1.28741    0.48034    0.05260
0.09441   0.05457   -0.01613    0.00976   -0.02394    0.06691
```

```
         0.01573    0.00022    0.00149    0.00094    0.00401    0.00355
  0.00501    0.00407    0.00394    0.00318    0.00373    0.00200

H20C         0.92293   -0.02717    1.31182    0.48034    0.08029
                                                 0.00401    0.00000

H20D         0.93391   -0.21251    1.36663    0.48034    0.08029
                                                 0.00401    0.00000

C21'         0.94535   -0.17416    1.17008    0.48034    0.06350
  0.10756    0.06153   -0.01127    0.01457   -0.01850    0.07705
     0.01759    0.00026    0.00159    0.00099    0.00401    0.00408
  0.00559    0.00435    0.00438    0.00366    0.00429    0.00226

H21'         0.93990   -0.27266    1.11666    0.48034    0.09246
                                                 0.00401    0.00000

C22'         0.97209   -0.07833    1.12997    0.48034    0.06251
  0.13060    0.06460    0.00888   -0.00025   -0.02631    0.08613
     0.01799    0.00025    0.00176    0.00098    0.00401    0.00432
  0.00702    0.00462    0.00519    0.00360    0.00482    0.00267

C23'         0.99167   -0.11870    1.00316    0.48034    0.07933
  0.19500    0.08515    0.02434    0.00025   -0.03709    0.12010
     0.03138    0.00033    0.00250    0.00199    0.00401    0.01156
  0.01378    0.00649    0.01219    0.00933    0.00884    0.00563

H23D         1.01738   -0.14902    1.02906    0.48034    0.18015
                                                 0.00401    0.00000

H23E         0.99101   -0.01917    0.94325    0.48034    0.18015
                                                 0.00401    0.00000

H23F         0.97933   -0.21409    0.95496    0.48034    0.18015
                                                 0.00401    0.00000
```

| | | | | | |
|---|---|---|---|---|---|
| C24' | 0.98287 | 0.08090 | 1.20165 | 0.48034 | 0.12470 |
| 0.12670 | 0.09922 | 0.02656 | 0.00427 | -0.03189 | 0.11705 |
| 0.02467 | 0.00046 | 0.00202 | 0.00144 | 0.00401 | 0.00857 |
| 0.00943 | 0.00766 | 0.00767 | 0.00696 | 0.00789 | 0.00416 |
| | | | | | |
| H24D | 0.96071 | 0.13996 | 1.22774 | 0.48034 | 0.17558 |
| | | | | 0.00401 | 0.00000 |
| | | | | | |
| H24E | 0.99624 | 0.15362 | 1.14105 | 0.48034 | 0.17558 |
| | | | | 0.00401 | 0.00000 |
| | | | | | |
| H24F | 0.99880 | 0.05468 | 1.28367 | 0.48034 | 0.17558 |
| | | | | 0.00401 | 0.00000 |

Final Structure Factor Calculation for xs0061 in C2

Total number of l.s. parameters = 403   Maximum vector length = 623
Memory required = 6827 / 30534 wR2 = 0.1486 before cycle 7 for 5499 data and 2 / 403 parameters

Disagreeable restraints before cycle 7

| Observed | Target | Error | Sigma | Restraint |
|---|---|---|---|---|
| | | -0.0389 | 0.0100 | SIMU U22 C21 C22' |
| | | -0.0688 | 0.0200 | SIMU U11 C22 C24' |
| | | -0.0644 | 0.0200 | SIMU U22 C22' C23' |
| | | -0.0622 | 0.0200 | SIMU U11 C22' C24' |

Summary of restraints applied in cycle    7

|        | ANTIBUMP | DFIX   | DANG   | SAME/SADI | CHIV/Z | CHIV/NZ | FLAT   |
|--------|----------|--------|--------|-----------|--------|---------|--------|
| DELU   | RIGU     | SIMU   | ISOR   | SUMP      |        |         |        |
| Number | 0        | 0      | 0      | 57        | 0      | 0       | 0      |
| 0      | 0        | 246    | 0      | 0         |        |         |        |
| rms sigma | 0.0000 | 0.0000 | 0.0000 | 0.0321    | 0.0000 | 0.0000  | 0.0000 |
| 0.0000 | 0.0000   | 0.0150 | 0.0000 | 0.0000    |        |         |        |
| rms deviation | 0.0000 | 0.0000 | 0.0000 | 0.0290 | 0.0000 | 0.0000 | 0.0000 |
| 0.0000 | 0.0000   | 0.0180 | 0.0000 | 0.0000    |        |         |        |

GooF = S =    1.054;    Restrained GooF =     1.060 for    304 restraints

Weight = 1 / [ sigma^2(Fo^2) + ( 0.1039 * P )^2 +   1.13 * P ]
where  P = ( Max ( Fo^2, 0 ) + 2 * Fc^2 ) / 3

R1 =  0.0498 for    5295 Fo > 4sig(Fo)  and  0.0522 for all    5499 data
wR2 =  0.1486,  GooF = S =    1.054,  Restrained GooF =    1.060 for all data Occupancy sum of asymmetric unit =    34.00 for non-hydrogen and 48.00 for H and D atoms Principal mean square atomic displacements U 0.0427   0.0302   0.0131   C1

| | | | |
|---|---|---|---|
| 0.0393 | 0.0233 | 0.0158 | C2 |
| 0.0388 | 0.0214 | 0.0145 | C3 |
| 0.0368 | 0.0227 | 0.0146 | C4 |
| 0.0377 | 0.0257 | 0.0162 | C5 |
| 0.0400 | 0.0295 | 0.0126 | C6 |
| 0.0457 | 0.0300 | 0.0164 | O1 |
| 0.0538 | 0.0292 | 0.0175 | O2 |
| 0.0455 | 0.0241 | 0.0218 | O3 |
| 0.0391 | 0.0261 | 0.0201 | O4 |
| 0.0377 | 0.0262 | 0.0180 | O5 |
| 0.0432 | 0.0255 | 0.0207 | O6 |
| 0.0477 | 0.0290 | 0.0164 | O7 |
| 0.0528 | 0.0304 | 0.0156 | O8 |
| 0.0497 | 0.0325 | 0.0272 | C7 |
| 0.0398 | 0.0301 | 0.0186 | N1 |
| 0.0486 | 0.0406 | 0.0307 | C8 |
| 0.0736 | 0.0544 | 0.0358 | C9 |
| 0.0571 | 0.0429 | 0.0380 | C10 |
| 0.0576 | 0.0506 | 0.0443 | C11 |
| 0.0830 | 0.0577 | 0.0463 | C12 |
| 0.1567 | 0.0596 | 0.0495 | C13 |
| 0.2939 | 0.0620 | 0.0429 | C14  may be split into  0.9339 -0.6521 0.9577  and  0.9412 -0.6396 0.9198 |
| 0.3063 | 0.1711 | 0.0483 | C15 |
| 0.0609 | 0.0345 | 0.0242 | C16 |
| 0.0425 | 0.0352 | 0.0161 | N2 |
| 0.0642 | 0.0475 | 0.0204 | C17 |
| 0.1212 | 0.0557 | 0.0240 | C18 |
| 0.0897 | 0.0516 | 0.0404 | C19 |
| 0.1153 | 0.0525 | 0.0495 | C20 |
| 0.1170 | 0.0659 | 0.0420 | C21 |
| 0.1065 | 0.0791 | 0.0460 | C22 |
| 0.1723 | 0.1156 | 0.0626 | C23 |
| 0.1468 | 0.1127 | 0.0569 | C24 |
| 0.0609 | 0.0345 | 0.0242 | C16' |

| | | | |
|---|---|---|---|
| 0.0425 | 0.0352 | 0.0161 | N2' |
| 0.0738 | 0.0350 | 0.0322 | C17' |
| 0.1251 | 0.0497 | 0.0296 | C18' |
| 0.0906 | 0.0394 | 0.0325 | C19' |
| 0.1097 | 0.0494 | 0.0417 | C20' |
| 0.1172 | 0.0629 | 0.0511 | C21' |
| 0.1414 | 0.0636 | 0.0534 | C22' |
| 0.2119 | 0.0804 | 0.0680 | C23' | may be split into 0.9904 - 0.0971 1.0071 and 0.9930 -0.1403 0.9992

| | | | |
|---|---|---|---|
| 0.1667 | 0.1080 | 0.0764 | C24' |

Warning: 2 atoms may be split and 0 atoms NPD

Analysis of variance for reflections employed in refinement     K = Mean[Fo^2] / Mean[Fc^2]  for group Fc/Fc(max)     0.000   0.013   0.020   0.027   0.036   0.045   0.057   0.074   0.098   0.145   1.000

Number in group    591.   528.   547.   565.   516.   579.   526.   550.   554.   543.

GooF    1.003   0.955   1.063   1.146   1.064   1.020   1.085   1.015   0.976   1.191

K    1.426   1.100   1.043   1.007   1.006   0.999   1.009   1.002   1.017   1.033

Resolution(A)   0.81   0.84   0.88   0.92   0.96   1.02   1.10   1.21   1.39   1.76   inf

| | | | | | |
|---|---|---|---|---|---|
| Number in group | 568. | 542. | 551. | 558. | 531. |
| 553. | 551. | 547. | 553. | 545. | |
| GooF | 1.065 | 1.051 | 0.858 | 0.778 | 0.853 |
| 0.849 | 0.897 | 0.994 | 1.188 | 1.698 | |
| K | 1.010 | 1.017 | 1.044 | 1.032 | 1.018 |
| 1.005 | 1.011 | 1.021 | 1.046 | 1.029 | |
| R1 | 0.084 | 0.071 | 0.066 | 0.057 | 0.044 |
| 0.039 | 0.038 | 0.043 | 0.047 | 0.058 | |

Recommended weighting scheme:  WGHT      0.1063      1.0583
Note that in most cases convergence will be faster if fixed weights (e.g. the
default WGHT 0.1) are retained until the refinement is virtually complete, and
only then should the above recommended values be used.

Most Disagreeable Reflections (* if suppressed or used for Rfree)

| h | k | l | Fo^2 | Fc^2 | Delta(F^2)/esd | Fc/Fc(max) | Resolution(A) |
|---|---|---|---|---|---|---|---|
| -21 | 1 | 11 | 203.32 | 25.49 | 10.15 | 0.020 | 0.81 |
| -10 | 2 | 11 | 294.06 | 77.21 | 9.15 | 0.035 | 0.86 |
| -2 | 0 | 2 | 866.06 | 333.02 | 8.64 | 0.074 | 4.82 |
| -5 | 3 | 11 | -4.98 | 90.47 | 8.02 | 0.038 | 0.84 |

| | | | | | | |
|---|---|---|---|---|---|---|
| -21 | 3 | 10 | 75.37 | 0.49 | 7.42 | 0.003 |
| 0.83 | | | | | | |
| -16 | 0 | 4 | 38.41 | 6.68 | 5.87 | 0.010 |
| 1.73 | | | | | | |
| -6 | 0 | 1 | 1242.62 | 2587.14 | 5.82 | 0.205 |
| 5.31 | | | | | | |
| -12 | 0 | 1 | 394.34 | 848.63 | 5.75 | 0.117 |
| 2.95 | | | | | | |
| 10 | 2 | 1 | 56.84 | 142.24 | 5.09 | 0.048 |
| 2.54 | | | | | | |
| 1 | -1 | 1 | 1067.68 | 1947.38 | 4.88 | 0.178 |
| 6.01 | | | | | | |
| 14 | 0 | 4 | 581.31 | 340.14 | 4.83 | 0.074 |
| 1.72 | | | | | | |
| 10 | -2 | 1 | 63.97 | 144.28 | 4.68 | 0.048 |
| 2.54 | | | | | | |
| 1 | 1 | 1 | 1103.40 | 1945.89 | 4.65 | 0.178 |
| 6.01 | | | | | | |
| -4 | 0 | 1 | 263.44 | 492.28 | 4.62 | 0.089 |
| 6.90 | | | | | | |
| -6 | 2 | 11 | 6.05 | 39.23 | 4.56 | 0.025 |
| 0.87 | | | | | | |
| -8 | 0 | 1 | 4115.56 | 7023.06 | 4.50 | 0.338 |
| 4.23 | | | | | | |
| -2 | 0 | 1 | 1139.43 | 1881.00 | 4.17 | 0.175 |
| 8.89 | | | | | | |
| 11 | 1 | 0 | 378.84 | 641.97 | 4.11 | 0.102 |
| 3.04 | | | | | | |
| 12 | 0 | 0 | 3598.80 | 2403.77 | 3.96 | 0.198 |
| 3.02 | | | | | | |
| -3 | 1 | 1 | 1137.77 | 1824.49 | 3.95 | 0.172 |
| 5.58 | | | | | | |
| 28 | 0 | 4 | 22.36 | 5.75 | 3.94 | 0.010 |
| 1.11 | | | | | | |

| | | | | | | |
|---|---|---|---|---|---|---|
| 14 | 0 | 1 | 220.28 | 368.39 | 3.79 | 0.077 |
| 2.46 | | | | | | |
| 1 | -3 | 3 | 2401.60 | 1628.19 | 3.77 | 0.163 |
| 2.04 | | | | | | |
| 20 | 0 | 4 | 255.92 | 159.93 | 3.68 | 0.051 |
| 1.41 | | | | | | |
| 12 | 0 | 1 | 184.94 | 113.18 | 3.68 | 0.043 |
| 2.83 | | | | | | |
| -3 | -1 | 1 | 1193.04 | 1834.16 | 3.63 | 0.173 |
| 5.58 | | | | | | |
| 11 | -1 | 0 | 405.36 | 641.18 | 3.63 | 0.102 |
| 3.04 | | | | | | |
| -18 | 2 | 11 | 17.12 | 52.02 | 3.63 | 0.029 |
| 0.82 | | | | | | |
| 20 | 0 | 0 | 171.68 | 104.43 | 3.63 | 0.041 |
| 1.81 | | | | | | |
| -18 | 0 | 8 | 20.68 | 54.26 | 3.62 | 0.030 |
| 1.08 | | | | | | |
| 4 | 0 | 1 | 39.43 | 80.71 | 3.61 | 0.036 |
| 6.43 | | | | | | |
| -2 | 0 | 4 | 36.77 | 15.59 | 3.56 | 0.016 |
| 2.45 | | | | | | |
| -28 | 0 | 6 | 61.09 | 112.56 | 3.47 | 0.043 |
| 1.05 | | | | | | |
| 13 | -3 | 0 | 447.80 | 300.99 | 3.45 | 0.070 |
| 1.91 | | | | | | |
| 2 | 0 | 1 | 22.19 | 49.84 | 3.39 | 0.028 |
| 8.37 | | | | | | |
| -2 | 0 | 6 | 443.55 | 301.01 | 3.34 | 0.070 |
| 1.64 | | | | | | |
| -24 | 2 | 10 | 29.37 | 7.17 | 3.33 | 0.011 |
| 0.83 | | | | | | |
| 1 | -5 | 0 | 199.61 | 125.71 | 3.32 | 0.045 |
| 1.58 | | | | | | |

| h | k | l | | | | | |
|---|---|---|---|---|---|---|---|
| -7 | 3 | 3 | 40.66 | 77.61 | 3.29 | 0.036 | 1.93 |
| 30 | 0 | 4 | 23.63 | 8.57 | 3.29 | 0.012 | 1.05 |
| -6 | -4 | 1 | 569.70 | 394.48 | 3.26 | 0.080 | 1.85 |
| -16 | 0 | 8 | 25.77 | 55.05 | 3.23 | 0.030 | 1.11 |
| 0 | 0 | 3 | 43.00 | 21.30 | 3.22 | 0.019 | 3.27 |
| -13 | -5 | 2 | 123.59 | 76.05 | 3.21 | 0.035 | 1.33 |
| -14 | 0 | 2 | 4288.61 | 3076.50 | 3.18 | 0.224 | 2.36 |
| -2 | 2 | 4 | 851.82 | 1239.06 | 3.16 | 0.142 | 2.08 |
| -26 | 2 | 9 | 43.17 | 81.81 | 3.15 | 0.036 | 0.87 |
| 2 | -6 | 6 | 115.37 | 69.45 | 3.13 | 0.034 | 1.02 |
| 6 | 2 | 0 | 740.79 | 1078.46 | 3.11 | 0.132 | 3.30 |
| 1 | 3 | 3 | 2257.59 | 1635.30 | 3.11 | 0.163 | 2.04 |

Bond lengths and angles

| C1 – | Distance | Angles | | |
|---|---|---|---|---|
| O2 | 1.2565 (0.0038) | | | |
| O1 | 1.2575 (0.0036) | 124.91 (0.23) | | |
| C2 | 1.5384 (0.0034) | 116.28 (0.23) | 118.80 (0.24) | |
| | C1 – | O2 | O1 | |

| C2 – | Distance | Angles | | |
|---|---|---|---|---|
| O3 | 1.4187 (0.0034) | | | |
| C3 | 1.5244 (0.0037) | 109.49 (0.19) | | |
| C1 | 1.5384 (0.0034) | 112.32 (0.21) | 109.55 (0.21) | |
| H2 | 1.0000 | 108.46 | 108.46 | 108.46 |
| | C2 – | O3 | C3 | C1 |

| C3 – | Distance | Angles | | |
|---|---|---|---|---|
| O4 | 1.4246 (0.0030) | | | |
| C2 | 1.5244 (0.0037) | 111.52 (0.22) | | |
| C4 | 1.5316 (0.0028) | 111.59 (0.17) | 111.39 (0.18) | |
| H3 | 1.0000 | 107.36 | 107.36 | 107.36 |
| | C3 – | O4 | C2 | C4 |

| C4 – | Distance | Angles | | |
|---|---|---|---|---|
| O5 | 1.4222 (0.0029) | | | |
| C3 | 1.5316 (0.0027) | 111.48 (0.17) | | |
| C5 | 1.5327 (0.0037) | 111.05 (0.22) | 111.43 (0.18) | |
| H4 | 1.0000 | 107.55 | 107.55 | 107.55 |
| | C4 – | O5 | C3 | C5 |

| C5 – | Distance | Angles | | |
|---|---|---|---|---|
| O6 | 1.4168 (0.0033) | | | |
| C4 | 1.5327 (0.0037) | 109.66 (0.19) | | |
| C6 | 1.5335 (0.0034) | 112.53 (0.22) | 109.17 (0.22) | |
| H5 | 1.0000 | 108.47 | 108.47 | 108.47 |
| | C5 – | O6 | C4 | C6 |

| C6 – | Distance | Angles | |
|---|---|---|---|
| O7 | 1.2613 (0.0034) | | |
| O8 | 1.2654 (0.0038) | 124.12 (0.23) | |
| C5 | 1.5335 (0.0034) | 119.53 (0.24) | 116.35 (0.23) |
| | C6 – | O7 | O8 |

| O1 – | Distance | Angles |
|---|---|---|

| | | |
|---|---|---|
| C1 | 1.2575 (0.0036) | |
| | O1 – | |
| | | |
| O2 – | Distance | Angles |
| C1 | 1.2565 (0.0038) | |
| | O2 – | |
| | | |
| O3 – | Distance | Angles |
| C2 | 1.4187 (0.0034) | |
| H3A | 0.8400 | 109.47 |
| | O3 – | C2 |
| | | |
| O4 – | Distance | Angles |
| C3 | 1.4246 (0.0030) | |
| H4A | 0.8400 | 109.47 |
| | O4 – | C3 |
| | | |
| O5 – | Distance | Angles |
| C4 | 1.4222 (0.0029) | |
| H5A | 0.8400 | 109.47 |
| | O5 – | C4 |
| | | |
| O6 – | Distance | Angles |
| C5 | 1.4168 (0.0033) | |
| H6 | 0.8400 | 109.47 |
| | O6 – | C5 |
| | | |
| O7 – | Distance | Angles |
| C6 | 1.2613 (0.0034) | |
| | O7 – | |
| | | |
| O8 – | Distance | Angles |
| C6 | 1.2654 (0.0038) | |
| | O8 – | |

| C7 - | Distance | Angles | | |
|---|---|---|---|---|
| N1 | 1.4980 (0.0038) | | | |
| H7A | 0.9800 | 109.47 | | |
| H7B | 0.9800 | 109.47 | 109.47 | |
| H7C | 0.9800 | 109.47 | 109.47 | 109.47 |
| | C7 - | N1 | H7A | H7B |

| N1 - | Distance | Angles | | |
|---|---|---|---|---|
| C7 | 1.4980 (0.0038) | | | |
| C8 | 1.4994 (0.0034) | 113.44 (0.25) | | |
| H1A | 0.9900 | 108.88 | 108.88 | |
| H1B | 0.9900 | 108.88 | 108.88 | 107.72 |
| | N1 - | C7 | C8 | H1A |

| C8 - | Distance | Angles | | |
|---|---|---|---|---|
| N1 | 1.4994 (0.0034) | | | |
| C9 | 1.5165 (0.0044) | 110.87 (0.23) | | |
| C10 | 1.5169 (0.0049) | 110.83 (0.27) | 114.66 (0.30) | |
| H8 | 1.0000 | 106.66 | 106.66 | 106.66 |
| | C8 - | N1 | C9 | C10 |

| C9 - | Distance | Angles | | |
|---|---|---|---|---|
| C8 | 1.5165 (0.0044) | | | |
| H9A | 0.9800 | 109.47 | | |
| H9B | 0.9800 | 109.47 | 109.47 | |
| H9C | 0.9800 | 109.47 | 109.47 | 109.47 |
| | C9 - | C8 | H9A | H9B |

| C10 - | Distance | Angles | | |
|---|---|---|---|---|
| C8 | 1.5169 (0.0049) | | | |
| C11 | 1.5281 (0.0049) | 115.97 (0.27) | | |
| H10A | 0.9900 | 108.29 | 108.29 | |
| H10B | 0.9900 | 108.29 | 108.29 | 107.40 |
| | C10 - | C8 | C11 | H10A |

| C11 -  | Distance        | Angles         |                |         |
|--------|-----------------|----------------|----------------|---------|
| C12    | 1.4951 (0.0054) |                |                |         |
| C10    | 1.5281 (0.0049) | 110.06 (0.28)  |                |         |
| H11A   | 0.9900          | 109.65         | 109.65         |         |
| H11B   | 0.9900          | 109.65         | 109.65         | 108.16  |
|        | C11 -           | C12            | C10            | H11A    |

| C12 -  | Distance        | Angles         |         |
|--------|-----------------|----------------|---------|
| C13    | 1.3094 (0.0059) |                |         |
| C11    | 1.4951 (0.0054) | 128.26 (0.48)  |         |
| H12    | 0.9500          | 115.87         | 115.87  |
|        | C12 -           | C13            | C11     |

| C13 -  | Distance        | Angles         |                |
|--------|-----------------|----------------|----------------|
| C12    | 1.3094 (0.0059) |                |                |
| C15    | 1.4843 (0.0109) | 123.04 (0.64)  |                |
| C14    | 1.5354 (0.0086) | 119.92 (0.59)  | 117.04 (0.60)  |
|        | C13 -           | C12            | C15            |

| C14 -  | Distance        | Angles  |         |         |
|--------|-----------------|---------|---------|---------|
| C13    | 1.5354 (0.0086) |         |         |         |
| H14A   | 0.9800          | 109.47  |         |         |
| H14B   | 0.9800          | 109.47  | 109.47  |         |
| H14C   | 0.9800          | 109.47  | 109.47  | 109.47  |
|        | C14 -           | C13     | H14A    | H14B    |

| C15 -  | Distance        | Angles  |         |         |
|--------|-----------------|---------|---------|---------|
| C13    | 1.4843 (0.0109) |         |         |         |
| H15A   | 0.9800          | 109.47  |         |         |
| H15B   | 0.9800          | 109.47  | 109.47  |         |
| H15C   | 0.9800          | 109.47  | 109.47  | 109.47  |
|        | C15 -           | C13     | H15A    | H15B    |

| C16 -  | Distance        | Angles  |
|--------|-----------------|---------|
| N2     | 1.4839 (0.0147) |         |

| | | | | |
|---|---|---|---|---|
| H16A | 0.9800 | 109.47 | | |
| H16B | 0.9800 | 109.47 | 109.47 | |
| H16C | 0.9800 | 109.47 | 109.47 | 109.47 |
| | C16 – | N2 | H16A | H16B |

| N2 – | Distance | Angles | | |
|---|---|---|---|---|
| C17 | 1.4809 (0.0136) | | | |
| C16 | 1.4839 (0.0147) | 115.21 (1.82) | | |
| H2A | 0.9900 | 108.47 | 108.47 | |
| H2B | 0.9900 | 108.47 | 108.47 | 107.50 |
| | N2 – | C17 | C16 | H2A |

| C17 – | Distance | Angles | | |
|---|---|---|---|---|
| N2 | 1.4809 (0.0136) | | | |
| C19 | 1.5122 (0.0138) | 111.30 (1.46) | | |
| C18 | 1.5365 (0.0141) | 110.38 (1.48) | 112.87 (1.58) | |
| H17 | 1.0000 | 107.34 | 107.34 | 107.34 |
| | C17 – | N2 | C19 | C18 |

| C18 – | Distance | Angles | | |
|---|---|---|---|---|
| C17 | 1.5365 (0.0141) | | | |
| H18A | 0.9800 | 109.47 | | |
| H18B | 0.9800 | 109.47 | 109.47 | |
| H18C | 0.9800 | 109.47 | 109.47 | 109.47 |
| | C18 – | C17 | H18A | H18B |

| C19 – | Distance | Angles | | |
|---|---|---|---|---|
| C17 | 1.5122 (0.0138) | | | |
| C20 | 1.5288 (0.0138) | 112.79 (1.24) | | |
| H19A | 0.9900 | 109.03 | 109.03 | |
| H19B | 0.9900 | 109.03 | 109.03 | 107.80 |
| | C19 – | C17 | C20 | H19A |

| C20 – | Distance | Angles |
|---|---|---|
| C21 | 1.4992 (0.0120) | |

| | | | | |
|---|---|---|---|---|
| C19 | 1.5288 (0.0138) | 111.02 (0.99) | | |
| H20A | 0.9900 | 109.43 | 109.43 | |
| H20B | 0.9900 | 109.43 | 109.43 | 108.03 |
| | C20 - | C21 | C19 | H20A |

| C21 - | Distance | Angles | |
|---|---|---|---|
| C22 | 1.3247 (0.0112) | | |
| C20 | 1.4992 (0.0120) | 128.14 (0.98) | |
| H21 | 0.9500 | 115.93 | 115.93 |
| | C21 - | C22 | C20 |

| C22 - | Distance | Angles | |
|---|---|---|---|
| C21 | 1.3247 (0.0112) | | |
| C24 | 1.5025 (0.0138) | 120.16 (1.00) | |
| C23 | 1.5322 (0.0144) | 125.03 (0.98) | 114.78 (0.95) |
| | C22 - | C21 | C24 |

| C23 - | Distance | Angles | | |
|---|---|---|---|---|
| C22 | 1.5322 (0.0144) | | | |
| H23A | 0.9800 | 109.47 | | |
| H23B | 0.9800 | 109.47 | 109.47 | |
| H23C | 0.9800 | 109.47 | 109.47 | 109.47 |
| | C23 - | C22 | H23A | H23B |

| C24 - | Distance | Angles | | |
|---|---|---|---|---|
| C22 | 1.5025 (0.0138) | | | |
| H24A | 0.9800 | 109.47 | | |
| H24B | 0.9800 | 109.47 | 109.47 | |
| H24C | 0.9800 | 109.47 | 109.47 | 109.47 |
| | C24 - | C22 | H24A | H24B |

| C16' - | Distance | Angles | |
|---|---|---|---|
| N2' | 1.4784 (0.0159) | | |
| H16D | 0.9800 | 109.47 | |
| H16E | 0.9800 | 109.47 | 109.47 |

| H16F | 0.9800 | 109.47 | 109.47 | 109.47 |
| | C16' – | N2' | H16D | H16E |

| N2' – | Distance | Angles | | |
|---|---|---|---|---|
| C16' | 1.4784 (0.0159) | | | |
| C17' | 1.5013 (0.0143) | 114.97 (1.98) | | |
| H2'1 | 0.9900 | 108.53 | 108.53 | |
| H2'2 | 0.9900 | 108.53 | 108.53 | 107.52 |
| | N2' – | C16' | C17' | H2'1 |

| C17' – | Distance | Angles | | |
|---|---|---|---|---|
| N2' | 1.5013 (0.0143) | | | |
| C19' | 1.5137 (0.0157) | 106.06 (1.51) | | |
| C18' | 1.5465 (0.0152) | 106.22 (1.54) | 116.38 (1.75) | |
| H17' | 1.0000 | 109.31 | 109.31 | 109.31 |
| | C17' – | N2' | C19' | C18' |

| C18' – | Distance | Angles | | |
|---|---|---|---|---|
| C17' | 1.5465 (0.0152) | | | |
| H18D | 0.9800 | 109.47 | | |
| H18E | 0.9800 | 109.47 | 109.47 | |
| H18F | 0.9800 | 109.47 | 109.47 | 109.47 |
| | C18' – | C17' | H18D | H18E |

| C19' – | Distance | Angles | | |
|---|---|---|---|---|
| C17' | 1.5137 (0.0157) | | | |
| C20' | 1.5305 (0.0128) | 116.78 (1.32) | | |
| H19C | 0.9900 | 108.10 | 108.10 | |
| H19D | 0.9900 | 108.10 | 108.10 | 107.30 |
| | C19' – | C17' | C20' | H19C |

| C20' – | Distance | Angles | | |
|---|---|---|---|---|
| C21' | 1.4797 (0.0110) | | | |
| C19' | 1.5305 (0.0128) | 114.39 (1.00) | | |
| H20C | 0.9900 | 108.66 | 108.66 | |

| | | | | |
|---|---|---|---|---|
| H20D | 0.9900 | 108.66 | 108.66 | 107.60 |
| | C20' - | C21' | C19' | H20C |

| C21' - | Distance | Angles | | |
|---|---|---|---|---|
| C22' | 1.3135 (0.0125) | | | |
| C20' | 1.4797 (0.0110) | 128.60 (1.02) | | |
| H21' | 0.9500 | 115.70 | 115.70 | |
| | C21' - | C22' | C20' | |

| C22' - | Distance | Angles | | |
|---|---|---|---|---|
| C21' | 1.3135 (0.0125) | | | |
| C24' | 1.4782 (0.0166) | 121.46 (1.04) | | |
| C23' | 1.5120 (0.0172) | 121.87 (1.13) | 116.55 (1.06) | |
| | C22' - | C21' | C24' | |

| C23' - | Distance | Angles | | |
|---|---|---|---|---|
| C22' | 1.5120 (0.0172) | | | |
| H23D | 0.9800 | 109.47 | | |
| H23E | 0.9800 | 109.47 | 109.47 | |
| H23F | 0.9800 | 109.47 | 109.47 | 109.47 |
| | C23' - | C22' | H23D | H23E |

| C24' - | Distance | Angles | | |
|---|---|---|---|---|
| C22' | 1.4782 (0.0166) | | | |
| H24D | 0.9800 | 109.47 | | |
| H24E | 0.9800 | 109.47 | 109.47 | |
| H24F | 0.9800 | 109.47 | 109.47 | 109.47 |
| | C24' - | C22' | H24D | H24E |

Selected torsion angles

-179.80 ( 0.22)  O2 - C1 - C2 - O3
   1.13 ( 0.33)  O1 - C1 - C2 - O3

```
 -57.89 ( 0.30)   O2  - C1  - C2  - C3
 123.04 ( 0.25)   O1  - C1  - C2  - C3
  63.86 ( 0.26)   O3  - C2  - C3  - O4
 -59.74 ( 0.27)   C1  - C2  - C3  - O4
 -61.54 ( 0.24)   O3  - C2  - C3  - C4
 174.87 ( 0.19)   C1  - C2  - C3  - C4
-179.43 ( 0.31)   O4  - C3  - C4  - O5
 -54.08 ( 0.24)   C2  - C3  - C4  - O5
  55.88 ( 0.24)   O4  - C3  - C4  - C5
-178.77 ( 0.25)   C2  - C3  - C4  - C5
 -62.17 ( 0.26)   O5  - C4  - C5  - O6
  62.76 ( 0.24)   C3  - C4  - C5  - O6
  61.53 ( 0.27)   O5  - C4  - C5  - C6
-173.54 ( 0.18)   C3  - C4  - C5  - C6
  -0.61 ( 0.32)   O6  - C5  - C6  - O7
-122.60 ( 0.25)   C4  - C5  - C6  - O7
 179.88 ( 0.20)   O6  - C5  - C6  - O8
  57.89 ( 0.29)   C4  - C5  - C6  - O8
 -60.32 ( 0.35)   C7  - N1  - C8  - C9
 171.17 ( 0.25)   C7  - N1  - C8  - C10
  71.47 ( 0.34)   N1  - C8  - C10 - C11
 -54.98 ( 0.38)   C9  - C8  - C10 - C11
-175.63 ( 0.30)   C8  - C10 - C11 - C12
-101.85 ( 0.50)   C10 - C11 - C12 - C13
  -4.07 ( 0.90)   C11 - C12 - C13 - C15
 176.12 ( 0.42)   C11 - C12 - C13 - C14
 153.80 ( 3.04)   C16 - N2  - C17 - C19
 -80.06 ( 3.32)   C16 - N2  - C17 - C18
-161.27 ( 1.78)   N2  - C17 - C19 - C20
  73.97 ( 2.15)   C18 - C17 - C19 - C20
-169.35 ( 1.35)   C17 - C19 - C20 - C21
 122.59 ( 1.29)   C19 - C20 - C21 - C22
 179.34 ( 1.00)   C20 - C21 - C22 - C24
  -2.79 ( 1.69)   C20 - C21 - C22 - C23
 175.70 ( 3.32)   C16' - N2' - C17' - C19'
```

```
 -59.88 ( 3.60)   C16' - N2' - C17' - C18'
-179.67 ( 1.92)   N2' - C17' - C19' - C20'
  62.48 ( 2.51)   C18' - C17' - C19' - C20'
  59.21 ( 2.12)   C17' - C19' - C20' - C21'
 144.43 ( 1.43)   C19' - C20' - C21' - C22'
  -1.48 ( 1.99)   C20' - C21' - C22' - C24'
-177.33 ( 1.26)   C20' - C21' - C22' - C23'
```

Hydrogen bonds with H..A < r(A) + 2.000 Angstroms and <DHA > 110 deg.

Appropriate HTAB instructions appended to .res file for future use.

```
D-H         d(D-H)    d(H..A)   <DHA     d(D..A)   A
O3-H3A      0.840     1.932     174.51   2.770     O2 [ -x+3/2, y-1/2, -z+2 ]
O4-H4A      0.840     2.017     161.65   2.827     O7 [ -x+3/2, y-1/2, -z+1 ]
O5-H5A      0.840     2.010     159.42   2.812     O1 [ -x+3/2, y+1/2, -z+2 ]
O6-H6       0.840     1.902     175.25   2.740     O8 [ -x+3/2, y+1/2, -z+1 ]
C7-H7A      0.980     2.497     132.67   3.243     O5
N1-H1A      0.990     1.829     167.42   2.804     O7 [ x, y-1, z ]
N1-H1B      0.990     2.593     149.08   3.480     O1 [ -x+3/2, y-1/2, -z+2 ]
N1-H1B      0.990     1.849     153.47   2.770     O2 [ -x+3/2, y-1/2, -z+2 ]
C10-H10A    0.990     2.496     151.54   3.399     O1 [ -x+3/2, y-1/2, -z+2 ]
```

FMAP and GRID set by program

```
FMAP    2     1    39
GRID   -0.694 -2   -2    0.694   2    2
```

R1 =  0.0511 for   2969 unique reflections after merging for Fourier

Electron density synthesis with coefficients Fo-Fc

Highest peak    0.38  at   0.1232   0.1726   0.9601  [  1.96 A from H14C ]
Deepest hole   -0.28  at   0.0756   0.3399  -0.0094  [  0.47 A from H14C ]

Mean =   0.00,   Rms deviation from mean =    0.05 e/A^3,   Highest memory used =    6161 /    23271

Fourier peaks appended to .res file x        y        z       sof      U       Peak   Distances to nearest atoms (including symmetry equivalents)

Q1   1   0.8768  -0.8274   1.0399   1.00000  0.05    0.38   1.96 H14C  2.37 H16D  2.42 H8   2.63 H21
 Q2   1   0.8686   0.1188   1.1070   1.00000  0.05    0.36   2.15 H19D  2.32 H19B  2.39 H16C  2.43 H21
 Q3   1   0.9594   0.0490   1.1863   1.00000  0.05    0.27   0.82 H24D  0.89 C24'  1.11 H21   1.21 C21
 Q4   1   0.7122   0.5541   0.7494   1.00000  0.05    0.26   0.55 O4    0.87 C3    1.14 H4A   1.52 H3
 Q5   1   0.7829   0.5651   0.7489   1.00000  0.05    0.25   0.69 O5    0.73 C4    1.24 H5A   1.42 H4
 Q6   1   0.9165   0.0553   1.2438   1.00000  0.05    0.25   0.62 H21   0.95 H20C  1.19 C21   1.68 C20'
 Q7   1   0.7350   0.4859   0.8517   1.00000  0.05    0.25   0.72 C2    0.81 C3    1.41 H2    1.45 H3
 Q8   1   0.8541   0.0200   0.7256   1.00000  0.05    0.23   0.72 N1    0.82 C8    1.33 H1B   1.33 H1A

```
Q9    1   0.7255  0.5694  1.0941  1.00000  0.05    0.23    0.80 O2
1.30 H3A   1.59 C1   2.13 O3
Q10   1   0.8749  0.1149  0.8857  1.00000  0.05    0.23    0.95 H8
1.59 C8   1.93 H10A  2.03 C10
```

Shortest distances between peaks (including symmetry equivalents)

```
  1   2  0.85       4   7  1.37      1  10  1.58      3   6  1.69
  8  10  1.85       5   7  2.17      2   6  2.18
      2  10  2.20       7   9  2.52      1   6  2.56      4   5  2.57
```

Time profile in seconds
------------------------

```
    0.01: Read and process instructions
    0.00: Fit rigid groups
    0.01: Interpret restraints etc.
    0.00: Generate connectivity array
    0.00: Analyse DFIX and DANG restraints
    0.00: Analyse SAME and SADI restraints
    0.00: Generate CHIV restraints
    0.00: Check if bonds in residues restrained
    0.00: Generate DELU and RIGU restraints
    0.00: Generate SIMU restraints
    0.00: Generate ISOR restraints
    0.00: Generate NCSY restraints
    0.00: Analyse other restraints etc.
    0.12: Read intensity data, sort/merge etc.
    0.00: Set up constraints
    0.00: OSF, H-atoms from difference map
    0.03: Set up l.s. refinement
    0.00: Generate idealized H-atoms
    0.30: Structure factors and derivatives
    0.50: Sum l.s. matrices
```

```
   0.00: Generate and apply antibumping restraints
   0.01: Apply other restraints
   0.08: Solve l.s. equations
   0.00: Generate HTAB table
   0.22: Other dependent quantities, CIF, tables
   0.03: Analysis of variance
   0.04: Merge reflections for Fourier and .fcf
   0.01: Fourier summations
   0.02: Peaksearch
   0.00: Analyse peaklist

** WARNING: These times are only approximate for multiple threads.
           To get better estimates run with -t1 **

+++++++++++++++++++++++++++++++++++++++++++++++++++++++++++++++++++++++
+++++++
 + xs0061a        finished at 14:26:56   Total elapsed time:       1.40
secs  +

+++++++++++++++++++++++++++++++++++++++++++++++++++++++++++++++++++++++
+++++++

Electron density synthesis with coefficients Fo-Fc

Highest peak    0.38  at  0.1232  0.1726  0.9601  [  1.96 A from H14C
]
 Deepest hole   -0.28  at  0.0756  0.3399 -0.0094  [  0.47 A from H14C
]

Mean =    0.00,   Rms deviation from mean =    0.05 e/A^3,   Highest
memory used =     6161 /   23271
```

Fourier peaks appended to .res file

```
                     x       y       z      sof      U     Peak    Distances
to nearest atoms (including symmetry equivalents)

Q1    1    0.8768  -0.8274  1.0399  1.00000  0.05   0.38   1.96 H14C
2.37 H16D  2.42 H8   2.63 H21
  Q2    1    0.8686   0.1188  1.1070  1.00000  0.05   0.36   2.15 H19D
2.32 H19B  2.39 H16C 2.43 H21
  Q3    1    0.9594   0.0490  1.1863  1.00000  0.05   0.27   0.82 H24D
0.89 C24'  1.11 H21  1.21 C21
  Q4    1    0.7122   0.5541  0.7494  1.00000  0.05   0.26   0.55 O4
0.87 C3    1.14 H4A  1.52 H3
  Q5    1    0.7829   0.5651  0.7489  1.00000  0.05   0.25   0.69 O5
0.73 C4    1.24 H5A  1.42 H4
  Q6    1    0.9165   0.0553  1.2438  1.00000  0.05   0.25   0.62 H21
0.95 H20C  1.19 C21  1.68 C20'
  Q7    1    0.7350   0.4859  0.8517  1.00000  0.05   0.25   0.72 C2
0.81 C3    1.41 H2   1.45 H3
  Q8    1    0.8541   0.0200  0.7256  1.00000  0.05   0.23   0.72 N1
0.82 C8    1.33 H1B  1.33 H1A
  Q9    1    0.7255   0.5694  1.0941  1.00000  0.05   0.23   0.80 O2
1.30 H3A   1.59 C1   2.13 O3
  Q10   1    0.8749   0.1149  0.8857  1.00000  0.05   0.23   0.95 H8
1.59 C8    1.93 H10A 2.03 C10

Shortest distances between peaks (including symmetry equivalents)

1    2    0.85        4    7   1.37        1   10   1.58       3    6   1.69
  8   10   1.85        5    7   2.17        2    6   2.18
       2   10   2.20        7    9   2.52        1    6   2.56       4    5   2.57
```

Time profile in seconds

------------------------

```
0.01: Read and process instructions
0.00: Fit rigid groups
0.01: Interpret restraints etc.
0.00: Generate connectivity array
0.00: Analyse DFIX and DANG restraints
0.00: Analyse SAME and SADI restraints
0.00: Generate CHIV restraints
0.00: Check if bonds in residues restrained
0.00: Generate DELU and RIGU restraints
0.00: Generate SIMU restraints
0.00: Generate ISOR restraints
0.00: Generate NCSY restraints
0.00: Analyse other restraints etc.
0.12: Read intensity data, sort/merge etc.
0.00: Set up constraints
0.00: OSF, H-atoms from difference map
0.03: Set up l.s. refinement
0.00: Generate idealized H-atoms
0.30: Structure factors and derivatives
0.50: Sum l.s. matrices
0.00: Generate and apply antibumping restraints
0.01: Apply other restraints
0.08: Solve l.s. equations
0.00: Generate HTAB table
0.22: Other dependent quantities, CIF, tables
0.03: Analysis of variance
0.04: Merge reflections for Fourier and .fcf
0.01: Fourier summations
0.02: Peaksearch
0.00: Analyse peaklist

** WARNING: These times are only approximate for multiple threads.
            To get better estimates run with -t1 **
```

```
+++++++++++++++++++++++++++++++++++++++++++++++++++++++++++++++++++++++
+++++++
+ xs0061a      finished at 14:26:56   Total elapsed time:    1.40
secs  +

+++++++++++++++++++++++++++++++++++++++++++++++++++++++++++++++++++++++
+++++++

Note:  atoms 1-82 are ordered.

CRYST1   36.341    7.883    9.823  90.00  94.10  90.00 C 1 2 1
SCALE1      0.027517  0.000000  0.001972        0.000000
SCALE2      0.000000  0.126861  0.000000        0.000000
SCALE3      0.000000  0.000000  0.102058        0.000000
ATOM     1   C1        0    24.962    3.384    9.773  1.000   2.29
ANISOU   1   C1        0      422      298      140       6      34      28
ATOM     2   C2        0    26.159    3.284    8.811  1.000   2.09
ANISOU   2   C2        0      387      222      175     -15      34      26
ATOM     3   H2        0    27.001    3.377    9.342  1.000   2.51
ATOM     4   C3        0    26.098    4.423    7.800  1.000   1.99
ANISOU   4   C3        0      379      210      158      -6      46      15
ATOM     5   H3        0    26.093    5.280    8.316  1.000   2.39
ATOM     6   C4        0    27.337    4.438    6.900  1.000   1.97
ANISOU   6   C4        0      364      227      150      10      25      10
ATOM     7   H4        0    27.337    3.589    6.372  1.000   2.37
ATOM     8   C5        0    27.291    5.601    5.903  1.000   2.12
ANISOU   8   C5        0      376      251      169      -2      17      23
ATOM     9   H5        0    26.440    5.539    5.383  1.000   2.54
ATOM    10   C6        0    28.467    5.475    4.927  1.000   2.19
ANISOU  10   C6        0      393      295      134     -28      10      34
ATOM    11   O1        0    24.183    2.403    9.873  1.000   2.46
ANISOU  11   O1        0      426      313      184     -54      61      14
ATOM    12   O2        0    24.856    4.457   10.418  1.000   2.68
```

| | | | | | | | | |
|---|---|---|---|---|---|---|---|---|
| ANISOU | 12 | O2 | 0 | 508 | 298 | 199 | -39 | 87 | -21 |
| ATOM | 13 | O3 | 0 | 26.196 | 2.043 | 8.124 | 1.000 | 2.43 | |
| ANISOU | 13 | O3 | 0 | 432 | 239 | 242 | 17 | 65 | 15 |
| ATOM | 14 | H3A | 0 | 26.781 | 1.549 | 8.470 | 1.000 | 3.65 | |
| ATOM | 15 | O4 | 0 | 24.896 | 4.380 | 7.036 | 1.000 | 2.27 | |
| ANISOU | 15 | O4 | 0 | 384 | 263 | 207 | 26 | 19 | -12 |
| ATOM | 16 | H4A | 0 | 24.918 | 3.719 | 6.517 | 1.000 | 3.41 | |
| ATOM | 17 | O5 | 0 | 28.536 | 4.468 | 7.665 | 1.000 | 2.18 | |
| ANISOU | 17 | O5 | 0 | 373 | 265 | 180 | 19 | 4 | 0 |
| ATOM | 18 | H5A | 0 | 28.542 | 5.155 | 8.148 | 1.000 | 3.27 | |
| ATOM | 19 | O6 | 0 | 27.299 | 6.832 | 6.605 | 1.000 | 2.38 | |
| ANISOU | 19 | O6 | 0 | 423 | 212 | 259 | 20 | 34 | 15 |
| ATOM | 20 | H6 | 0 | 26.681 | 7.323 | 6.317 | 1.000 | 3.57 | |
| ATOM | 21 | O7 | 0 | 29.293 | 6.423 | 4.822 | 1.000 | 2.48 | |
| ANISOU | 21 | O7 | 0 | 438 | 320 | 172 | -77 | 26 | 21 |
| ATOM | 22 | O8 | 0 | 28.532 | 4.401 | 4.262 | 1.000 | 2.63 | |
| ANISOU | 22 | O8 | 0 | 487 | 328 | 174 | -67 | 76 | -15 |
| ATOM | 23 | C7 | 0 | 29.319 | 1.599 | 6.372 | 1.000 | 2.92 | |
| ANISOU | 23 | C7 | 0 | 497 | 323 | 274 | 6 | -6 | 10 |
| ATOM | 24 | H7A | 0 | 29.625 | 2.344 | 6.931 | 1.000 | 4.37 | |
| ATOM | 25 | H7B | 0 | 28.340 | 1.575 | 6.368 | 1.000 | 4.37 | |
| ATOM | 26 | H7C | 0 | 29.647 | 1.722 | 5.457 | 1.000 | 4.37 | |
| ATOM | 27 | N1 | 0 | 29.848 | 0.311 | 6.924 | 1.000 | 2.36 | |
| ANISOU | 27 | N1 | 0 | 390 | 302 | 193 | -20 | 31 | 13 |
| ATOM | 28 | H1A | 0 | 29.657 | -0.416 | 6.280 | 1.000 | 2.83 | |
| ATOM | 29 | H1B | 0 | 29.369 | 0.102 | 7.765 | 1.000 | 2.83 | |
| ATOM | 30 | C8 | 0 | 31.322 | 0.341 | 7.199 | 1.000 | 3.19 | |
| ANISOU | 30 | C8 | 0 | 402 | 467 | 329 | -25 | -21 | -46 |
| ATOM | 31 | H8 | 0 | 31.484 | 1.116 | 7.810 | 1.000 | 3.83 | |
| ATOM | 32 | C9 | 0 | 32.104 | 0.616 | 5.929 | 1.000 | 4.36 | |
| ANISOU | 32 | C9 | 0 | 442 | 656 | 538 | -29 | 91 | 123 |
| ATOM | 33 | H9A | 0 | 31.769 | 0.042 | 5.209 | 1.000 | 6.54 | |
| ATOM | 34 | H9B | 0 | 33.053 | 0.428 | 6.083 | 1.000 | 6.54 | |
| ATOM | 35 | H9C | 0 | 31.994 | 1.557 | 5.676 | 1.000 | 6.54 | |
| ATOM | 36 | C10 | 0 | 31.755 | -0.903 | 7.952 | 1.000 | 3.68 | |

| | | | | | | | | | |
|---|---|---|---|---|---|---|---|---|---|
| ANISOU | 36 | C10 | | 0 | 411 | 568 | 402 | 22 | -23 | 11 |
| ATOM | 37 | H10 | | 0 | 31.155 | -1.020 | 8.730 | 1.000 | 4.41 |
| ATOM | 38 | H10 | | 0 | 32.668 | -0.752 | 8.302 | 1.000 | 4.41 |
| ATOM | 39 | C11 | | 0 | 31.758 | -2.204 | 7.149 | 1.000 | 4.06 |
| ANISOU | 39 | C11 | | 0 | 511 | 555 | 459 | 18 | -22 | -37 |
| ATOM | 40 | H11 | | 0 | 30.865 | -2.348 | 6.746 | 1.000 | 4.88 |
| ATOM | 41 | H11 | | 0 | 32.420 | -2.141 | 6.416 | 1.000 | 4.88 |
| ATOM | 42 | C12 | | 0 | 32.101 | -3.355 | 8.039 | 1.000 | 4.98 |
| ANISOU | 42 | C12 | | 0 | 616 | 586 | 668 | 73 | -165 | -31 |
| ATOM | 43 | H12 | | 0 | 31.399 | -3.673 | 8.595 | 1.000 | 5.98 |
| ATOM | 44 | C13 | | 0 | 33.245 | -3.981 | 8.151 | 1.000 | 7.08 |
| ANISOU | 44 | C13 | | 0 | 775 | 648 | 1236 | 203 | -387 | -252 |
| ATOM | 45 | C14 | | 0 | 33.412 | -5.091 | 9.198 | 1.000 | 10.63 |
| ANISOU | 45 | C14 | | 0 | 1536 | 637 | 1815 | 392 | -1154 | -297 |
| ATOM | 46 | H14 | | 0 | 34.024 | -4.788 | 9.901 | 1.000 | 15.94 |
| ATOM | 47 | H14 | | 0 | 33.778 | -5.892 | 8.769 | 1.000 | 15.94 |
| ATOM | 48 | H14 | | 0 | 32.540 | -5.301 | 9.593 | 1.000 | 15.94 |
| ATOM | 49 | C15 | | 0 | 34.421 | -3.675 | 7.298 | 1.000 | 14.01 |
| ANISOU | 49 | C15 | | 0 | 699 | 1593 | 2965 | 423 | 218 | -369 |
| ATOM | 50 | H15 | | 0 | 34.752 | -4.502 | 6.889 | 1.000 | 21.02 |
| ATOM | 51 | H15 | | 0 | 35.129 | -3.277 | 7.848 | 1.000 | 21.02 |
| ATOM | 52 | H15 | | 0 | 34.160 | -3.044 | 6.596 | 1.000 | 21.02 |
| ATOM | 53 | C16A | | 0 | 28.919 | -4.536 | 11.219 | 0.520 | 3.19 |
| ANISOU | 53 | C16A | | 0 | 597 | 338 | 261 | -33 | -49 | 39 |
| ATOM | 54 | H16A | | 0 | 29.236 | -4.553 | 10.292 | 0.520 | 4.78 |
| ATOM | 55 | H16A | | 0 | 27.939 | -4.554 | 11.229 | 0.520 | 4.78 |
| ATOM | 56 | H16A | | 0 | 29.264 | -5.319 | 11.697 | 0.520 | 4.78 |
| ATOM | 57 | N2 | A | 0 | 29.399 | -3.300 | 11.884 | 0.520 | 2.50 |
| ANISOU | 57 | N2 | A | 0 | 362 | 392 | 183 | -44 | 42 | 44 |
| ATOM | 58 | H2AA | | 0 | 29.149 | -2.524 | 11.322 | 0.520 | 3.00 |
| ATOM | 59 | H2BA | | 0 | 28.926 | -3.205 | 12.749 | 0.520 | 3.00 |
| ATOM | 60 | C17A | | 0 | 30.856 | -3.245 | 12.138 | 0.520 | 3.52 |
| ANISOU | 60 | C17A | | 0 | 395 | 598 | 328 | -86 | 109 | 98 |
| ATOM | 61 | H17A | | 0 | 31.311 | -3.684 | 11.363 | 0.520 | 4.23 |
| ATOM | 62 | C18A | | 0 | 31.211 | -4.055 | 13.395 | 0.520 | 5.35 |

| | | | | | | | | | |
|---|---|---|---|---|---|---|---|---|---|
| ANISOU | 62 | C18A | | 0 | 545 | 1080 | 383 | 133 | -49 | 304 |
| ATOM | 63 | H18A | | 0 | 30.758 | -3.667 | 14.172 | 0.520 | 8.03 |
| ATOM | 64 | H18A | | 0 | 32.181 | -4.031 | 13.536 | 0.520 | 8.03 |
| ATOM | 65 | H18A | | 0 | 30.921 | -4.984 | 13.278 | 0.520 | 8.03 |
| ATOM | 66 | C19A | | 0 | 31.350 | -1.817 | 12.200 | 0.520 | 4.84 |
| ANISOU | 66 | C19A | | 0 | 571 | 801 | 445 | -176 | 53 | 15 |
| ATOM | 67 | H19A | | 0 | 31.110 | -1.430 | 13.079 | 0.520 | 5.81 |
| ATOM | 68 | H19A | | 0 | 30.893 | -1.287 | 11.500 | 0.520 | 5.81 |
| ATOM | 69 | C20A | | 0 | 32.862 | -1.704 | 12.003 | 0.520 | 5.79 |
| ANISOU | 69 | C20A | | 0 | 602 | 997 | 574 | -231 | 75 | -153 |
| ATOM | 70 | H20A | | 0 | 33.320 | -2.358 | 12.589 | 0.520 | 6.95 |
| ATOM | 71 | H20A | | 0 | 33.089 | -1.922 | 11.064 | 0.520 | 6.95 |
| ATOM | 72 | C21A | | 0 | 33.345 | -0.322 | 12.325 | 0.520 | 6.00 |
| ANISOU | 72 | C21A | | 0 | 682 | 917 | 651 | -350 | 53 | 8 |
| ATOM | 73 | H21A | | 0 | 32.944 | 0.384 | 11.831 | 0.520 | 7.19 |
| ATOM | 74 | C22A | | 0 | 34.260 | 0.039 | 13.212 | 0.520 | 6.17 |
| ANISOU | 74 | C22A | | 0 | 539 | 947 | 830 | -154 | 130 | -83 |
| ATOM | 75 | C23A | | 0 | 34.991 | -0.916 | 14.160 | 0.520 | 9.34 |
| ANISOU | 75 | C23A | | 0 | 1019 | 1114 | 1372 | -88 | -488 | -148 |
| ATOM | 76 | H23A | | 0 | 34.656 | -1.828 | 14.028 | 0.520 | 14.01 |
| ATOM | 77 | H23A | | 0 | 34.833 | -0.641 | 15.088 | 0.520 | 14.01 |
| ATOM | 78 | H23A | | 0 | 35.952 | -0.892 | 13.972 | 0.520 | 14.01 |
| ATOM | 79 | C24A | | 0 | 34.619 | 1.489 | 13.378 | 0.520 | 8.43 |
| ANISOU | 79 | C24A | | 0 | 743 | 999 | 1422 | -270 | 14 | -125 |
| ATOM | 80 | H24A | | 0 | 34.226 | 2.009 | 12.646 | 0.520 | 12.65 |
| ATOM | 81 | H24A | | 0 | 35.594 | 1.588 | 13.363 | 0.520 | 12.65 |
| ATOM | 82 | H24A | | 0 | 34.271 | 1.815 | 14.234 | 0.520 | 12.65 |
| ATOM | 83 | C16B | | 0 | 29.077 | -4.589 | 11.340 | 0.480 | 3.19 |
| ANISOU | 83 | C16B | | 0 | 597 | 338 | 261 | -33 | -49 | 39 |
| ATOM | 84 | H16B | | 0 | 29.533 | -4.801 | 10.499 | 0.480 | 4.78 |
| ATOM | 85 | H16B | | 0 | 28.107 | -4.598 | 11.197 | 0.480 | 4.78 |
| ATOM | 86 | H16B | | 0 | 29.314 | -5.256 | 12.017 | 0.480 | 4.78 |
| ATOM | 87 | N2'B | | 0 | 29.494 | -3.248 | 11.802 | 0.480 | 2.50 |
| ANISOU | 87 | N2'B | | 0 | 362 | 392 | 183 | -44 | 42 | 44 |
| ATOM | 88 | H2'B | | 0 | 29.038 | -3.055 | 12.659 | 0.480 | 3.00 |

```
ATOM     89  H2'B        0    29.186   -2.578  11.143 0.480  3.00
ATOM     90  C17B        0    30.973   -3.078  12.000 0.480  3.76
ANISOU   90  C17B        0      345      655     410     -3    -14    165
ATOM     91  H17B        0    31.446   -3.275  11.142 0.480  4.51
ATOM     92  C18B        0    31.389   -4.118  13.066 0.480  5.45
ANISOU   92  C18B        0      494     1102     449      8    -26    345
ATOM     93  H18B        0    30.881   -3.963  13.890 0.480  8.17
ATOM     94  H18B        0    32.347   -4.031  13.251 0.480  8.17
ATOM     95  H18B        0    31.202   -5.020  12.732 0.480  8.17
ATOM     96  C19B        0    31.181   -1.623  12.364 0.480  4.33
ANISOU   96  C19B        0      471      721     433   -240     69   -118
ATOM     97  H19B        0    30.653   -1.431  13.179 0.480  5.20
ATOM     98  H19B        0    30.809   -1.067  11.634 0.480  5.20
ATOM     99  C20B        0    32.623   -1.175  12.614 0.480  5.35
ANISOU   99  C20B        0      517      944     546   -228     59   -161
ATOM    100  H20B        0    32.619   -0.214  12.854 0.480  6.42
ATOM    101  H20B        0    32.980   -1.675  13.391 0.480  6.42
ATOM    102  C21B        0    33.533   -1.373  11.465 0.480  6.16
ANISOU  102  C21B        0      621     1076     615   -177    102   -113
ATOM    103  H21B        0    33.373   -2.149  10.941 0.480  7.39
ATOM    104  C22B        0    34.534   -0.617  11.072 0.480  6.89
ANISOU  104  C22B        0      632     1306     646   -270    -49     89
ATOM    105  C23B        0    35.334   -0.936   9.829 0.480  9.60
ANISOU  105  C23B        0      801     1950     852   -389    -59    243
ATOM    106  H23B        0    36.250   -1.175  10.083 0.480 14.40
ATOM    107  H23B        0    35.352   -0.151   9.242 0.480 14.40
ATOM    108  H23B        0    34.919   -1.688   9.357 0.480 14.40
ATOM    109  C24B        0    34.875    0.638  11.774 0.480  9.36
ANISOU  109  C24B        0     1252     1267     992   -339    -28    266
ATOM    110  H24B        0    34.051    1.103  12.030 0.480 14.04
ATOM    111  H24B        0    35.403    1.211  11.180 0.480 14.04
ATOM    112  H24B        0    35.396    0.431  12.578 0.480 14.04
```

```
data_xcalibur
_audit_creation_date
;
'Fri Apr 19 10:58:55 2013'
;
_audit_creation_method
;
CrysAlisPro, Agilent Technologies,
Version 1.171.36.28 (release 01-02-2013 CrysAlis171 .NET)
(compiled Feb  1 2013,16:14:44)
;
_computing_data_collection
;
CrysAlisPro, Agilent Technologies,
Version 1.171.36.28 (release 01-02-2013 CrysAlis171 .NET)
(compiled Feb  1 2013,16:14:44)
;
_computing_cell_refinement
;
CrysAlisPro, Agilent Technologies,
Version 1.171.36.28 (release 01-02-2013 CrysAlis171 .NET)
(compiled Feb  1 2013,16:14:44)
;
_computing_data_reduction
;
CrysAlisPro, Agilent Technologies,
Version 1.171.36.28 (release 01-02-2013 CrysAlis171 .NET)
(compiled Feb  1 2013,16:14:44)
;
_cell_length_a                 36.3410(7)
_cell_length_b                 7.88266(12)
_cell_length_c                 9.82344(18)
_cell_angle_alpha              90.0
_cell_angle_beta               94.0983(17)
_cell_angle_gamma              90.0
```

```
_cell_volume                              2806.87(9)
_cell_formula_units_Z                        4.00000
_cell_measurement_reflns_used   17242
_cell_measurement_theta_min     4.4860
_cell_measurement_theta_max     71.8310
_cell_oxdiff_length_a                     36.3488(7)
_cell_oxdiff_length_b                     7.88405(14)
_cell_oxdiff_length_c                     9.81993(14)
_cell_oxdiff_angle_alpha                  90.0166(14)
_cell_oxdiff_angle_beta                   94.1239(15)
_cell_oxdiff_angle_gamma                  89.9831(16)
_cell_oxdiff_volume                       2806.87(9)
_cell_oxdiff_measurement_reflns_used   17242
_exptl_crystal_description                   ''
_exptl_crystal_colour                        ''
_exptl_crystal_size_max                                 0.5596
_exptl_crystal_size_mid                                 0.2583
_exptl_crystal_size_min                                 0.0761
loop_
_exptl_crystal_face_index_h
_exptl_crystal_face_index_k
_exptl_crystal_face_index_l
_exptl_crystal_face_perp_dist
_exptl_oxdiff_crystal_face_indexfrac_h
_exptl_oxdiff_crystal_face_indexfrac_k
_exptl_oxdiff_crystal_face_indexfrac_l
_exptl_oxdiff_crystal_face_x
_exptl_oxdiff_crystal_face_y
_exptl_oxdiff_crystal_face_z
 -24   0   1 0.0537 -24.0070 -0.0074  1.0005  0.7822  0.6022  0.2604
  23   0   0 0.0378  23.0057  0.0066 -0.0012 -0.7785 -0.5824 -0.1018
  -2   4   4 0.2168  -2.0122  3.9977  3.9960  0.4078 -0.5996  0.6923
  -2  -5   3 0.2310  -1.9945 -5.0028  2.9993 -0.5983  0.8191  0.3877
   2  -4  -4 0.2657   2.0122 -3.9977 -3.9960 -0.4078  0.5996 -0.6923
   4   1  -6 0.1209   4.0056  1.0045 -5.9960  0.1604 -0.2251 -0.9259
```

```
    4    2   -6 0.1242   4.0038   2.0046  -5.9963   0.2756  -0.3821  -0.9092
   -4   -1    6 0.1317  -4.0056  -1.0045   5.9960  -0.1604   0.2251   0.9259
   -3   -4    5 0.1996  -2.9987  -4.0040   4.9975  -0.5096   0.6763   0.7172
    1    5    0 0.2656   0.9910   5.0009  -0.0014   0.5418  -0.8104   0.0792
  -23    0   -1 0.0526 -23.0046  -0.0060  -0.9980   0.8086   0.5880  -0.0523
  -24    0    0 0.0383 -24.0060  -0.0069   0.0013   0.8123   0.6077   0.1063
   23    0    1 0.0445  23.0046   0.0060   0.9980  -0.8086  -0.5880   0.0523
   21    1   -3 0.0509  21.0066   1.0077  -2.9992  -0.5053  -0.6722  -0.5387
   20    2    2 0.1042  19.9991   2.0049   1.9969  -0.5069  -0.8316   0.2532
  -23   -1    1 0.0833 -23.0049  -1.0072   1.0008   0.6332   0.7339   0.2393
  -20   -1    3 0.0938 -20.0064  -1.0074   2.9991   0.4715   0.6468   0.5343
   22   -2    1 0.0985  22.0081  -1.9945   0.9986  -1.0050  -0.2486   0.0233
   19   -2   -4 0.1476  19.0127  -1.9927  -3.9975  -0.7529  -0.1449  -0.7342
   13   -1    5 0.1090  12.9997  -0.9991   4.9958  -0.7057  -0.1999   0.6965
```
_exptl_absorpt_coefficient_mu                    0.710
_exptl_absorpt_correction_T_min                  0.764
_exptl_absorpt_correction_T_max                  0.955
_exptl_absorpt_correction_type              'analytical'
_exptl_absorpt_process_details
;
CrysAlisPro, Agilent Technologies,
Version 1.171.36.28 (release 01-02-2013 CrysAlis171 .NET)
(compiled Feb  1 2013,16:14:44)
Analytical numeric absorption correction using a multifaceted crystal
               model based on expressions derived by R.C. Clark
& J.S. Reid.
(Clark, R. C. & Reid, J. S. (1995). Acta Cryst. A51, 887-897)
;
_diffrn_radiation_wavelength 1.5418
_diffrn_radiation_type 'Cu K\a'
_diffrn_radiation_source 'SuperNova (Cu) X-ray Source'
_diffrn_radiation_monochromator 'mirror'
_diffrn_measurement_device_type 'SuperNova, Dual, Cu at zero, Atlas'
_diffrn_detector_area_resol_mean 10.3875
_diffrn_reflns_number 31163

_diffrn_reflns_av_R_equivalents 0.0343
_diffrn_reflns_av_sigmaI/netI 0.0239
_diffrn_reflns_limit_h_min -44
_diffrn_reflns_limit_h_max 44
_diffrn_reflns_limit_k_min -9
_diffrn_reflns_limit_k_max 9
_diffrn_reflns_limit_l_min -10
_diffrn_reflns_limit_l_max 12
_diffrn_reflns_theta_min 4.5126
_diffrn_reflns_theta_max 72.0945
_diffrn_measured_fraction_theta_max 0.9975
_diffrn_reflns_theta_full 71.9829
_diffrn_measured_fraction_theta_full 0.9997
_diffrn_orient_matrix_UB_11      -0.0338732000
_diffrn_orient_matrix_UB_12       0.1150518000
_diffrn_orient_matrix_UB_13      -0.0301133000
_diffrn_orient_matrix_UB_21      -0.0252721000
_diffrn_orient_matrix_UB_22      -0.1570496000
_diffrn_orient_matrix_UB_23      -0.0056593000
_diffrn_orient_matrix_UB_31      -0.0044233000
_diffrn_orient_matrix_UB_32       0.0167496000
_diffrn_orient_matrix_UB_33       0.1542751000
_diffrn_measurement_details
;
__ type_ start__ end____ width___ exp.time_
   1 omega    0.00   25.00   1.0000    5.0000
omega____ theta____ kappa____ phi_____ frames
    -         40.0000   93.0000   147.3583  25

__ type_ start__ end____ width___ exp.time_
   2 omega    0.00   25.00   1.0000    5.0000
omega____ theta____ kappa____ phi_____ frames
    -         40.0000   93.0000   -13.1658  25

__ type_ start__ end____ width___ exp.time_

```
   3 omega  -114.00   -14.00    1.0000    5.0000
omega____  theta____  kappa____  phi_____  frames
   -        -40.6162  -57.0000   120.0000  100

#__ type_  start__   end____   width___   exp.time_
   4 omega   -74.00    -5.00    1.0000    5.0000
omega____  theta____  kappa____  phi_____  frames
   -        -40.6162  125.0000   120.0000  69

#__ type_  start__   end____   width___   exp.time_
   5 omega  -116.00   -16.00    1.0000    5.0000
omega____  theta____  kappa____  phi_____  frames
   -        -40.6162  -38.0000  -150.0000  100

#__ type_  start__   end____   width___   exp.time_
   6 omega  -116.00    -9.00    1.0000    5.0000
omega____  theta____  kappa____  phi_____  frames
   -        -40.6162  -77.0000    0.0000  107

#__ type_  start__   end____   width___   exp.time_
   7 omega    22.00    84.00    1.0000    5.0000
omega____  theta____  kappa____  phi_____  frames
   -         40.6162 -122.0000   -78.0000  62

#__ type_  start__   end____   width___   exp.time_
   8 omega    17.00    42.00    1.0000    5.0000
omega____  theta____  kappa____  phi_____  frames
   -         52.0000   82.0000  -130.6528  25

#__ type_  start__   end____   width___   exp.time_
   9 omega  -140.00   -80.00    1.0000   20.0000
omega____  theta____  kappa____  phi_____  frames
   -        -61.5000 -111.0000  -150.0000  60

#__ type_  start__   end____   width___   exp.time_
```

| 10 | omega | -139.00 | -89.00 | 1.0000 | 20.0000 |
|---|---|---|---|---|---|
| omega | theta | kappa | phi | | frames |
| - | -61.5000 | -77.0000 | -41.4811 | | 50 |

| # | type | start | end | width | exp.time |
|---|---|---|---|---|---|
| 11 | omega | -62.00 | -30.00 | 1.0000 | 20.0000 |
| omega | theta | kappa | phi | | frames |
| - | -61.5000 | -77.0000 | 60.0000 | | 32 |

| # | type | start | end | width | exp.time |
|---|---|---|---|---|---|
| 12 | omega | -56.00 | -29.00 | 1.0000 | 20.0000 |
| omega | theta | kappa | phi | | frames |
| - | -61.5000 | -77.0000 | 120.0000 | | 27 |

| # | type | start | end | width | exp.time |
|---|---|---|---|---|---|
| 13 | omega | -89.00 | -4.00 | 1.0000 | 20.0000 |
| omega | theta | kappa | phi | | frames |
| - | -61.5000 | 111.0000 | 30.0000 | | 85 |

| # | type | start | end | width | exp.time |
|---|---|---|---|---|---|
| 14 | omega | -56.00 | -29.00 | 1.0000 | 20.0000 |
| omega | theta | kappa | phi | | frames |
| - | -61.5000 | -77.0000 | -41.4811 | | 27 |

| # | type | start | end | width | exp.time |
|---|---|---|---|---|---|
| 15 | omega | -66.00 | -28.00 | 1.0000 | 20.0000 |
| omega | theta | kappa | phi | | frames |
| - | -61.5000 | -77.0000 | -90.0000 | | 38 |

| # | type | start | end | width | exp.time |
|---|---|---|---|---|---|
| 16 | omega | -56.00 | -29.00 | 1.0000 | 20.0000 |
| omega | theta | kappa | phi | | frames |
| - | -61.5000 | -77.0000 | 90.0000 | | 27 |

| # | type | start | end | width | exp.time |
|---|---|---|---|---|---|

```
 17 omega   -58.00   -31.00    1.0000    20.0000
omega____  theta____  kappa____  phi_____  frames
   -        -61.5000  -77.0000  150.0000 27

#__ type_ start__ end____ width___ exp.time_
 18 omega   -56.00   -28.00    1.0000    20.0000
omega____  theta____  kappa____  phi_____  frames
   -        -61.5000  -77.0000 -150.0000 28

#__ type_ start__ end____ width___ exp.time_
 19 omega    35.00   108.00    1.0000     5.0000
omega____  theta____  kappa____  phi_____  frames
   -         68.0000   75.0000   76.6790 73

#__ type_ start__ end____ width___ exp.time_
 20 omega    39.00    69.00    1.0000     5.0000
omega____  theta____  kappa____  phi_____  frames
   -         68.0000   63.0000  123.0535 30

#__ type_ start__ end____ width___ exp.time_
 21 omega    40.00    74.00    1.0000     5.0000
omega____  theta____  kappa____  phi_____  frames
   -         68.0000   71.0000  -46.4378 34

#__ type_ start__ end____ width___ exp.time_
 22 omega    35.00    62.00    1.0000     5.0000
omega____  theta____  kappa____  phi_____  frames
   -         68.0000   76.0000   -1.1268 27

#__ type_ start__ end____ width___ exp.time_
 23 omega   109.00   141.00    1.0000     5.0000
omega____  theta____  kappa____  phi_____  frames
   -         68.0000   75.0000   76.6790 32

#__ type_ start__ end____ width___ exp.time_
```

```
 24 omega   39.00   85.00   1.0000    5.0000
omega____ theta____ kappa____ phi_____ frames
    -        72.0000   77.0000  -157.6806 46

#__ type_ start__ end____ width___ exp.time_
 25 omega   48.00  133.00   1.0000   20.0000
omega____ theta____ kappa____ phi_____ frames
    -        80.0000   76.0000   18.7656 85

#__ type_ start__ end____ width___ exp.time_
 26 omega   49.00   84.00   1.0000   20.0000
omega____ theta____ kappa____ phi_____ frames
    -        80.0000   67.0000 -167.4197 35

#__ type_ start__ end____ width___ exp.time_
 27 omega   67.00   93.00   1.0000   20.0000
omega____ theta____ kappa____ phi_____ frames
    -       100.0000   75.0000  -42.1709 26

#__ type_ start__ end____ width___ exp.time_
 28 omega  121.00  178.00   1.0000   20.0000
omega____ theta____ kappa____ phi_____ frames
    -       113.0000   77.0000   90.0000 57

#__ type_ start__ end____ width___ exp.time_
 29 omega   79.00  115.00   1.0000   20.0000
omega____ theta____ kappa____ phi_____ frames
    -       113.0000   77.0000   90.0000 36

#__ type_ start__ end____ width___ exp.time_
 30 omega   35.00   83.00   1.0000   20.0000
omega____ theta____ kappa____ phi_____ frames
    -       113.0000  -94.0000 -180.0000 48

#__ type_ start__ end____ width___ exp.time_
```

```
 31 omega   119.00   176.00    1.0000    20.0000
omega____  theta____  kappa____  phi_____  frames
   -       113.0000   77.0000  -180.0000  57

#__ type_  start__  end____  width___  exp.time_
 32 omega    79.00   116.00    1.0000    20.0000
omega____  theta____  kappa____  phi_____  frames
   -       113.0000   77.0000  -180.0000  37

#__ type_  start__  end____  width___  exp.time_
 33 omega    79.00   176.00    1.0000    20.0000
omega____  theta____  kappa____  phi_____  frames
   -       113.0000   77.0000   150.0000  97

#__ type_  start__  end____  width___  exp.time_
 34 omega    82.00   116.00    1.0000    20.0000
omega____  theta____  kappa____  phi_____  frames
   -       113.0000 -111.0000  -120.0000  34

#__ type_  start__  end____  width___  exp.time_
 35 omega    45.00    81.00    1.0000    20.0000
omega____  theta____  kappa____  phi_____  frames
   -       113.0000 -111.0000  -120.0000  36

#__ type_  start__  end____  width___  exp.time_
 36 omega    82.00   109.00    1.0000    20.0000
omega____  theta____  kappa____  phi_____  frames
   -       113.0000 -122.0000   101.0000  27

#__ type_  start__  end____  width___  exp.time_
 37 omega    79.00   169.00    1.0000    20.0000
omega____  theta____  kappa____  phi_____  frames
   -       113.0000   77.0000  -120.0000  90

#__ type_  start__  end____  width___  exp.time_
```

```
 38 omega   83.00  113.00   1.0000   20.0000
omega____  theta____  kappa____  phi_____  frames
    -      113.0000   61.0000   30.0000 30

#__ type_ start__ end____ width___ exp.time_
 39 omega   69.00  131.00   1.0000   20.0000
omega____  theta____  kappa____  phi_____  frames
    -      113.0000  -61.0000  -30.0000 62

#__ type_ start__ end____ width___ exp.time_
 40 omega   35.00  142.00   1.0000   20.0000
omega____  theta____  kappa____  phi_____  frames
    -      113.0000  -77.0000 -120.0000 107

#__ type_ start__ end____ width___ exp.time_
 41 omega   80.00  107.00   1.0000   20.0000
omega____  theta____  kappa____  phi_____  frames
    -      113.0000   77.0000   30.0000 27

#__ type_ start__ end____ width___ exp.time_
 42 omega   79.00  165.00   1.0000   20.0000
omega____  theta____  kappa____  phi_____  frames
    -      113.0000   77.0000  -30.0000 86

#__ type_ start__ end____ width___ exp.time_
 43 omega   79.00  177.00   1.0000   20.0000
omega____  theta____  kappa____  phi_____  frames
    -      113.0000   77.0000   60.0000 98

#__ type_ start__ end____ width___ exp.time_
 44 omega   84.00  118.00   1.0000   20.0000
omega____  theta____  kappa____  phi_____  frames
    -      113.0000   61.0000  120.0000 34

#__ type_ start__ end____ width___ exp.time_
```

```
              45 omega   83.00   167.00    1.0000    20.0000
       omega____  theta____  kappa____  phi_____  frames
                -         113.0000    61.0000   -60.0000 84

#__ type_ start__ end____ width___ exp.time_
              46 omega   79.00   171.00    1.0000    20.0000
       omega____  theta____  kappa____  phi_____  frames
                -         113.0000   -77.0000   120.0000 92

#__ type_ start__ end____ width___ exp.time_
              47 omega   83.00   111.00    1.0000    20.0000
       omega____  theta____  kappa____  phi_____  frames
                -         113.0000    61.0000  -120.0000 28

#__ type_ start__ end____ width___ exp.time_
              48 omega   117.00  166.00    1.0000    20.0000
       omega____  theta____  kappa____  phi_____  frames
                -         113.0000    77.0000     0.0000 49

#__ type_ start__ end____ width___ exp.time_
              49 omega   133.00  165.00    1.0000    20.0000
       omega____  theta____  kappa____  phi_____  frames
                -         113.0000    61.0000    30.0000 32

#__ type_ start__ end____ width___ exp.time_
              50 omega   83.00   110.00    1.0000    20.0000
       omega____  theta____  kappa____  phi_____  frames
                -         113.0000    61.0000   150.0000 27

#__ type_ start__ end____ width___ exp.time_
              51 omega   79.00   106.00    1.0000    20.0000
       omega____  theta____  kappa____  phi_____  frames
                -         113.0000    77.0000     0.0000 27

#__ type_ start__ end____ width___ exp.time_
```

```
 52 omega   86.00  113.00   1.0000   20.0000
omega____ theta____ kappa____ phi_____ frames
    -       113.0000   61.0000 -180.0000 27

#__ type_ start__ end____ width___ exp.time_
 53 omega   83.00  110.00   1.0000   20.0000
omega____ theta____ kappa____ phi_____ frames
    -       113.0000   61.0000   90.0000 27

#__ type_ start__ end____ width___ exp.time_
 54 omega   79.00  154.00   1.0000   20.0000
omega____ theta____ kappa____ phi_____ frames
    -       113.0000   77.0000  -90.0000 75

#__ type_ start__ end____ width___ exp.time_
 55 omega   85.00  112.00   1.0000   20.0000
omega____ theta____ kappa____ phi_____ frames
    -       113.0000 -111.0000   30.0000 27

#__ type_ start__ end____ width___ exp.time_
 56 omega   79.00  106.00   1.0000   20.0000
omega____ theta____ kappa____ phi_____ frames
    -       113.0000   77.0000 -150.0000 27

#__ type_ start__ end____ width___ exp.time_
 57 omega   84.00  176.00   1.0000   20.0000
omega____ theta____ kappa____ phi_____ frames
    -       113.0000   61.0000 -150.0000 92

#__ type_ start__ end____ width___ exp.time_
 58 omega   45.00  115.00   1.0000   20.0000
omega____ theta____ kappa____ phi_____ frames
    -       113.0000 -111.0000  150.0000 70

#__ type_ start__ end____ width___ exp.time_
```

```
 59 omega   83.00  162.00   1.0000   20.0000
omega____  theta____  kappa____  phi_____  frames
   -        113.0000   61.0000   60.0000 79

#__ type_  start__  end____  width___  exp.time_
 60 omega    1.00   28.00    1.0000    5.0000
omega____  theta____  kappa____  phi_____  frames
   -         40.0000   92.0000 -168.5442 27

#__ type_  start__  end____  width___  exp.time_
 61 omega  -116.00  -56.00   1.0000    5.0000
omega____  theta____  kappa____  phi_____  frames
   -        -40.6162 -151.0000   15.0000 60

#__ type_  start__  end____  width___  exp.time_
 62 omega   37.00  115.00    1.0000    5.0000
omega____  theta____  kappa____  phi_____  frames
   -         40.6162 -151.0000  -59.0000 78

#__ type_  start__  end____  width___  exp.time_
 63 omega    1.00   83.00    1.0000    5.0000
omega____  theta____  kappa____  phi_____  frames
   -         40.6162  -99.0000    0.0000 82

#__ type_  start__  end____  width___  exp.time_
 64 omega   17.00   45.00    1.0000    5.0000
omega____  theta____  kappa____  phi_____  frames
   -         52.0000   82.0000  -87.0034 28

#__ type_  start__  end____  width___  exp.time_
 65 omega   37.00  143.00    1.0000    5.0000
omega____  theta____  kappa____  phi_____  frames
   -         68.0000   63.0000  123.0535 106

#__ type_  start__  end____  width___  exp.time_
```

```
 66 omega    34.00   147.00   1.0000    5.0000
omega____  theta____  kappa____  phi_____  frames
   -        68.0000   77.0000   31.5989   113

#__ type_ start__ end____ width___ exp.time_
 67 omega    35.00   146.00   1.0000    5.0000
omega____  theta____  kappa____  phi_____  frames
   -        68.0000   75.0000   76.6790   111

#__ type_ start__ end____ width___ exp.time_
 68 omega    36.00   144.00   1.0000    5.0000
omega____  theta____  kappa____  phi_____  frames
   -        68.0000   71.0000  -46.4378   108

#__ type_ start__ end____ width___ exp.time_
 69 omega    38.00   151.00   1.0000    5.0000
omega____  theta____  kappa____  phi_____  frames
   -        72.0000   77.0000 -157.6806   113
```

;
_diffrn_measurement_method '\w scans'
_reflns_odcompleteness_completeness        99.97
_reflns_odcompleteness_theta               71.98
_reflns_odcompleteness_iscentric           1
_chemical_oxdiff_formula 'C24 H44 N2 O8'

While the invention has been particularly shown and described with reference to particular embodiments, it will be appreciated that variations of the above-disclosed and other features and functions, or alternatives thereof, may be desirably combined into many other different systems or applications. Also that various presently unforeseen or unanticipated alternatives, modifications, variations or improvements therein may be subsequently made by those skilled in the art which are also intended to be encompassed by the following claims.

What is claimed is:

1. An isolated (R)-Isometheptene enantiomer compound, comprising the structure according to Formula (Ib),

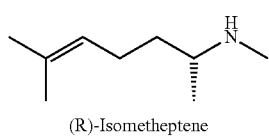

(R)-Isometheptene or a hydrochloride, or a pharmaceutically acceptable addition salt thereof.

2. The compound of claim 1, wherein the pharmaceutically acceptable addition salt is selected from the group consisting of mucate and bitartrate.

3. An (R)-Isometheptene mucate salt comprising the structure according to Formula (III):

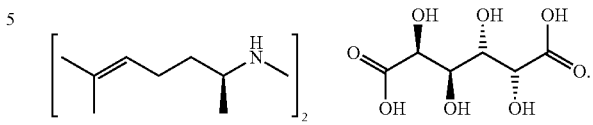

4. An HPLC purified (R)-Isometheptene enantiomer mucate salt according to claim 3 in crystal form.

5. The (R)-enantiomeric Isometheptene mucate salt according to claim 4, wherein an X-ray crystallography analysis showed a poor structural overlap between the dimethylalkene portion of the (R)-Isometheptene molecule and the mucate molecule as compared to a better structural overlap between the nitrogen moiety of the (R)-Isometheptene molecule and the mucate molecule.

6. The (R)-enantiomeric Isometheptene mucate salt compound of claim 3, capable of selectively or specifically binding to Imidazoline receptor type 1 ($I_1$).

7. The compound according to claim 1 which is chromatographically purified.

* * * * *